(12) United States Patent
Bailey et al.

(10) Patent No.: US 7,851,199 B2
(45) Date of Patent: Dec. 14, 2010

(54) PRODUCTION OF CAROTENOIDS IN OLEAGINOUS YEAST AND FUNGI

(75) Inventors: Richard Bailey, South Natick, MA (US); Kevin T. Madden, Arlington, MA (US); Joshua Trueheart, Concord, MA (US)

(73) Assignee: Microbia, Inc., Lexington, MA (US)

( * ) Notice: Subject to any disclaimer, the term of this patent is extended or adjusted under 35 U.S.C. 154(b) by 465 days.

(21) Appl. No.: 11/385,580

(22) Filed: Mar. 20, 2006

(65) Prior Publication Data

US 2007/0015237 A1 Jan. 18, 2007

Related U.S. Application Data

(60) Provisional application No. 60/663,621, filed on Mar. 18, 2005.

(51) Int. Cl.
   *C12N 1/19* (2006.01)
   *C12N 1/00* (2006.01)
   *C12N 15/70* (2006.01)
   *C12P 21/00* (2006.01)
   *C12Q 1/68* (2006.01)

(52) U.S. Cl. .......... 435/254.2; 435/255.1; 435/471; 435/71.1; 435/6

(58) Field of Classification Search ............ None
   See application file for complete search history.

(56) References Cited

U.S. PATENT DOCUMENTS

| | | |
|---|---|---|
| 4,318,987 A | 3/1982 | Murillo Araujo et al. |
| 4,439,629 A | 3/1984 | Ruegg |
| 4,680,314 A | 7/1987 | Nonomura |
| 4,851,339 A | 7/1989 | Hills |
| 4,870,011 A | 9/1989 | Suzuki et al. |
| 4,880,741 A | 11/1989 | Davidow |
| 4,937,189 A | 6/1990 | Davidow |
| 5,071,764 A | 12/1991 | Davidow et al. |
| 5,164,308 A | 11/1992 | Kyle |
| 5,182,208 A | 1/1993 | Johnson et al. |
| 5,212,088 A | 5/1993 | Prevatt |
| 5,310,554 A | 5/1994 | Haigh |
| 5,328,845 A | 7/1994 | Finkelstein et al. |
| 5,349,126 A | 9/1994 | Chappell et al. |
| 5,356,809 A | 10/1994 | Johnson et al. |
| 5,356,810 A | 10/1994 | Fleno et al. |
| 5,360,730 A | 11/1994 | Orndorff et al. |
| 5,365,017 A | 11/1994 | Chappell |
| 5,374,657 A | 12/1994 | Kyle |
| 5,378,369 A | 1/1995 | Rose et al. |
| 5,422,247 A | 6/1995 | Finkelstein et al. |
| 5,429,939 A | 7/1995 | Misawa et al. |
| 5,460,949 A | 10/1995 | Saunders et al. |
| 5,466,599 A | 11/1995 | Jacobson et al. |
| 5,550,156 A | 8/1996 | Kyle |
| 5,583,019 A | 12/1996 | Barclay |
| 5,589,581 A | 12/1996 | Misawa et al. |
| 5,589,619 A | 12/1996 | Chappell et al. |
| 5,591,343 A | 1/1997 | Kitaoka et al. |
| 5,599,711 A | 2/1997 | Flenoet et al. |
| 5,607,839 A | 3/1997 | Tsubokura et al. |
| 5,643,719 A | 7/1997 | Cerda-Olmedo et al. |
| 5,648,261 A | 7/1997 | De Boer et al. |
| 5,679,567 A | 10/1997 | Fleno et al. |
| 5,691,190 A | 11/1997 | Girard et al. |
| 5,709,856 A | 1/1998 | Flenoet et al. |
| 5,712,110 A | 1/1998 | Fleno et al. |
| 5,766,911 A | 6/1998 | Koike et al. |
| 5,773,265 A | 6/1998 | Koike et al. |
| 5,773,273 A | 6/1998 | Nishino et al. |
| 5,786,193 A | 7/1998 | Greene et al. |
| 5,786,212 A | 7/1998 | James |
| 5,792,903 A | 8/1998 | Hirschberg et al. |
| 5,807,725 A | 9/1998 | Ohto et al. |
| 5,811,273 A | 9/1998 | Misawa et al. |
| 5,840,528 A | 11/1998 | Van Ooyen |
| 5,849,524 A | 12/1998 | Kondo et al. |
| 5,858,700 A | 1/1999 | Ausich et al. |
| 5,858,761 A | 1/1999 | Tsubokura et al. |
| 5,879,927 A | 3/1999 | De Boer et al. |
| 5,882,909 A | 3/1999 | Ohto et al. |
| 5,885,810 A | 3/1999 | Ohto et al. |
| 5,910,433 A | 6/1999 | Kajiwara et al. |
| 5,916,791 A | 6/1999 | Hirschberg et al. |
| 5,922,560 A | 7/1999 | Jacobson et al. |

(Continued)

FOREIGN PATENT DOCUMENTS

EA    00438182 A1    7/1991

(Continued)

OTHER PUBLICATIONS

Echavarri-Erasun et al. Stimulation of astaxanthin formation in the yeast Xanthophyllomyces dendrorhous by the fungus Epicoccum nigrum. FEMS Yeast Res. Jan. 2004;4(4-5):511-9.*

(Continued)

*Primary Examiner*—Michele J Joike
(74) *Attorney, Agent, or Firm*—Choate, Hall & Stewart, LLP; Brenda Herschbach Jarrell

(57) ABSTRACT

The present invention provides systems for producing engineered oleaginous yeast or fungi that express carotenoids.

53 Claims, 26 Drawing Sheets

U.S. PATENT DOCUMENTS

| | | | |
|---|---|---|---|
| 5,928,696 | A | 7/1999 | Best et al. |
| 5,928,924 | A | 7/1999 | Greene et al. |
| 5,935,808 | A | 8/1999 | Hirschberg et al. |
| 5,935,832 | A | 8/1999 | Nakane et al. |
| 5,965,795 | A | 10/1999 | Hirschberg et al. |
| 5,972,642 | A | 10/1999 | Fleno et al. |
| 5,972,690 | A | 10/1999 | Misawa et al. |
| 6,015,684 | A | 1/2000 | Jacobson et al. |
| 6,020,177 | A | 2/2000 | Koike et al. |
| 6,022,701 | A | 2/2000 | Boussiba et al. |
| 6,040,165 | A | 3/2000 | Narita et al. |
| 6,071,733 | A | 6/2000 | Muramatsu et al. |
| 6,087,152 | A | 7/2000 | Hohmann et al. |
| 6,107,072 | A | 8/2000 | Ishida |
| 6,124,113 | A | 9/2000 | Hohmann et al. |
| 6,150,130 | A | 11/2000 | Misawa et al. |
| 6,166,231 | A | 12/2000 | Hoeksema |
| 6,207,409 | B1 | 3/2001 | Hohmann et al. |
| 6,218,599 | B1 | 4/2001 | Hirschberg et al. |
| 6,225,096 | B1 | 5/2001 | Narita et al. |
| 6,255,505 | B1 | 7/2001 | Bijl et al. |
| 6,265,185 | B1 | 7/2001 | Muller |
| 6,284,506 | B1 | 9/2001 | Hoshino et al. |
| 6,291,204 | B1 | 9/2001 | Pasamontes et al. |
| 6,316,216 | B1 | 11/2001 | Ohto et al. |
| 6,329,141 | B1 | 12/2001 | Van Ooijen et al. |
| 6,365,386 | B1 | 4/2002 | Hoshino et al. |
| 6,407,306 | B1 | 6/2002 | Peter et al. |
| 6,410,288 | B1 | 6/2002 | Knutzon et al. |
| 6,413,736 | B1 | 7/2002 | Jacobson et al. |
| 6,420,135 | B1 | 7/2002 | Kunsch et al. |
| 6,448,043 | B1 | 9/2002 | Choi et al. |
| 6,531,292 | B1 | 3/2003 | Rine et al. |
| 6,531,303 | B1 | 3/2003 | Millis |
| 6,541,049 | B2 | 4/2003 | Barclay |
| 6,551,807 | B1 | 4/2003 | Cunningham et al. |
| 6,582,951 | B1 | 6/2003 | Nicaud et al. |
| 6,586,202 | B2 | 7/2003 | Hoshino et al. |
| 6,596,538 | B1 | 7/2003 | Lardizabal et al. |
| 6,600,089 | B1 | 7/2003 | Cahoon et al. |
| 6,613,543 | B2 | 9/2003 | Hohmann et al. |
| 6,627,795 | B1 | 9/2003 | Coughlan et al. |
| 6,645,767 | B1 | 11/2003 | Villa |
| 6,660,507 | B2 | 12/2003 | Cheng et al. |
| 6,677,134 | B2 | 1/2004 | Pasamontes et al. |
| 6,689,593 | B2 | 2/2004 | Millis et al. |
| 6,696,293 | B2 | 2/2004 | Hoshino et al. |
| 6,709,688 | B1 | 3/2004 | Breivik et al. |
| 6,727,373 | B2 | 4/2004 | Bijl et al. |
| 6,750,048 | B2 | 6/2004 | Ruecker et al. |
| 6,753,459 | B2 | 6/2004 | Keller et al. |
| 6,753,460 | B2 | 6/2004 | Fabijanski et al. |
| 6,812,001 | B2 | 11/2004 | Sibeijn et al. |
| 6,812,009 | B2 | 11/2004 | Gladue et al. |
| 6,818,239 | B2 | 11/2004 | Kagan et al. |
| 6,818,424 | B2 | 11/2004 | DiCosimo et al. |
| 6,821,749 | B1 | 11/2004 | Kajiwara et al. |
| 6,849,434 | B2 | 2/2005 | Ingram et al. |
| 6,863,914 | B1 | 3/2005 | Auweter et al. |
| 6,869,773 | B2 | 3/2005 | Hoshino et al. |
| 6,872,556 | B2 | 3/2005 | Hoshino et al. |
| 6,929,928 | B2 | 8/2005 | Cheng |
| 6,969,595 | B2 | 11/2005 | Brzostowicz |
| 6,972,191 | B2 | 12/2005 | Muramatsu |
| 7,015,014 | B2 | 3/2006 | Schaap et al. |
| 7,064,196 | B2 * | 6/2006 | Cheng et al. .......... 536/23.7 |
| 7,070,952 | B2 | 7/2006 | Cheng |
| 7,125,672 | B2 | 10/2006 | Picataggio et al. |
| 7,202,356 | B2 | 4/2007 | Pollak et al. |
| 7,214,491 | B2 | 5/2007 | Yadav et al. |
| 7,238,482 | B2 | 7/2007 | Picataggio et al. |
| 7,335,476 | B2 | 2/2008 | Picataggio et al. |
| 7,384,788 | B2 | 6/2008 | Van Dyk |
| 7,511,128 | B2 | 3/2009 | Picataggio et al. |
| 7,553,628 | B2 | 6/2009 | Picataggio et al. |
| 2002/0039758 | A1 | 4/2002 | De Laat et al. |
| 2002/0051998 | A1 | 5/2002 | Schmidt-Dannert et al. |
| 2002/0146784 | A1 | 10/2002 | Suzuki et al. |
| 2002/0147371 | A1 | 10/2002 | Hohmann et al. |
| 2002/0168703 | A1 | 11/2002 | Hoshino et al. |
| 2003/0022273 | A1 | 1/2003 | Pasamontes et al. |
| 2003/0033626 | A1 | 2/2003 | Hahn et al. |
| 2003/0044499 | A1 | 3/2003 | Zelkha et al. |
| 2003/0049720 | A1 | 3/2003 | Hoshino et al. |
| 2003/0054070 | A1 | 3/2003 | Bridges et al. |
| 2003/0054523 | A1 | 3/2003 | Hoshino et al. |
| 2003/0077691 | A1 | 4/2003 | Hoshino et al. |
| 2003/0087337 | A1 | 5/2003 | Giraud et al. |
| 2003/0092144 | A1 | 5/2003 | Millis et al. |
| 2003/0096385 | A1 | 5/2003 | Muramatsu et al. |
| 2003/0134353 | A1 | 7/2003 | Wolff et al. |
| 2003/0143705 | A1 | 7/2003 | Roberts et al. |
| 2003/0148319 | A1 | 8/2003 | Brzostowicz |
| 2003/0148416 | A1 | 8/2003 | Berry et al. |
| 2003/0157592 | A1 | 8/2003 | Lerchl et al. |
| 2003/0190734 | A1 | 10/2003 | Hoshino et al. |
| 2003/0207947 | A1 | 11/2003 | DeSouza et al. |
| 2004/0058410 | A1 | 3/2004 | Pasamontes et al. |
| 2004/0067550 | A1 | 4/2004 | Costa Perez et al. |
| 2004/0077068 | A1 | 4/2004 | Brzostowicz |
| 2004/0078846 | A1 | 4/2004 | Desouza et al. |
| 2004/0091958 | A1 | 5/2004 | Van Oouijen et al. |
| 2004/0115309 | A1 | 6/2004 | Harris |
| 2004/0116514 | A1 | 6/2004 | Nishino et al. |
| 2004/0127554 | A1 | 7/2004 | Ghisalberti |
| 2004/0152154 | A1 | 8/2004 | Perez et al. |
| 2004/0191877 | A1 | 9/2004 | Roberts et al. |
| 2004/0219629 | A1 | 11/2004 | Cheng et al. |
| 2004/0224383 | A1 | 11/2004 | Cheng et al. |
| 2004/0234579 | A1 | 11/2004 | Finke |
| 2004/0241672 | A1 | 12/2004 | Goldsmith et al. |
| 2004/0248266 | A1 | 12/2004 | Barclay |
| 2004/0253621 | A1 | 12/2004 | Picataggio et al. |
| 2004/0259959 | A1 | 12/2004 | Sharoni et al. |
| 2004/0268439 | A1 | 12/2004 | Cheng et al. |
| 2004/0268442 | A1 | 12/2004 | Miller et al. |
| 2005/0003474 | A1 | 1/2005 | Desouza et al. |
| 2005/0014219 | A1 | 1/2005 | Cheng et al. |
| 2005/0014270 | A1 | 1/2005 | Picataggio et al. |
| 2005/0019852 | A1 | 1/2005 | Cheng et al. |
| 2005/0037995 | A1 | 2/2005 | Lockwood et al. |
| 2005/0049248 | A1 | 3/2005 | Lockwood et al. |
| 2005/0096477 | A1 | 5/2005 | Gloor et al. |
| 2005/0124031 | A1 | 6/2005 | Saiz |
| 2005/0266132 | A1 | 12/2005 | Temelli et al. |
| 2006/0099670 | A1 | 5/2006 | Matuschek |
| 2006/0148049 | A1 | 7/2006 | Fukuchi et al. |
| 2006/0234333 | A1 | 10/2006 | Matuschek |
| 2007/0238160 | A1 | 10/2007 | Millis |
| 2008/0020438 | A1 | 1/2008 | Matsuda |
| 2008/0233620 | A1 | 9/2008 | Okubo |
| 2009/0233346 | A1 | 9/2009 | Picataggio et al. |
| 2009/0233347 | A1 | 9/2009 | Picataggio et al. |

FOREIGN PATENT DOCUMENTS

| | | | |
|---|---|---|---|
| EA | 00454024 | A2 | 10/1991 |
| EA | 00474347 | A1 | 3/1992 |
| EA | 00955363 | A2 | 11/1999 |
| EA | 01035206 | A1 | 9/2000 |
| EA | 01111067 | A2 | 6/2001 |
| EA | 01158081 | A1 | 11/2001 |
| EA | 01203818 | A2 | 5/2002 |
| EP | 00005277 | B1 | 1/1982 |

| | | | | | | |
|---|---|---|---|---|---|---|
| EP | 00166659 | B1 | 8/1989 | WO | 9837179 A2 | 8/1998 |
| EP | 427405 | A1 | 5/1991 | WO | 9843620 A1 | 10/1998 |
| EP | 00138508 | B1 | 4/1992 | WO | 9858943 A1 | 12/1998 |
| EP | 367765 | B1 | 8/1993 | WO | 9906585 A1 | 11/1999 |
| EP | 00367765 | B1 | 8/1993 | WO | 9964618 | 12/1999 |
| EP | 670306 | A1 | 9/1995 | WO | WO/00/01650 | 1/2000 |
| EP | 674000 | A2 | 9/1995 | WO | 0012725 A2 | 3/2000 |
| EP | 674000 | A3 | 9/1995 | WO | 0037660 A1 | 6/2000 |
| EP | 812360 | A1 | 6/1996 | WO | 0005382 A2 | 9/2000 |
| EP | 735137 | A1 | 10/1996 | WO | WO/00/53768 | 9/2000 |
| EP | 00436562 | B1 | 1/1997 | WO | 0061764 A1 | 10/2000 |
| EP | 769551 | A1 | 4/1997 | WO | 0065062 A2 | 11/2000 |
| EP | 812914 | A2 | 6/1997 | WO | 0078935 A1 | 12/2000 |
| EP | 812914 | A3 | 6/1997 | WO | 0112832 A1 | 2/2001 |
| EP | 870042 | A1 | 7/1997 | WO | WO/01/20011 | 3/2001 |
| EP | 551676 | A1 | 4/1998 | WO | 01/48163 A1 | 5/2001 |
| EP | 00551676 | B1 | 4/1998 | WO | 0142455 A1 | 6/2001 |
| EP | 877811 | B1 | 11/1998 | WO | 0144276 A2 | 6/2001 |
| EP | 587872 | B1 | 5/2000 | WO | 0166703 A1 | 9/2001 |
| EP | 1070759 | A1 | 1/2001 | WO | 0183437 A1 | 11/2001 |
| EP | 1070759 | A4 | 1/2001 | WO | 0218617 A2 | 3/2002 |
| EP | 719866 | B1 | 12/2001 | WO | 0220733 A2 | 3/2002 |
| EP | 1196583 | B1 | 4/2002 | WO | 0220815 A2 | 3/2002 |
| EP | 725137 | A1 | 5/2002 | WO | 0226933 A2 | 4/2002 |
| EP | 00725137 | B1 | 5/2002 | WO | 0241833 A2 | 5/2002 |
| EP | 1203818 | A2 | 5/2002 | WO | 02053745 A1 | 7/2002 |
| EP | 590707 | B1 | 11/2002 | WO | 02053746 A1 | 7/2002 |
| EP | 00590707 | B1 | 11/2002 | WO | 02053747 A1 | 7/2002 |
| EP | 872554 | B1 | 6/2003 | WO | 02059290 A2 | 8/2002 |
| EP | 1476546 | A2 | 8/2003 | WO | 02059297 A2 | 8/2002 |
| EP | 1367131 | A1 | 12/2003 | WO | 02070721 A2 | 9/2002 |
| EP | 747483 | B1 | 3/2004 | WO | 02079395 A2 | 10/2002 |
| EP | 1219704 | B1 | 8/2004 | WO | 02088365 A1 | 11/2002 |
| EP | 870042 | B1 | 9/2004 | WO | 02094867 | 11/2002 |
| EP | 00870042 | B1 | 9/2004 | WO | 02094868 | 11/2002 |
| EP | 1306444 | B1 | 9/2004 | WO | 02099095 A2 | 12/2002 |
| EP | 674000 | B1 | 10/2004 | WO | WO/02/099095 | 12/2002 |
| EP | 1471151 | A1 | 10/2004 | WO | 03000902 A1 | 1/2003 |
| EP | 1140043 | B1 | 3/2005 | WO | WO/03/012056 | 2/2003 |
| EP | 1510583 | A1 | 3/2005 | WO | 03020936 A1 | 3/2003 |
| EP | 00832258 | B1 | 1/2007 | WO | 03023016 A2 | 3/2003 |
| EP | 1947189 | A1 | 7/2008 | WO | 03027293 A1 | 4/2003 |
| JP | 2006008712 | | 1/2006 | WO | 03031642 A2 | 4/2003 |
| JP | 2006008713 | | 1/2006 | WO | 03038064 A2 | 5/2003 |
| JP | 2006008714 | | 1/2006 | WO | 03044205 A1 | 5/2003 |
| JP | 2006008715 | | 1/2006 | WO | 03047547 A2 | 6/2003 |
| JP | 2006008716 | | 1/2006 | WO | 03062416 A1 | 7/2003 |
| JP | 2006008717 | | 1/2006 | WO | 03076575 | 9/2003 |
| JP | 2006008718 | | 1/2006 | WO | 03097798 A2 | 11/2003 |
| JP | 2006008719 | | 1/2006 | WO | 2004001057 A1 | 12/2003 |
| JP | 2006008720 | | 1/2006 | WO | 2004013345 A1 | 2/2004 |
| JP | 2006016407 | | 1/2006 | WO | 2004016791 A1 | 2/2004 |
| JP | 2006016408 | | 1/2006 | WO | 2004018385 A2 | 3/2004 |
| JP | 2006016409 | | 1/2006 | WO | 2004018688 A1 | 3/2004 |
| JP | 2006022121 | | 1/2006 | WO | 2004018694 A2 | 3/2004 |
| WO | 8808025 | A1 | 10/1988 | WO | 2004022765 A2 | 3/2004 |
| WO | 9001552 | A1 | 2/1990 | WO | 2004029232 A2 | 4/2004 |
| WO | 9102060 | A1 | 2/1991 | WO | 2004029255 A2 | 4/2004 |
| WO | 9221764 | A1 | 12/1992 | WO | 2004029261 A2 | 4/2004 |
| WO | 9320183 | A1 | 10/1993 | WO | 2004029263 A2 | 4/2004 |
| WO | 9406918 | A2 | 3/1994 | WO | 2004029275 A1 | 4/2004 |
| WO | 9612013 | A1 | 4/1996 | WO | WO/2004/029255 | 4/2004 |
| WO | 96/021736 | | 7/1996 | WO | 2004039991 A2 | 5/2004 |
| WO | 9621736 | | 7/1996 | WO | 2004047763 A2 | 6/2004 |
| WO | 9633276 | | 7/1996 | WO | 04056972 A2 | 7/2004 |
| WO | 9628545 | A1 | 9/1996 | WO | 2004056974 A2 | 7/2004 |
| WO | WO/96/28014 | | 9/1996 | WO | 2004056975 A2 | 7/2004 |
| WO | 96/033276 | | 10/1996 | WO | 2004057012 A1 | 7/2004 |
| WO | 9707219 | A2 | 2/1997 | WO | 2004063358 A1 | 7/2004 |
| WO | 9723633 | A1 | 7/1997 | WO | 2004063359 A2 | 7/2004 |
| WO | 9729114 | A1 | 10/1997 | WO | 2004063366 A1 | 7/2004 |
| WO | 9807830 | A2 | 2/1998 | WO | 2004067709 | 8/2004 |
| WO | 9820138 | A1 | 5/1998 | WO | 2004070035 A2 | 8/2004 |

| | | |
|---|---|---|
| WO | 2004074440 A2 | 9/2004 |
| WO | 2004074490 A2 | 9/2004 |
| WO | 0047746 A1 | 10/2004 |
| WO | 2004087883 A2 | 10/2004 |
| WO | 2004098530 A2 | 11/2004 |
| WO | 2004101753 A2 | 11/2004 |
| WO | 2004101757 A2 | 11/2004 |
| WO | 2004104167 A2 | 12/2004 |
| WO | 2004104180 A2 | 12/2004 |
| WO | 2004111214 A1 | 12/2004 |
| WO | 2005001024 A2 | 1/2005 |
| WO | 2005007826 A2 | 1/2005 |
| WO | 2005010156 A2 | 2/2005 |
| WO | 2005010174 A2 | 2/2005 |
| WO | 2005014828 A2 | 2/2005 |
| WO | 2005019467 A1 | 3/2005 |
| WO | 2005011712 A1 | 5/2005 |
| WO | WO/2006/014837 | 2/2006 |
| WO | WO/2006/091924 | 8/2006 |
| WO | 2006102342 | 9/2006 |
| WO | WO/2006/096392 | 9/2006 |
| WO | WO/2006/102342 A | 9/2006 |
| WO | WO/2007/095007 | 8/2007 |
| WO | 2008/042338 | 4/2008 |
| WO | WO/2008/073367 | 6/2008 |
| WO | WO/2008/076758 | 6/2008 |
| WO | WO/2009/010826 | 1/2009 |

OTHER PUBLICATIONS

Flikweert et al. Pyruvate decarboxylase: an indispensable enzyme for growth of Saccharomyces cerevisiae on glucose. Yeast. Mar. 15, 1996;12(3):247-57.*

Iturriaga et al. Structure and function of the genes involved in the biosynthesis of carotenoids in the mucorales. Biotech. Bioprocess Eng. 5(4): 263-274, 2000.*

Mlíčková et al. Lipid Accumulation, Lipid Body Formation, and Acyl Coenzyme A Oxidases of the Yeast Yarrowia lipolytica. Applied and Environmental Microbiology, Jul. 2004, p. 3918-3924, vol. 70, No. 7.*

Search Report and Written Opinion from the Austrian Patent Office Service and Information Center received in Singapore App. No. 200706626-9, Date of Mailing Dec. 10, 2009.

Mehta et al., "New Mutants of Phycomyces blakesleeanus for β-Carotene Production," *Applied and Environmental Microbiology* 63(9):3657-3661 (1997).

Barth et al., "Yarrowia lipolytica", Nonconventional Yeasts in Genetics, Biochemistry and Biotechnology, 1(Springer-Verlag, Berlin, Germany): 335-408, 2003.

Barth et al., "Physiology and genetics of the dimorphic fungus Yarrowia lipolytica", FEMS Microbiol Rev., 19: 219, 1997.

Miura et al., "Production of lycopene by the food yeast, Candida utilis that does not naturally synthesize carotenoid", Biotechnol Bioeng, 58: 306-8, 1998.

Bertram, "Carotenoids and Gene Regulation", Nutr. Rev., 57: 182, 1999.

Boeke, et al.,"Fluoroorotic Acid as a Selective Agent in Yeast Molecular Genetics", Methods Enzymol,. 154: 164-175, 1987.

Chew et al., "A Comparison of the Anticancer Activities of Dietary β-Carotene, Canthaxanthin and Astaxanthin in Mic in Vivo", Anticancer Res., 19: 1849, 1999.

Downing et al., "The isolation of two mutants of Saccharomyces cerevisiae which demonstrate increased activity of 3-hydroxy-3-methylglutaryl coenzyme A reductase", Chem. Abs., 93: 65791y, 484, 1980.

Edge et al., "The Carotenoids as anti-oxidants—a review", J. Photochem Photobiol, 41:189, 1997.

Evans et al., "A Comparison of the Oleaginous Yeast, Candida Curvata, Grown on Different Carbon Sources in Continuous and Batch Culture", Lipids, 18(9): 623-29, 1983.

Gil, et al., "Membrane-bound domain of HMG CoA reductase is required for sterol-enhanced degradation of the enzyme", Cell, 41: 249, 1985.

Giovannucci et al., "Intake of Carotenoids and Retinol in Relation to Risk of Prostate Cancer", J. Natl. Cancer Inst., 87: 1767, 1995.

Jitrapakdee et al., "The Biotin Enzyme Family: Conserved Structural Motifs and Domain Rearrangements", Curr Protein Pept Sci., 4: 217, 2003.

Juretzek et al., "Vectors for gene expression and amplification in the yeast Yarrowia lipolytica", Yeast 2001, 18 (2001): 97-113.

Jyonouchi et al., "Studies of Immunomodulating Actions of Carotenoids. I. Effects of β-Carotene and Astaxanthin on Murine Lymphocyte Functions and Cell Surface Marker Expression in In Vitro Culture System", Nutr. Cancer, 16: 93, 1991.

Kim et al., "Cloning of the Ribosomal Protein L41 Gene of Phaffia rhodozyma and Its Use as a Drug Resistance Marker for Transformation", Appl Environ Microbiol., 64(5): 1947-9, 1998.

Koyama "New Trends in Photobiology: Structures and functions of carotenoids in photosynthetic systems", J. Photochem Photobiol, 9: 265, 1991.

Krinski, "The antioxidants and biological properities of carotenoids", Pure Appl. Chem., 66: 1003, 1994.

Madzak et al., "Heterologous protein expression and secretion in the non-conventional yeast Yarrowia lipolytica: a review", J Biotechnol., 109: 63, 2004.

Madzak, "Functional analysis of upstream regulating regions from the Yarrowia lipolytica XPR2 promoter", Microbiology, 145 (Pt 1): 75-87, 1999.

Kurischko, "The MATA locus of the dimorphic yeast Yarrowia lipolytica consists of two divergently oriented genes", Mol Gen Genet, 262: 180-8, 1999.

Athenstaedt, "Identification and characterization of major lipid particle proteins of the yeast Saccharomyces cerevisiae", J Bacteriol, 181: 6441-8, 1999.

Boone et al., "Bimodal activation of acetyl-CoA carboxylase by glutamate", J Biol Chem, 275: 10819-25, 2000.

Nowrousian et al., "The fungal acl1 and acl2 genes encode two polypeptides with homology to the N- and C-terminal parts of the animal ATP citrate lyase polypeptide", Curr Genet, 37: 189-93, 2000.

Malmstrom et al., "Secondary metabolites characteristic of *Penicillium citrinum*, *Penicillium steckii* and related species", Phytochemistry, 54: 301-9, 2000.

Kroken et al., "Phylogenomic analysis of type I polyketide synthase genes in pathogenic and saprobic ascomycetes", PNAS, 100: 15670-15675, 2003.

Aharonowitz et al., "Penicillin and cephalosporin biosynthetic genes: structure, organization, regulation, and evolution", Annu. Rev. Microbiol., 46: 461-95, 1992.

Silva et al., "Production of Amylases from Rice by Solid-State Fermentation in a Gas-Solid Spouted-Bed Bioreactor", Biotechnol Prog, 14: 580-587, 1998.

Townsend, "New reactions in clavulanic acid biosynthesis", Current Opinion in Chemical Biology, 6: 583-589, 2002.

Wang et al., "A bacterial cell-cell communication signal with cross-kingdom structural analogues", Molecular Biology, 51: 903-912, 2004.

Nonaka et al., "A downstream target of RHO1 small GTP-binding protein is PKC1, a homolog of protein kinase C, which leads to activation of the MAP kinase cascade in *Saccharomyces cerevisiae*", EMBO Journal, 14: 5931-5938, 1995.

Bundgaard et al., "A new spectrophotometric method for the determination of *penicillins*", J. Pharm. Pharmac., 24: 790-794, 1972.

Wang et al., "A novel Two-Component System amrB-amkB Involved in the Regulation of Central Carbohydrate Metabolism in Rifamycin SV-Producing Amycolatopsis mediterranei U32", Current Microbiology, 48: 14-19, 2004.

Muhlrad and Parker, "A Rapid Method for Localized Mutagenesis of Yeast Genes", Yeast, 8: 79-82, 1992.

Kato et al., "Functional Expression of Genes Involved in the Biosynthesis of the Novel Polyketide Chain Extension Unit, Methoxymalonyl-Acyl Carrier Protein, and Engineered Biosynthesis of 2-Desmethyl-2-Methoxy-6-Deoxyerythronolide B", JAGS Communications, 124: 5268-5269, 2002.

Casqueiro et al., "Gene Targeting in *Penicillium chrysogenum*: Disruption of the lys2 Gene Leads to *Penicillin* Overproduction", Journal of Bacteriology, 181: 1181-1188, 1999.

O'Toole et al., "Genetic Approaches to Study of Biofilms", Genetic Approaches, 310: 91-109, 1999.
Woloshuk et al., "Genetic Transformation System for the Aflatoxin-Producing Fungus *Aspergillus flavus*", Applied and Environmental Microbiology, 55: 86-90, 1989.
Hendrickson et al., "Lovastatin biosynthesis in *Aspergillus terreus*: characterization of blocked mutants, enzyme activities and a multifunctional polyketide synthase gene", Chemistry and Biology, 6: 429-439, 1999.
Fierro et al., "High efficiency transformation of *Penicillium nalgiovense* with integrative and autonomously replicating plasmids", International Journal of Food Microbiology, 90: 237-248, 2004.
Carroll et al., "Identification of a Set of Genes Involved in the Formation of the Substrate for the Incorporation of the Unusual 'Glycolate' Chain Extension Unit in Ansamitocin Biosynthesis", J. Am. Chem. Soc., 124: 4176-4177, 2002.
Su and Mitchell, "Identification of Functionally Related Genes That Stimulate Early Meiotic Gene Expression in Yeast", Genetics, 133: 67-77, 1993.
Qadota et al., "Identification of Yeast Rho1p GTPase as a Regulatory Subunit of 1,2-$/beta$-Glucan Synthase", Science, 272: 279-281, 1996.
Jin et al., "Improvement of industry-applied rifamycin B-producing strain, Amycolatopsis mediterranei, by rational screening", J. Gen. Appl. Microbiol., 48: 329-334, 2002.
Dannaoui et al., "In Vitro Evaluation of Double and Triple Combinations of Antifungal Drugs against *Aspergillus fumigatus* and *Aspergillus terreus*", Antimicrobial Agents and Chemotherapy, 48: 970-978, 2004.
Samson et al., "Isolation, sequence determination and expression in *Escherichia coli* of the isopenicilln N synthetase gene from *Cephalosporium acremonium*", Nature, 318: 191-194, 1985.
Brock et al., "Methylcitrate synthase from *Aspergillus nidulans*: implications for propionate as an antifungal agent", Molecular Microbiology, 35: 961-973, 2000.
Zhang and Keller, "Blockage of methylcitrate cycle ingibits polyketide production in *Aspergillus nidulans*", Molecular Microbiology, 52: 541-550, 2004.
Kelly and Hynes, "Transformation of *Aspergillus niger* by the amdS gene of *Aspergillus nidulans*", EMBO Journal, 4: 475-479, 1985.
Kimura et al., "Trichothecene 3-O-Acetyltransferase Protects Both the Producing Organism and Transformed Yeast from Related Mycotoxins", The Journal of Biological Chemistry, 273: 1654-1661, 1998.
Bok and Keller, "LaeA, a Regulator of Secondary Metabolism in *Aspergillus* spp.", Eukaryotic Cell, 3: 527-535, 2004.
Chen et al., "Mapping Mutations in Genes Encoding the Two Large Subunits of *Drosophila* RNA Polymerase II Defines Domains Essential for Basic Transcription Functions and for Proper Expression of Developmental Genes", Molecular and Cellular Biology, 13: 4212-4222, 1993.
McCluskey, "The Fungal Genetics Stock Center: From Molds to Molecules", Advances in Applied Microbiology, 52: 245-263, 2003.
Kimura, "Metabolic Engineering of Glutamate Production", Advances in Biochemical Engineering, 79: 37-57, 2003.
Alberts et al., "Mevinolin: A Highly Potent Competitive Inhibitor of Hydroxymethylglutaryl-Coenzyme a Reductase and a Cholesterol-Lowering Agent", Proc. Natl. Acad. Sci USA, 77: 3957-3961, 1980.
Demain, "Microbial secondary metabolism: a new theoretical frontier for academia, a new opportunity for industry", Microbial secondary metabolism for academia and industry, 171: 3-23, 1992.
Woloshuk et al., "Molecular Characterization of aflR, a Regulatory Locus fo Aflatoxin Biosynthesis", Applied and Environmental Microbiology, 60: 2408-2414, 1994.
Mullaney et al., "Primary structure of the trpC gene from *Aspergillus nidulans*", Mol Gen Genet, 199: 37-45, 1985.
Atalla et al., "Mycotoxin production in wheat grains by different *Aspergilli* in relation to different relative humidities and storage periods", Nahrung/Food, 47: 6-10, 2003.
Kholsa and Keasling, "Metabolic engineering for drug discovery and development", Nature, 2: 1019-1025, 2003.

Nikolaev et al., "Nuclear Import of Zinc Binuclear Cluster Proteins Proceeds through Multiple, Overlapping Transport Pathways", Eukaryotic Cell, 2: 209-221, 2003.
Parekh et al., "Improvement of microbial strains and fermentation processes", Appl Microbiol Biotechnol, 54: 287-301, 2000.
Watanabe, et al., "Cloning, characterization and expression of the gene encoding cytochrome P-450 from Streptomyces carbophilus involved in production of pravastatin, a specific HMG-CoA reductatse inhibitor", Gene, 163: 81-85, 1995.
Drake and Daniel, "Physiology of the thermophilic acetogen Moorella thermoacetica", Research in Microbiology, 155: 422-436, 2004.
Li et al., "Identification and chemial profiling of monacolins in red eyast rice using high-performance liquid chromoatography with photodiode array detector and mass spectrometry", Journal of Pharaceutical and Biomedical Analysis, 35: 1101-1112, 2004.
Bentley, "Secondary Metabolite Biosynthesis: The First Century", Critical Reviews in Biotechnology, 19: 1-40, 1999.
Kumari et al., "Secretion of ligninperoxidase by *Penicillium citrinum, Fusarium oxysporum* and *Aspergillus terreus*", Indian Journal of Experimental Biology, 40: 802-806, 2002.
Seng et al., "Cyclohexanedione Herbicides are Inhibitors of Rat Heart Acetyl-CoA Carboxylase", Bioorganic and Medicinal Chemistry Letters, 13: 3237-3242, 2003.
Shimizu et al., "Pka, Ras and RGS Protein Interactions Regulate Activity of AflR, a Zn(II)2Cys6 Transcription Factor in *Aspergillus nidulans*", Genetics, 165: 1095-1104, 2003.
Fauser and Wissinger, "Simultaneous Detection of Multiple Point Mutations Using Fluorescence-Coupled Competitive Primer Extension", BioTechniques, 22: 964-968, 1997.
Schimmel and Parsons, "High purity, high yield procedure for butyrolactone I production from *Aspergillus terreus*", Biotechnology Techniques, 13: 379-384, 1999.
Swart et al., "Genetic Analysis in the Asexual Fungus *Aspergillus Niger*", Acta Biiologica Hungarica, 52: 335-343, 2001.
Cardenas et al., "Targets of immunophilin-immunosuppressant complexes are distinct highly conserved regions of calcineurin A", The EMBO Journal, 14: 2772-2783, 1995.
Kim et al., "Terreulactones A, B, C, and D: Novel Acetylcholinesterase Inhibitors Produced by *Aspergillus terreus*", The Journal of Antibiotics, 56: 351-357, 2003.
Tilburn et al., "The *Aspergillus* PacC zinc finger transcription factor mediates regulation of both acid- and alkaline- expressed genes by ambient pH", The EMBO Journal, 14: 779-790, 1995.
Penalva et al., "The optimization of *penicillin* boisynthesis in fungi", Tibetch, 16: 483-489, 1998.
Spiteller et al., "The Post-Polyketide Synthase Modification Steps in the Biosynthesis of the Antitumor Agent Ansamitocin by *Actinosynnema pretiosum*", J. Am. Chem. Soc., 125: 14236-14237, 2003.
Matsumoto et al., "The Trichothecene Biosynthesis Regulatory Gene from the Type B Producer Fusarium Strains: Sequence of Tri6 and It's Expression in *Escherichia coli*", Biosci. Biotechnol. Biochem., 63: 2001-2004, 1999.
Tilburn et al., "Transformation by intergration in *Aspergillus nidulans*", Gene, 914: 205-221, 1983.
Katzmann et al., "Transcriptional Control of the Yeast PDR5 Gene by the PDR3 Gene Product", Molecular and Cellular Biology, 14: 4653-4661, 1994.
Kanamasa et al., "Transformation of *Aspergillus aculeatus* Using the Drug Resistance Gene of *Aspergillus oryzae* and the pyrG Gene of *Aspergillus nidulans*", Biosci. Biotechnol. Biochem., 67: 2661-2663, 2003.
Trapp et al., "Characterizaion of the gene cluster for biosynthesis of macrocyclic trichothecenes in Myrothecium roridum", Mol Gen Genet, 257: 421-432, 1998.
Alexander et al., "TRI12, a trichothecene efflux pump from Fusarium sportrichioides: gene isolation and expression in yeast", Mol Gen Genet, 261: 977-984, 1999.
Thampy et al., "Troglitazone stimulates acetyl-CoA carboxylase activity through a post-translational mechanism", Life Sciences, 68: 699-708, 2000.

Prasad et al., "Tryptophan Accumulation in *Saccharomyces cerevisiae* Under the Influence of an Artificial Yeast TRP Gene Cluster", Yeast, 3: 95-105, 1987.
Pisano and Vellozzi, "Production of Cephalosporin C by *Paecilimyces persicinus* P-10", Antimicrobial Agents and Chemotherapy, 6: 447-451, 1974.
Davies, Chapter 21, Heterologous Gene Expression and Protein Secretion in *Aspergillus*, 527-560.
Hancock and Viola, "Biotechnological approaches for L-ascorbic acid production", Trends in Biotechnology, 20: 299-305, 2002.
Oskouian and Saba, "YAP1 confers resistance to the fatty acid synthase inhibitor cerulenin through the transporter Flr1p in *Saccharomyces cerevisiae*", Mol Gen Genet, 261: 346-353, 1999.
Mlickova et al., "Lipid Accumulation, Lipid Body Formation, and Acyl Coenzyme a Oxidases of the Yeast *Yarrowia lipolytica*", Applied and Environmental Microbiology, 70: 3918-3924, 2004.
Yelton et al., "Transformation of *Aspergillus nidulans* by using a trpC plasmid", Proc. Natl. Acad. Sci. USA, 81: 1470-1474, 1984.
Han et al., "A putative G protein-coupled receptor negatively controls sexual development in *Aspergillus nidulans*", Molecular Microbiology, 51: 1333-1345, 2004.
Guo et al., "Synthesis of aminoshikimic acid", Org Lett, 6: 1585-8, 2004.
Hasper et al., "Functional analysis of the transcriptional activator XlnR from *Aspergillus niger*", Microbiology, 150: 1367-75, 2004.
Lodato et al., "Study of the expression of carotenoid biosynthesis genes in wild-type and deregulated strains of *Xanthophyllomyces dendrorhous*" (Ex.: *Phaffia rhodozyma*), 37: 83-93, 2004.
Mlmckova, et al., "Lipid accumulation, lipid body formation, and acyl coenzyme A oxidases of the yeast *Yarrowia lipolytica*", Appl Environ Microbiol, 70: 3918-24, 2004.
Lopez-Nieto et al., "Biotechnological lycopene production by mated fermentation of *Blakeslea trispora*", Appl Microbiol Biotechnol, 2004.
Steiger et al., "Cloning of two carotenoid ketolase genes from Nostoc punctiformie for the heterologous production of canthaxanthin and astaxanthin", Biotechnol Lett, 26: 813-7, 2004.
Rodriguez-Saiz et al., "*Blakeslea trispora* genes for carotene biosynthesis", Appl Environ Microbiol, 70: 5589-94, 2004.
Papanikolaou et al., "Repression of reserve lipid turnover in *Cunninghamella echinulata* and *Mortierella isabellina* cultivated in multiple-limited media", J Appl Microbiol, 97: 867-75, 2004.
Takahashi, et al., "Efficient gene disruption in the koji-mold *Aspergillus sojae* using a novel variation of the positive-negative method", Mol Genet Genomics, 272: 344-52, 2004.
Hall, et al., "Regulation of gene expression by a metabolic enzyme", Science, 306: 482-4, 2004.
Cannizzaro, et al., "Metabolic network analysis on *Phaffia rhodozyma* yeast using 13C-labeled glucose and gas chromatography-mass spectrometry", Metab Eng, 6: 340-51, 2004.
Inoue, "Carotenoid hydroxylation—P450 finally", Trends Plant Sci, 9: 515-7, 2004.
Yelton et al., "A Cosmid for Selecting Genes by Complementation is *Aspergillus nidulans*: Selection of the Developmentally Regulated yA Locus", Proceedings of the National Academy of Sciences of the USA, 70: 834-838, 1985.
Liras et al., "Evolution of the clusters of genes for B-lactam antibiotics: a model for evolutive combinatorial assembly of new B-lactams", Internatl Microbiol, 1: 271-278, 1998.
Oda et al., "Coupling of Fermentation and Esterification: Microbial Esterification of Decanoic Acid with Ethanol Produced via Fermentation", Biosci Biotechnol Biochem, 65: 1388-1390, 2001.
Ohara et al., "REN1 is Required for Development of Microconidia and Macroconidia, but Not of Chlamydospores, in the Plant Pathogenic Fungus *Fusarium oxysporum*", Genetics Society of America, 166: 113-124, 2004.
Seo et al., "Suppressor Mutations Bypass the Requirement of fluG for Asexual Sporulation and Sterigmatocystin Production in *Aspergillus nidulans*", Genetics Society of America, 165: 1083-1093, 2003.
Kato et al., "The Expression of Sterigmatocystin and *Penicillin* Genes in *Aspergillus nidulans* Is Controlled by veA, a Gene Required for Sexual Development", Eukaryotic Cell, 2: 1178-1186, 2003.

Mannhaupt et al., What's in the genome of a filamentous fungus? Analysis of the Neurospora genome sequence, Nucleic Acids Research, 31: 1944-1954, 2003.
Liu et al., "Extra Copies of the *Aspergillus fumigaus* Squalene Epoxidase Gene Confer Resistance to Terbinafine: Genetic Approach to Studying Gene Dose-Dependent Resistance to Antifungals in a. fumigatus", Antimicrobial Agents and Chemotherapy, 48: 2490-2496, 2004.
Schmidt-Dannert et al., "Molecular breeding of carotenoid biosynthetic pathways", Nat Biotechnol, 18: 750-3, 2000.
Flores et al., "Carbohydrate and energy-yielding metabolism in non-conventional yeasts", FEMS Microbiol Rev, 24: 507-29, 2000.
Kamisaka et al., "Intracellular transport of phosphatidic acid and phosphatidylcholine into lipid bodies: use of fluorescent lipids to study lipid-body formation in an oleaginous fungus", Biochem Soc Trans, 28: 723-5, 2000.
Titorenko et al., "Peroxisome biogenesis in the yeast *Yarrowia lipolytica*", Cell Biochem Biophys, 32: 21-6, 2000.
Wynn et al., "Biochemical events leading to the diversion of carbon into storage lipids in the oleaginous fungi *Mucor circinelloides* and *Mortierella alpina*", Microbiology, 147: 2857-64, 2001.
Arrach et al., "Mutants of the carotene cyclase domain of al-2 from *Neurospora crassa*", Mol Genet Genomics, 266: 914-21, 2002.
Park et al., "Bioconverstion of compactin into pravastatin by *Streptomyces* sp.", Biotechnology Letters, 25: 1827-1831, 2003.
Bradamante et al., "Production of Lovastatin Examined by an Integrated Approach Based on Chemometrics and DOSY-NMR", Biotechnology and Bioengineering, 80: 589-593.
Junker et al., "Early Phase Process Scale-Up Challenges for Fungal and Filamentous Bacterial Cultures", Applied Biochemistry and Biotechnology, 119: 241-277, 2004.
Baddley et al., "Epidemiology of *Aspergillus terreus* at a University Hospital", Journal of Clinical Microbiology, 41: 5525-5529, 2003.
Taylor and Deeble, "Enzymatic methods for mutation scanning", Genetic Analysis, 14: 181-186, 1999.
Roberts and Fink, "Elements of a single MAP kinase cascade in *Saccharomyces cerevisiae* mediate two developmental programs in the same cell type: mating and invasive growth", Genes and Development, 8: 2974-2985, 1994.
Skatrud, et al., "Efficient integrative transformation of *Cephalosporium acremonium*", Current Genetics, 12: 337-348, 1987.
Boyum and Guidotti, "Effect of ATP Binding Cassette/Multidrug Resistance Proteins on ATP Efflux of *Saccharomyces cerevisiae*", Biochemical and Biophysical Research Communications, 230: 22-26, 1997.
Borel "Editorial: Ciclosporin and Its Future", Prog. Allergy, 38: 9-18, 1986.
Durand et al., "Randomly amplified polymorphic DNAs assess recombination following an induced parasexual cycle in *Penicillium roqueforti*", Current Genetics, 24: 417-420, 1993.
Buchholz et al., "Quantification of Intracellular Metabolites in *Escherichia coli* K12 Using Liquid Chromatographic-Elctrospray Ionization Tandem Mass Spectrometric Techniques", Analytical Biochemistry, 295: 129-137, 2001.
Varga et al., "Diversity of polyketide synthase gene sequences in *Aspergillus* species", Research in Microbiology, 154: 593-600, 2003.
Robertson et al., "Exploring Nitrilase Sequence Sapce for Enantioselective Catalysis", Applied and Environmental Microbiology, 70: 2429-2436, 2004.
Cooke et al., "Disseminated *Aspergillus terreus* infection arising from cutaneous inoculation treated with caspofungin", Clinical Microbiology and Infection, 9: 1238-1241, 2003.
Devchand and Gwynne, "Expression of heterologous proteins in *Aspergillus*", Journal of Biotechnology, 17: 3-10, 1991.
Willinger et al., "Detection and Identification of Fungi from Fungus Balls of the Maxillary Sinus by Molecular Techniques", Journal of Clinical Microbiology, 41: 581-585, 2003.
Kloosterman et al., "(De)regulation if key enzyme steps in the shikimate pathway and phenylalanine-specific pathway of the actinomycete *Amycolatopsis methanolica*", Microbiology, 149: 3321-3330, 2003.

Cove, "The induction and repression of nitrate reductase in the fungus *aspergillus nidulans*", Biochimica et Biophysica Acta, 113: 51-56, 1966.

Abe et al., "Molecular cloning and characterization of an LM-236B (compactin) biosynthetic gene cluster in *Penicillium citrinum*", Mol Genet Genomics, 267: 636-646, 2002.

Manzoni and Rollini, "Biosynthesis and biotechnoligical production of statins by filamentous fungi and application of these cholesterol-lowering drugs", Appl Microbiol Biotechnol, 58: 555-564, 2002.

Abe et al., "Functional analysis of mlcR, a regulatory gene for ML-236B (compactin) biosynthesis in *Penicillium citrinum*", Mol Genet Genomics, 268: 352-361, 2002.

Abe et al., "Effect of increased dosage of the ML-236B (compactin) biosynthetic gene cluster on ML-236B production in *Penicillium citrinum*", Mol Genet Genomics, 268: 130-137, 2002.

Jadoun et al., "Disruption of the *Aspergillus fumigatus* argB gene using a novel in vitro transposon-based mutagenesis approach", Curr Genet, 45: 235-241, 2004.

Decottignies and Goffeau, "Complete inventory of the yeast ABC proteins", nature genetics, 15: 137-145, 1997.

Chakravarti and Sahai, "Compactin-a review", Appl Microbiol Biotechnol, 64: 618-624, 2004.

Endo et al., "The Synthesis of Compactin (ML-236B) and Monacolin K in Fungi", the Journal of Antibiotics, 39: 1609-1610, 1986.

Nelissen, et al., "Classification of all putative permeases and other membrane plurispanners of the major facilitator superfamily encoded by the complete genome of *Saccharomyces cerevisiae*", FEMS Microbiology Reviews, 21: 113-134, 1997.

Suarez and Penalva, Characterization of a *Penicillium chrysogenum* gene encoding a PacC transcription factor and its binding sites in the divergent pcbAB-pcbC promoter of the penicillin biosynthetic cluster, Molecular Microbiolgy, 20: 529-540, 1996.

Gutierrez et al., "The cefG Gene of *Cephalosporium acremonium* Is Linked to the cefEF Gene and Encodes a Deacetylcephalosporin C Acetyltransferase Closely Related to Homoserine 0-Acetyltransferase", Journal of Bacteriology, 174: 3056-3064, 1992.

Baillie and Douglas, "Candida Biofilms and Their Susceptibility to Antifungal Agents", Methods in Enzymology, 310: 644-657, 1999.

Buxton and Radford, "Cloning of the Structural Gene for Orotidine 5'-Phosphate Carboxylase of Neurospora crassa by Expression in *Escherichia coli*", Mol Gen Genet, 193: 403-405.

Brown et al., "Twenty-five coregulated transcripts define a sterigmatocystin gene cluster in *Aspergillus nidulans*", Proc. Natl. Acad. Sci. USA, 93: 1418-1422, 1996.

Bray et al., "Kinetic Studies of the Metabolism of Foreign Organic Compounds", Kinetics of Glucuronide Formation in vivo, 52: 416-419, 1952.

Takahashi et al., "Purification and Characterization of Dimethylallyl Pyrophosphate: Aspulvinone Dimethylallyltransferase from *Aspergillus terreus*", Biochemistry, 17: 2696-2702, 1978.

Balance et al., "Transformation of *Aspergillus nidulans* by the Orotidine-5'-Phosphate Decarboxylase Gene of Neurospora Crass", Biochemical and Biophysical Research Communications, 112: 284-289, 1983.

Hutchinson et al., "Aspects of the biosynthesis of non-aromatic fungal polyketides by iterative polyketide synthases", Antonie van Leeusenhoek, 78: 287-295, 2000.

Arst et al., "Do the Tightly Linked Structural Genes for Nitrate and Nitritie Reductases in Aspergillus nidulans Form an Operon? Evidence from an Insertional Translocation Which Separates Them", Molec gen Genet, 174: 89-100, 1979.

Kaster et al., "Analysis of a bacterial hygromycin B resistance gene by transcriptional and translational fusions and by DNA sequencing", Nucleic Acids Research, 11: 6895-6911, 1983.

Abe et al., "Molecular basis of ML-236B production in the high-producing mutant No. 41520 of *Penicillium citrinum*", J. Gen. Appl. Microbiol., 50: 169-176, 2004.

Kyte and Doolittle, "A Simple Method for Displaying the Hydropathic Character of a Protein", J. Mol. Biol., 157: 105-132, 1982.

Edwards et al., "A simple and rapid method for the preparation of plant genomic DNA for PCR analysis", Nucleic Acids Research, 19: 1349, 1991.

Todd and Andrianopoulos, "Evolution of a Fungal Regulatory Gene Family: The Zn(II) 2Cys6 Binuclear Cluster DNA Binding Motif", Fungal Genetics and Biology, 21: 388-405, 1997.

Roncal and Ugalde, "Conidiation induction in *Penicillium*", Research in Microbiology, 154: 539-546, 2003.

Helmuth, "Microbiology: Bakers' Yeast Blooms Into Biofilms", Science, 291: 806-807, 2001.

Wentzell et al., "The Sfil Restriction Endonuclease Makes a Four-strand DNA Break at Two Copies of its Recognition Sequence", J. Mol. Biol., 248: 581-595, 1995.

Titorenko and Rachubinski, "Dynamics of peroxisome assembly and function", Trends in Cell Biology, 11: 22-29, 2001.

Murphy et al., "PCR-mediated gene replacement in *Escherichia coli*", Gene, 246: 321-330, 2000.

Nobbs and Halford, "DNA Cleavage at Two Recoginition Sites by the Sfil Restriction Endonuclease: Salt Dependence of Cis and Trans Interactions between Distant DNA Sites", J. Mol. Biol., 252: 399-411, 1995.

Schmitt and Kuck, "The Fungal CPCR1 Protein, Which Binds Specifically to B-Lactam Biosynthesis Genes, Is Related to Human Regulatory Factor X Transcription Factors", The Journal of Biological Chemistry, 275: 9348-9357, 2000.

Sagami et al., "Aspulvinone Dimethylallyltransferase", Methods in Enzymology, 110: 320-327, 1985.

Jensen and Demain, Chapter 8, Beta-Lactams, 239-268.

Drgonova et al., "Rho1p, a Yeast Protein at the Interface Between Cell Polarization and Morphogenesis", Science, 272: 277-279, 1996.

Hacia, "Resequencing and mutational analysis using oligonucleotide microarrays", nature genetics supplement, 21: 41-47, 1999.

Shearer and Hampton, "Lipid-mediated. reversible misfolding of a sterol-sensing domain protein", The EMBO Journal, 24: 149-159, 2005.

Rand and Arst, "A Mutation in *Aspergillus nidulans* which Affects the Regulation of Nitrite Reductase and is Tightly Linked to Its Structural Gene", Molec. Gen. Genet., 155: 67-75, 1977.

Peng et al., "Production of Plyclonal Antibodies against Territrem B and Detection of Territrem B in the Conidia of *Aspergillus Terreus* 23-1 by Immunelectron Microscopy", J. Agric. Food Chem., 52: 3360-3365, 2004.

Poteete, "What makes the bacteriophage Red system useful for genetic engineering: molecular mechanism and biological function", FEMS Microbiology Letters, 201: 9-14, 2001.

Pines et al. "They cytosolic pathway of L-malic acid synthesis in *Saccharomyces cerevisiae*: the role of fumarase", Appl Microbiol Biotechnol, 46: 393-399, 1996.

Dowzer and Kelly, "Analysis of the creA Gene, a Regulatro of Carbon Catabolite Repression in *Aspergillus nidulans*", Molecular and Cellular Biology, 11: 5701-5709, 1991.

Nannini et al., "Peritonitis due to *Aspergillus* and zygomycetes in patients undergoing peritoneal dialysis: report of 2 cases and review of the literature", Diagnostic Microbiology and Infectious Disease, 46: 49-54, 2003.

Luengo and Penalva, Chapter 23, *Penicillin* Biosynthesis, 603-638.

Peng et al., "Biotransformation of Compactin to Pravastatin by *Actinomadura* sp. 2966", The Journal of Antibiotics, 50: 1032-1035, 1997.

Hall and Keller, "mitochondrial B-oxidation in *Aspergillus nidulans*", Molecular Microbiology, 54: 1173-1185, 2004.

Bhosale, et al., *Applied Microbiology and Biotechnology*, 55(4): 423-427, 2001.

Cerda-Olmedo, et al., *Progress in Lipid Res.*, 33(1-2): 185-192, 1994.

Lee, et al., *Applied Microbiology and Biotechnology*, 60(1-2): 1-11, 2002.

Misawa, et al., *J. of Biotechnology*, 59(3): 169-181, 1998.

Schmidt-Dannert, *Current Opin. In Biotechnology*, 11(3): 255-261, 2000.

International Search Report, PCT/US2006/010271, date of mailing Jul. 31, 2007.

Written Opinion of International Searching Authority, PCT/US2006/010271, date of mailing Jul. 31, 2007.

Dyal, et al., "Implications for the use of *Mortierella* fungi in the industrial production of essential fatty acids," Food Res. Int., 38(4): 445-467, May 2005.
Prado-Cabrero, et al., "Retinal biosynthesis in fungi: Characterization of the carotenoid oxygenase CarX from *Fusarium fujikuroi*," Eukaryotic Cell, (6)4: 650-657, Apr. 2007.
International Search Report, PCT/US2007/021092, date of mailing Aug. 11, 2008.
Written Opinion of the International Searching Authority, PCT/US2007/021092, date of mailing Aug. 11, 2008.
Tuveson, et al., *J. of Bacteriology*, 170:4675-4680, 1988.
Hundle, et al., *Fed. of Eur. Biochem. Soc.*, 315:329-334, 1993.
Nakagawa, et al., *Agric. Biol. Chem.*, 58:2147-2148, 1991.
Perry, et al., *J. of Bacteriology*, 168:607-612, 1986.
Misawa, et al., *J. of Biotech.*, 59:169-181, 1998.
International Search Report, PCT/US2006/010271, filed on Sep. 27, 2007.
Madzak et al., "Strong Hybrid Promoters and Integrative Expression/Secretion Vectors for Quasi-Constitutive Expression of Heterologous Proteins in the Yeast *Yarrowia lipolytica*", J. Mol. Microbiol. Biotechnol., 2(2000): 207-216.
Martinez et al., "Genetic transformation of astaxanthin mutants of *Phaffia rhodozyma*", Antonie Van Leeuwenhoek, 73(2): 147-53, 1998.
Miki, "Biological functions and activities of animal carotenoids", Pure Appl. Chem., 63: 141, 1991.
Misawa et al., "Metabolic engineering for the production of carotenoids in non-carotenogenic bacteria and yeasts", J. Biotechnol., 59: 169, 1998.
Miura et al., "Production of the Carotenoids Lycopene, β-Carotene, and Astaxanthin in the Food Yeast Candida utilis", Appl. Environ. Microbiol., 64: 1226, 1998.
Muhlrad and Parker, "Aberrant mRNAs with extended 3' UTRs are substrates for rapid degradation by mRNA surveillance", RNA 5: 1299-1307, 1999.
Palozza et al., "Antioxidant Effects of Carotenoids in Vivo and in Vitro: An Overview", Meth Enzymol., 213: 403, 1992.
Papanikolaou et al., "Single cell oil (SCO) production by *Mortierella isabellina* grown on high-sugar content media", Bioresour Technol., 95(3): 287, 2004.
Ratlegde, "Fatty acid biosynthesis in microorganisms being used for Single Cell Oil Production", Biochimie, 86: 207, 2004.
Rock, "Carotenoids: Biology and Treatment", Pharmacol. Ther., 75: 185, 1997.
Schuldiner et al., "Exploration of the Function and Organization of the Yeast Early Secretory Pathway through an Epistatic Miniarray Profile", Cell 123: 507-519, 2005.
Sherman et al., "Genolevures: comparative genomics and molecular evolution of hemiascomycetous yeasts", Nucleic Acids, Res. 32(Database Issue): D315-8, 2004.
Singh et al., "Cancer Chemoprevention Part 1: Retinoids and Carotenoids and Other Classic Antioxidants", Oncology, 12: 1643, 1998.
Thaker et al., "Lipid production by Candida Y-1", Indian J. Exp. Biol., 35(3): 313, 1997.
Verdoes et al., "Metabolic Engineering of the Carotenoid Biosynthetic Pathway in Yeast Xanthophyllomyces dendrorhous (*Phaffia rhodzyma*)", Appl Environ Microbiol, 69: 3728-3738, 2003.
Visser et al., "Metabolic engineering of the astaxanthin-biosynthetic pathway of *Xanthophyllomyces dendrorhous*", FEMS Yeast Res, 4: 221-231, 2003.
Wang et al., "Astaxanthin-Rich Algal Meal and Vitamin C Inhibit Helicobacter pylori Infection in BALB/cA Mice", Antimicrob. Agents Chemother., 44: 2452, 2000.
Wery et al., "High copy number integration into the ribosomal DNA of the yeast *Phaffia rhodozyma*", Gene., 184(1): 89-97, 1997.
Wynn et al., "The role of malic enzyme in the regulation of lipid accumulation in *filamentous* fungi", Microbiol, 145: 1911, 1999.
Zhu et al., "An inexpensive medium for production of arachidonic acid by *Mortierella alpina*", J. Ind. Microbiol. Biotechnol., 30(1): 75-79, 2003.

Kendrick et al., "Desaturation of polyunsaturated fatty acids in Mucor circinelloides and the involvement of a novel membrane-bound malic enzyme", Eur J Biochem, 209: 667-673, 1992.
Fabre et al., "Role of the proregion in the production and secretion of the *Yarrowia lipolytica* alkaline extracellular protease", J Biol Chem, 266: 3782-3790, 1991.
Golubev, "Perfect state of Rhodomyces dendrorhous (*Phaffia rhodozyma*)",Yeast, 11: 101-110, 1995.
Yamano et al., "Metabolic engineering for production of beta-carotene and lycopene in *Saccharomyces cerevisiae*", Biosci Biotechnol Biochem, 58: 1112-1114, 1994.
Vahlensieck et al., "Identification of the yeast ACC1 gene product (acetyl-CoA carboxylase) as the target of the polyketide fungicide soraphen A", Curr Genet, 25: 95-100, 1994.
Lum et al., "Molecular, functional and evolutionary characterization of the gene encoding HMG-CoA reductase in the fission yeast, *Schizosaccharomyces pombe*", Yeast: 1107-1124, 1996.
Van Der Giezen et al., "A mitochondrial-like targeting signal on the hydrogenosomal malic enzyme from the anaerobic fungus *Neocallimastix frontalis*: support for the hypothesis that hydrogenosomes are modified mitochondria", Moll Microbiol, 23: 11-21, 1997.
Park et al., "Expression, secretion, and processing of rice alpha-amylase in the yeast *Yarrowia lipolytica*", J Biol Chem, 272: 6876-6781, 1997.
Leman "Oleaginous microorganisms: an assessment of the potential", Adv Appl Microbiol, 43: 195-243, 1997.
Pines et al., "Overexpression of cytosolic malate dehydrogenase (MDH2) causes overproduction of specific organic acids in *Saccharomyces cerevisiae*", Appl Microbiol Biotechnol, 48: 248-255, 1997.
Shimada et al., "Increased carotenoid production by the food yeast Candida utilis through metabolic engineering of the isoprenoid pathway", Appl Environ Microbiol, 64: 2676-2680, 1998.
Levert et al., "A bisubstrate analog inhibitor of the carboxyltransferase component of acetyl-CoA carboxylase", Biochem Biophys Res Commun, 291: 1213-1217, 2002.
Bauernfeind, "Carotenoids as colorants and vitamin A precursors", Academic Press, NY, 1981.(1&2).
Adams et al., "The distinctiveness of ATP:citrate lyase from *Aspergillus nidulans*", Biochim Biophys Acta, 1597: 36-41, 2002.
Ratledge, "Regulation of lipid accumulation in oleaginous microorganisms", Biochem Soc Trans, 30: 1047-50, 2002.
Papanikolaou et al., "Accumulation of a cocoa-butter-like lipid by *Yarrowia lipolytica* cultivatied on agro-industrial residues", Curr Microbiol, 46: 124-130, 2003.
Wang, et al., "Amplication of HMG-CoA reductase production enhances carotenoid accumulation in *Neurospora crassa*", Metab Eng, 4: 193-201, 2002.
Nicaud, et al., "Protein expression and secretion in the yeast *Yarrowia lipolytica*", FEMS Yeast Res, 2: 371-9, 2002.
Gadanho et al., "Polyphasic taxonomy of the basidiomycetous yeast genus *Rhodotorula*: Rh. glutinis sensu stricto and Rh. dairenensis comb. Nov", FEMS Yeast Res, 2: 47-58, 2002.
Song, "Detection of farnesyl diphosphate accumulation in yeast ERG9 mutants", Anal Biochem. 317: 180-5, 2003.
Verdoes et al., "Metabolic engineering of the carotenoid biosynthetic pathway in the yeat *Xanthophyllomyces dendrorhous* (*Phaffia rhodozyma*)", Appl Environ Microbiol, 69: 3728-38, 2003.
Johnson, "*Phaffia rhodozyma*: colorful odyssey", Int Microbiol, 6: 169-174, 2003.
Fickers et al., "New disruption cassettes for rapid gene disruption and marker rescue in the yeast *Yarrowia lipolytica*", J Microbiol Methods, 55: 727-37, 2003.
Del Campo et al., "Accumulation of astaxanthin and lutein in *Chlorella zofingiensis* (*Chlorophyta*)", Appl Microbiol Biotechnol, 64: 848-54, 2004.
Dominguez-Bochanegra et al., "Influence of environmental and nutritional factors in the production of astaxanthin from *Haematococcus pluvialis*", Bioresour Technol, 92: 209-14, 2004.
Echavarri-Erasun, et al., "Stimulation of astaxanthin formation in the yeast *Xanthophyllomyces dendrorhous* by the fungus *Epicoccum nigrum*", FEMS Yeast Res, 4: 511-9, 2004.

Sallam et al., "Role of some fermentation parameters on cyclosporin A production by a new isolate of *Aspergillus terreus*", J Gen Appl Microbiol, 49: 321-8, 2003.

Kimura et al., "Rapid estimation of lipids in oleaginous fungi and yeasts using Nile red fluorescence", 56: 331-338, 2004.

Zhang et al., "Molecular basis for the inhibition of the carboxyltransferase domain of acetyl-conenzyme-A carboxylase by haloxyfop and diclofop", Proc Natl Acad Sci U S A, 101: 5910-5, 2004.

Appel et al., "A multicopy vector system for genetic studies in Mucor circinellodies and other zygomycetes", Mol Genet Genomics, 271, 595-602, 2004.

\* cited by examiner

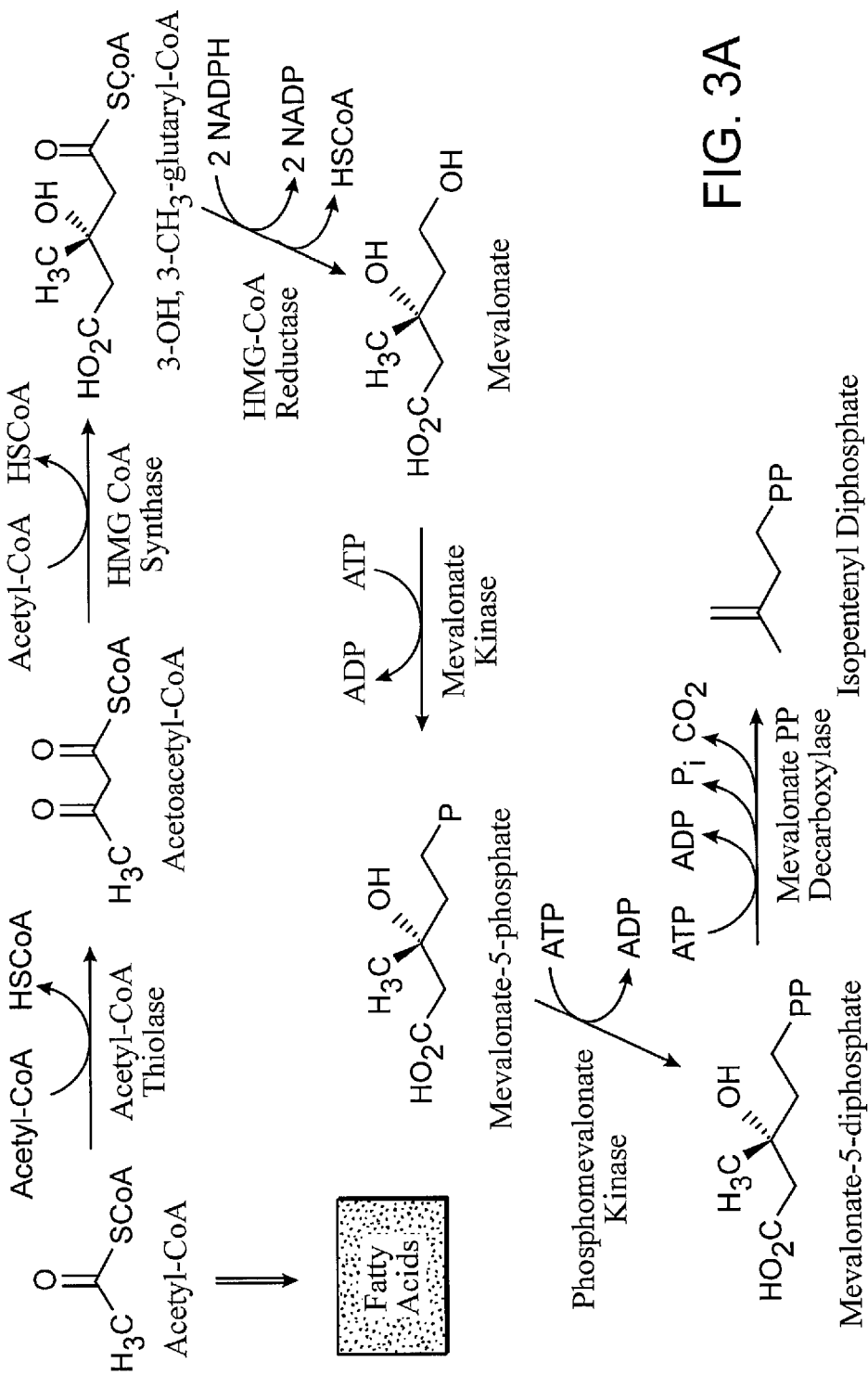

FIG. 7A

Alignment of representative fungal HMG-CoA reductase polypeptides.

```
                            1                                                        50
A. nidulans HMG    (1) -MASVLIRRKFGTE--GGSDAEPSWLKRQVTGCLQSISRRACIHPIHTIV
G. zeae HMG        (1) -MASILPKKFRGETAPAEKTTPSWASKRLTPIAQFISRLACSHPIHTVV
N. crassa HMG      (1) MIASSLLPSKFRGEQPATQAATPSWINKKVTPLQKITSSNPIHTIV
S. cerevisea HMG2  (1) ----------------MSLPKTIVHLVKPFACTARFSARYPIHVIV
S. cerevisiae HMG1 (1) ----------------MPPLFKGLKQMAKPLAYVSRFSAKPPIHIIL
Y. lipolytica HMG  (1) ----------------MLQAAIGKIVGFAVNRPIHTVV
Consensus              MAS LL  RF  E      A PSW  K LT PIQ ISRFAA HPIHTIV 51                                                       100
A. nidulans HMG   (48) VIALLASTTIYVGLLEGSLFDSFRNSNNVAGHVDVDSLLLGNRSLRLGEGT
G. zeae HMG       (50) IVAVLASTSYVGLLQESFFSTDLP--TVGKADWSSLVEGSRVLRAGPET
N. crassa HMG     (51) LVALLASISSYIGLLQNSLFNVTR--SVRKAEWESLQAGSRMLRAGANT
S. cerevisea HMG2 (32) MAVLLSAAAYLSVTQSYLNEWKLDSN-----QYSTYLSIKPDELFEKCTH
S. cerevisiae HMG1(32) FSLIISAFAYLSVIQYYFNGWQLDSNS-----VFFETAPNKDSNTLFQECSH
Y. lipolytica HMG (23) LTISIVASTAYLALLDIAIPGEEG-------TQPISYYHPAAKSYDNPAD
Consensus              LVALLASTAYLGLLQ SLF W L SN        D TSL GSR LR G  T
```

```
                              101                                                       150
A. nidulans HMG    (98)  SWKWQVEDSLNQDDQKVGNPELKREVDQHLALTTLIFPDSISKS-ASTAP
G. zeae HMG        (97)  AWNWKAIEQDSIQ------------HAGADADHLALLTLVFPDTHSAESSTAP
N. crassa HMG      (97)  EWNWQNHDPEAP-------------VPANANHLALLTLVFPDTAES--GPVVA
S. cerevisea HMG2  (77)  YYRSPVSDTWKLS------------SKEAADIYTPFHYYLSTISFQSKDNSTTLP
S. cereviseae HMG1 (78)  YYRDSSLDGWVSIT-----------AHEASELPAPHHYYLLNLNFSPNETDSIP
Y. lipolytica HMG  (65)  ---WTHIAEADIP------------SDAYRLAFAQIRVSDVQGGE-APTIP
      Consensus   (101)  WRW  ID   I                AADA HLAL TLVFPDTQS E ASTIP 151                                                       200
A. nidulans HMG   (147)  AADALPVPANASAQLPHTPNLFSPEISHDSSLVFTLPFDQVPQFLRAVQE----
G. zeae HMG       (139)  RSSHVPVPQNLSITPLPSTKNSFTAYSQDSILAYSLPYAEG------------
N. crassa HMG     (135)  QTNTVPLPSNLSITPLPSTAISFT-YSQDSALAFSLPYSQAPEFLANAQE----
S. cerevisea HMG2 (121)  SLDDVIYSVDHTRYLSEEPKIPTELVSENGTKWRLRNNSN-------------
S. cereviseae HMG1(122)  ELANTVFEKDNTKYLLQEDLSVSKEISSTDGTKWRLRSDRK------------
Y. lipolytica HMG (100)  GAVAVSDLDHRIVMDYKQWAPWTASNEQIASENHIWKHSFK-------D----
      Consensus  (151)  A  VPVP N SI LLP T   IFT YSQDSSL FSLPYS 201                                                       250
A. nidulans HMG   (197)  LPDPTLEDDEGEQKR---WIMRATRGPVSGPNGTISSWLSDAWSSFVDLI
G. zeae HMG       (180)  ----------------------------PDVVQWANNAWTEFLDLL
N. crassa HMG     (184)  IPNAVSSQETIETERGHEKKMWIMKAARVQTRSSTVKWVQNAWVEFTDLL
S. cerevisea HMG2 (162)  -----------------------------FILDIHNIYRNMVKQFSNKT
S. cereviseae HMG1(163)  -----------------------------SLFDVKTLAYSLYDVFSENV
Y. lipolytica HMG (142)  -----------------------------HVAFSWIKWFRWAYLRLSTLI
      Consensus  (201)                                DIV W  NAW   FSDLI
```

FIG. 7B

```
                     251                                                         300
A. nidulans HMG (244) KHAETIDIIIMTLGYLAMYLSFASLEFSMKQLGSKFWLATTVLFSGMFAF
    G. zeae HMG (198) KNAETLDIVIMFLGYTAMHLTFVSLFLSMRKIGSKFWLGICTLFSSVFAF
 N. crassa HMG  (234) RNAETLDIIIMALGYISMHLTFVSLFLSMRRMGSNFWLATSVIFSSIFAF
S. cereviseae HMG2 (182) SEFDQFDLFIILAAYLTFYTLCCLFNDMRKIGSKFWLSFSALSNSACAL
S. cereviseae HMG1 (183) TQADPFDVLIMVTAYLMMFYTIFGLFNDMRKTGSNFWLSASTVNSASSL
 Y. lipolytica HMG (163) QGADNFDIAVVALGYLAMHYTFFSLFRSKRKVGSHEWLASMALVSSFFAF
      Consensus (251) KNADTFDIIIM LGYLAMHYTF SLF SMRKLGSKFWLATS LFSSIFAF 301                                                         350
A. nidulans HMG (294) LFGLIVTTKFG-VPINLLLSEGLPFIVTTIGFEKPIILTRAVLSASIDK
    G. zeae HMG (248) LFGLIVTTKLG-VPISVILLSEGLPFIVTIGFEKNIVLTRAVMSHAIEH
 N. crassa HMG  (284) LFGLIVTTKLG-VPMNMVLLSEGLPFIVTIGFEKNIVLTRAVLSHAIDH
S. cereviseae HMG2 (232) YLSLYTTHSLLKKPASLLSLVIGLPFTVIIGLPFTVVIIGEKHHKVRLAAFSLQKFHRI
S. cereviseae HMG1 (233) FLALYVTQCILGKEVSALTFEGLPFLVVVGFKHKIKIAQYALEKFERV
 Y. lipolytica HMG (213) LLAVVASSSLG-YRPSMITMSEGLPFIVAIGEDRKVNLASEVLTSKSSQ
      Consensus (301) LLGLIVTTKLG VPISMLLSEGLPFLVVTIGFEKKIVLTRAVLS AID 351                                                         400
A. nidulans HMG (343) KRQGS-------ATSTPSSIQDSIQTAIREQGFEIIRDYCIEISILIA
    G. zeae HMG (297) RRQIQNSKGKGSPERSMQNVIQYAVQSAIKEKGFEIMRDYAIEIVILAL
 N. crassa HMG  (333) RRPTE--KSGKPSKQADSAHSIQSAIQLAIKEKGFDIVKDYAIEAGILVL
S. cereviseae HMG2 (282) S-------IDKKITVSNIIYEAMFQEGAYLIRDYLFYISSFIG
S. cereviseae HMG1 (283) G-------LSKRITTDEIVFESVSEEGGRLIQDHLLCIFAFIG
 Y. lipolytica HMG (262) --------LAPMVQVITKIASKALFEYSLEVAALFA
      Consensus (351) RR           S  SIQ AIQ AIKE GFEIIRDYAIEISILIA
```

FIG. 7C

```
                          401                                               450
A. nidulans HMG  (384)  GAASGVQGG-LQQFCFLAAWILFFDCILLFTFYTTICIKLFITRIRRHV
     G. zeae HMG (347)  GAASGVQGG-LQHFCFLAAWILFFDFILLFTFYTAILSIKLEINRIKRHV
   N. crassa HMG (381)  GAASGVQGG-LQQFCFLAAWILFFDCILLFSFYTAILCIKLEINRIKRHV
S. cerevisea HMG2 (318) CAIYARHLPGLVNFCILSTFMLVFDILLSATFYSAILSMKLFINIIHRST
S. cereviseae HMG1 (319) CSMYAHQLKTLTNFGILSAFILIFELILTPTFYSAILALRLFMNVIHRST
  Y. lipolytica HMG (290) GAYTGVPR--LSQFCFLSAWILIFDYMFLLTFYSAVIAIKFLINHIKFNR
          Consensus (401) GAASGVQGG L QFCFLAAWILFFD ILLFTFYSAILAIKLEINRIKRHV
                          451                                               500
A. nidulans HMG  (433)  TLRKALEEDGTTQSVAEKVASSN-DWFGAGSDNSDADDASVFGRKIKSNN
     G. zeae HMG (396)  DMRMALEEDGVSRRVAENVAKSDGDWTRVKGDSSLFG------RKSSS
   N. crassa HMG (430)  QMRKALEEDGVSRRVAEKVAQSN-DWPRADGKDQPGTTI--FGRQLKSTH
S. cerevisea HMG2 (368) VIRQTLEEDGVVPTTADIIYKDE--------TASEPHFLR------SNVA
S. cereviseae HMG1 (369) IIKQTLEEDGVVPSTARIISKAE--------KKSVSSFLN------LSVV
  Y. lipolytica HMG (338) MIQDALKEDGVSAAVAEKVADSSPDAKLDRKSDVSLFG------ASGA
          Consensus (451) IIR ALEEDGVS SVAEKVAKSE DW         KGSDS F       KS  A
                          501                                               550
A. nidulans HMG  (482)  VRRFKFETMVGGFVIVNVVNMTAIPFRNS-S------LSPLCNVFSPTPI
     G. zeae HMG (438)  VPTFKVIMILGFIFVNIVNICSIPFRNPRSLSTIRTWASSLGVVAPLSV
   N. crassa HMG (477)  IPKFKVVMVTGFVLINVLNLCTIPFRSANSISSISSWARGLGVTPPPV
S. cerevisea HMG2 (404) IITGKASVIGLILINJYVFTDKLNATILN------------TVYFD
S. cereviseae HMG1 (405) VITMKLSVILLFVEINFYNFGANWVNDAFN------------SLYFD
  Y. lipolytica HMG (380) IAVFKIFMVLGFLGLNLINLTAIPHLGK------------AAAAAQSV
          Consensus (501) I IFKVLMILGFVLINLVNLTAIPFR A S              L GV SP  V
```

FIG. 7D

```
                       551                                                        600
A. nidulans HMG  (524) DPFKVAENGLDATYVSAKSQKLETLVTVVPPIKVKLEYPSVHYAKLGES-
     G. zeae HMG (488) DPFKVASNGLDAILAAAKSNNRPTLVTVLTPIKYELEYPSIHYALGSAIN
   N. crassa HMG (527) DPFKVASNGLDIILEAARADGRETTVTVLTPIRYELEYPSTHYDLPQKS-
S. cereviseae HMG2 (439) S---TIYSLPNFINYKDIGNLSNQVIISVLPKQYTPLKKYHQIEDSVL-
S. cereviseae HMG1 (440) K---ERVSLPDFITSNASENFKEQAIVSVTPLLYKPIKSYQRIEDMVL-
 Y. lipolytica HMG (416) TPITLSPELLHAIPASVP-----VVVTFVPSVVYEHSQLILQLEDALTE-
       Consensus  (551) DPFKVA NLLDAI AAAKSN RETLVTVTPIKYELEYPSIHY E    S
                       601                                                        650
A. nidulans HMG  (573) -----QSIEIEYTDQLLDAVGGHVLNGVLKSIEDPVISKWITAVLTISIVL
     G. zeae HMG (538) GNNAEYTDAFHHHFQGYGVGGRMVGILKSIEDPVLSKWIVIALAISVAL
   N. crassa HMG (576) -----AEVEGGDYANLGGYGGRMVGSILKSIEDPTLSKWIVVALAISVAL
S. cereviseae HMG2 (485) ------------------IIDSVSNAIRDQFISKILFFAFAVSISI
S. cereviseae HMG1 (486) ------------------LLRNVSVAIRDRFVSKLVLSALVCSAVI
 Y. lipolytica HMG (460) -----------------------FIAACISKTIGDPVISKYIFLCLMVSTAL
       Consensus  (601)                     L    G GG MLGSVSKSIEDPVISKWIVIALALSIAL
                       651                                                        700
A. nidulans HMG  (619) NGYLFNAARWSIKEPQAAPAPKEP-----------------
     G. zeae HMG (588) NGYLFNVARWGIKDPNVPEHNIDRNELARAQQFNDTGSATLPLGEYVPPT
   N. crassa HMG (621) NGYLFNAARWGIKDPNVPDHPINPKELDEAQKFNDTASATLPLGEYMKPT
S. cereviseae HMG2 (514) NVYLLNAAKIHTGYMNFQPQSNKIDDLVQQKSATIEFSETRSMPLASGL
S. cereviseae HMG1 (515) NVYLLNAARIHTSYTADQLVKTEVTKKSFTAPVQKASTPVLTNKTVISGS
 Y. lipolytica HMG (488) NVYLFGATREVRTQSVKVVEKHVPIVIE----K---------
       Consensus  (651) NVYLFNAARW IKDPNV     EV EL  Q    N   SA L     I T
```

FIG. 7E

```
                         701                                                            750
A. nidulans HMG  (643)   ------------------------------------AKPKVYPKTDLNAGPKRSMEECEAMLKA
G. zeae HMG      (638)   PMR---TEPSTPAITDDEAEGLQMTKARSDKLPNRPNEE-----LEKLIAE
N. crassa HMG    (671)   APSSPVAPLTPSSTDDENDAQAKENRAVTLAAQRATTIRSQGELDKMTAE
S. cerevisea HMG2(564)   E----TPVTAKDIIISEEIQNN----ECVYALSSQDEPIRPLSNLVELMEK
S. cereviseae HMG1(565)  K----VKSLSAQSSSSGPSSSSEEDDSRDIESLDKKIRPLELEALLSS
Y. lipolytica HMG (518)  -------PSEKEEDTSSEDSIELTVGKPKPVTETRSLDDLEATMKA
Consensus        (701)                 TPA TDDE  S  S    V KI   IRSLEELEALLAA 751                                                            800
A. nidulans HMG  (671)   KKAAYLSDELLIETSLSGKLPGYALLKSLENEELMSRVDAFLTRAVKLRRA
G. zeae HMG      (681)   KRVKEMSDEEIVSLSMRCKIPGYALLKTLG------------DFTRAVKIRRS
N. crassa HMG    (721)   KRTHELNDEETVHLSLKGKIPGYALEKTLK------------DFTRAVKVRRS
S. cerevisea HMG2(607)   EQLKNMNNTEVSNIVNGKLPLYSLEKKLE------------DTLRAVLVRRK
S. cereviseae HMG1(611)  GNTKQLKNKEVAALVTHGKLPLYALEKKLG------------DTTRAVAVRRK
Y. lipolytica HMG (558)  GKTKLLEDHEVVKLSLEGKLPLYALFKQLG------------DNTRAVGIRRS
Consensus        (751)   KKTK L DEEVV LSL GKLPLYALEKTLG             DFTRAVKIRRS 801                                                            850
A. nidulans HMG  (721)   VVSRTPATSAVTSSLETSKLFYKDYNYALVHGACCENVIGTLPLPLGVAG
G. zeae HMG      (722)   IIARNRATSDLTHSLERSKLPFEKYNWERVFCACCENVIGYMPLPVGVAG
N. crassa HMG    (762)   IISRTKATTELTNILDRSKLPYQNVNWAQVHGACCENVIGYMPLPVGVAG
S. cerevisea HMG2(648)   ALST---L-AESPILVSEKLPFRNYDYDRVFGACCENVIGYMPIPVGVIG
S. cereviseae HMG1(652)  ALSI---L-AEAPVLASDRLFYKNYDYDRVFGACCENVIGYMPLPVGVIG
Y. lipolytica HMG (599)  IISQ---Q-SNTKTLETSKLPYLHYDYDRVFGACCENVIGYMPLPVGVAG
Consensus        (801)   IISR   ATSALT SLESSKLPYKNYNYDRVFGACCENVIGYMPLPVGVAG
```

FIG. 7F

```
                            851                                                      900
A. nidulans HMG   (771)  PLVTDGQSYFIPMATIEGVLVASASRGAKAINAGGAVIVLTGDGMTRGP
      G. zeae HMG (772)  RLVTDGQSYFIPMATIEGVLVASASRGCKAINAGGAVTVLTADGMTRGP
    N. crassa HMG (812)  PLVTDGQSEFVPMATIEGVLVASTSRGCKAINSGGAVTVLTADGMTRGP
 S. cereviseae HMG2 (694) PLITDGTSYHIPMATTEGCLVASAMPGCKAINAGGATTVLTKDGMTRGP
 S. cereviseae HMG1 (698) PLVTDGTSYHIPMATTEGCLVASAMRGCKAINAGGATTVLTKDGMIRGP
  Y. lipolytica HMG (645) PMNTDGKNYHIPMATTEGCLVASTMRGCKAINAGGVTTVLTQDGMTRGP
         Consensus (851) PLVIDGQSYHIPMATTEGVLVASASRGCKAINAGGAVTVLTADGMTRGP 901                                                      950
A. nidulans HMG   (821)  CVGFPTIARAAAAKVWLDSEEGKSVMTAAFNSTSRFARLQHLKTALAGTY
      G. zeae HMG (822)  CVAFETIERAGAAKLWIDSEAGSDIMKKAFNSTSRFARLQSMKTALAGTN
    N. crassa HMG (862)  CVQFETIERAGAAKIWLDSEKGQSIMKKAFNSTSRFARLETMKTAMAGTN
 S. cereviseae HMG2 (744) VVRFPTLIRSGACKIWLDSEEGQNSIKKAFNSTSRFARLQHTQTCLAGDL
 S. cereviseae HMG1 (748) VVRFPTIKRSGAQKIWLDSEEGQNALIKKAFNSTSRFARLQHIQTCLAGDL
  Y. lipolytica HMG (695) CVSEFSIKRAGAAKIWLDESEGLKSMRKAFNSTSRFARLQSLHSTLAGNL
         Consensus (901) CV FPTL RAGAAKIWLDSEEGQ SMKKAFNSTSRFARLQHIKTALAGTL 951                                                      1000
A. nidulans HMG   (871)  LYIRFKTTGDAMGMNMISKGVEKALHVMATECGFDDMATISVSGNFCTD
      G. zeae HMG (872)  LYIRFKTTGDAMGMNIISKGVEHALSVMSNEAGFDDMQIVSVSGNYCTD
    N. crassa HMG (912)  LYIRFKITTGDAMGMNMISKGVEHALSVMYNEG-FEDMNIVSLSGNYCTD
 S. cereviseae HMG2 (794) LFMRFRTTTGDAMGMNMISKGVEYSLKQMVEEYGWEDMEVVSVSGNYCTD
 S. cereviseae HMG1 (798) LFMRFRTTTSDAMGMNMISKGVEYSLKQMVEEYGWEDMEVVSVSGNYCTD
  Y. lipolytica HMG (745) LFIRFRTTTGDAMGMNMISKGVEHSLAVMVKEYGFPLMDIVSVSGNYCTD
         Consensus (951) LFIRFKTTTGDAMGMNMISKGVEHALSVMV EYGFEDMEIVSVSGNYCTD
```

```
                      1151                                                     1200
A. nidulans HMG  (1071) AAVLAGELSLCSALAAGHLVRAHMAHNRSAAPTRSATPVSAAVGATRGLS
    G. zeae HMG  (1072) ASVLAGELSLCSALAAGHLVRAHMQHNRSAAPSRSTTPAPMTPVRSFDTK
  N. crassa HMG  (1111) AAVLAGELSLCSALAAGHLVKAHMAHNRSAPPTRTSTPAPAAAGLTMTS
S. cereviseа HMG2 (994) CAVLAGELSLCSALAAGHLVQSHMTHNRKTNKANELP----QPSNKGPPC
S. cereviseae HMG1 (998) CAVLAGELSLCAALAAGHLVQSHMTHNRKPAEPTKPNNLDATDINRLKDG
Y. lipolytica HMG (945) SGVLAAELSLQSALAAGHLVQSHMTIHNRSQAPTPAKQSQADLQRLQNGSN
      Consensus  (1151) AAVLAGELSLCSALAAGHLVQAHMTHNRSAAPTRS TP  A
                      1201                                                     1250
A. nidulans HMG  (1121) MTSR----------------------------------------------
    G. zeae HMG  (1122) VRCQPNNKDIRNILLTQHPSKPTITYSKRVIKSTIHLNPLILALFDNSVQ
  N. crassa HMG  (1161) S------------N----PNAAAVERSRR---------------------
S. cereviseа HMG2 (1040) KTSALL--------------------------------------------
S. cereviseae HMG1 (1048) SVTCIKS-------------------------------------------
Y. lipolytica HMG (995) ICIRS---------------------------------------------
      Consensus  (1201) I S
                      1251                        1289
A. nidulans HMG  (1126) --------------------------------------  (SEQ ID NO: 75)
    G. zeae HMG  (1172) TRDVQLGDQVSTRGTLDAVGGPQGGVAAGGVARRVVGS  (SEQ ID NO: 76)
  N. crassa HMG  (1174) --------------------------------------  (SEQ ID NO: 77)
S. cereviseа HMG2 (1046) --------------------------------------  (SEQ ID NO: 78)
S. cereviseae HMG1 (1055) --------------------------------------  (SEQ ID NO: 79)
Y. lipolytica HMG (1000) --------------------------------------  (SEQ ID NO: 80)
      Consensus  (1251) --------------------------------------  (SEQ ID NO: 81)
```

FIG. 71

PRODUCTION OF CAROTENOIDS IN OLEAGINOUS YEAST AND FUNGI

RELATED APPLICATIONS

This application claims the benefit of U.S. Provisional Application No. 60/663,621, filed Mar. 18, 2005, the contents of which are hereby incorporated by reference in their entirety.

BACKGROUND OF THE INVENTION

Carotenoids are organic pigments ranging in color from yellow to red that are naturally produced by certain organisms, including photosynthetic organisms (e.g., plants, algae, cyanobacteria), and some fungi. Carotenoids are responsible for the orange color of carrots, as well as the pink in flamingos and salmon, and the red in lobsters and shrimp. Animals, however, cannot produce carotenoids and must receive them through their diet.

Carotenoid pigments (e.g., β-carotene and astaxanthin) are used industrially as ingredients for food and feed stocks, both serving a nutritional function and enhancing consumer acceptability. For example, astaxanthin is widely used in salmon aquaculture to provide the orange coloration characteristic of their wild counterparts. Some carotenoids are also precursors of vitamin A. Also, carotenoids have antioxidant properties, and may have various health benefits (see, for example, Jyonouchi et al., *Nutr. Cancer* 16:93, 1991; Giovannucci et al., *J. Natl. Cancer Inst.* 87:1767, 1995; Miki, *Pure Appl. Chem* 63:141, 1991; Chew et al., *Anticancer Res.* 19:1849, 1999; Wang et al., *Antimicrob. Agents Chemother.* 44:2452, 2000). Some carotenoids such as β-carotene, lycopene, and lutein are currently sold as nutritional supplements.

In general, the biological systems that produce carotenoids are industrially intractable and/or produce the compounds at such low levels that commercial scale isolation is not practicable. Thus, most carotenoids used in industry are produced by chemical synthesis. There is a need for improved biological systems that produce carotenoids. Some efforts have previously been made to genetically engineer certain bacteria or fungi to produce higher levels of carotenoids (see, for example, Misawa et al., *J. Biotechnol.* 59:169, 1998; Visser et al., *FEMS Yeast Research* 4:221, 2003). However, improved systems, allowing higher levels of production and greater ease of isolation, are needed.

SUMMARY OF THE INVENTION

The present invention provides improved systems for the biological production of carotenoids. In one aspect, the invention encompasses the discovery that it is desirable to produce carotenoids in oleaginous organisms. Without wishing to be bound by any particular theory, the present inventors propose that biological systems may be able to accumulate higher levels of carotenoids if the compounds are sequestered in lipid bodies. Regardless of whether absolute levels are higher, however, carotenoids that are accumulated within lipid bodies in oleaginous organisms are readily isolatable through isolation of the lipid bodies.

The present invention therefore provides oleaginous fungi (including, for example, yeast or other unicellular fungi) that produce one or more carotenoids. The present invention also provides methods of constructing such yeast and fungi, methods of using such yeast and fungi to produce carotenoids, and methods of preparing carotenoid-containing compositions, such as food or feed additives, or nutritional supplements, using carotenoids produced in such oleaginous yeast or fungi. In particular, the present invention provides systems and methods for generating yeast and fungi containing one or more oleaginic and/or carotenogenic modifications that increase the oleaginicity and/or alter their carotenoid-producing capabilities as compared with otherwise identical organisms that lack the modification(s).

The present invention further encompasses the general recognition that lipid-accumulating systems are useful for the production and/or isolation of lipophilic agents (such as, but not limited to isoprenoids, or isoprenoid-derived compounds). Thus, according to the present invention, it is desirable to engineer organisms to produce such lipophilic agents and/or to accumulate lipid.

Various other aspects of the present invention will be apparent to those of ordinary skill in the art from the present description, including the appended claims.

BRIEF DESCRIPTION OF THE DRAWING

FIGS. 3A and 3B depict the mevalonate isoprenoid biosynthesis pathway, which typically operates in eukaryotes, including fungi.

FIG. 6A highlights branches leading to various cyclic and acyclic xanthophylls; FIG. 6B shows certain X. dendrorhous pathways that generate dicyclic and monocyclic carotenoids, including astaxanthin; FIG. 6C shows interconnecting pathways for converting β-carotene into any of a variety of other carotenoids, including astaxanthin; FIG. 6D depicts possible routes of synthesis of cyclic carotenoids and common plant and algal xanthophylls from neurosporene.

FIGS. 7A-7I show an alignment of certain representative fungal HMG-CoA reductase polypeptides. As can be seen, these polypeptides show very high identity across the catalytic region, and also have complex membrane spanning domains. In some embodiments of the invention, these membrane-spanning domains are disrupted or are removed, so that, for example, a hyperactive version of the polypeptide may be produced.

DEFINITIONS

Figure 1A:
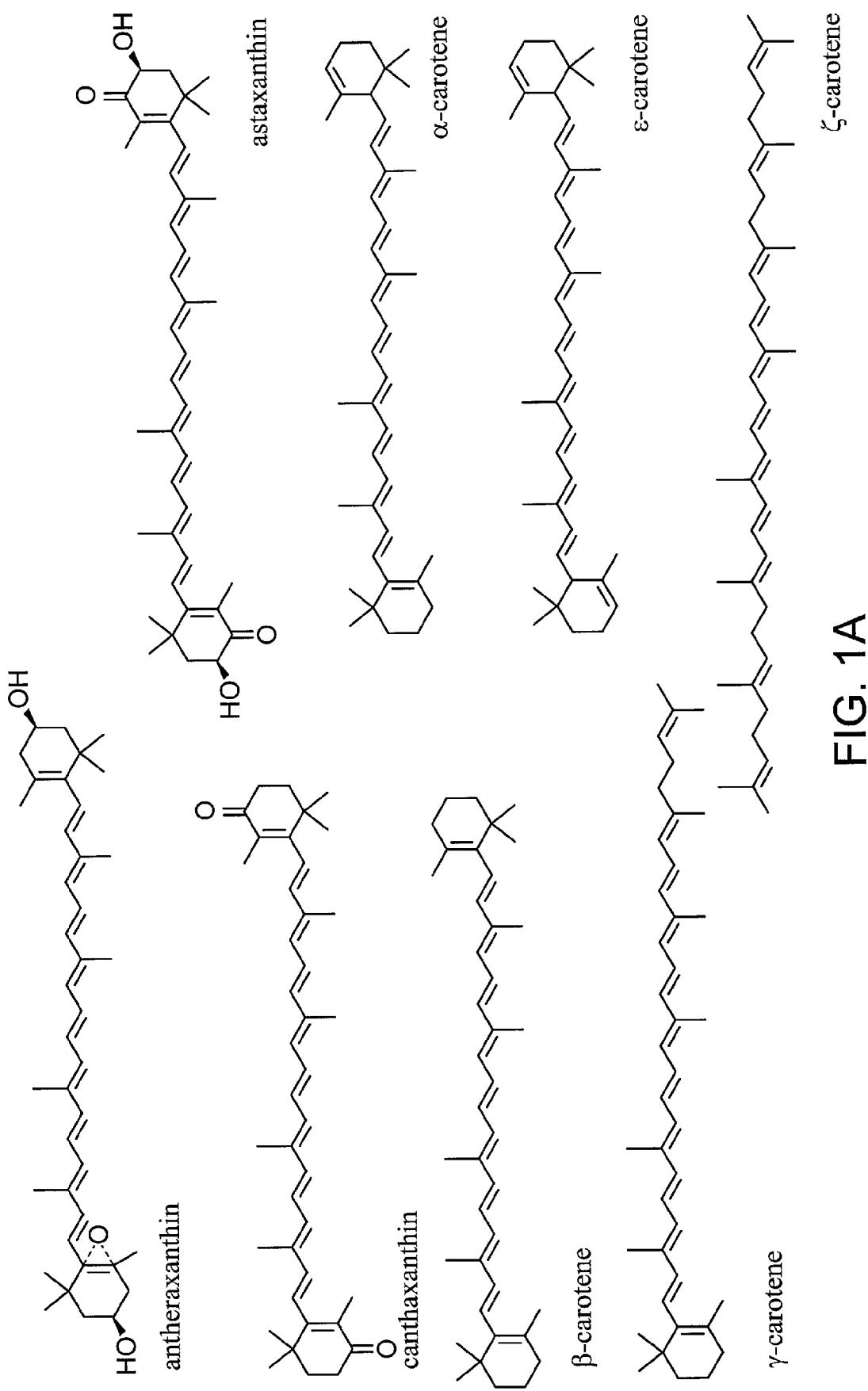
FIG. 1A-1D depicts certain common carotenoids.
Figure 1B:
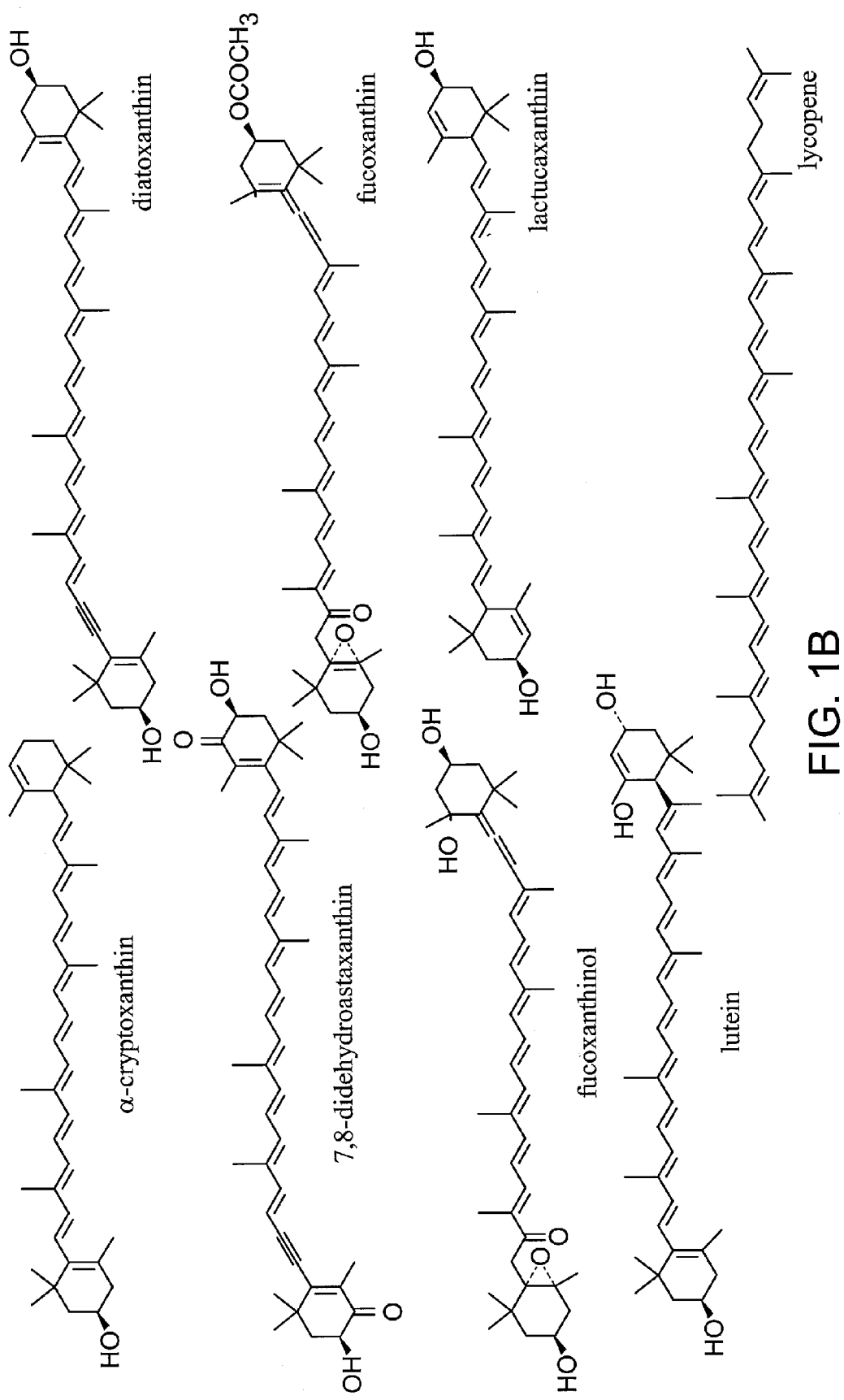
Figure 1C:
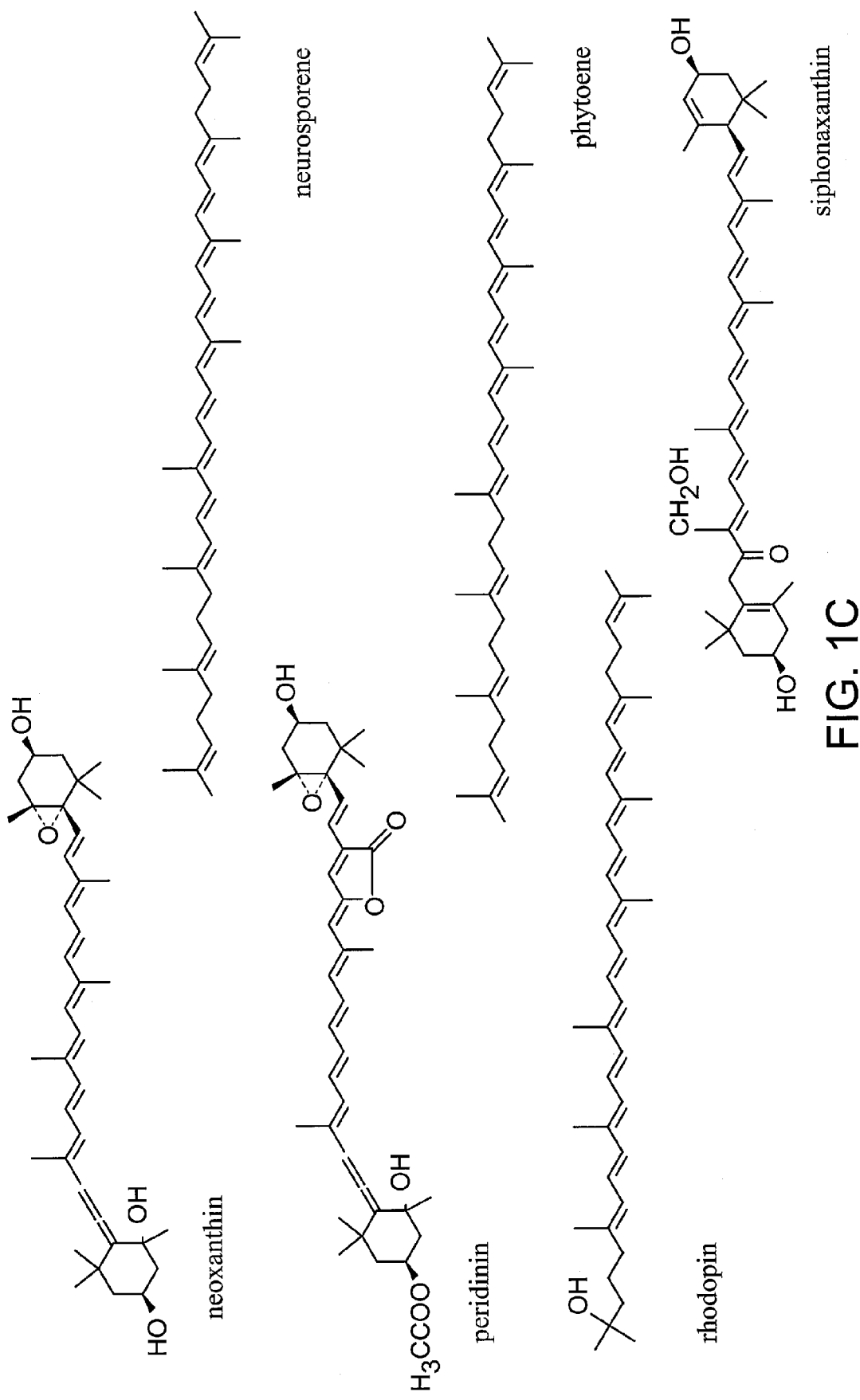
Figure 1D:
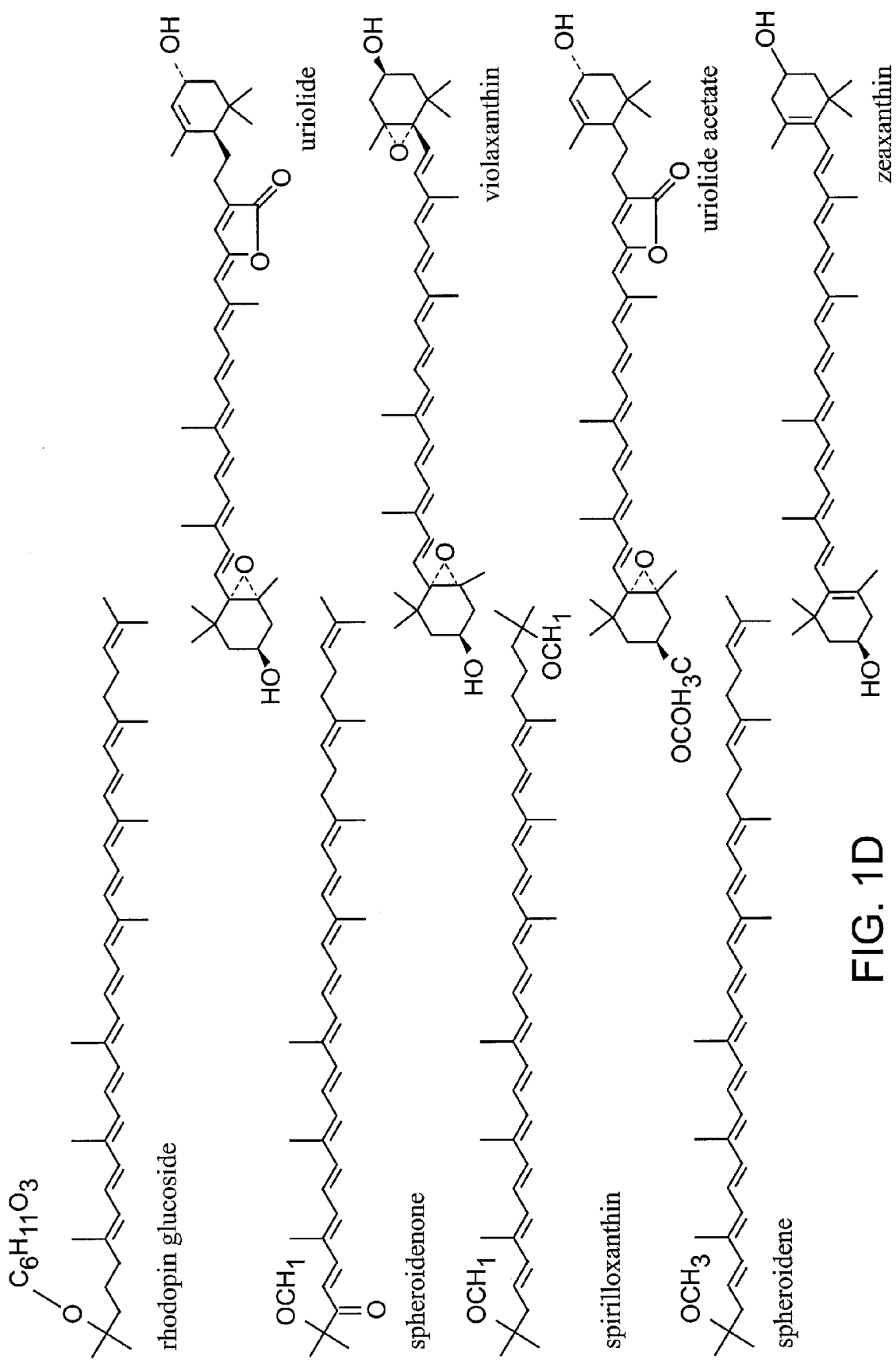

Carotenogenic modification: The term "carotenogenic modification", as used herein, refers to a modification of a host organism that adjusts production of one or more carotenoids, as described herein. For example, a carotenogenic modification may increase the production level of one or more carotenoids, and/or may alter relative production levels of different carotenoids. In principle, an inventive carotenogenic modification may be any chemical, physiological, genetic, or other modification that appropriately alters production of one or more carotenoids in a host organism produced by that organism as compared with the level produced in an otherwise identical organism not subject to the same modification. In most embodiments, however, the carotenogenic modification will comprise a genetic modification, typically resulting in increased production of one or more selected carotenoids. In some embodiments, the selected carotenoid is one or more of astaxanth in, β-carotene, canthaxanth in, lutein, lycopene, phytoene, zeaxanth in, and/or modifications of zeaxanthin or astaxanthin (e.g., glucoside, esterified zeaxanthin or astaxanthin). In some embodiments, the selected carotenoid is one or more xanthophylls, and/or a modification thereof (e.g., glucoside, esterified xanthophylls). In certain embodiments, the selected xanthophyl is selected from the group consisting of astaxanthin, lutein, zeaxanthin, lycopene, and modifications thereof. In some embodiments, the selected carotenoid is one or more of astaxanthin, β-carotene, canthaxanthin, lutein, lycopene, and zeaxanthin and/or modifications of zeaxanthin or astaxanthin. In some embodiments, the carotenoid is β-carotene. In some embodiments, the selected carotenoid is astaxanthin. In some embodiments, the selected carotenoid is other than β-carotene.

Carotenogenicpolypeptide: The term "carotenogenic polypeptide", as used herein, refers to any polypeptide that is involved in the process of producing carotenoids in a cell, and may include polypeptides that are involved in processes other than carotenoid production but whose activities affect the extent or level of production of one or more carotenoids, for example by scavenging a substrate or reactant utilized by a carotenoid polypeptide that is directly involved in carotenoid production. Carotenogenic polypeptides include isoprenoid biosynthesis polypeptides, carotenoid biosynthesis polypeptides, and isoprenoid biosynthesis competitor polypeptides, as those terms are defined herein. The term also encompasses polypeptides that may affect the extent to which carotenoids are accumulated in lipid bodies.

Carotenoid: The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound 1PP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{200}$. $C_{30}$ diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature; certain common carotenoids are depicted in FIG. 1. Carotenoids include but are not limited to: antheraxanthin, adonirubin, adonixanthin, astaxanthin, canthaxanthin, capsorubrin, β-cryptoxanthin, α-carotene, β-carotene, β,ψ-carotene, δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester) and sulfate derivatives (e.g., esterified xanthophylls).

Carotenoid biosynthesis polypeptide: The term "carotenoid biosynthesis polypeptide" refers to any polypeptide that is involved in the synthesis of one or more carotenoids. To mention but a few, these carotenoid biosynthesis polypeptides include, for example, polypeptides of phytoene synthase, phytoene dehydrogenase (or desaturase), lycopene cyclase, carotenoid ketolase, carotenoid hydroxylase, astaxanthin synthase, carotenoid epsilon hydroxylase, lycopene cyclase (beta and epsilon subunits), carotenoid glucosyltransferase, and acyl CoA:diacyglycerol acyltransferase. Representative examples of carotenoid biosynthesis polypeptide sequences are presented in Tables 17-25.

Gene: The term "gene", as used herein, generally refers to a nucleic acid encoding a polypeptide, optionally including certain regulatory elements that may affect expression of one or more gene products (i.e., RNA or protein).

Heterologous: The term "heterologous", as used herein to refer to genes or polypeptides, refers to a gene or polypeptide that does not naturally occur in the organism in which it is being expressed. It will be understood that, in general, when a heterologous gene or polypeptide is selected for introduction into and/or expression by a host cell, the particular source organism from which the heterologous gene or polypeptide may be selected is not essential to the practice of the present invention. Relevant considerations may include, for example, how closely related the potential source and host organisms are in evolution, or how related the source organism is with other source organisms from which sequences of other relevant polypeptides have been selected.

Host cell: As used herein, the "host cell" is a yeast or fungal cell that is manipulated according to the present invention to accumulate lipid and/or to express one or more carotenoids as described herein. A "modified host cell", as that term is used herein, is a host cell that contains at least one oleaginic modification and/or at least one carotenogenic modification according to the present invention.

Isolated: The term "isolated", as used herein, means that the isolated entity has been separated from at least one component with which it was previously associated. When most other components have been removed, the isolated entity is "purified". Isolation and/or purification may be performed using any techniques known in the art including, for example, fractionation, extraction, precipitation, or other separation.

Figure 5:
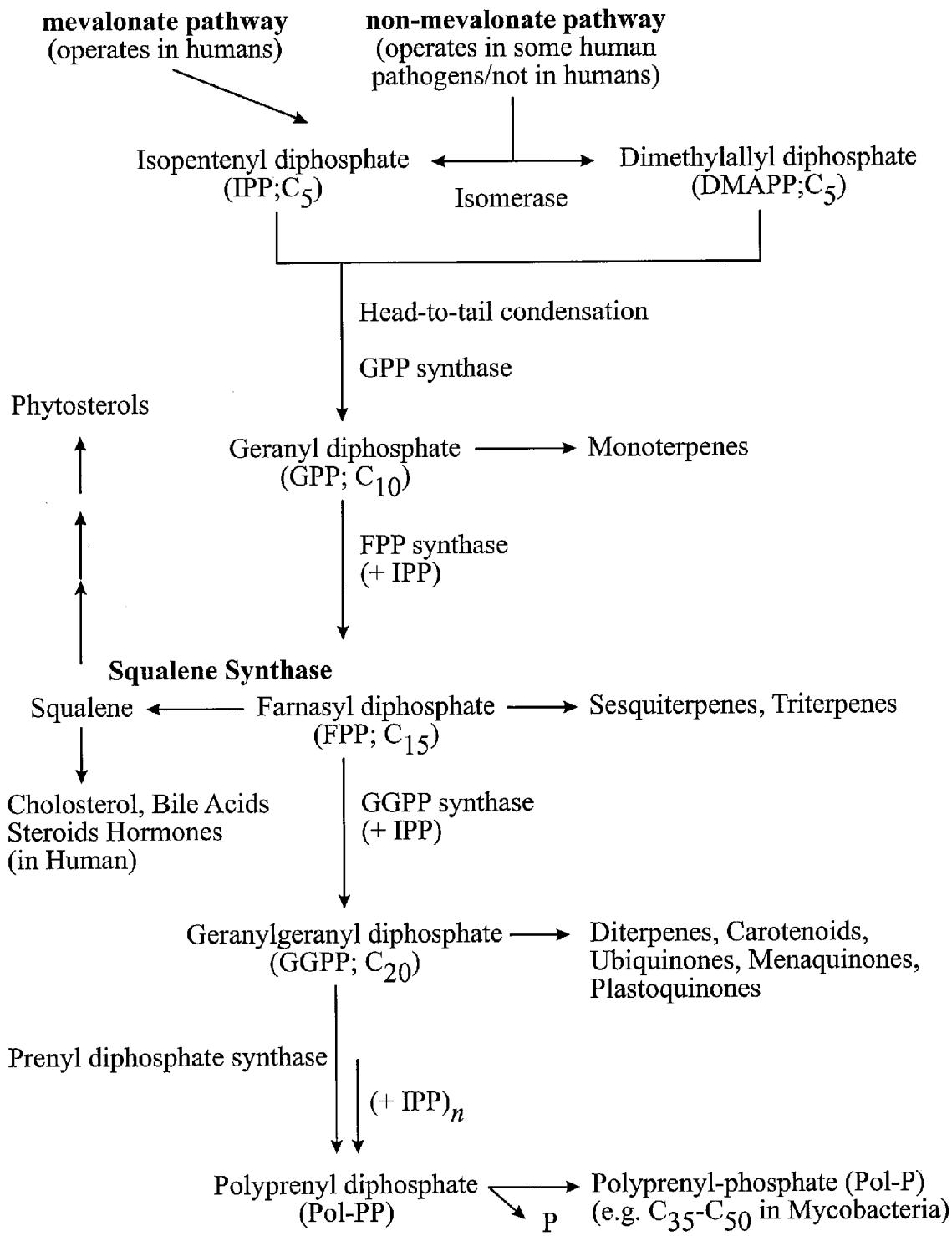
FIG. 5 depicts intermediates in the isoprenoid biosynthesis pathway and how they feed into biosynthetic pathways of other biomolecules, including carotenoids as well as non-carotenoid compounds such as sterols, steroids, and vitamins, such as vitamin E or vitamin K.

Isoprenoid biosynthesis competitor polypeptide: The term "isoprenoid biosynthesis competitor polypeptide", as used herein, refers to a polypeptide whose expression in a cell reduces the level of geranylgeranyl diphosphate (GGPP) available to enter the carotenoid biosynthesis pathway. For example, isoprenoid biosynthesis competitor polypeptides include enzymes that act on isoprenoid intermediates prior to GGPP, such that less GGPP is generated (see, for example, FIG. 5). Squalene synthase is but one isoprenoid biosynthesis competitor polypeptide according to the present invention; representative squalene synthase sequences are presented in Table 16. Prenyldiphosphate synthase enzymes and para-hydroxybenzoate (PHB) polyprenyltransferase are yet additional isoprenoid biosynthesis competitor polypeptides according to the present invention; representative prenyl-diphosphate synthase enzymes and PHB polyprenyltransferase polypeptides are presented in Table 29 and 30 respectively.

Isoprenoid biosynthesis polypeptide: The term "isoprenoid biosynthesis polypeptide" refers to any polypeptide that is involved in the synthesis of isoprenoids. For example, as discussed herein, acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase, are all involved in the mevalonate pathway for isoprenoid biosynthesis. Each of these proteins is also an isoprenoid biosynthesis polypeptide for purposes of the present invention, and sequences of representative examples of these enzymes are provided in Tables 7-15.

Isoprenoid pathway: The "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway". The term "soprenoid pathway" is sufficiently general to encompass both of these types of pathway. Biosynthesis of isoprenoids from IPP occurs by polymerization of several five-carbon isoprene subunits. Isoprenoid metabolites derived from IPP are of varying size and chemical structure, including both cyclic and acyclic molecules. Isoprenoid metabolites include, but are not limited to, monoterpenes, sesquiterpenes, diterpenes, sterols, and polyprenols such as carotenoids.

Oleaginic modification: The term "oleaginic modification", as used herein, refers to a modification of a host organism that adjusts the desirable oleaginy of that host organism, as described herein. In some cases, the host organism will already be oleaginous in that it will have the ability to accumulate lipid to at least about 20% of its dry cell weight. It may nonetheless be desirable to apply an oleaginic modification to such an organism, in accordance with the present invention, for example to increase (or, in some cases, possibly to decrease) its total lipid accumulation, or to adjust the types or amounts of one or more particular lipids it accumulates (e.g., to increase relative accumulation of triacylglycerol). In other cases, the host organism may be non-oleaginous (though may contain some enzymatic and regulatory components used in other organisms to accumulate lipid), and may require oleaginic modification in order to become oleaginous in accordance with the present invention. The present invention also contemplates application of oleaginic modification to non-oleaginous host strains such that their oleaginicity is increased even though, even after being modified, they may not be oleaginous as defined herein. In principle, the oleaginic modification may be any chemical, physiological, genetic, or other modification that appropriately alters oleaginy of a host organism as compared with an otherwise identical organism not subjected to the oleaginic modification. In most embodiments, however, the oleaginic modification will comprise a genetic modification, typically resulting in increased production and/or activity of one or more oleaginic polypeptides. In some embodiments, the oleaginic modification comprises at least one chemical, physiological, genetic, or other modification; in other embodiments, the oleaginic modification comprises more than one chemical, physiological, genetic, or other modification. In certain aspects where more than one modification is utilized, such modifications can comprise any combination of chemical, physiological, genetic, or other modification (e.g., one or more genetic modification and chemical or physiological modification).

Oleaginicpolypeptide: The term "oleaginic polypeptide", as used herein, refers to any polypeptide that is involved in the process of lipid accumulation in a cell and may include polypeptides that are involved in processes other than lipid biosynthesis but whose activities affect the extent or level of accumulation of one or more lipids, for example by scavenging a substrate or reactant utilized by an oleaginic polypeptide that is directly involved in lipid accumulation. For example, as discussed herein, acetyl-CoA carboxylase, pyruvate decarboxylase, isocitrate dehydrogenase, ATP-citrate lyase, malic enzyme, and AMP deaminase, among other proteins, are all involved in lipid accumulation in cells. In general, reducing the activity of pyruvate decarboxylase or isocitrate dehydrogenase, and/or increasing the activity of acetyl CoA carboxylase, ATP-citrate lyase, malic enzyme and/or AMP deaminase is expected to promote oleaginy. Each of these proteins is an oleaginic polypeptide for purposes of the present invention, and sequences of representative examples of these enzymes are provided in Tables 1-6.

Oleaginous: The term "oleaginous", refers to the ability of an organism to accumulate lipid to at least about 20% of its dry cell weight. In certain embodiments of the invention, oleaginous yeast or fungi accumulate lipid to at least about 25% of their dry cell weight. In other embodiments, inventive oleaginous yeast or fungi accumulate lipid within the range of about 20-45% of their dry cell weight. In some embodiments, oleaginous organisms may accumulate lipid to as much as about 70% of their dry cell weight. In some embodiments of the invention, oleaginous organisms may accumulate a large fraction of total lipid accumulation in the form of triacylglycerol. In certain embodiments, the majority of the accumulated lipid is in the form of triacylglycerol. Alternatively or additionally, the lipid may accumulate in the form of intracellular lipid bodies, or oil bodies. In certain embodiments, the present invention utilizes yeast or fungi that are naturally oleaginous. In some aspects, naturally oleaginous organisms are manipulated (e.g., genetically, chemically, or otherwise) so as to futher increase the level of accumulated lipid in the organism. In other embodiments, yeast or fungi that are not naturally oleaginous are manipulated (e.g., genetically, chemically, or otherwise) to accumulate lipid as described herein. For the purposes of the present invention, *Xanthophyl-*

*lomyces dendrorhous* (*Phaffia rhodozyma*) and *Candida utilis* are not naturally oleaginous fungi.

Figure 7H:
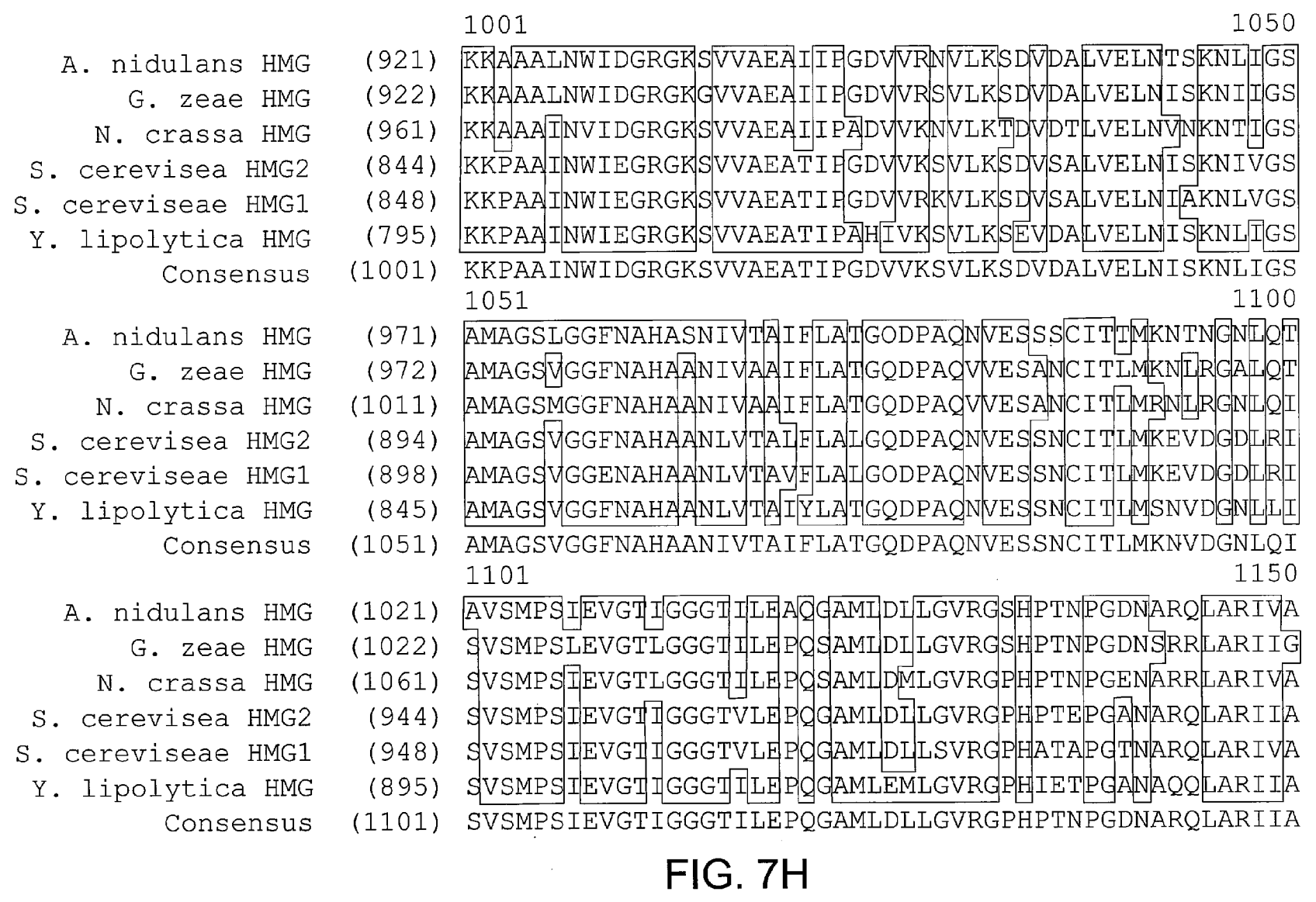

Polypeptide: The term "polypeptide", as used herein, generally has its art-recognized meaning of a polymer of at least three amino acids. However, the term is also used to refer to specific functional classes of polypeptides, such as, for example, oleaginic polypeptides, carotenogenic polypeptides, isoprenoid biosynthesis polypeptides, carotenoid biosynthesis polypeptides, and isoprenoid biosynthesis competitor polypeptides. For each such class, the present specification provides several examples of known sequences of such polypeptides. Those of ordinary skill in the art will appreciate, however, that the term "polypeptide" is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions (e.g., isocitrate dehydrogenase polypeptides often share a conserved AMP-binding motif; HMG-CoA reductase polypeptides typically include a highly conserved catalytic domain (see, for example, FIG. 7); acetyl coA carboxylase typically has a carboxyl transferase domain; see, for example, Downing et al., *Chem. Abs.* 93:484, 1980; Gil et al., *Cell* 41:249, 1985; Jitrapakdee et al. *Curr Protein Pept Sci.* 4:217, 2003; U.S. Pat. No. 5,349,126, each of which is incorporated herein by reference in its entirety), usually encompassing at least 3-4 and often up to 20 or more amino acids, with another polypeptide of the same class, is encompassed within the relevant term "olypeptide" as used herein.

Source organism: The term "source organism", as used herein, refers to the organism in which a particular polypeptide sequence can be found in nature. Thus, for example, if one or more heterologous polypeptides is/are being expressed in a host organism, the organism in which the polypeptides are expressed in nature (and/or from which their genes were originally cloned) is referred to as the "source organism". Where more than one heterologous polypeptides are being expressed in a host organism, one or more source organism(s) may be utilized for independent selection of each of the heterologous polypeptide(s). It will be appreciated that any and all organisms that naturally contain relevant polypeptide sequences may be used as source organisms in accordance with the present invention. Representative source organisms include, for example, animal, mammalian, insect, plant, fungal, yeast, algal, bacterial, cyanobacterial, archaebacterial and protozoal source organisms.

DETAILED DESCRIPTION OF CERTAIN PREFERRED EMBODIMENTS OF THE INVENTION

As noted above, the present invention encompasses the discovery that carotenoids can desirably be produced in oleaginous yeast and fungi. According to the present invention, strains that both (i) accumulate lipid, often in the form of cytoplasmic oil bodies and typically to at least about 20% of their dry cell weight; and (ii) produce carotenoid(s) at a level at least about 1%, and in some embodiments at least about 3-20%, of their dry cell weight, are generated through manipulation of host cells (i.e., strains, including, e.g., naturally-occurring strains, strains which have been previously modified, etc.). These manipulated host cells are then used to produce carotenoids, so that carotenoids that partition into the lipid bodies can readily be isolated.

In general, it will be desirable to balance oleaginy and carotenoid production in inventive cells such that, as soon as a minimum desirable level of oleaginy is achieved, substantially all further carbon which is capable of being utilized and diverted into biosynthesis of products is diverted into a carotenoid production pathway. In some embodiments of the invention, this strategy involves engineering cells to be oleaginous; in other embodiments, it involves engineering cells to accumulate a higher level of lipid, particularly cytoplasmic lipid, than they would accumulate in the absence of such engineering even though the engineered cells may not become "oleaginous" as defined herein. In other embodiments, the extent to which an oleaginous host cell accumulates lipid is actually reduced so that remaining carbon can be utilized in carotenoid production.

Host Cells

Those of ordinary skill in the art will readily appreciate that a variety of yeast and fungal strains exist that are naturally oleaginous or that naturally produce carotenoids. Any of such strains may be utilized as host strains according to the present invention, and may be engineered or otherwise manipulated to generate inventive oleaginous, carotenoid-producing strains. Alternatively, strains that naturally are neither oleaginous nor carotenoid-producing may be employed. Furthermore, even when a particular strain has a natural capacity for oleaginy or for carotenoid production, its natural capabilities may be adjusted as described herein, so as to change the production level of lipid and/or carotenoid. In certain embodiments engineering or manipulation of a strain results in modification of a type of lipid and/or carotenoid which is produced. For example, a strain may be naturally oleaginous and/or carotenogenic, however engineering or modification of the strain may be employed so as to change the type of lipid which is accumulated and or to change the type of carotenoid which is produced.

When selecting a particular yeast or fungal strain for use in accordance with the present invention, it will generally be desirable to select one whose cultivation characteristics are amenable to commercial scale production. For example, it will generally (though not necessarily always) be desirable to avoid filamentous organisms, or organisms with particularly unusual or stringent requirements for growth conditions. However, where conditions for commercial scale production can be applied which allow for utilization of filamentous organisms, these may be selected as host cells. In some embodiments of the invention, it will be desirable to utilize edible organisms as host cells, as they may optionally be formulated directly into food or feed additives, or into nutritional supplements, as desired. For ease of production, some embodiments of the invention utilize host cells that are genetically tractable, amenable to molecular genetics (e.g., can be efficiently transformed, especially with established or available vectors; optionally can incorporate and/or integrate multiple genes, for example sequentially; and/or have known genetic sequence; etc), devoid of complex growth requirements (e.g., a necessity for light), mesophilic (e.g., prefer growth temperatures with in the range of about 25-32° C.), able to assimilate a variety of carbon and nitrogen sources and/or capable of growing to high cell density. Alternatively or additionally, various embodiments of the invention utilize host cells that grow as single cells rather than multicellular organisms (e.g., as mycelia).

In general, when it is desirable to utilize a naturally oleaginous organism in accordance with the present invention, any modifiable and cultivatable oleaginous organism may be employed. In certain embodiments of the invention, yeast or fungi of genera including, but not limited to, *Blakeslea, Candida, Cryptococcus, Cunninghamella, Lipomyces, Mortierella, Mucor, Phycomyces, Pythium, Rhodosporidium, Rhodotorula, Trichosporon*, and *Yarrowia* are employed. In certain particular embodiments, organisms of species that include, but are not limited to, *Blakeslea trispora, Candida pulcherrima, C. revkaufi, C. tropicalis, Cryptococcus curvatus, Cunninghamella echinulata, C. elegans, C. japonica, Lipomyces starkeyi, L. lipoferus, Mortierella alpina, M. isabellina, M. ramanniana, M. vinacea, Mucor circinelloides, Phycomyces blakesleanus, Pythium irregulare, Rhodosporidium toruloides, Rhodotorula glutin is, R. gracilis, R. graminis, R. mucilaginosa, R. pinicola, Trichosporon pullans, T. cutaneum*, and *Yarrowia lipolytica* are used.

Of these naturally oleaginous strains, some also naturally produce carotenoids and some do not. In most cases, only low levels (less than about 0.05% dry cell weight) of carotenoids are produced by naturally-occurring carotenogenic, oleaginous yeast or fungi. Higher levels of βcarotene are sometimes produced, but high levels of other carotenoids are generally not observed.

In general, any organism that is naturally oleaginous and non-carotenoid-producing (e.g., produce less than about 0.05% dry cell weight, do not produce the carotenoid of interest) may be utilized as a host cell in accordance with the present invention. In some embodiments, the organism is a yeast or fungus from a genus such as, but not limited to, *Candida, Cryptococcus, Cunninghamella, Lipomyces, Mortierella, Pythium, Trichosporon*, and *Yarrowia*; in some embodiments, the organism is of a species including, but not limited to, *Mortierella alpina* and *Yarrowia lipolytica*.

Comparably, the present invention may utilize any naturally oleaginous, carotenoid-producing organism as a host cell. In general, the present invention may be utilized to increase carbon flow into the isoprenoid pathway in naturally carotenoid-producing organisms (particularly for organisms other than *Blakeslea* and *Phycomyces*), and/or to shift production from one carotenoid (e.g., β-carotene) to another (e.g., astaxanthin). Introduction of one or more carotenogenic modifications (e.g., increased expression of one or more endogenous or heterologous carotenogenic polypeptides), in accordance with the present invention, can achieve these goals.

In certain embodiments of the invention, the utilized oleaginous, carotenoid-producing organism is a yeast or fungus, for example of a genus such as, but not limited to, *Blakeslea, Mucor, Phycomyces, Rhodosporidium*, and *Rhodotorula*; in some embodiments, the organism is of a species such as, *Mucor circinelloides* and *Rhodotorula glutinis*.

When it is desirable to utilize strains that are naturally non-oleaginous as host cells in accordance with the present invention, genera of non-oleaginous yeast or fungi include, but are not limited to, *Aspergillus, Botrytis, Cercospora, Fusarium (Gibberella), Kluyveromyces, Neurospora, Penicillium, Pichia (Hansenula), Puccinia, Saccharomyces, Sclerotium, Trichoderma*, and *Xanthophyllomyces (Phaffia)*; in some embodiments, the organism is of a species including, but not limited to, *Aspergillus nidulans, A. niger, A. terreus, Botrytis cinerea, Cercospora nicotianae, Fusarium fujikuroi (Gibberella zeae), Kluyveromyces lactis, K. lactis, Neurospora crassa, Pichia pastoris, Puccinia distincta, Saccharomyces cerevisiae, Sclerotium rolfsii, Trichoderma reesei*, and *Xanthophyllomyces dendrorhous (Phaffia rhodozyma)*.

It will be appreciated that the term "non-oleaginous", as used herein, encompasses both strains that naturally have some ability to accumulate lipid, especially cytoplasmically, but do not do so to a level sufficient to qualify as "oleaginous" as defined herein, as well as strains that do not naturally have any ability to accumulate extra lipid, e.g., extra-membranous lipid. It will further be appreciated that, in some embodiments of the invention, it will be sufficient to increase the natural level of oleaginy of a particular host cell, even if the modified cell does not qualify as oleaginous as defined herein.

As with the naturally oleaginous organisms, some of the naturally non-oleaginous fungi naturally produce carotenoids, whereas others do not. Genera of naturally non-oleaginous fungi that do not naturally produce carotenoids (e.g., produce less than about 0.05% dry cell weight, do not produce carotenoid of interest) may desirably be used as host cells in accordance with the present invention include, but are not limited to, *Aspergillus, Kluyveromyces, Penicillium, Saccharomyces*, and *Pichia*; species include, but are not limited to, *Aspergillus niger* and *Saccharomyces cerevisiae*. Genera of naturally non-oleaginous fungi that do naturally produce carotenoids and that may desirably be used as host cells in accordance with the present invention include, but are not limited to, *Botrytis, Cercospora, Fusarium (Gibberella), Neurospora, Puccinia, Sclerotium, Trichoderma*, and *Xanthophyllomyces (Phaffia)*; species include, but are not limited to, *Xanthophyllomyces dendrorhous (Phaffia rhodozyma)*.

As discussed above, any of a variety of organisms may be employed as host cells in accordance with the present invention. In certain embodiments of the invention, host cells will be *Yarrowia lipolytica* cells. Advantages of *Y. lipolytica* include, for example, tractable genetics and molecular biology, availability of genomic sequence (see, for example. Sherman et al. *Nucleic Acids Res.* 32(Database issue):D315-8, 2004), suitability to various cost-effective growth conditions, and ability to grow to high cell density. In addition, *Y. lipolytica* is naturally oleaginous, such that fewer manipulations may be required to generate an oleaginous, carotenoid-producing *Y. lipolytica* strain than might be required for other organisms. Furthermore, there is already extensive commercial experience with *Y. lipolytica*.

*Saccharomyces cerevisiae* is also a useful host cell in accordance with the present invention, particularly due to its experimental tractability and the extensive experience that researchers have accumulated with the organism. Although cultivation of *Saccharomyces* under high carbon conditions may result in increased ethanol production, this can generally be managed by process and/or genetic alterations.

Additional useful hosts include *Xanthophyllomyces dendrorhous (Phaffia rhodozyma)*, which is experimentally tractable and naturally carotenogenic. *Xanthophyllomyces dendrorhous (Phaffia rhodozyma)* strains can produce several carotenoids, including astaxanthin.

*Aspergillus niger* and *Mortierella alpina* accumulate large amounts of citric acid and fatty acid, respectively; *Mortierella alpina* is also oleaginous.

*Neurospora* or *Gibberella* are also useful. They are not naturally oleaginous and tend to produce very low levels of carotenoids, thus extensive modification may be required in accordance with the present invention. *Neurospora* and *Gibberella* are considered relatively tractable from an experimental standpoint. Both are filamentous fungi, such that production at commercial scales can be a challenge necessary to overcome in utilization of such strains.

*Mucor circinelloides* is another available useful species. While its molecular genetics are generally less accessible than are those of some other organisms, it naturally produces β-carotene, thus may require less modification than other species available.

Molecular genetics can be performed in *Blakeslea*, though significant effort may be required. Furthermore, cost-effective fermentation conditions can be challenging, as, for example, it may be required that the two mating types are mixed. Fungi of the genus *Phycomyces* are also possible sources which have the potential to pose fermentation process challenges, and these fungi are also may be less amenable to manipulate than several other potential host organisms.

Those of ordinary skill in the art will appreciate that the selection of a particular host cell for use in accordance with the present invention will also affect, for example, the selection of expression sequences utilized with any heterologous polypeptide to be introduced into the cell, and will also influence various aspects of culture conditions, etc. Much is known about the different gene regulatory requirements, protein targeting sequence requirements, and cultivation requirements, of different host cells to be utilized in accordance with the present invention (see, for example, with respect to *Yarrowia*, Barth et al. *FEMS Microbiol Rev.* 19:219, 1997; Madzak et al. *J Biotechnol.* 109:63, 2004; see, for example, with respect to *Xanthophyllomyces*, Verdoes et al. *Appl Environ Microbiol* 69: 3728-38, 2003; Visser et al. FEMS Yeast Res 4: 221-31, 2003; Martinez et al. Antonie Van Leeuwenhoek. 73(2):147-53, 1998; Kim et al. Appl Environ Microbiol. 64(5):1947-9, 1998; Wery et al. Gene. 184(1):89-97, 1997; see, for example, with respect to *Saccharomyces*, Guthrie and Fink *Methods in Enzymology* 194:1-933, 1991). In certain aspects, for example, targeting sequences of the host cell (or closely related analogs) may be useful to include for directing heterologous proteins to subcellular localization. Thus, such useful targeting sequences can be added to heterologous sequence for proper intracellular localization of activity. In other aspects (e.g., addition of mitochondrial targeting sequences), heterologous targeting sequences may be eliminated or altered in the selected heterologous sequence (e.g., alteration or removal of source organism plant chloroplast targeting sequences).

Engineering Oleaginy

All living organisms synthesize lipids for use in their membranes and various other structures. However, most organisms do not accumulate in excess of about 10% of their dry cell weight as total lipid, and most of this lipid generally resides within cellular membranes.

Significant biochemical work has been done to define the metabolic enzymes necessary to confer oleaginy on microorganisms (primarily for the purpose of engineering single cell oils as commercial sources of arachidonic acid and docosahexaenoic acid; see for example Ratledge *Biochimie* 86:807, 2004, the entire contents of which are incorporated herein by reference). Although this biochemical work is compelling, prior to the present invention, there have been no reports of de novo oleaginy being established through genetic engineering with the genes encoding the key metabolic enzymes.

It should be noted that oleaginous organisms typically only accumulate lipid when grown under conditions of carbon excess and nitrogen or other nutrient limitation. Under these conditions, the organism readily depletes the limiting nutrient but continues to assimilate the carbon source. The "excess" carbon is channeled into lipid biosynthesis so that lipids (usually triacylglycerols) accumulate in the cytosol, typically in the form of bodies.

In general, it is thought that, in order to be oleaginous, an organism must produce both acetyl-CoA and NADPH in the cytosol, which can then be utilized by the fatty acid synthase machinery to generate lipids. In at least some oleaginous organisms, acetyl-CoA is generated in the cytosol through the action of ATP-citrate lyase, which catalyzes the reaction:

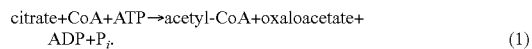

citrate+CoA+ATP→acetyl-CoA+oxaloacetate+ ADP+P$_i$.                                                     (1)

Of course, in order for ATP-citrate lyase to generate appropriate levels of acetyl-CoA in the cytosol, it must first have an available pool of its substrate citric acid. Citric acid is generated in the mitochondria of all eukaryotic cells through the tricarboxylic acid (TCA) cycle, and can be moved into the cytosol (in exchange for malate) by citrate/malate translocase.

In most oleaginous organisms, and in some non-oleaginous organisms, the enzyme isocitrate dehydrogenase, which operates as part of the TCA cycle in the mitochondria, is strongly AMP-dependent. Thus, when AMP is depleted from the mitochondria, this enzyme is inactivated. When isocitrate dehydrogenase is inactive, isocitrate accumulates in the mitochondria. This accumulated isocitrate is then equilibrated with citric acid, presumably through the action of aconitase. Therefore, under conditions of low AMP, citrate accumulates in the mitochondria. As noted above, mitochondrial citrate is readily transported into the cytosol.

AMP depletion, which in oleaginous organisms is believed to initiate the cascade leading to accumulation of citrate (and therefore acetyl-CoA) in the cytoplasm, occurs as a result of the nutrient depletion mentioned above. When oleaginous cells are grown in the presence of excess carbon source but under conditions limiting for nitrogen or some other nutrient(s), the activity of AMP deaminase, which catalyzes the reaction:

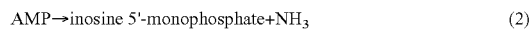

Figure 2:
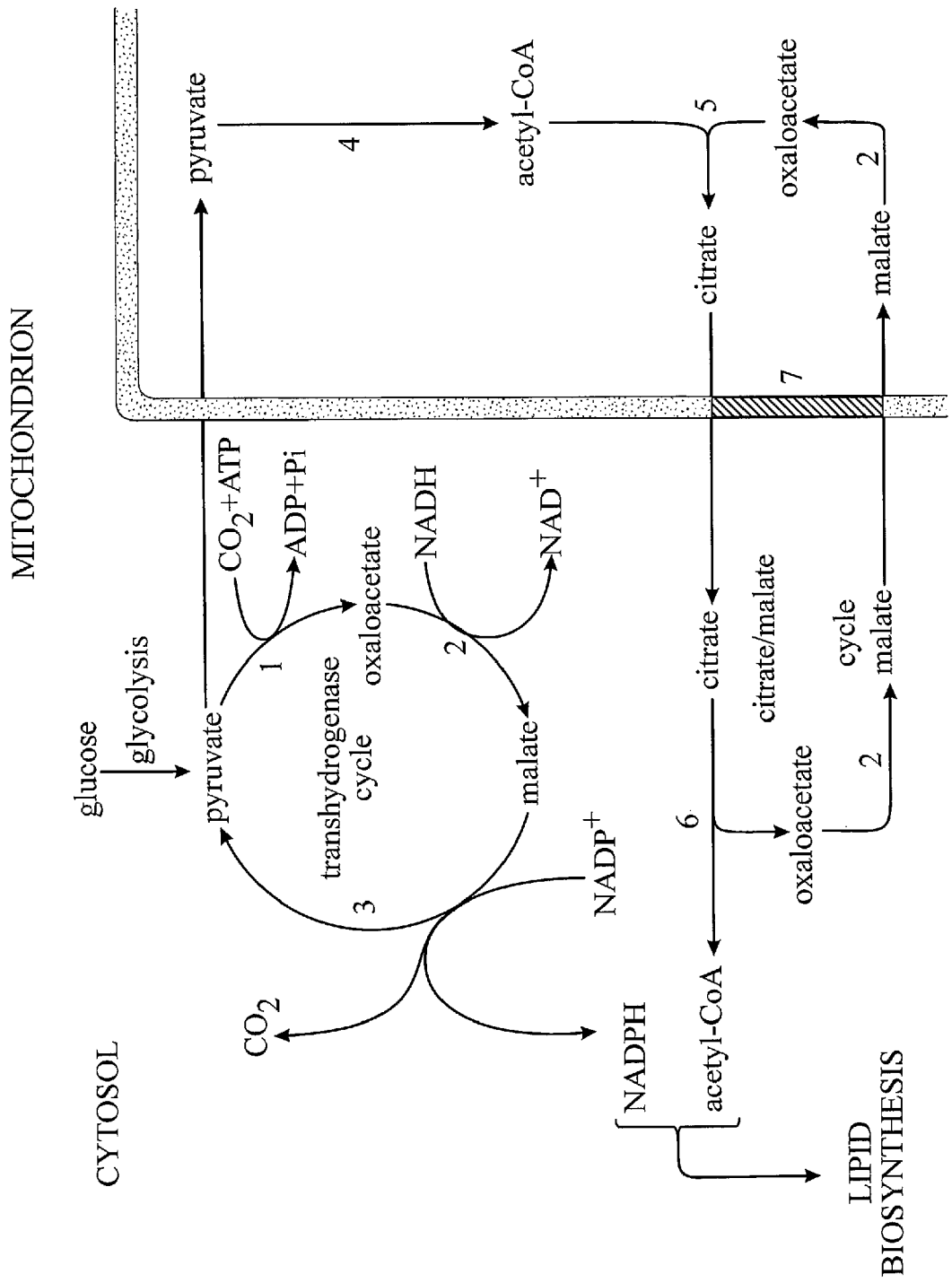
FIG. 2 depicts how sufficient levels of acetyl-CoA and NADPH may be accumulated in the cytosol of oleaginous organisms to allow for production of significant levels of cytosolic lipids. Enzymes: 1, pyruvate decarboxylase; 2, malate dehydrogenase; 3, malic enzyme; 4, pyruvate dehydrogenase; 5, citrate synthase; 6, ATP-citrate lyase; 7, citrate/malate translocase.

AMP→inosine 5'-monophosphate+NH$_3$                    (2)

is strongly induced. The increased activity of this enzyme depletes cellular AMP in both the cytosol and the mitochondria. Depletion of AMP from the mitochondria is thought to inactivate the AMP-dependent isocitrate dehydrogenase, resulting in accumulation of citrate in the mitochondria and, therefore, the cytosol. This series of events is depicted diagrammatically in FIG. 2.

As noted above, oleaginy requires both cytosolic acetyl-CoA and cytosolic NADPH. It is believed that, in many oleaginous organisms, appropriate levels of cytosolic NADPH are provided through the action of malic enzyme (Enzyme 3 in FIG. 2). Some oleaginous organisms (e.g., *Lipomyces* and some *Candida*) do not appear to have malic enzymes, however, so apparently other enzymes can provide comparable activity, although it is expected that a dedicated source of NADPH is probably required for fatty acid synthesis (see, for example, Wynn et al., *Microbiol* 145:1911, 1999; Ratledge *Adv. Appl. Microbiol.* 51:1, 2002, each of which is incorporated herein by reference in its entirety).

Thus, according to the present invention, the oleaginy of a host organism may be enhanced by modifying the expression or activity of one or more polypeptides involved in generating cytosolic acetyl-CoA and/or NADPH. For example, modification of the expression or activity of one or more of acetyl-CoA carboxylase, pyruvate decarboxylase, isocitrate dehydrogenase, ATP-citrate lyase, malic enzyme, and AMP-deaminase can enhance oleaginy in accordance with the present invention. Exemplary polypeptides which can be utilized or derived so as to enhance oleaginy in accordance with the present invention include, but are not limited to those acetyl-CoA carboxylase, pyruvate decarboxylase, isocitrate dehydrogenase, ATP-citrate lyase, malic enzyme, and AMP-deaminase polypeptides provided in Table 1, Table 2, Table 3, Table 4, Table 5, and Table 6, respectively.

In some embodiments of the invention, where an oleaginous host cell is employed, enzymes and regulatory components relevant to oleaginy are already in place but could be modified, if desired, by for example altering expression or activity of one or more oleaginic polypeptides and/or by introducing one or more heterologous oleaginic polypeptides. In those embodiments of the invention where a non-oleaginous host cell is employed, it is generally expected that at least one or more heterologous oleaginic polypeptides will be introduced.

The present invention contemplates not only introduction of heterologous oleaginous polypeptides, but also adjustment of expression or activity levels of heterologous or endogenous oleaginic polypeptides, including, for example, alteration of constitutive or inducible expression patterns. In some embodiments of the invention, expression patterns are adjusted such that growth in nutrient-limiting conditions is not required to induce oleaginy. For example, genetic modifications comprising alteration and/or addition of regulatory sequences (e.g., promoter elements, terminator elements) may be utilized to confer particular regulation of expression patterns. Such genetic modifications may be utilized in conjunction with endogenous genes (e.g., for regulation of endogenous oleaginic polypeptide(s)); alternatively, such genetic modifications may be included so as to confer regulation of expression of at least one heterologous polypeptide (e.g., oleaginic polypeptide(s)). For example, promoters including, but not limited to Tef1, Gpd1 promoters can be used in conjunction with endogenous genes and/or heterologous genes for modification of expression patterns of endogenous oleaginic polypeptides and/or heterolous oleagenic polypeptides. Similarly, exemplary terminator sequences include, but are not limited to, use of *Y. lipolytica* XPR2 terminator sequences.

In some embodiments, at least one oleaginic polypeptide is introduced into a host cell. In some embodiments of the invention, a plurality (e.g., two or more) of different oleaginic polypeptides is introduced into the same host cell. In some embodiments, the plurality of oleaginic polypeptides contains polypeptides from the same source organism; in other embodiments, the plurality includes polypeptides independently selected from different source organisms.

Representative examples of a variety of oleaginic polypeptides that may be introduced into or modified within host cells according to the present invention, include, but are not limited to, those provided in Tables 1-6. As noted above, it is expected that at least some of these polypeptides (e.g., malic enzyme and ATP-citrate lyase) should desirably act in concert, and possibly together with one or more components of fatty acid synthase, such that, in some embodiments of the invention, it will be desirable to utilize two or more oleaginic polypeptides from the same source organism.

In general, source organisms for oleaginic polypeptides to be used in accordance with the present invention include, but are not limited to, *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium (Gibberella), Kluyveromyces, Neurospora, Penicillium, Pichia (Hansenula), Puccinia, Saccharomyces, Sclerotium, Trichoderma,* and *Xanthophyllomyces (Phaffia)*. In some embodiments, the source species for acetyl CoA carboxylase, ATP-citrate lyase, malice enzyme and/or AMP deaminase polypeptides include, but are not limited to, *Aspergillus nidulans, Cryptococcus neoformans, Fusarium fujikuroi, Kluyveromyces lactis, Neurospora crassa, Saccharomyces cerevisiae, Schizosaccharomyces pombe, Ustilago maydis,* and *Yarrowia lipolytica*; in some embodiments, source species for pyruvate decarboxylase or isocitrate dehydrogenase polypeptides include, but are not limited to *Neurospora crassa, Xanthophyllomyces dendrorhous (Phaffia rhodozyma), Aspergillus niger, Saccharomyces cerevisiae, Mucor circinelloides, Rhodotorula glutinis, Candida utilis, Mortierella alpina* and *Yarrowia lipolytica*.

Engineering Carotenoid Production

Figure 3B:
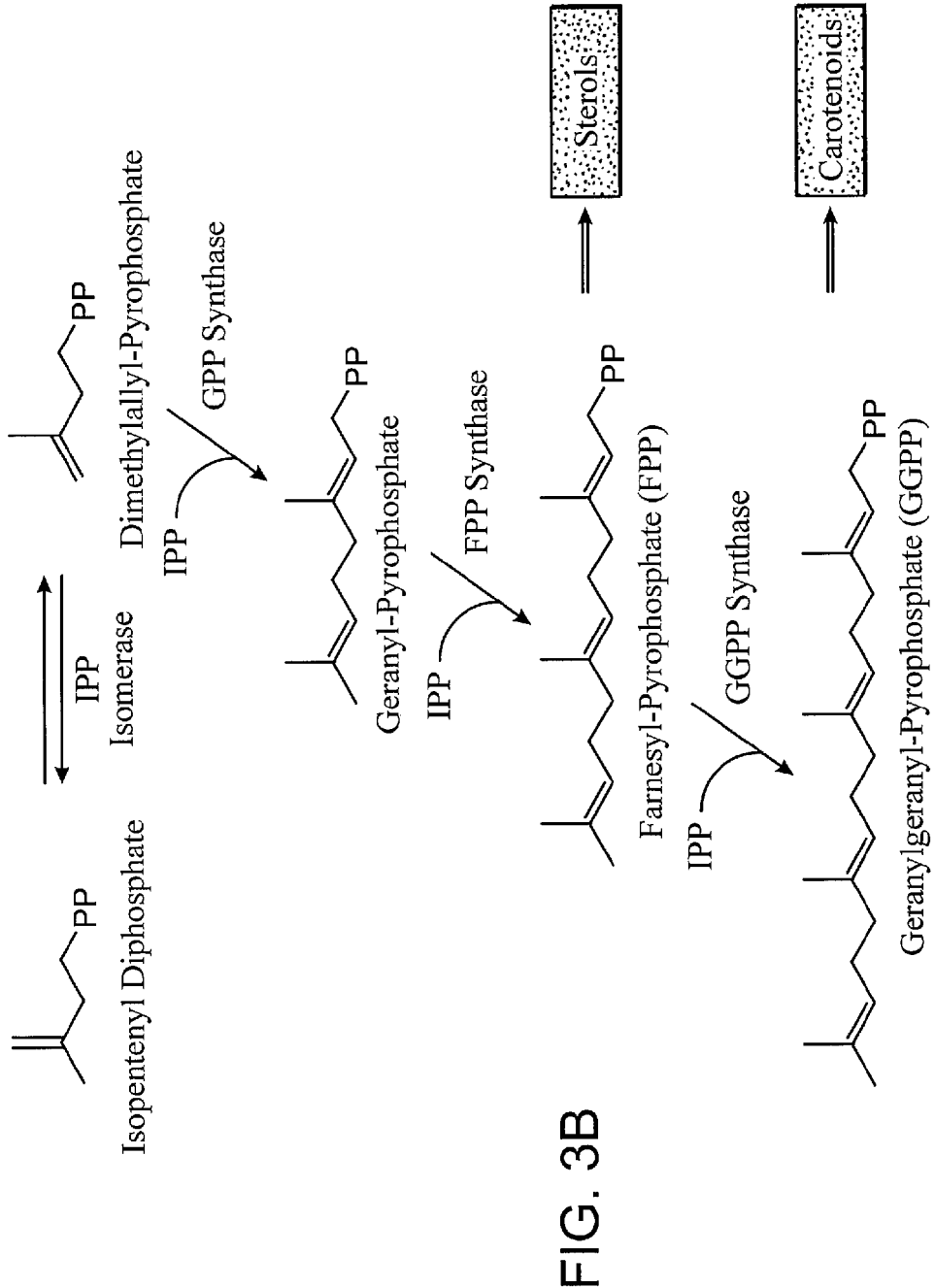

Carotenoids are synthesized from isoprenoid precursors, some of which are also involved in the production of steroids and sterols. The most common isoprenoid biosynthesis pathway, sometimes referred to as the "mevalonate pathway", is generally depicted in FIG. 3. As shown, acetyl-CoA is converted, via hydroxymethylglutaryl-CoA (HMG-CoA), into mevalonate. Mevalonate is then phosphorylated and converted into the five-carbon compound isopentenyl pyrophosphate (IPP). Following isomerization of IPP into dimethylallyl pyrophosphate (DMAPP), three sequential condensation reactions with additional molecules of IPP generate the ten-carbon molecule geranyl pyrophosphate (GPP), followed by the fifteen-carbon molecule farnesyl pyrophosphate (FPP), and finally the twenty-carbon compound geranylgeranyl pyrophosphate (GGPP).

Figure 4:
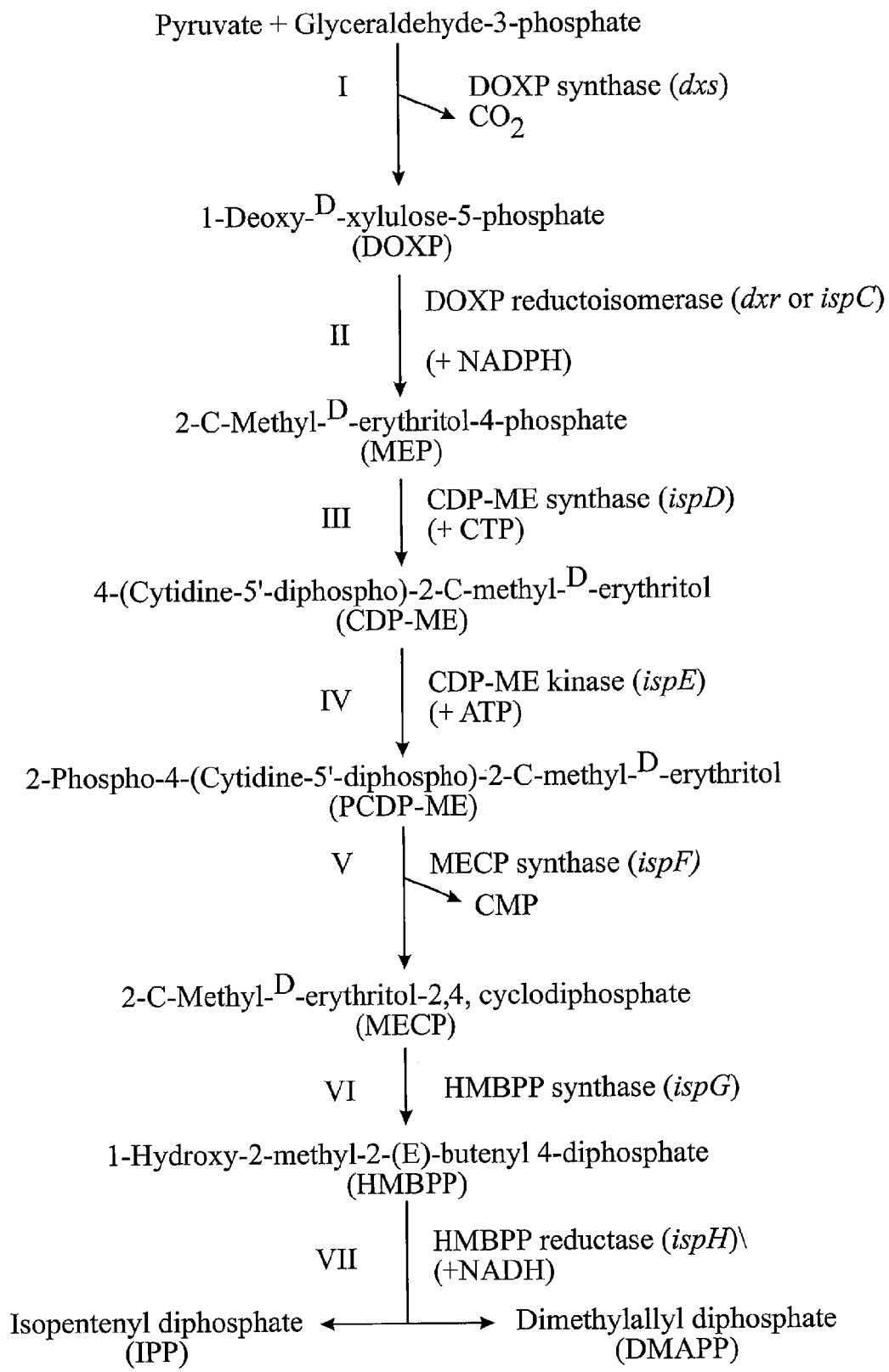
FIG. 4 depicts the mevalonate-independent isoprenoid biosynthesis pathway, also known as the DXP pathway, which typically operates in bacteria and in the plastids of plants.

An alternative isoprenoid biosynthesis pathway, that is utilized by some organisms (particularly bacteria) and is sometimes called the "mevalonate-independent pathway", is depicted in FIG. 4. This pathway is initiated by the synthesis of 1-deoxy-D-xyloglucose-5-phosphate (DOXP) from pyruvate and glyceraldehyde-3-phosphate. DOXP is then converted, via a series of reactions shown in FIG. 4, into IPP, which isomerizes into DMAPP and is then converted, via GPP and FPP, into GGPP as shown in FIG. 3 and discussed above.

Various proteins involved in isoprenoid biosynthesis have been identified and characterized in a number of organisms. Moreover, various aspects of the isoprenoid biosynthesis pathway are conserved throughout the fungal, bacterial, plant and animal kingdoms. For example, polypeptides corresponding to the acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase shown in FIG. 3 have been identified in and isolated from a wide variety of organisms and cells. Representative examples of a wide variety of such polypeptides are provided in Tables 7-15. One or more of the polypeptides selected from those provided in any one of Tables 7-15 may be utilized or derived for use in the methods and compositions in accordance with the present invention.

According to the present invention, carotenoid production in a host organism may be adjusted by modifying the expression or activity of one or more proteins involved in isoprenoid biosynthesis. In some embodiments, such modification involves introduction of one or more heterologous isoprenoid biosynthesis polypeptides into the host cell; alternatively or additionally, modifications may be made to the expression or activity of one or more endogenous or heterologous isoprenoid biosynthesis polypeptides. Given the considerable conservation of components of the isoprenoid biosynthesis polypeptides, it is expected that heterologous isoprenoid biosynthesis polypeptides will often function even in significantly divergent organisms. Furthermore, should it be desirable to introduce more than one heterologous isoprenoid biosynthesis polypeptide, in many cases polypeptides from different source organisms will function together. In some embodiments of the invention, a plurality of different heterologous isoprenoid biosynthesis polypeptides is introduced into the same host cell. In some embodiments, this plurality contains only polypeptides from the same source organism (e.g., two or more sequences of, or sequences derived from, the same source organism); in other embodiments the plurality includes polypeptides independently selected from from different source organisms (e.g., two or more sequences of, or sequences derived from, at least two independent source organisms).

In some embodiments of the present invention that utilize heterologous isoprenoid biosynthesis polypeptides, the source organisms include, but are not limited to, fungi of the genera *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium (Gibberella), Kluyveromyces, Neurospora, Penicillium, Pichia (Hansenula), Puccinia, Saccharomyces, Schizosaccharomyces, Sclerotium, Trichoderms, Ustilago,* and *Xanthophyllomyces (Phaffia)*. In certain embodiments, the source organisms are of a species including, but not limited to, *Cryptococcus neoformans, Fusarium fujikuroi, Kluyverimyces lactis, Neurospora crassa, Saccharomyces cerevisiae, Schizosaccharomyces pombe, Ustilago maydis,* and *Yarrowia lipolytica*.

As noted above, the isoprenoid biosynthesis pathway is also involved in the production of non-carotenoid compounds, such as sterols, steroids, and vitamins, such as vitamin E or vitamin K. Proteins that act on isoprenoid biosynthesis pathway intermediates, and divert them into biosynthesis of non-carotenoid compounds are therefore indirect inhibitors of carotenoid biosynthesis (see, for example, FIG. 5, which illustrates points at which isoprenoid intermediates are channeled into other biosynthesis pathways). Such proteins are therefore considered isoprenoid biosynthesis competitor polypeptides. Reductions of the level or activity of such isoprenoid biosynthesis competitor polypeptides are expected to increase carotenoid production in host cells according to the present invention.

In some embodiments of the present invention, production or activity of endogenous isoprenoid biosynthesis competitor polypeptides may be reduced or eliminated in host cells. In some embodiments, this reduction or elimination of the activity of an isoprenoid biosynthesis competitor polypeptide can be achieved by treatment of the host organism with small molecule inhibitors of enzymes of the ergosterol biosynthetic pathway. Enzymes of the ergosterol biosynthetic pathway include, for example, squalene synthase, squalene epoxidase, 2,3-oxidosqualene-lanosterol cyclase, cytochrome P450 lanosterol 14α-demethylase, C-14 sterol reductase, C-4 sterol methyl oxidase, SAM:C-24 sterol methyltransferase, C-8 sterol isomerase, C-5 sterol desaturase, C-22 sterol desaturase, and C-24 sterol reductase. Each of these enzymes is considered an isoprenoid biosynthesis competitor polypeptide. Regulators of these enzymes may also be considered isoprenoid biosynthesis competitor polypeptides (e.g., the yeast proteins Sut1 (Genbank Accession JC4374 GI:2133159) and Mot3 (Genbank Accession NP_013786 GI:6323715), which may or may not have homologs in other organisms.

In other embodiments, reduction or elimination of the activity of an isoprenoid biosynthesis competitor polypeptide can be achieved by decreasing activity of the ubiquinone biosynthetic pathway. The commitment step in ubiquinone biosynthesis is the formation of para-hydroxybenzoate (PHB) from tyrosine or phenylalanine in mammals or chorismate in bacteria, followed by condensation of PHB and isoprene precursor, resulting in addition of the prenyl group. This reaction is catalyzed by PHB-polyprenyltransferase. The isoprenoid side chain of ubiquinone is determined by the prenyidiphosphate synthase enzyme. The 3-decaprenyl-4-hydroxybenzoic acid resulting from the condensation of PHB and decaprenyldiphosphate reaction undergoes further modifications, which include hydroxylation, methylation and decarboxylation, in order to form ubiquinone (CoQ10). Thus, inhibition of prenyidiphosphate synthase leading from famesyldiphosphate to extended isoprenoids, or inhibition of PHB polyprenyltransferase may be useful in increasing the amount of isoprenoid available for carotenoid biosynthesis. (Examples of prenyldiphosphate synthase and PHB-polyprenyltransferase enzymes are depicted in Tables 29 and 30, respectively).

Known small molecule inhibitors of isoprenoid biosynthesis competitor enzymes include, but are not limited to, zaragosic acid (including analogs thereof such as TAN1607A (Biochem Biophys Res Commun 1996 Feb. 15;219(2):515-520)), RPR 107393 (3-hydroxy-3-[4-(quinolin-6-yl)phenyl]-1-azabicyclo[2-2-2]octane dihydrochloride; J Pharmacol Exp Ther. 1997 May;281(2):746-52), ER-28448 (5-{N-[2-butenyl-3-(2-methoxyphenyl)]-N-methylamino}-1,1-penthylidenebis(phosphonic acid) trisodium salt; Journal of Lipid Research, Vol. 41, 1136-1144, July 2000), BMS-188494 (The Journal of Clinical Pharmacology, 1998; 38:1116-1121), TAK-475 (1-[2-[(3R,5S)-1-(3-acetoxy-2,2-dimethylpropyl)-7-chloro-1,2,3,5-tetrahydro-2-oxo-5-(2,3-dimethoxyphenyl)-4,1-benzoxazepine-3-yl]acetyl]piperidin-4-acetic acid; Eur J Pharmacol. 2003 April 11;466(1-2):155-61), YM-5360 ((E)-2-[2-fluoro-2-(quinuclidin-3-ylidene)ethoxy]-9H-carbazole monohydrochloride; Br J Pharmacol. 2000 September;131(1):63-70), or squalestatin I that inhibit squalene synthase; terbinafine that inhibits squalene epoxidase; various azoles that inhibit cytochrome P450 lanosterol 14α-demethylase; and fenpropimorph that inhibits the C-14 sterol reductase and the C-8 sterol isomerase. In other embodiments, heterologous isoprenoid biosynthesis competitor polypeptides may be utilized (whether functional or non-functional; in some embodiments, dominant negative mutants are employed).

One particular isoprenoid biosynthesis competitor polypeptide useful according to the present invention is squalene synthase which has been identified and characterized from a variety of organisms; representative examples of squalene synthase polypeptide sequences are included in Table 16. In some embodiments of the invention that utilize squalene synthase (or modifications of squalene synthase) source organisms include, but are not limited to, *Neurospora crassa, Xanthophyllomyces dendrorhous (Phaffia rhodozyma), Aspergillus niger, Saccharomyces cerevisiae, Mucor circinelloides, Rhotorula glutinis, Candida utilis, Mortierella alpina,* and *Yarrowia lipolytica*.

Figure 6A:
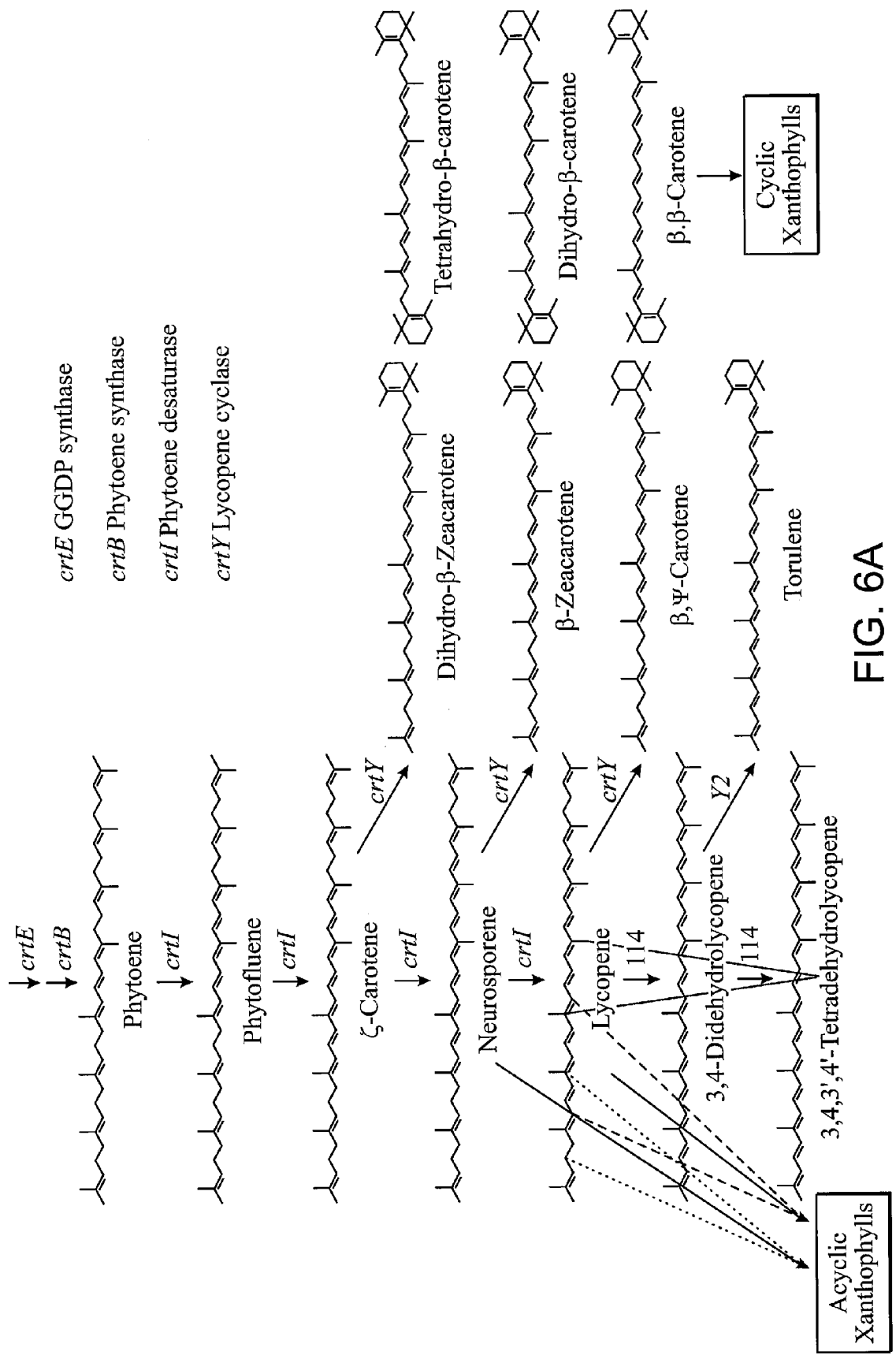
FIGS. 6A-6D illustrate various carotenoid biosynthetic pathways.
Figure 6B:
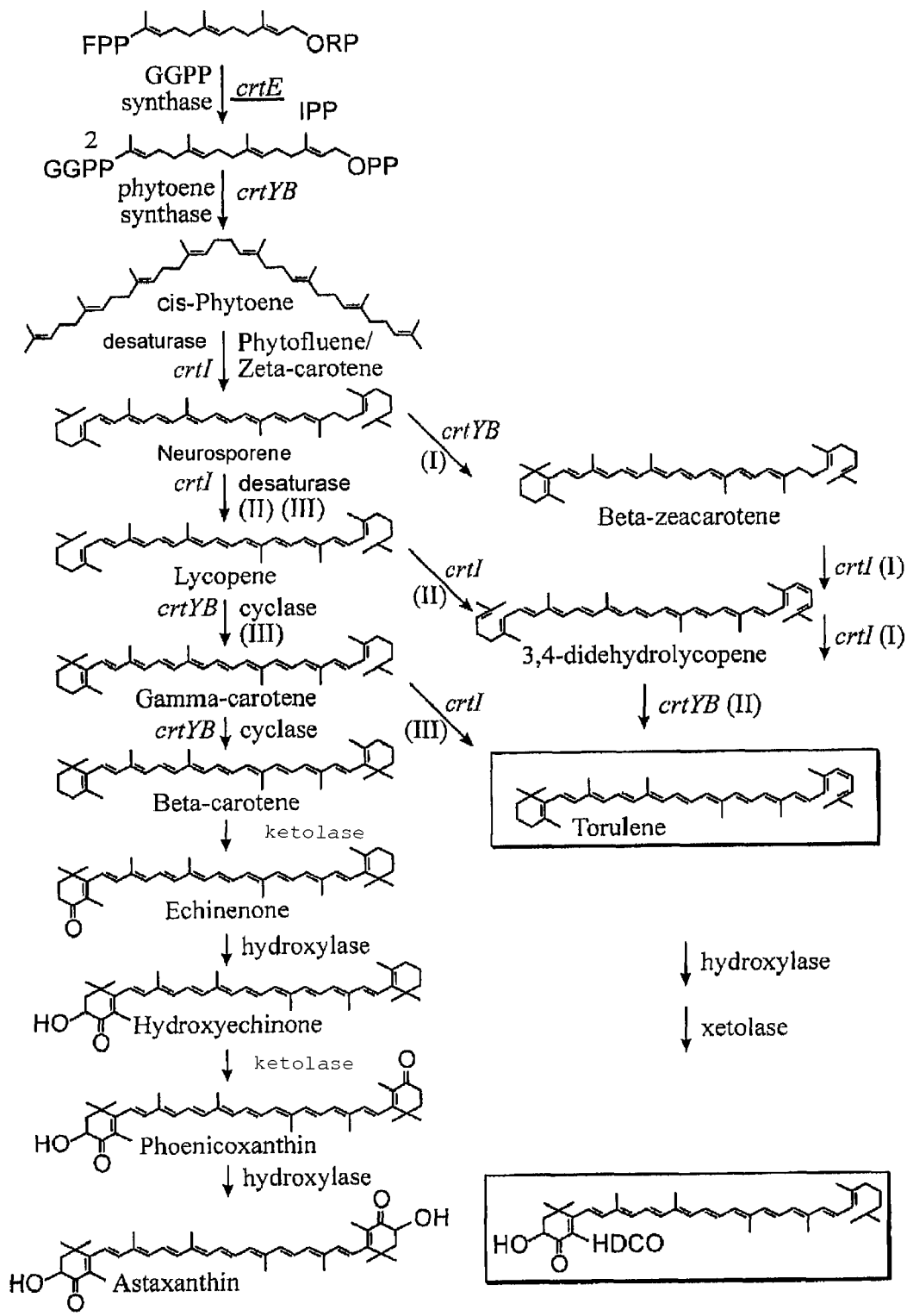
Figure 6C:
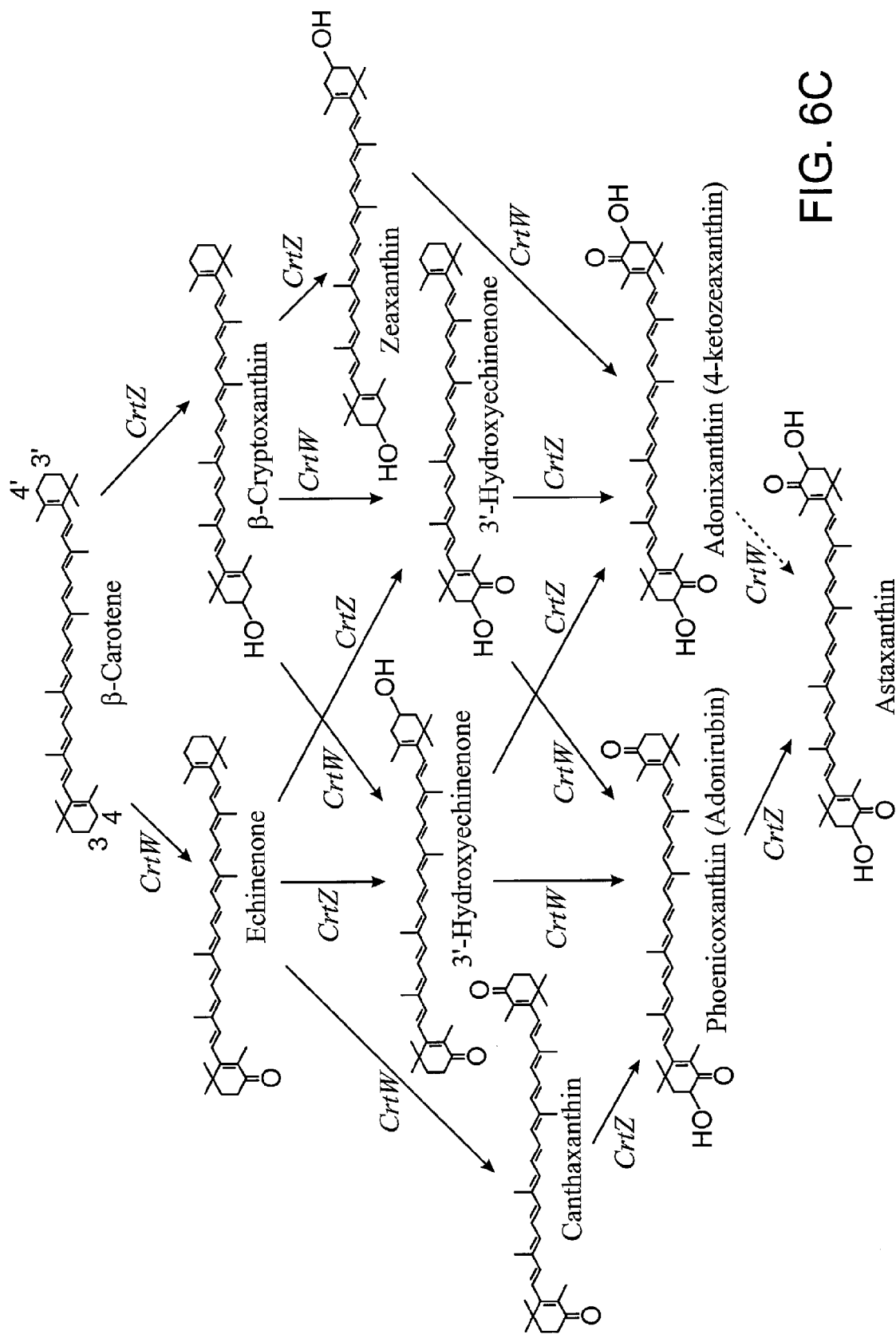
Figure 6D:
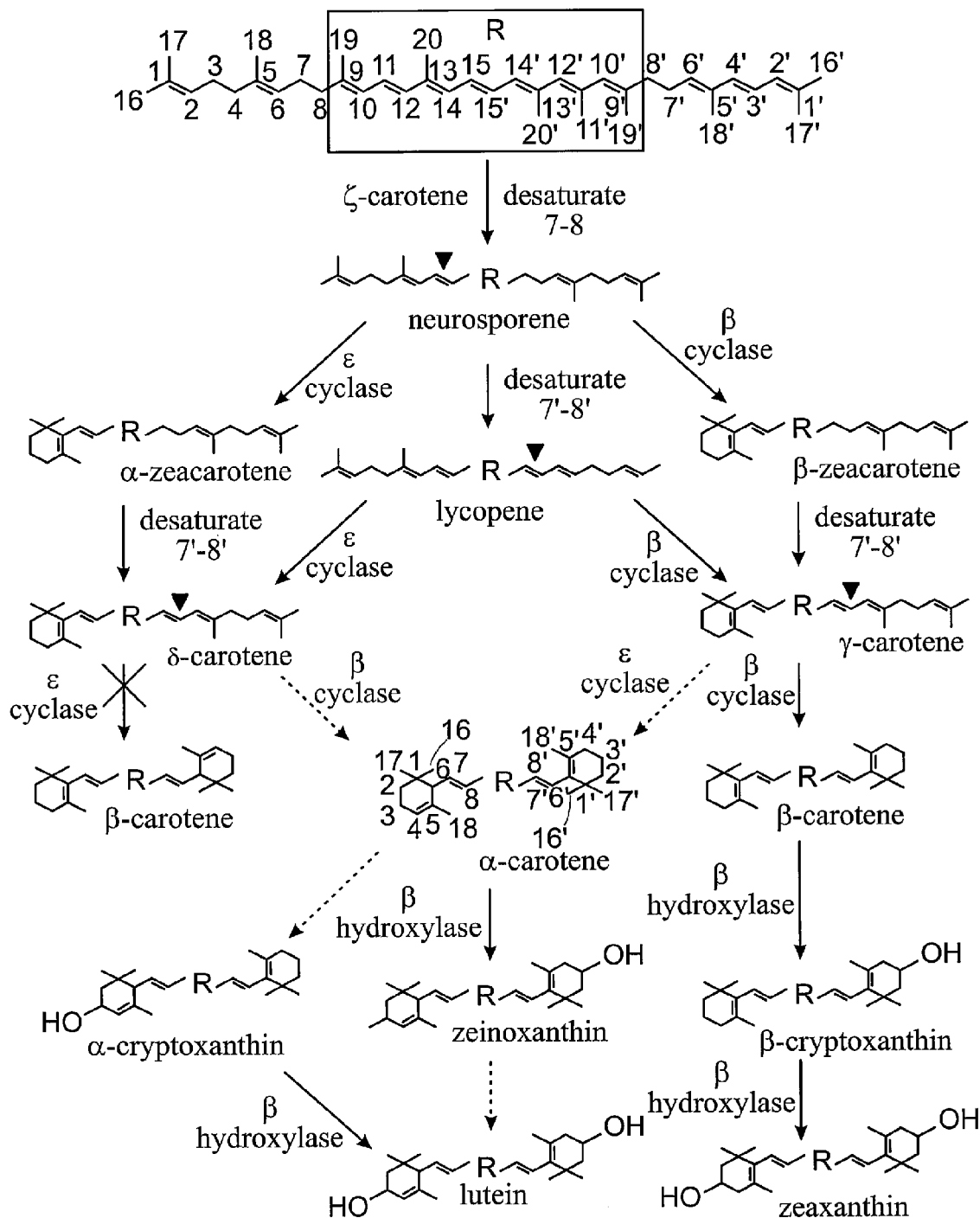
Figure 8A:
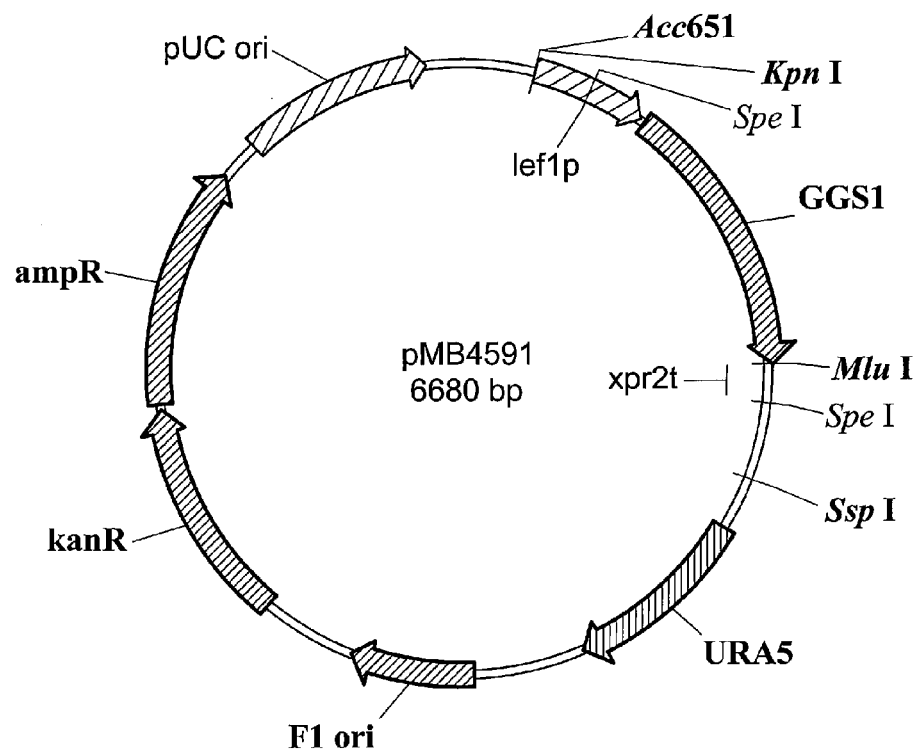
FIGS. 8A-8D depict schematic representations of plasmids generated and described in detail in the exemplification.
Figure 8A:
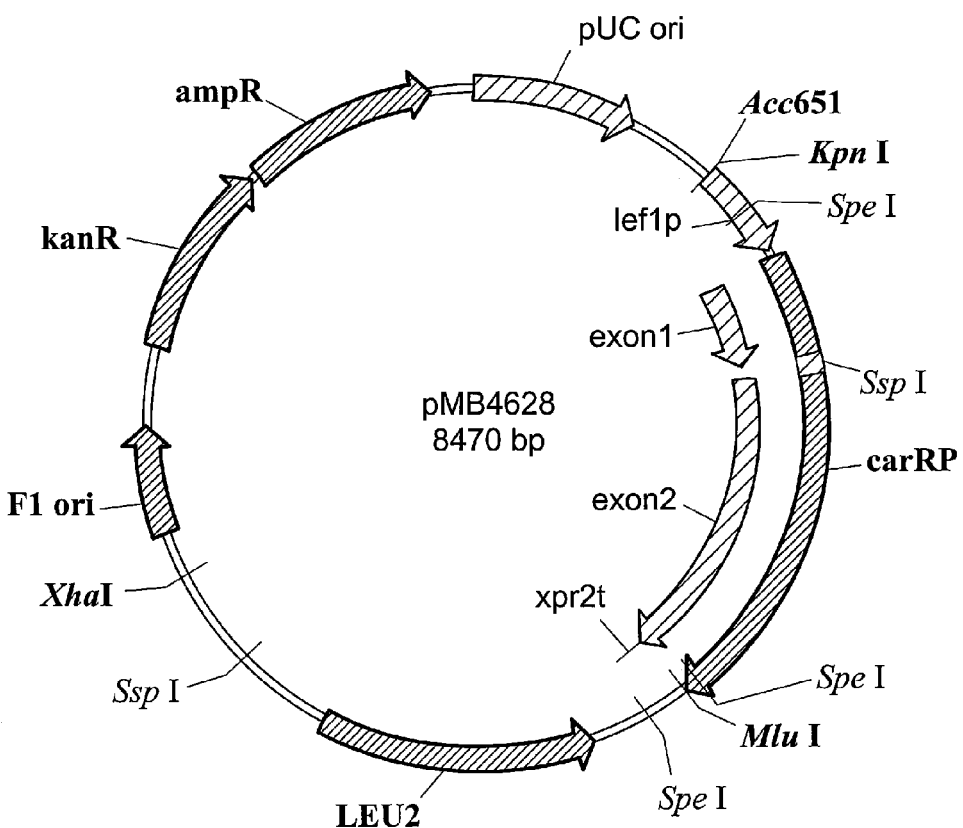
Figure 8B:
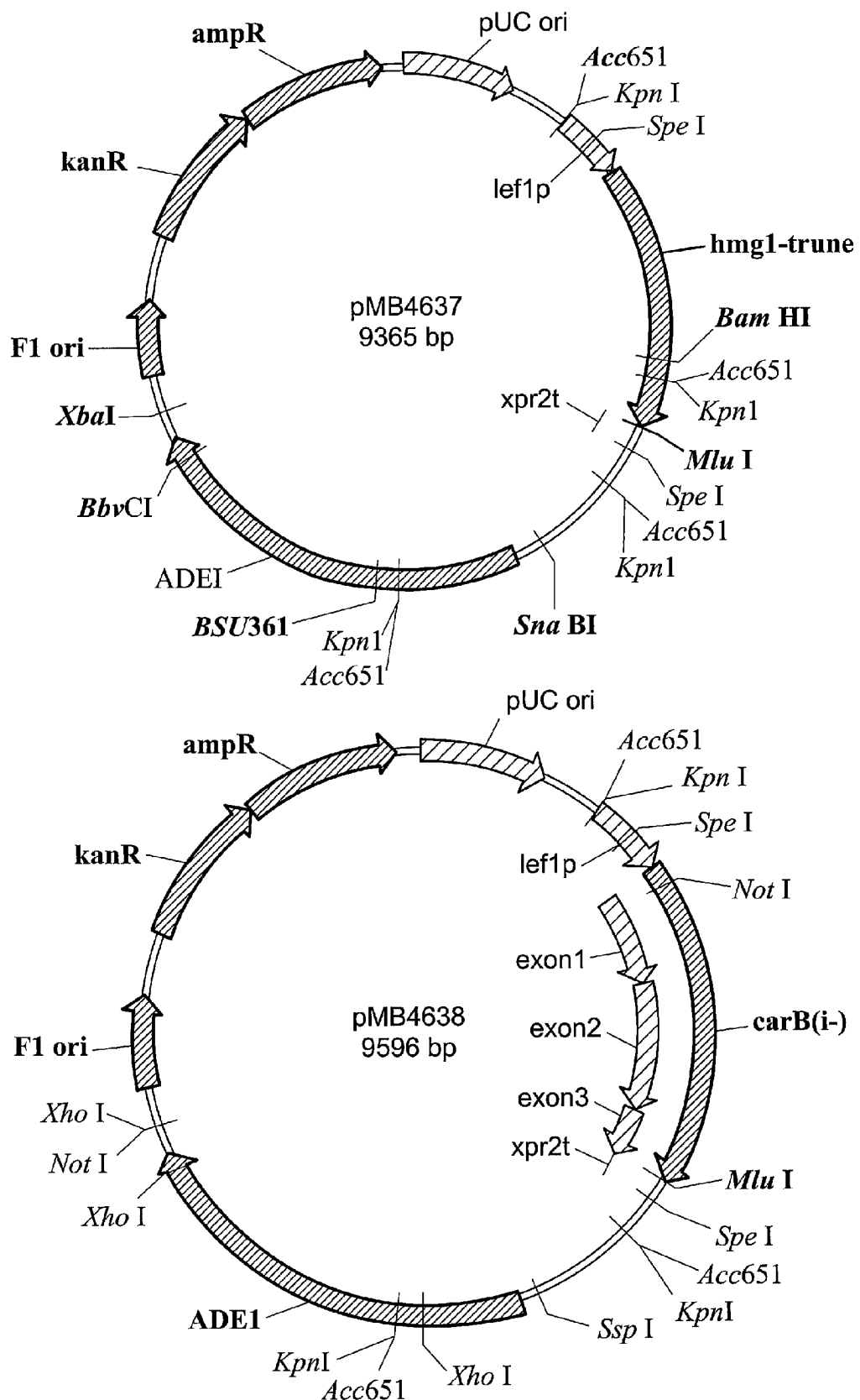
Figure 8C:
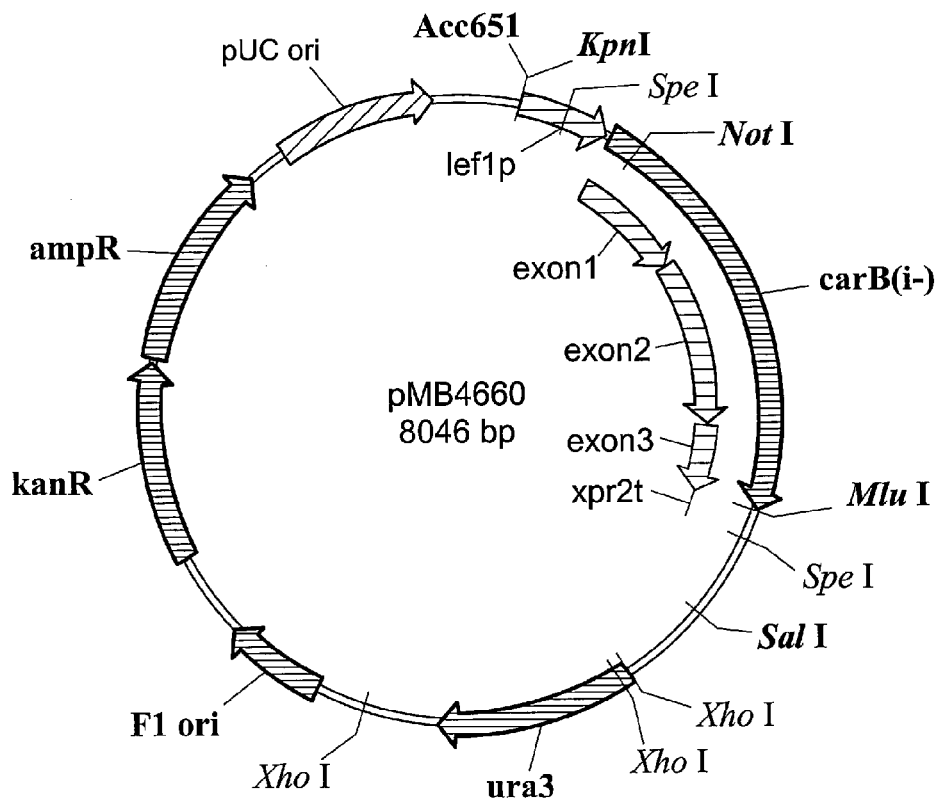
Figure 8C:
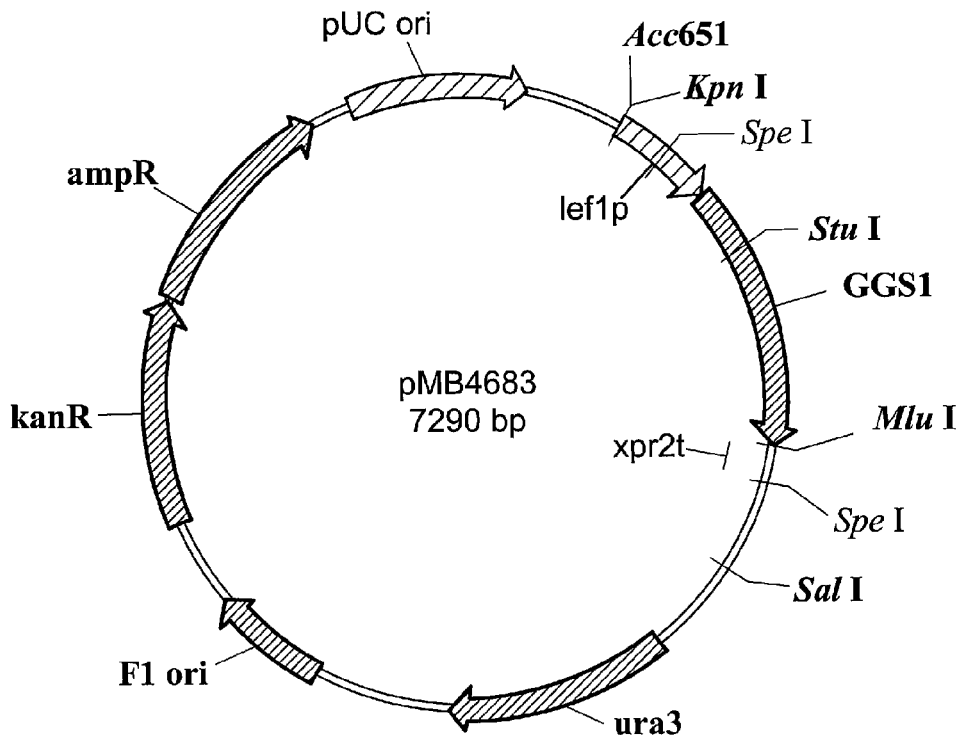
Figure 8D:
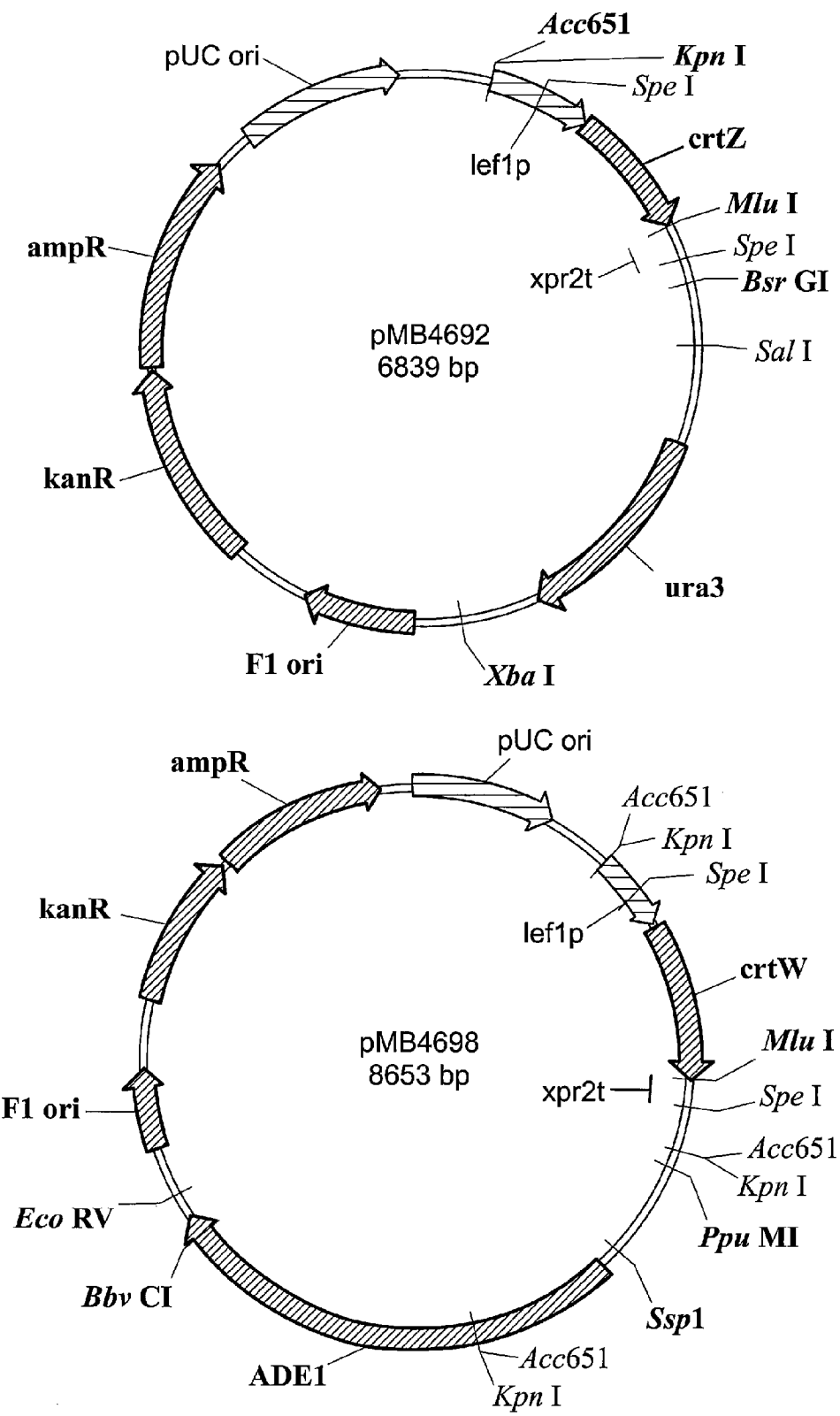

The carotenoid biosynthesis pathway branches off from the isoprenoid biosynthesis pathway at the point where GGPP is formed. The commitment step in carotenoid biosynthesis is the formation of phytoene by the head-to-head condensation of two molecules of GGPP, catalyzed by phytoene synthase (often called crtB; see FIG. 6). A series of dehydrogenation reactions, each of which increases the number of conjugated double bonds by two, converts phytoene into lycopene via neurosporene. The pathway branches at various points, both before and after lycopene production, so that a wide range of carotenoids can be generated. For example, action of a cyclase enzyme on lycopene generates γ-carotene; action of a desaturase instead produces 3,4-didehydrolycopene. γ-carotene is converted to β-carotene through the action of a cyclase. β-carotene can be processed into any of a number of products (see, for example, FIG. 6C), including astaxanthin (via echinone, hydroxyechinone, and phoenicoxanthin).

According to the present invention, carotenoid production in a host organism may be adjusted by modifying the expression or activity of one or more proteins involved in carotenoid biosynthesis. As indicated, in some embodiments, it will be desirable to utilize as host cells organisms that naturally produce one or more carotenoids. In some such cases, the focus will be on increasing production of a naturally-produced carotenoid, for example by increasing the level and/or activity of one or more proteins involved in the synthesis of that carotenoid and/or by decreasing the level or activity of one or more proteins involved in a competing biosynthetic pathway. Alternatively or additionally, in some embodiments it will be desirable to generate production of one or more carotenoids not naturally produced by the host cell.

According to some embodiments of the invention, it will be desirable to introduce one or more heterologous carotenogenic polypeptides into a host cell. As will be apparent to those of ordinary skill in the art, any of a variety of heterologous polypeptides may be employed; selection will consider, for instance, the particular carotenoid whose production is to be enhanced. The present invention contemplates not only introduction of heterologous carotenogenic polypeptides, but also adjustment of expression or activity levels of heterologous or endogenous carotenogenic polypeptides, including, for example, alteration of constitutive or inducible expression patterns. In some embodiments of the invention, expression patterns are adjusted such that growth in nutrient-limiting conditions is not required to induce oleaginy. For example, genetic modifications comprising alteration and/or addition of regulatory sequences (e.g., promoter elements, terminator elements) may be utilized to confer particular regulation of expression patterns. Such genetic modifications may be utilized in conjunction with endogenous genes (e.g., for regulation of endogenous carotenogenic); alternatively, such genetic modifications may be included so as to confer regulation of expression of at least one heterologous polypeptide (e.g., carotenogenic polypeptide(s)). For example, promoters including, but not limited to Tef1, Gpd1 promoters can be used in conjunction with endogenous genes and/or heterologous genes for modification of expression patterns of endogenous carotenogenic polypeptide(s) and/or heterolous carotenogenic polypeptide(s). Similarly, exemplary terminator sequences include, but are not limited to, use of *Y. lipolytica* XPR2 terminator sequences.

As indicated in FIG. 6 and in the literature, proteins involved in carotenoid biosynthesis include, but are not limited to, phytoene synthase, phytoene dehydrogenase, lycopene cyclase, carotenoid ketolase, carotenoid hydroxylase, astaxanthin synthase (a single multifunctional enzyme found in some source organisms that typically has both ketolase and hydroxylase activities), carotenoid epsilon hydroxylase, lycopene cyclase (beta and epsilon subunits), carotenoid glucosyltransferase, and acyl CoA:diacyglycerol acyltransferase. Representative example sequences for these carotenoid biosynthesis polypeptides are provided in Tables 17-25.

Xanthophylls can be distinguished from other carotenoids by the presence of oxygen containing functional groups on their cyclic end groups. For instance, lutein and zeaxanthin contain a single hydroxyl group on each of their terminal ring structures, while astaxanthin contains both a keto group and a hydroxyl on each terminal ring. This property makes xanthophylls more polar than carotenes such as beta-carotene and lycopene, and thus dramatically reduces their solubility in fats and lipids. Naturally occurring xanthophylls are often found as esters of the terminal hydroxyl groups, both mono- and diesters of fatty acids. They also occur as glucosides in certain species of bacteria. The solubility and dispersibility of xanthophylls can be greatly modified by the addition of ester moieties, and it is known that esterification can also affect the absorbability and/or bioavailability of a given carotenoid. It is an objective of this invention to maximize the amount of a particular xanthophyll accumulating within the intracellular triacylglyceride fraction of oleaginous yeasts, and one mechanism for achieving this goal is to increase the hydrophobic nature of the xanthophyll product that accumulates. One way of achieving this is to engineer the production of fatty-acyl mono- and/or diesters of the target xanthophyll compound.

A variety of enzymes can function to esterify carotenoids. For example, carotenoid glucosyltransferases have been identified in several bacterial species (see, e.g., Table 24). In addition, acyl CoA:diacyglycerol acyltransferase (DGAT) and acyl CoA:monoacylglycerol acyltransferases (MGAT), which function in the final steps of triacylglycerol biosynthesis, are likely to serve an additional role in the esterification of xanthophylls. Representative DGAT polypetides are shown in Table 25. Furthermore, other enzymes may specifically modify carotenoids and molecules of similar structure (e.g. sterols) and be available for modification and ester production.

In some embodiments of the invention, potential source organisms for carotenoid biosynthesis polypeptides include, but are not limited to, genera of naturally oleaginous or non-oleaginous fungi that naturally produce carotenoids. These include, but are not limited to, *Botrytis, Cercospora, Fusarium (Gibberella), Mucor, Neurospora, Phycomyces, Puccina, Rhodotorula, Sclerotium, Trichoderma,* and *Xanthophyllomyces*. Exemplary species include, but are not limited to, *Neurospora crassa, Xanthophyllomyces dendrorhous (Phaffia rhodozyma), Mucor circinelloildes,* and *Rhodotorula glutinis*. Of course, carotenoids are produced by a wide range of diverse organisms such as plants, algae, yeast, fungi, bacteria, cyanobacteria, etc. Any such organisms may be source organisms for carotenoid biosynthesis polypeptides according to the present invention.

It will be appreciated that the particular carotenogenic modification to be applied to a host cell in accordance with the present invention will be influenced by which carotenoid(s) is desired to be produced. For example, isoprenoid biosynthesis polypeptides are relevant to the production of most carotenoids. Carotenoid biosynthesis polypeptides are also broadly relevant. Ketolase is particularly relevant for production of canthaxanthin, as hydroxylase is for production of lutein and zeaxanthin, among others. Both hydroxylase and ketolase (or astaxanthin synthase) are particularly useful for production of astaxanthin.

Production and Isolation of Carotenoids

As discussed above, accumulation of lipid bodies in oleaginous organisms is generally induced by growing the relevant organism in the presence of excess carbon source and limiting nitrogen. Specific conditions for inducing such accumulation have previously been established for a number of different oleaginous organisms (see, for example, Wolf (ed.) *Nonconventionalyeasts in biotechnology* Vol. 1, Springer-Verlag, Berlin, Germany, pp. 313-338; *Lipids* 18(9):623, 1983; *Indian J. Exp. Biol.* 35(3):313, 1997; *J. Ind. Microbiol. Biotechnol.* 30(1):75, 2003; *Bioresour. Technol.* 95(3):287, 2004, each of which is incorporated herein by reference in its entirety).

In general, it will be desirable to cultivate inventive modified host cells under conditions that allow accumulation of at least about 20% of their dry cell weight as lipid. In other embodiments, the inventive modified host cells are grown under conditions that permit accumulation of at least about 15%, 16%, 17%, 18%, 19%, 20%, 21%, 22%, 23%, 24%, 25%, 30%, 35%, 40%, 45%, 50%, 55%, 60%, 65%, 70%, 75%, or even 80% or more of their dry cell weight as lipid. In certain embodiments, the host cells utilized are cells which are naturally oleaginous, and induced to produce lipid to the desired levels. In other embodiments, the host cells are cells which naturally produce lipid, but have been engineered to increase production of lipid such that desired levels of lipid production and accumulation are achieved.

In certain embodiments, the host cells of the invention are not naturally oleaginous, but have been engineered to produce lipid such that desired levels of lipid production are obtained. Those of ordinary skill in the art will appreciate that, in general, growth conditions that are effective for inducing lipid accumulation in a source organism, may well also be useful for inducing lipid accumulation in a host cell into which the source organism's oleaginic polypeptides have been introduced. Of course, modifications may be required in light of characteristics of the host cell, which modifications are within the skill of those of ordinary skill in the art.

It will also be appreciated by those of ordinary skill in the art that it will generally be desirable to ensure that production of the desired carotenoid by the inventive modified host cell occurs at an appropriate time in relation to the induction of oleaginy such that the carotenoid(s) accumulate(s) in the lipid bodies. In some embodiments, it will be desirable to induce production of the carotenoid(s) in a host cell which does not naturally produce the carotenoid(s), such that detectable levels of the carotenoid(s) is/are produced. In certain aspects the host cells which do not naturally produce a certain carotenoid(s) are capable of production of other carotenoid(s) (e.g. certain host cells may, for example, naturally produce β-carotene but may not naturally produce astaxanthin); in other aspects the host cells do not naturally produce any carotenoid(s). In other embodiments, it will be desirable to increase production levels of carotenoid(s) in a host cell which does naturally produce low levels of the carotenoid(s), such that increased detectable levels of the carotenoid(s) are produced. In certain aspects, the host cells which do naturally produce the carotenoid(s) (e.g., β-carotene) also produce additional carotenoid(s) (e.g., astaxanthin, etc.); in still other aspects, the cells which naturally produce the carotenoid(s) (e.g., β-carotene) do not produce additional carotenoid(s).

In certain embodiments of the invention, it will be desirable to accumulate carotenoids to levels (i.e., considering the total amount of all produced carotenoids together) that are greater than at least about 1% of the dry weight of the cells. In some embodiments, the total carotenoid accumulation in the lipid bodies will be to a level at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20% or more of the total dry weight of the cells. In certain embodiments of the invention, it will be desirable to achieve total levels of carotenoid accumulation in the lipid bodies (i.e., considering the total amount of all produced carotenoids together) that are greater than at least about 1% of the dry weight of the cells. In some embodiments, the total carotenoid accumulation in the lipid bodies will be to a level at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20% or more of the total dry weight of the cells.

Bacterial carotenogenic genes have already been demonstrated to be transferrable to other organisms, and are therefore particularly useful in accordance with the present invention (see, for example, Miura et al., *Appl. Environ. Microbiol.* 64:1226, 1998). In other embodiments, it may be desirable to utilize genes from other source organisms such as plant, alga, or microalgae; these organisms provide a variety of potential sources for ketolase and hydroxylase polypeptides. Still additional useful source organisms include fungal, yeast, insect, protozoal, and mammalian sources of polypeptides.

In certain embodiments, the *Mucor circinelloides* multifunctional phytoene synthase/lycopene cyclase and the *Neurospora crassa* phytoene dehydrogenase genes can be expressed in *Yarrowia lipolytica*. Subsequent overexpression of the catalytic domain from *N. crassa* hydroxymethylglutaryl-CoA reductase and/or treatment of the modified *Y. lipolytica* strains with the squalene synthase inhibitor zaragozic acid further increases carotenoid production. Finally, *Paracoccus marcusii* genes encoding carotenoid hydroxylase and carotenoid ketolase enzymes are expressed in *Y. lipolytica* β-carotene-producing strains, and this modification results in the accumulation of astaxanthin. Similar approaches to enhance carotenoid production could be employed in other oleaginous or non-oleaginous host organisms can be undertaken, using the same, homologous, or functionally similar carotogenic polypeptides.

It should be noted that, for inventive organisms that produce more than one carotenoid, it will sometimes be possible to adjust the relative amounts of individual carotenoids produced by adjusting growth conditions. For example, it has been reported that controlling the concentration of dissolved oxygen in a culture during cultivation can regulate relative production levels of certain carotenoids such as β-carotene, echinenone, β-cryptoxanthin, 3-hydroxyechinenone, asteroidenone, canthaxanthin, zeaxanthin, adonirubin, adonixanthin and astaxanthin (see, for example, U.S. Pat. No. 6,825,002 to Tsubokura et al., the entire contents of which are incorporated herein by reference).

Particularly for embodiments of the present invention directed toward production of astaxanthin, it will often be desirable to utilize one or more genes from a natural astaxanthin-producing organism. Where multiple heterologous polypeptides are to be expressed, it may be desirable to utilize the same source organism for all, or to utilize closely related source organisms.

One advantage provided by the present invention is that, in addition to allowing the production of high levels of carotenoids, the present invention allows those produced compounds to be readily isolated because they accumulate in the lipid bodies within oleaginous organisms. Methods and systems for isolating lipid bodies have been established for a wide variety of oleaginous organisms (see, for example, U.S. Pat. Nos. 5,164,308; 5,374,657; 5,422,247; 5,550,156; 5,583, 019; 6,166,231; 6,541,049; 6,727,373; 6,750,048; and 6,812, 001, each of which is incorporated herein by reference in its entirety). In brief, cells are typically recovered from culture, often by spray drying, filtering or centrifugation. In some instances, cells are homogenized and then subjected to supercritical liquid extraction or solvent extraction (e.g., with solvents such as chloroform, hexane, methylene chloride, methanol, isopropanol, ethyl acetate, etc.), yielding a crude oil suspension. This oil suspension may optionally be refined as known in the art. Refined oils may be used directly as feed or food additives. Alternatively or additionally, carotenoids can be isolated from the oil using conventional techniques.

Given the sensitivity of carotenoids generally to oxidation, many embodiments of the invention employ oxidative stabilizers (e.g., tocopherols, vitamin C; ethoxyquin; vitamin E, BHT, BHA, TBHQ, etc, or combinations thereof) during and/or after carotenoid isolation. Alternatively or additionally, microencapsulation, for example with proteins, may be employed to add a physical barrier to oxidation and/or to improve handling (see, for example, U.S. Patent Application 2004/0191365).

Uses

Carotenoids produced according to the present invention can be utilized in any of a variety of applications, for example exploiting their biological or nutritional properties (e.g., antioxidant, anti-proliferative, etc.) and/or their pigment properties. For example, according to the present invention, carotenoids may be used in pharmaceuticals (see, for example, Bertram, *Nutr. Rev.* 57.182, 1999; Singh et al., *Oncology* 12:1643, 1998; Rock, *Pharmacol. Ther.* 75:185, 1997; Edge et al, *J. Photochem Photobiol* 41:189, 1997; U.S. Patent Application 2004/0116514; U.S. Patent Application 2004/0259959), food supplements (see, for example, Koyama et al, *J. Photochem Photobiol* 9:265, 1991; Bauemfeind, *Carotenoids as colorants and vitamin A precursors*, Academic Press, NY, 1981; U.S. Patent Application 2004/0115309; U.S. Patent Application 2004/0234579), electro-optic applications, animal feed additives (see, for example, Krinski, *Pure Appl. Chem.* 66:1003,1994; Polazza et al., *Meth. Enzymol.* 213:403, 1992), cosmetics (as anti-oxidants and/or as cosmetics, including fragrances; see for example U.S. Patent Application 2004/0127554), etc. Carotenoids produced in accordance with the present invention may also be used as intermediates in the production of other compounds (e.g., steroids, etc.).

For example, astaxanthin and/or esters thereof may be useful in a variety of pharmaceutical applications and health foods including treatment of inflammatory diseases, asthma, atopic dermatitis, allergies, multiple myeloma, arteriosclerosis, cardiovascular disease, liver disease, cerebrovascular disease, thrombosis, neoangiogenesis-related diseases, including cancer, rheumatism, diabetic retinopathy; macular degeneration and brain disorder, hyperlipidemia, kidney ischemia, diabetes, hypertension, tumor proliferation and metastasis; and metabolic disorders. Additionally, carotenoids and astaxanthin may be useful in the prevention and treatment of fatigue, for improving kidney function in nephropathy from inflammatory diseases, as well as prevention and treatment of other life habit-related diseases. Still further, astaxanthin has been found to play a role as inhibitors of various biological processes, including interleukin inhibitors, phosphodiesterase inhibitors inhibitors, phospholipase A2 inhibitors, cyclooxygenase-2 inhibitors, matrix metalloproteinase inhibitors, capillary endothelium cell proliferation inhibitors, lipoxygenase inhibitors. See, e.g., Japanese Publication No. 2006022121, published Jan. 26, 2000(JP Appl No. 2005-301156 filed Oct. 17, 2005); Japanese Publication No. 2006016408, published Jan. 19, 2006(JP Appl No. 2005-301155 filed Oct. 17, 2005); Japanese Publication No. 2006016409, published Jan. 19, 2006(JP Appl No. 2005-301157 filed Oct. 17, 2005); Japanese Publication No. 2006016407, published Jan. 19, 2006(JP Appl No. 2005-301153 filed Oct. 17, 2005); Japanese Publication No. 2006008717, published Jan. 12, 2006(JP Appl No. 2005-301151 filed Oct. 17, 2005); Japanese Publication No. 2006008716, published Jan. 12, 2006(JP Appl No. 2005-301150 filed Oct. 17, 2005); Japanese Publication No. 2006008720, published Jan. 12, 2006(JP Appl No. 2005-301158 filed Oct. 17, 2005); Japanese Publication No. 2006008719, published Jan. 12, 2006(JP Appl No. 2005-301154 filed Oct. 17, 2005); Japanese Publication No. 2006008718, published Jan. 12, 2006(JP Appl No. 2005-301152 filed Oct. 17, 2005); Japanese Publication No. 2006008713, published Jan. 12, 2006(JP Appl No. 2005-301147 filed Oct. 17, 2005); Japanese Publication No. 2006008715, published Jan. 12, 2006(JP Appl No. 2005-301149 filed Oct. 17, 2005); Japanese Publication No. 2006008714, published Jan. 12, 2006(JP Appl No. 2005-301148 filed Oct. 17, 2005); and Japanese Publication No. 2006008712, published Jan. 12, 2006(JP Appl No. 2005-301146 filed Oct. 17, 2005).

It will be appreciated that, in some embodiments of the invention, carotenoids produced by manipulated host cells as described herein are incorporated into a final product (e.g., food or feed supplement, pharmaceutical, cosmetic, dye-containing item, etc.) in the context of the host cell. For example, host cells may be lyophilized, freeze dried, frozen or otherwise inactivated, and then whole cells may be incorporated into or used as the final product. The host cell may also be processed prior to incorporation in the product to increase bioavailability (e.g., via lysis). Alternatively or additionally, a final product may incorporate only a portion of the host cell (e.g., fractionated by size, solubility), separated from the whole. For example, in some embodiments of the invention, lipid droplets are isolated from the host cells and are incorporated into or used as the final product. In other embodiments, the carotenoids themselves, or individual carotenoid compounds are isolated and reformulated into the final product.

As stated above, fatty acid and glucoside esters are the predominant carotenoid esters found in nature, whereas additional esters (e.g. with organic acids or inorganic phosphate) can be synthesized to generate useful product forms. For delivery, carotenoid esters can also be formulated as salts of the ester form. See, e.g., US Publication No. 20050096477.

The amount of carotenoid incorporated into a given product may vary dramatically depending on the product, and the particular carotenoid(s) involved. Amounts may range, for example, from less than 0.01% by weight of the product, to more than 1%, 10%, 20%, 30% or more; in some cases the carotenoid may comprise 100% of the product.

In some embodiments of the invention, one or more produced carotenoids is incorporated into a component of food or feed (e.g., a food supplement). Types of food products into which carotenoids can be incorporated according to the present invention are not particularly limited, and include beverages such as teas, juices, and liquors; confections such as jellies and biscuits; fat-containing foods and beverages such as dairy products; processed food products such as rice and soft rice (or porridge); infant formulas; or the like. In some embodiments of this aspect of the invention, it may be useful to incorporate the carotenoids within bodies of edible lipids as it may facilitate incorporation into certain fat-containing food products.

Examples of feedstuffs into which carotenoids produced in accordance with the present invention may be incorporated include, for instance, pet foods such as cat foods, dog foods and the like, feeds for aquarium fish, cultured fish or crustaceans, etc., feed for farm-raised animals (including livestock and further including fish or crustaceans raised in aquaculture). Food or feed material into which the carotenoid(s) produced in accordance with the present invention is incorporated is preferably palatable to the organism which is the intended recipient. This food or feed material may have any physical properties currently known for a food material (e.g., solid, liquid, soft).

In some embodiments of the invention, one or more produced carotenoids is incorporated into a cosmetic product. Examples of such cosmetics include, for instance, skin cosmetics (e.g., lotions, emulsions, creams and the like), lipsticks, anti-sunburn cosmetics, makeup cosmetics, fragrances, products for daily use (e.g., toothpastes, mouthwashes, bad breath preventive agents, solid soaps, liquid soaps, shampoos, conditioners), etc.

In some embodiments, one or more produced carotenoids is incorporated into a pharmaceutical. Examples of such pharmaceuticals include, for instance, various types of tablets, capsules, drinkable agents, troches, gargles, etc. In some embodiments, the pharmaceutical is suitable for topical application. Dosage forms are not particularly limited, and include capsules, oils, granula, granula subtilae, pulveres, tabellae, pilulae, trochisci, or the like. Oils and oil-filled capsules may provide additional advantages both because of their lack of ingredient decomposition during manufacturing, and because inventive carotenoid-containing lipid droplets may be readily incorporated into oil-based formulations.

Pharmaceuticals according to the present invention may be prepared according to techniques established in the art including, for example, the common procedure as described in the United States Pharmacopoeia, for example.

Carotenoids produced according to the present invention may be incorporated into any pigment-containing product including, for example, fabric, paint, etc. They may also be incorporated into a product which is an environmental indicator, or an instrument such as a biosensor for use as a detection agent.

EXEMPLIFICATION

Table 26 below describes certain *Yarrowia lipolytica* strains used in the following exemplification:

TABLE 26

*Yarrowia lipolytica* strains.

| | | |
|---|---|---|
| NRRL Y-1095 | Wild type diploid | |
| ATCC76861 | MATB ura2-21 lyc1-5 LYS1-5B | |
| ATCC76982 | MATB ade1 leu2-35 lyc1-5 xpr2 | |
| ATCC201249 | MATA ura3-302 leu2-270 lys8-11 PEX17-HA | |
| MF346 | MATA ura2-21 | ATCC76861 × ATCC201249 |
| MF350 | MATB ura2-21 leu2-35 ade1 | ATCC76982 × MF346 |

(The genotypes at LYC1, LYS1, XPR2, and PEX17 were not determined in crosses nor verified for ATCC strains.)

All basic molecular biology and DNA manipulation procedures described herein are generally performed according to Sambrook et al. or Ausubel et al. (Sambrook J, Fritsch E F, Maniatis T (eds). 1989. *Molecular Cloning. A Laboratory Manual.* Cold Spring Harbor Laboratory Press: New York; Ausubel F M, Brent R, Kingston R E, Moore D D, Seidman J G, Smith J A, Struhl K (eds). 1998. *Current Protocols in Molecular Biology.* Wiley: New York).

Example 1

Production of Plasmids for Carotenoid Strain Construction

Plasmids were generated for construction of carotenoid producing strains. The following subparts describe production of plasmids encoding carotenogenic polypeptides. Plasmids used in these studies and details of their construction are described in Table 27. Additional plasmid construction details and descriptions of their use are found in the text of the relevant subsection. All PCR amplifications used NRRL Y-1095 genomic DNA as template unless otherwise specified. The URA5 gene described below is allelic with the ura2-21 auxotrophy above. The GPD1 and TEF1 promoters are from *Y. lipolytica* as is the XPR2 terminator.

GGS1 is the gene encoding the *Y. lipolytica* gene encoding geranylgeranylpyrophosphate synthase. The nucleic acid coding sequence, and encoded Ggs1 protein of pMB4591 and pMB4683 are as follows:

```
atggattataacagcgcggatttcaaggagatatggggcaaggccgccgacaccgcgctgctgggaccgtacaactac ctcgccaacaaccggggccacaacatcagagaacacttgatcgcagcgttcggagcggttatcaaggtggacaagagcgatctcgagaccattt cgcacatcaccaagattttgcataactcgtcgctgcttgttgatgacgtggaagacaactcgatgctccgacgaggcctgccggcagcccattgtc tgtttggagtcccccaaaccatcaactccgccaactacatgtactttgtggctctgcaggaggtgctcaagctcaagtcttatgatgccgtctccattt caccgaggaaatgatcaacttgcatagaggtcagggtatggatctctactggagagaaacactcacttgcccctcggaagacgagtatctggaga tggtggtgcacaagaccggtggactgtttcggctggctctgagacttatgctgtcggtggcatcgaaacaggaggaccatgaaaagatcaactttg atctcacacaccttaccgacacactgggagtcatttaccagattctggatgattacctcaacctgcagtccacggaattgaccgagaacaagggatt ctgcgaagatatcagcgaaggaaagttttcgtttccgctgattcacagcatacgccaccaacccggataaccacgagattctcaacattctcaaacag cgaacaagcgacgcttcactcaaaaagtacgccgtggactacatgagaacagaaaccaagagtttcgactactgcctcaagaggatacaggcca tgtcactcaaggcaagttcgtacattgatgatctagcagcagctggccacgatgtctccaagctacgagccattttgcattattttgtgtccacctctg actgtgaggagagaaagtactttgaggatgcgcagtga
(SEQ ID NO: 1)
``` mdynsadfkeiwgkaadtallgpynylannrghnirehliaafgavikvdksdletishitkilhnssllvddvedns

-continued

```
mlrrglpaahclfgvpqtinsanymyfvalqevlklksydavsifteeminlhrgqgmdlywretltcpsedeylemvvhktgglfrlalrlm lsvaskqedhekinfdlthltdtlgviyqilddylnlqsteltenkgfcedisegkfsfplihsirtnpdnheilnilkqrtsdaslkkyavdymrte tksfdyclkriqamslkassyiddlaaaghdvsklrailhyfvstsdceerkyfedaq
(SEQ ID NO: 2)
```

TABLE 27

Plasmids

| Plasmid | Backbone | Insert | Oligos or source |
|---|---|---|---|
| pMB4529 | PCR2.1 | 3.4 kb ADE1 PCR product | MO4475 & MO4476 |
| pMB4534 | PCR2.1 | 2.1 kb LEU2 PCR product | MO4477 & MO4478 |
| pMB4535 | PCR2.1 | 1.2 kb URA5 PCR product | MO4471 & MO4472 |
| pMB4589 | pMB4535 (KpnI + SpeI) | 1.2 kb GPD1 promoter (KpnI + NotI); 0.14 kb XPR2 terminator (NotI + SpeI) | MO4568 & MO4591; MO4566 & MO4593 |
| pMB4590 | pMB4535 (KpnI + SpeI) | 0.4 kb TEF1 promoter (KpnI + NotI); 0.14 kb XPR2 terminator (NotI + SpeI) | MO4571 & MO4592; MO4566 & MO4593 |
| pMB4591 | pMB4590 (NheI + MluI) | 1.0 kb GGS1 ORF (XbaI + MluI) | MO4534 & MO4544 |
| pMB4597 | pMB4534 (Acc65I + SpeI) | GPD1 promoter & XPR2 terminator (Acc65I + SpeI) | From pMB4589 |
| pMB4603 | pMB4597 (RsrII + MluI) | Residual backbone & TEF1 promoter (RsrII + MluI) | From pMB4590 |
| pMB4616 | pMB4529 (RsrII + SpeI) | Residual backbone & GPD1 promoter & XPR2 terminator (RsrII + SpeI) | From pMB4589 |
| pMB4629 | pMB4616 (RsrII + MluI) | Residual backbone & TEF1 promoter (RsrII + MluI) | From pMB4590 |
| pMB4631 | pMB4603 (KpnI + NheI) | 1.2 kb GPD1 promoter (KpnI + NheI); | MO4568 & MO4659 |
| pMB4628 | pMB4603 | Carp | See 1A |
| pMB4637 | pMB4629 (NheI + MluI) | 1.5 kb hmg1$^{trunc}$ ORF (XbaI + MluI) | See 1D |
| pMB4638 | pMB4629 | carB(i⁻) | See 1B |
| pMB4660 | pMB4638 (+URA3) | carB(i⁻) | See 1C |
| pMB4662 | pMB4631 (SpeI + XhoI) | 1.8 kb URA3 fragment (SpeI + BsaI) | MO4684 & MO4685 See 1C |
| pMB4683 | pMB4662 (Acc65I + MluI) | 1.4 kb tef1p-GGS1 fragment (Acc65I + MluI) | From pMB4591 |
| pMB4692 | pMB4662 (Acc65I + MluI) | 0.4 kb TEF1 promoter (Acc65I + NheI); 0.55 kb crtZ ORF (XbaI + MluI) | See 1E |
| pMB4698 | pMB4629 (NheI + MluI) | 0.9 kb crtW ORF (XbaI + MluI) | See 1F |
| pMB4599 | pBluescriptSKII- (EcoRV) | 1.9 kb carRP gene | MO4525 & MO4541 |
| pMB4606 | pBluescriptSKII- (EcoRV) | 1.9 kb carB gene | MO4530 & MO4542 |
| pMB4613 | pMB4599 (Acc65I + PpuMI) | carRP(i⁻) | See text |
| pMB4619 | pBluescriptSKII- (BamHI + Acc65I)) | carB(i⁻) | See text |

Certain oligonucleotides referred to in Table 27 above are as follows:

```
MO4471 5'-CTGGGTGACCTGGAAGCCTT
       (SEQ ID NO: 3)

MO4472 5'-AAGATCAATCCGTAGAAGTTCAG
       (SEQ ID NO: 4)

MO4475 5'-AAGCGATTACAATCTTCCTTTGG
       (SEQ ID NO: 5)

MO4476 5'-CCAGTCCATCAACTCAGTCTCA
       (SEQ ID NO: 6)

MO4477 5'-GCATTGCTTATTACGAAGACTAC
       (SEQ ID NO: 7)

MO4478 5'-CCACTGTCCTCCACTACAAACAC
       (SEQ ID NO: 8)

MO4534 5-CACAAACGCGTTCACTGCGCATCCTCAAAGT
       (SEQ ID NO: 9)

MO4544 5'-CACAATCTAGACACAAATGGATTATAACAGCGCGGAT
       (SEQ ID NO: 10)

MO4566 5'-CACAAACTAGTTTGCCACCTACAAGCCAGAT
       (SEQ ID NO: 11)

MO4568 5'-CACAAGGTACCAATGTGAAAGTGCGCGTGAT
       (SEQ ID NO: 12)

MO4571 5'-CACAAGGTACCAGAGACCGGGTTGGCGG
       (SEQ ID NO: 13)

MO4591 5'-CACAAGCGGCCGCGCTAGCATGGGGATCGATCTCTTATAT
       (SEQ ID NO: 14)
```

-continued

```
MO4592  5'-CACAAGCGGCCGCGCTAGCGAATGATTCTTATACTCAGAAG
        (SEQ ID NO: 15)

MO4593  5'-CACAAGCGGCCGCACGCGTGCAATTAACAGATAGTTTGCC
        (SEQ ID NO: 16)

MO4659  5'-CACAAGCTAGCTGGGGATGCGATCTCTTATATC
        (SEQ ID NO: 17)
```

1A: Production of pMB4628 (tef1p-carRP LEU2) encoding phytoene synthase/lycopene cyclase: Intron-containing carRP was amplified from *M. circinelloides* (ATCC 90680) genomic DNA using MO4525 and MO4541:

```
MO4525  5'-CACAAACGCGTTTAAATGGTATTTAGATTTCTCATT
        (SEQ ID NO: 18)

MO4541  5'-CACAATCTAGACACAAATGCTGCTCACCTACATGGA
        (SEQ ID NO: 19)
``` and the resulting 1.9 kb fragment was phosphorylated with T4 polynucleotide kinase. The resulting fragment was blunt-end ligated into pBluescriptSKII-cleaved with EcoRV, yielding pMB4599. The 1.9 kb XbaI-MluI fragment from pMB4599 was inserted into NheI- and MluI-cleaved pMB4603, yielding pMB4628. The intron containing nucleic acid coding sequence, and encoded CarRP protein of pMB4628 are as follows:

```
atgctgctcacctacatggaagtccacctctactacacgctgcctgtgct
gggcgtcctgtcctggctgtcgcggccgtactacacagccaccgatgcgc
tcaaattcaaatttctgacactggttgccttcacgaccgcctccgcctgg
gacaactacattgtctaccacaaggcgtggtcctactgcccacctgcgt
caccgctgtcattggctacgtgcccttggaggagtacatgttcttcatca
tcatgactctgttgaccgtggcattcaccaatctggtgatgcgctggcac
ctgcacagcttctttatcaggcctgaaacgcccgtcatgcagtccgtcct
ggtccgtcttgtccccataacagccttattaatcactgcatacaaggctt
gggtaagcaaacaaacaaatgatgtgccgcatcgcattttaatattaacc
attgcatacacagcattggcggtccgctggcggtgctcgtctccattgc
gctgccacgctgtttctctgctgggtcgatgtcgtcgctattggcgccg
gcacatgggacatttcgctggccacaagcaccggcaagttcgtcgtgccc
cacctgcccgtggaggaattcatgttctttgcgctaattaataccgttttt
ggtatttggtacgtgtgcgatcgatcgcacgatggcgatcctccacctgt
tcaaaaacaagagtcctctcagcgcccataccagcacagcaagtcgttc
ctccaccagatcctcgagatgacctgggccttctgtttacccgaccaagt
gctgcattcagacacattccacgacctgtccgtcagctgggacatcctgc
gcaaggcctccaagtcctttttacacggcctctgctgtctttccggcgac
gtgcgccaagagctcggtgtgctatacgcctttgcagagccacggacga
tctctgcgacaacgagcaggtccctgtgcagacgcgaaaggagcagctga
tactgacacatcagttcgtcagcgatctgtttggccaaaagacaagcgcg
ccgactgccattgactgggacttttacaacgaccaactgcctgcctcgtg
catctctgccttcaagtcgttcacccgtttgcgccatgtgctggaagctg
gagccatcaaggaactgctcgacgggtacaagtgggatttggagcgtcgc
tccatcagggatcaggaggatctcagatattactcagcttgtgtcgccag
cagtgttggtgaaatgtgcactcgcatcatactggcccacgccgacaagc
ccgcctcccgccagcaaacacagtggatcattcagcgtgcgcgtgaaatg
ggtctggtactccaatatacaaacattgcaagagacattgtcaccgacag
cgaggaactgggcagatgctacctgcctcaggattggcttaccgagaagg
aggtggcgctgattcaaggcggccttgcccgagaaattggcgaggagcga
ttgctctcactgtcgcatcgcctcatctaccaggcagacgagctcatggt
ggttgccaacaagggcatcgacaagctgcccagccattgtcaaggcggcg
tgcgtgcggcctgcaacgtctatgcttccattggcaccaagctcaagtct
tacaagcaccactatcccagcagagcacatgtcggcaattcgaaacgagt
ggaaattgctcttcttagcgtatacaaccttttacaccgcgccaattgcga
ctagtagtaccacacattgcagacagggaaaaatgagaaatctaaatacc
atttaa
(SEQ ID NO: 20)

mlltymevhlyytlpvlgvlswlsrpyytatdalkfkfltlvafttasaw
dnyivyhkawsycptcvtavigyvpleeymffiimtlltvaftnlvmrwh
lhsffirpetpvmqsvlvrlvpitallitaykawhlavpgkplfygscil
wyacpvlallwfgageymmrrplavlvsialptlflcwvdvvaigagtwd
```

-continued
```
islatstgkfvvphlpveefmffalintvlvfgtcaidrtmailhlfknk
spyqrpyqhsksflhqilemtwafclpdqvlhsdtflidlsvswdilrka
sksfytasavfpgdvrqelgvlyafcratddlcdneqvpvqtrkeqlilt
hqfvsdlfgqktsaptaidwdfyndqlpascisafksftrlrhvleagai
kelldgykwdlerrsirdqedlryysacvassvgemctriilahadkpas
rqqtqwiiqraremglvlqytniardivtdseelgrcylpqdwltekeva
liqgglareigeerllslshrliyqadelmvvankgidklpshcqggvra
acnvyasigtklksykhhypsrahvgnskrveiallsvynlytapiatss
tthcrqgkmrnlnti
(SEQ ID NO: 21)
```

Alternatively, pMB4599 was also used as a template for PCR amplification using MO4318, MO4643, MO4644, and MO4639 and

```
MO4318  5'-GTAAAACGACGGCCAGT
        (SEQ ID NO: 22)

MO4643  5'-CACACGGTCTCATGCCAAGCCTTGTATGCAGTGATTAA
        (SEQ ID NO: 23)

MO4639  5'-CCACTGTGTTTGCTGGCGG
        (SEQ ID NO: 24)

MO4644  5'-CACACGGTCTCTGGCATTTGGCGGTCCCTGGAAA
        (SEQ ID NO: 25)
``` producing fragments of 0.5 and 0.95 kb, that were subsequently cleaved with Acc65I and BsaI, and BsaI and PpuMI, respectively. These fragments were ligated to pMB4599 that had been digested with Acc65I and PpuMI, yielding pMB4613, harboring intronless carRP. The 1.85 kb XbaI-MluI fragment from pMB4613 can be inserted into NheI- and MluI-cleaved pMB4603 to yield pCarRPdelI.

1B: Production of pMB4638 (tef1p-carB ADE1), encoding phytoene dehydrogenase: Intron-containing carB was amplified from *M. circinelloides* (ATCC 90680) genomic DNA using MO4530 and MO4542:

```
MO4530  5'-CACAAACGCGTTTAAATGACATTAGAGTTATGAAC
        (SEQ ID NO: 26)

MO4542  5'-CACAATCTAGACACAAATGTCCAAGAAACACATTGTC
        (SEQ ID NO: 27)
``` and the resulting 1.9 kb fragment was phosphorylated with T4 polynucleotide kinase and blunt-end ligated into pBS-SKII-cleaved with EcoRV, yielding pMB4606. pMB4606 was then used as a template for PCR amplification using MO4318 and MO4648, and MO4646 and MO4647, and MO4343 and MO4645:

```
MO4318  5'-GTAAAACGACGGCCAGT
        (SEQ ID NO: 28)

MO4648  5'-CACAAGGTCTCAAGCACGCATCCCGGAACTG
        (SEQ ID NO: 29)

MO4646  5'-CACACGGTCTCAGGCATGTCGCCCTACGATGC
        (SEQ ID NO: 30)

MO4647  5'-CACACGGTCTCATGCTTGCACCCACAAAGAATAGG
        (SEQ ID NO: 31)

MO4343  5'-CAGGAAACAGCTATGAC
        (SEQ ID NO: 32)

MO4645  5'-CACACGGTCTCTTGCCCATATACATGGTCTGAAACG
        (SEQ ID NO: 33)
``` producing fragments of 0.4 and 0.85 and 0.7 kb, that were subsequently cleaved with Acc65I and BsaI, and BsaI, and BsaI and BamHI, respectively. These fragments were ligated to pBS-SKII- that had been cut with Acc65I and BamHI, yielding pMB4619, harboring intronless carB. The 1.75 kb XbaI-MluI fragment from pMB4619 was inserted into NheI- and MluI-cleaved pMB4629, yielding pMB4638. The resulting nucleic acid coding sequence and encoded CarB protein of pMB4638 are as follows:

```
atgtccaagaaacacattgtcattatcggtgctggcgtgggtggcacggc
tacagctgctcgtttggcccgcgaaggcttcaaggtcactgtggtggaga
aaaacgactttggtggcggccgctgctccttgatccatcaccagggccat
cgctttgatcagggcccgtcgctctacctgatgcccaagtactttgagga
cgcctttgccgatctggacgagcgcattcaagaccacctggagctgctgc
gatgcgacaacaactacaaggtgcactttgacgacggtgagtcgatccag
ctgtcgtctgacttgacacgcatgaaggctgaattggaccgcgtggaggg
ccccttggttttggccgattcctggatttcatgaaagagacacacatcc
actacgaaagcggcaccctgattgcgctcaagaagaatttcgaatccatc
tgggacctgattcgcatcaagtacgctccagagatctttcgcttgcacct
gtttggcaagatctacgaccgcgcttccaagtacttcaagaccaagaaga
tgcgcatggcattcacgtttcagaccatgtatatgggcatgtcgccctac
gatgcgcctgctgtctacagcctgttgcagtacaccgagttcgctgaagg
catctggtatcccgtggcggcttcaacatggtggttcagaagctagagg
cgattgcaaagcaaaagtacgatgccgagtttatctacaatgcgcctgtt
gccaagattaacaccgatgatgccaccaaacaagtgacaggtgtaaccct
ggaaaatggccacatcatcgatgccgatgcggttgtgtgtaacgcagatc
tggtctatgcttatcacaatctgttgcctccctgccgatggacgcaaaac
acactggcttccaagaaattgacgtcttcttccatttccttctactggtc
catgtccaccaaggtgcctcaattggacgtgcacaacatcttttggccg
aggcttatcaggagagctttgacgaaatcttcaaggactttggcctgcct
gaagagcaagacgggcgatgcttccaccgagaactacccggccatggtgg
acaaggcacgcaagatggtgctggctgtgattgagcgtcgtctgggcatg
tcgaatttcgccgacttgattgagcatgagcaagtcaatgatcccgctgt
atggcagagcaagttcaatctgtggagaggctcaattctgggtttgtctc
atgatgtgcttcaggtgctgtggttccgtcccagcacaaaggattctacc
ggtcgttatgataacctattctttgtgggtgcaagcacgcatcccggaac
tggtgttcccattgtccttgcaggaagcaagctcacctctgaccaagttg
tcaagagctttggaaagacgcccaagccaagaaagatcgagatggagaac
acgcaagcaccttggaggagcctgatgctgaatcgacattccctgtgtg
gttctggttgcgcgctgccttttgggtcatttaa
(SEQ ID NO: 34)
``` mskkhiviigagvggtataarlaregfkvtvvekndfgggrcslihhqgh
rfdqgpslylmpkyfedafadlderiqdhlellrcdnnykvhfddgesiq
lssdltrmkaeldrvegplgfgrfldfmkethihyesgtlialkknfesi
wdlirikyapeifrlhlfgkiydraskyfktkkmrmaftfqtmymgmspy
dapavysllqytefaegiwyprggfnmvvqkleaiakqkydaefiynapv
akintddatkqvtgvtlenghiidadavvcnadlvyayhnllppcrwtqn
tlaskkltsssisfywsmstkvpqldvhniflaeayqesfdeiflcdfgl
pseasfyvnvpsridpsaapdgkdsvivlvpighmksktgdastenypam
vdkarkmvlavierrlgmsnfadlieheqvndpavwqskfnlwrgsilgl
shdvlqvlwfrpstkdstgrydnlffvgasthpgtgvpivlagskltsdq
vvksfgktpkprkiementqapleepdaestfpvwfwlraafwvmfmffy
ffpqsngqtpasfinnllpevfrvhnsnvi
(SEQ ID NO: 35)

1C. Production of pMB4660 (tef1p-carB URA3) encoding encoding, phytoene dehydrogenase: The 4.3 kb XhoI-NotI fragment and the 1.8 kb NotI-SpeI fragment from pMB4638 were ligated to the 1.9 kb BsaI- and SpeI-cleaved URA3 gene generated by PCR amplification of *Y. lipolytica* genomic DNA using MO4684 and MO4685 to create pMB4660:

```
MO4684   5'-CATTCACTAGTGGTGTGTTCTGTGGAGCATTC
         (SEQ ID NO: 36)

MO4685   5'-CACACGGTCTCATCGAGGTGTAGTGGTAGTGCAGTG
         (SEQ ID NO: 37)
```

The resulting nucleic acid coding sequence and encoded CarB(i) protein of pMB4660 are as follows:

```
atgtccaagaaacacattgtcattatcggtgctggcgtgggtggcacggc
tacagctgctcgtttggcccgcgaaggcttcaaggtcactgtggtggaga
aaaacgactttggtggcggccgctgctccttgatccatcaccagggccat
cgctttgatcagggcccgtcgctctacctgatgcccaagtactttgagga
cgcctttgccgatctggacgagcgcattcaagaccacctggagctgctgc
gatgcgacaacaactacaaggtgcactttgacgacggtgagtcgatccag
ctgtcgtctgacttgacacgcatgaaggctgaattggaccgcgtggaggg
ccccttggttttggccgattcctggatttcatgaaagagacacacatcc
actacgaaagcggcaccctgattgcgctcaagaagaatttcgaatccatc
tgggacctgattcgcatcaagtacgctccagagatctttcgcttgcacct
gtttggcaagatctacgaccgcgcttccaagtacttcaagaccaagaaga
tgcgcatggcattcacgtttcagaccatgtatatgggcatgtcgccctac
gatgcgcctgctgtctacagcctgttgcagtacaccgagttcgctgaagg
catctggtatcccgtggcggcttcaacatggtggttcagaagctagagg
cgattgcaaagcaaaagtacgatgccgagtttatctacaatgcgcctgtt
gccaagattaacaccgatgatgccaccaaacaagtgacaggtgtaaccct
ggaaaatggccacatcatcgatgccgatgcggttgtgtgtaacgcagatc
tggtctatgcttatcacaatctgttgcctccctgccgatggacgcaaaac
acactggcttccaagaaattgacgtcttcttccatttccttctactggtc
catgtccaccaaggtgcctcaattggacgtgcacaacatcttttggccg
aggcttatcaggagagctttgacgaaatcttcaaggactttggcctgcct
gaagagcaagacgggcgatgcttccaccgagaactacccggccatggtgg
acaaggcacgcaagatggtgctggctgtgattgagcgtcgtctgggcatg
tcgaatttcgccgacttgattgagcatgagcaagtcaatgatcccgctgt
atggcagagcaagttcaatctgtggagaggctcaattctgggtttgtctc
atgatgtgcttcaggtgctgtggttccgtcccagcacaaaggattctacc
ggtcgttatgataacctattctttgtgggtgcaagcacgcatcccggaac
tggtgttcccattgtccttgcaggaagcaagctcacctctgaccaagttg
tcaagagctttggaaagacgcccaagccaagaaagatcgagatggagaac
acgcaagcaccttggaggagcctgatgctgaatcgacattccctgtgtg
gttctggttgcgcgctgccttttgggtcatttaa
(SEQ ID NO: 38)
``` mskkhiviigagvggtataarlaregfkvtvvekndfgggrcslihhqgh
rfdqgpslylmpkyfedafadlderiqdhlellrcdnnykvhfddgesiq
lssdltrmkaeldrvegplgfgrfldfmkethihyesgtlialkknfesi
wdlirikyapeifrlhlfgkiydraskyfktkkmrmaftfqtmymgmspy
dapavysllqytefaegiwyprggfnmvvqkleaiakqkydaefiynapv
akintddatkqvtgvtIenghiidadavvcnadlvyayhnllppcrwtqn
tlaskkltsssisfywsmstkvpqldvhniflaeayqesfdeiflcdfgl
pseasfyvnvpsridpsaapdgkdsvivlvpighmksktgdastenypam
vdkarkmvlavierrlgmsnfadlieheqvndpavwqskfnlwrgsilgl
shdvlqvlwfrpstkdstgrydnlffvgasthpgtgvpivlagskltsdq
vvksfgktpkprkiementqapleepdaestfpvwfwlraafwvmfmffy
ffpqsngqtpasfinnllpevfrvhnsnvi
(SEQ ID NO: 39)

1D. Production of pMB4637 and pTef-HMG encoding a truncated HMG1. For production of a truncated variant of the HMG-CoA reductase gene, which also encodes a 77 amino acid leader sequence derived from *S. cerevisiae*, the following oligonucleotides are synthesized:

```
PRIMER O   5'-TTCTAGACACAAAAATGGCTGCAGACCAATTGGTGA
           (SEQ ID NO: 40)

PRIMER P   5'-CATTAATTCTTCTAAAGGACGTATTTTCTTATC
           (SEQ ID NO: 41)

PRIMER Q   5'-GTTCTCTGGACGACCTAGAGG
           (SEQ ID NO: 42)

MO4658     5'-CACACACGCGTACACCTATGACCGTATGCAAAT
           (SEQ ID NO: 43)
```

Primers O and P are used to amplify a 0.23 kb fragment encoding Met-Ala followed by residues 530 to 604 of the Hmg1 protein of *S. cerevisiae*, using genomic DNA as template. Primers Q and MO4658 are used to amplify a 1.4 kb fragment encoding the C-terminal 448 residues of the Hmg1 protein of *Y. lipolytica*, using genomic DNA as template. These fragments are ligated to the appropriate cloning vector, and the resultant plasmids, designated pOP and pQMO4658, are verified by sequencing. The OP fragment is liberated with XbaI and AseI, and the QMO4658 fragment is liberated with MaeI and MluI. These fragments are then ligated to the ADE1 TEF1p expression vector pMB4629 cut with XbaI and MluI to produce pTefHMG.

Alternatively, the native HMG1 gene from *Y. lipolytica* may be modified without *S. cerevisiae* sequences as described in the table above using primers MO4658 (described above) and MO4657, to create pMB4637:

MO4657 5'-CACACTCTAGACACAAAAATGACCCAGTCTGTGAAGGTGG
(SEQ ID NO: 44)

The resulting nucleic acid coding sequence and encoded Hmg1$^{trunc}$ protein of pMB4637 are as follows:

```
atgacccagtctgtgaaggtggttgagaagcacgttcctatcgtcattga
gaagcccagcgagaaggaggaggacacctcttctgaagactccattggc
tgactgtcggaaagcagcccaagcccgtgaccgagacccgttctctggac
gacctagaggctatcatgaaggcaggtaagaccaagcttctggaggacca
cgaggttgtcaagctctctctcgagggcaagcttcctttgtatgctcttg
agaagcagcttggtgacaacaccgagctgttggcatccgacgatctatc
atctcccagcagtctaataccaagactttagagacctcaaagcttcctta
cctgcactacgactacgaccgtgtttttggagcctgttgcgagaacgtta
ttggttacatgcctctcccgttggtgttgctggcccatgaacattgat
ggcaagaactaccacattcctatggccaccactgagggttgtcttgttgc
ctcaaccatgcgaggttgcaaggccatcaacgccggtggcggtgttacca
ctgtgcttactcaggacggtatgacacgaggtccttgtgtttccttcccc
tctctcaagcgggctggagccgctaagatctggcttgattccgaggaggg
tctcaagtccatgcgaaaggccttcaactccacctctcgatttgctcgtc
tccagtctcttcactctaccctgctggtaacctgctgtttattcgattc
cgaaccaccactggtgatgccatgggcatgaacatgatctccaagggcgt
cgaacactctctggccgtcatggtcaaggagtacggcttccctgatatgg
acattgtgtctgtctcgggtaactactgcactgacaagaagcccgcagcg
atcaactggatcgaaggccgaggcaagagtgttgttgccgaagccaccat
ccctgctcacattgtcaagtctgttctcaaaagtgaggttgacgctcttg
ttgagctcaacatcagcaagaatctgatcggtagtgccatggctggctct
gtgggagggtttcaatgcacacgccgcaaacctggtgaccgccatctacct
tgccactggccaggatcctgctcagaatgtcgagtcttccaactgcatca
cgctgatgagcaacgtcgacggtaacctgctcatctccgtttccatgcct
tctatcgaggtcggtaccattggtggaggtactatttttggagccccaggg
ggctatgctggagatgcttggcgtgcgaggtcctcacatcgagaccccg
gtgccaacgcccaacagcttgctcgcatcattgcttctggagttcttgca
gcggagctttcgctgtgttctgctcttgctgccggccatcttgtgcaaag
tcatatgaccacaaccggtcccaggctcctactccggccaagcagtctc
aggccgatctgcagcgtctacaaaacggttcgaatatttgcatacggtca
tag
(SEQ ID NO: 45)
```

```
mtqsvkvvekhvpiviekpsekeedtssedsieltvgkqpkpvietrsld
dleaimkagktklledhevvklslegklplyalekqlgdntravgirrsi
isqqsntktletsklpylhydydrvfgaccenvigympvgvagpmnid
gknyhipmattegclvastmrgckainagggvttvltqdgmtrgpcvsfp
slkragaakiwldseeglksmrkafnstsrfarlqslhstlagnllfirf
rtttgdamgmnmiskgvehslavmvkeygfpdmdivsvsgnyctdkkpaa
inwiegrgksvvaeatipahivksvlksevdalvelnisknligsamags
vggfnahaanlvtaiylatgqdpaqnvessncitlmsnvdgnllisvsmp
sievgtigggtilepqgamlemlgvrgphietpganaqqlariiasgvla
aelslcsalaaghlvqshmthnrsqaptpakqsqadlqrlqngsnicirs
(SEQ ID NO: 46)
```

1E. Production of pMB4692 (URA3 tef1p-crtZ), encoding carotene hydroxylase. The following carotene hydroxylase (CrtZ) ORF sequence was synthesized; based on protein sequence of *Novosphingobium aromaticivorans*, using *Y. lipolytica* codon bias:

```
5'-ttctagacacaaaaatgggtggagccatgcagaccctcgctgctatc
ctgatcgtcctcggtacagtgctgctatgagtttgtcgcttgtcttct
cataagtatatcatgcatggcttcggatgggatggcatagagaccatca
cgagcccatgagggatttcttgaagaatgacttatacgccatcgttg
gcgctgccctctcgatactcatgtttgccctcggctctcccatgatcatg
ggcgctgacgcctggtggcccggaacctggatcggactcggtgtcctctt
ctatggtgtcatctatacctcgtgcacgacggtctggtgcaccaacgat
ggtttagatgggtgcctaaacgaggttacgccaaacgactcgtgcaggcc
cataagctgcaccacgccaccattggcaaggaaggaggcgtctcattcgg
tttcgtgttcgcccgagatcccgccgttctgaagcaggagcttcgagctc
aacgagaagcaggtatcgccgtgctgcgagaggctgtggacggctagacg
cgt
(SEQ ID NO: 47)
```

This sequence was cleaved using XbaI and MluI and ligated, along with an Acc65I-NheI TEF1 promoter fragment from pMB4629, to pMB4662 cut with Acc65I and MluI to produce pMB4692. The nucleic acid coding sequence is depicted in bold underline above. The resulting encoded crtZ protein of pMB4692 is as follows:

```
mggamqtlaailivlgtvlamefvawsshkyimhgfgwgwhrdhhepheg
flekndlyaivgaalsilmfalgspmimgadawwpgtwiglgvlfygviy
tlvhdglvhqrwfrwvpkrgyakrlvqahklhhatigkeggvsfgfvfar
dpavlkqelraqreagiavlreavdg
(SEQ ID NO: 82)
```

1F. Production of pMB4698 (ADE1 tef1p-crtW), encoding carotene ketolase. The following carotene ketolase (CrtW) ORF sequence was synthesized, based on protein sequence of an environmental sequence isolated from the Sargasso Sea (Genbank accession AACY01034193.1):

```
5'-ttctagacacaaaaatgactcgatctatttcctggccttccacctac
tggcacctccagccctcctgttcttcttgggtcgcaaacgaattctctcc
tcaagcccgaaaaggtctcgtcctcgctggtctcattggttccgcttggc
tgcttactctcggacttggcttttccttccctccatcaaacgagctgg
cttctcatcggttgtcgttctccttagatctttcctgcacaccggact
tttatcgttgcccatgacgctatgcacgcttctcttgttcctgaccacc
ctggccttaaccgttggattggacgtgtctgtcttctcatgatatgctgg
actctcctacaaaagatgctgccgaaatcaccgtcgacaccaccaagccc
ctgaaacagttgaagaccctgactaccaacgatgcactaacaacaatatc
ctcgactggtacgttcactttatgggaaattacctcggatggcaacaatt
gcttaatctctcttgcgtttggctcgctctcaccttccgtgtttctgact
actctgctcaattcttccacctgctccttttctctgtccttcctctcatc
gtctcctcctgtcaactcttcctcgtgggaacctggctgccacaccgacg
aggcgctactactcgaccggcgttaccactcgatcctgaacttccaccc
tgctctttccttcgctgctgctaccacttcggttaccaccgtgaacacc
atgaatctccctctactccttggttccaacttcctaaactccgagaaggt
tctctcatctaaacgcgt
(SEQ ID NO: 48)
```

This sequence was cleaved using XbaI and MluI and ligated to pMB4629 cut with NheI and MluI to produce pMB4698. The nucleic acid coding sequence is depicted in bold underline above. The resulting encoded crtW protein of pMB4698 is as follows:

```
mtrsiswpstywhlqpscsswvanefspqarkglvlagligsawlltlgl
gfslplhqtswlligclvllrsflhtglfivahdamhaslvpdhpqlnrw
igrvcllmyaglsykrccrnhrrhhqapetvedpdyqrctnnnildwyvh
fmgnylgwqqllnlscvwlaltfrvsdysaqffhllllfsvlplivsscql
flvgtwlphrrgattrpgvttrslnfbpalsfaacyhfgyhrehhespst
pwfqlpklregsli
(SEQ ID NO: 83)
```

Example 2

Engineering *Yarrowia lipolyvtica* for Increased Carotenoid Production

2A. Production of *Y. lipolytica* expressing geranylgeranylpyrophosphate synthase and phytoene dehydrogenase: MF350 (MATB ura2-21 leu2-35 ade1) was transformed with pMB4591 (tef1p-GGS1) that had been cleaved upstream of URA5 with SspI; a Ura⁺ transformant carrying the plasmid at the ura2 locus was identified and named MF364. It was subsequently transformed with pMB4638 (tef1p-carB) that had been cleaved at ADE1 with SspI and a prototrophic transformant was chosen that harbored the plasmid at the ade1 locus. This strain was named MF502.

2B. Production of *Y. lipolytica* expressing geranylgeranylpyrophosphate synthase, phytoene dehydrogenase and phytoene synthase/lycopene cyclase MF502 was transformed with pMB4628 (tef1p-carRP) that had been treated with SspI. Nine prototrophic colonies were chosen that were uncolored, orange, or very orange on the transformation plate (YNB agar with 1% glucose and 0.1% glutamate [YNBglut]) after two to three days of growth. Two, MF597 and MF600 (the very orange ones), produced greater than 4 mg carotene per g dry cell weight (DCW) after four days of growth in YPD at 30° C. Southern analysis reveals a different single KpnI-HindIII band in genomic DNA from MF597 and MF600, neither of which suggested that homologous integration occurred at leu2-270.

2C. Production of *Y. lipolytica* expressing phytoene synthase/lycopene cyclase and phytoene dehydrogenase: ATCC201249 (MATA ura3-302 leu2-270 lys8-11) was transformed with SspI-cleaved pMB4628. Hundreds of Leu⁺ colonies were pooled, re-grown, and transformed with pMB4660 (tef1p-carB) that had been cleaved upstream of URA3 with SalI. One colony that was noticeably yellow after 5 days at 30° C. on YNBglut plus 0.6 mM lysine was selected, named MF447, and found to produce 0.2 mg carotene per gram dry cell weight after 4 days of growth in YPD.

MF447 was challenged with 1 g/L 5-fluoroorotic acid and Ura⁻ segregants selected. Surprisingly, they were all found to retain the identical yellow appearance of their parent, implying that the loss of a functional URA3 gene did not coincide with the loss of a functional CarB enzyme. Southern analysis demonstrates that two fragments from a KpnI-HindIII digest of MF447 DNA contain URA3p-hybridizing sequences, only one of which also hybridizes to carB. The other is absent in MF578, the Ura3⁻ segregant chosen for further manipulation. Plasmid rescue and analysis of the DNA sequence encompassing the carRP intron in strains MF447, MF597 (example 2c), and MF600 (example 2c) revealed that exons 1 and 2 were contiguous and were each separated by an intron sequence that lacked the original internal SspI site (present in pMB4628).

2D. Production of *Y. lipolytica* expressing phytoene synthase/lycopene cyclase, phytoene dehydrogenase and geranylgeranylpyrophosphate synthase: MF578 was transformed with pMB4683 (tef1p-GGS1) that had been cleaved with SalI (upstream of URA3) or with StuI (within the GGS1 ORF). Ura⁺ Leu⁺ colonies in both cases appeared bright orange on YNBglut+Lys and on YPD, and several produced greater than 4 mg carotene per gram of dry cell weight when grown as above. One, MF633, contained a single copy of the plasmid at the GGS1 locus, as inferred from Southern analysis. The others arose by non-homologous or more complex integrations.

2E. Production of *Y. lipolytica* expressing phytoene synthase/lycopene cyclase, phytoene dehydrogenase and geranylgeranylpyrophosphate synthase: MF364 is crossed with MF578, and spores from the resulting diploid are plated on YPD for two to three days at 30° C. Orange Leu⁺ Ade⁻ Ura⁻ colonies are screened for the presence of tefp-carB, tefp-carRP, and tefp-GGS1 by PCR, and for high carotenoid (>4 mg/g dry cell weight) production after growth in YPD liquid medium. Colonies meeting these criteria, as well as displaying resistance to 5-fluorootic acid, an indication that they harbor the ura3-302 allele, are chosen for further studies and hereafter referred to as GBRPua strains. Such a strain is selected for further analysis and modification.

Example 3

Extraction of Carotenoids from *Yarrowia lipolytica* Cells

Shake-flask testing of generated strains was conducted using YPD medium (1% yeast extract, 2% peptone, 2% glucose). 20 ml cultures in 125 ml flasks were grown at 30° C. *Y. lipolytica* cells were harvested from 72-96 hour cultures, and extractions were performed to determine carotenoid form and quantity. 1.8 ml of culture was placed into an Eppendorf tube. Cells were pelleted and washed twice with 1 ml $H_2O$. After the second wash, the resuspended cells were transferred to a pre-weighed snap-cap tube with a hole poked in the top, and the cells were lyophilized overnight. After drying to completion, the tube was weighed in order to calculate dry cell weight. 0.25 ml from the same shake flask culture was placed into a 2 ml screw-cap tube for carotenoid extraction. Cells were pelleted and the supernatant was aspirated. Pelleted cells may be frozen at −80° C. and stored. An equal volume of cubic zirconia beads was added to cell pellets, along with 1 ml ice-cold extraction solvent (a 50/50 v/v mix of hexane and ethyl acetate containing 0.01% butylhydroxytoluene (BHT)). The mixture was then agitated (Mini-BeadBeater-8, BioSpec Products, Inc.) at maximum speed for 5 minutes at 4° C. The mixture was then spun at maximum speed for 1 minute, and the supernatant was collected and deposited in a cold 16 ml glass vial. The remaining cell debris was re-extracted at least three times, without the addition of zirconia beads; all supernatants were pooled in the 16 ml glass vial. Following extraction, the glass vial was spun for 5 minutes at 2000 rpm at 4° C. in a Sorvall tabletop centrifuge, and the supernatant was transferred to a new cold 16 ml glass vial. A Speed Vac was used to concentrate the supernatant (room temperature in dark), and the samples were stored at −20° C. or −80° C. until immediately before HPLC analysis. Prior to HPLC analysis, the samples were resuspended in 1 ml ice-cold solvent and then transferred to a cold amber vial. Throughout the protocol, care was taken to avoid contact with oxygen, light, heat, and acids.

Example 4

Quantification of Carotenoid Production by HPLC

For carotenoid analysis, samples were resuspended in ice-cold extraction solvent (a 50/50 v/v mix of hexane and ethyl acetate containing 0.01% butylhydroxytoluene (BHT)). An Alliance 2795 HPLC (Waters) equipped with a Waters XBridge C18 column (3.5 um, 2.1×50 mm) and Thermo Basic 8 guard column (2.1×10 mm) was used to resolve carotenoid at 25° C.; authentic carotenoid samples were used as standards. The mobile phases and flow rates are shown below (Solvent A=Ethyl Acetate; Solvent B=Water; Solvent C=Methanol; Solvent D=Acetonitrile). The injection volume was 10 μL. The detector is a Waters 996 photodiode array detector. The retention times for lipophilic molecules include astaxanthin (1.159 min), zeaxanthin (1.335), β-apo-8'-carotenal (2.86 min), ergosterol (3.11 min), lycopene (3.69 min), β-Carotene (4.02 min), and phytoene (4.13 min). Astaxanthin, zeaxanthin, β-apo-8'-carotenal, lycopene and β-Carotene are detected at 475 nm, whereas ergosterol and phytoene were detected at 286 nm.

TABLE 28

Retention Times for Lipophilic Molecules

| Time (min) | Flow (mL/min) | % A | % B | % C | % D | Curve |
|---|---|---|---|---|---|---|
|  | 0.50 | 0.0 | 20.0 | 0.0 | 80.0 |  |
| 3.00 | 1.00 | 20.0 | 0.0 | 0.0 | 80.0 | 6 |
| 4.50 | 1.00 | 80.0 | 0.0 | 20.0 | 0.0 | 6 |
| 5.50 | 1.00 | 0.0 | 0.0 | 60.0 | 40.0 | 6 |
| 6.50 | 1.00 | 0.0 | 0.0 | 80.0 | 20.0 | 6 |
| 7.50 | 1.00 | 0.0 | 0.0 | 100.0 | 0.0 | 6 |
| 8.50 | 1.00 | 0.0 | 0.0 | 100.0 | 0.0 | 6 |
| 9.50 | 1.00 | 0.0 | 20.0 | 0.0 | 80.0 | 6 |
| 10.50 | 0.50 | 0.0 | 20.0 | 0.0 | 80.0 | 6 |

Example 5

Expression of a Truncated form of HMG-CoA Reductase Results in Increased Carotenoid Production In order to increase carotenoid production, carbon flow through the isoprenoid pathway is enhanced by introducing a truncated variant of the HMG-CoA reductase gene.

In one approach, a truncated variant of the HMG-CoA reductase gene which also encodes a 77 amino acid leader sequence derived from *S. cerevisiae* Hmg1 is introduced into a GRPBua strain (described in Example 2E above). Plasmid pTefHMG can be cleaved with SnaBI, BbvCI, or Bsu36I to direct integration at the ade1 locus, or with BamHI to direct integration at the HMG1 locus, or with EcoRV to promote random integration, in the GRPBua strains, restoring them to adenine prototrophy. Resulting Ade$^+$ transformants are screened for increased carotenoid production.

Alternatively, the native HMG1 gene from *Y. lipolytica* may be modified without *S. cerevisiae* sequences as described in Example 1D above, to create pMB4637. This plasmid can be digested as described for pTefHMG and transformed into GRPBua strains, and resulting transformants screened as described for increased carotenoid production.

In still another approach, a truncated variant of the *N. crassa* HMG-CoA reductase gene may be utilized and introduced into *Y. lipolytica* strains. In order to generate a plasmid suitable for expression of the heterologous HMG-CoA reductase, p641P (Yeast 2001; 18 (2001): 97-113) is modified by replacing the ICL1 promoter with the GPD promoter, and by the addition of sequences conferring resistance to phleomycin. *Y. lipolytica* genomic DNA is amplified with two primers.

GPDdist:
5' CACACGGTacctgtaggttgggttgggtg
(SEQ ID NO: 49)

GPDprox:
5' CACACGGATCCtgtttaattcaagaatgaatatagagaagagaag,
(SEQ ID NO: 50)

and the resulting fragment (0.7 kb) is cleaved with BamHI and KpnI, and ligated to BamHI- and KpnI-cleaved p641P, creating the plasmid "p641Pgpd". The ble gene under the control of the *A. nidulans* GPD promoter is then excised from pBCphleo (Silar, Fungal Genetics Newsletter 42:73) as a 3.2 kb BclI-BamHI fragment and inserted into the unique BamHI site of "p641Pgpd", in the orientation that preserves the BamHI site proximal to the GPD promoter, to create "p641Pgpdble",

*N. crassa* genomic DNA is amplified with two primers:

Neuhmg fwd:
5' CACACGGATCCACATCAACAatggcatctgccacccttcccc
(SEQ ID NO: 51)

Neuhmg rev:
5' CACACGGATCcaagtgctgacgcggaacttg,
(SEQ ID NO: 52)

and the resulting fragment is cleaved with BamHI and inserted into BamHI-digested "p641Pgpdble" in the correct orientation. The resulting plasmid, "pZg", contains sequences encoding a truncated cytosolic catalytic domain of hydroxymethylglutaryl-CoA reductase from *N. crassa* (Genbank accession: XP_324892) under the control of the constitutive GPD promoter. This plasmid can be introduced into the *Y. lipolytica* strain created in Example 2E above, and transformants are selected by their resistance to phleomycin (100 µg/ml). Resulting transformants are tested for β-carotene production, as described above.

Example 6

Introduction of Heterologous Carotene Hydroxylase and Carotene Ketolase Genes Into *Y. lipolytica* Strains Producing Carotenoid for Production of Astaxanthin For introduction of carotene hydroxylase and carotene ketolase into carotenoid producting *Y. lipolytica*, pMB4692 and pMB4698, described as in Example 1E and 1F above, can be sequentially introduced into the GRPBua strain (described in Example 2E). For the introduction of pMB4692, the plasmid may be cleaved with SalI or BsrGI to direct integration at the ura3 locus, or with XbaI to promote random integration, selecting for uracil prototrophy. GRPBua Ura$^+$ transformants harboring pMB4692 are screened for zeaxanthin production in YPD. Zeaxanthin-producing cells are transformed with pMB4698 (which can be cleaved with PpuMI, SspI or BbvCI to direct integration at the ade1 locus, or with EcoRV to promote random integration) and prototrophic colonies are screened for astaxanthin production.

Alternatively, the order of plasmid transformation may be reversed wherein pMB4698 is transformed first and transformants are selected for adenine prototrophy. GRPBua Ade$^+$ transformants harboring pMB4698 are screened for canthaxanthin production. Canthaxanthin-producing GRPBua [pMB4698] cells are transformed with pMB4692 and prototrophic colonies are screened for astaxanthin production.

In another approach, the carotenoid ketolase and carotenoid hydroxylase genes from *P. marcusii* can be introduced into the strains described in Example 2 above, in order to convert β-carotene into astaxanthin. *P. marcusii* genomic DNA is amplified with two primers.

CrtZfwd: 5' CACACCGTCTCAAatgaccaatttcctgatcgtcgtc
(SEQ ID NO: 53)

CrtZrev: 5' CACACAGATCtcacgtgcgctcctgcgcc,
(SEQ ID NO: 54)

and the resulting fragment is cleaved with BsmBI, modified with the Klenow fragment of DNA polymerase, and cleaved with BglII. This fragment is inserted into PmlI- and BamHI-cleaved pINA1269 (J. Mol. Microbiol. Biotechnol. 2 (2000): 207-216), containing the hp4d promoter, the XPR2 terminator, the selectable LEU2 gene, and sequences necessary for selection and propagation in *E. coli*. The resulting plasmid "pA" contains sequences encoding carotene hydroxylase from *P. marcusii* (crtZ gene)(Genbank accession: CAB56060.1) under the control of the hp4d promoter.

"pYEG1TEF" is modified by substituting the LIP2 terminator for the XPR2 terminator as follows. pINA1291 is digested with AvrII, modified with the Klenow fragment of DNA polymerase, and cleaved with EcoRI, and the small LIP2t containing fragment is ligated to "YEG1TEF" that has been digested with SacII, modified with T4 DNA polymerase in the presence of dNTP, and cleaved with EcoRI. The resulting plasmid is named "pYEG1TEF-LIP2t".

In order to amplify the carotenoid ketolase gene, *P. marcusii* genomic DNA is amplified with two primers.

```
CrtWfwd:   5' CACACCCTAGGCCatgagcgcacatgccctgc
              (SEQ ID NO: 55)

CrtWrev:   5' CACACAAGCTTtcatgcggtgtccccttg,
              (SEQ ID NO: 56)
``` and the resulting fragment is cleaved with AvrII and HindIII, and inserted into AvrII- and HindIII-cleaved "pYEG1TEF-LIP2t". The resulting plasmid, "pBt", contains sequences encoding the carotene ketolase (crtW gene)(Genbank accession: CAB56059.1) under the control of the constitutive TEF1 promoter.

In order to combine the two expression cassettes into a single plasmid, "pBt" is cleaved with ClaI, modified with the Klenow fragment of DNA polymerase, and cleaved with EcoRI, and the crtW-containing fragment is isolated, mixed with the phosphorylated oligonucleotide adaptor pair:

```
5' AATTCGCGGCCGCT
(SEQ ID NO: 57)
and

5' AGCGGCCGCG,
(SEQ ID NO: 58)
``` cleaved with NotI, and ligated to NotI-digested "pA". The resulting plasmid, "pABt", contains both the TEF1p/crtW/LIP2t cassette and the hp4d/crtZ/XPR2t cassette as well as the selectable LEU2 gene.

"pABt" can be introduced into the *Y. lipolytica* strain described above in Example 4 (TEF1p/al-1/XPR2t; hp4d/carRP/LIP2t; GPDp/HMGR$_{trunc}$), and transformants selected for leucine prototrophy.

Example 7

Partial Inactivation of *Y. lipolytica* ERG9 Gene Encoding Squalene Synthase Results in Increased Carotenoid Production 7A. In order to partially inactivate the ERG9 gene encoding squalene synthase, the neighboring FOL3 gene is disrupted, resulting in a folinic acid requirement. This strain is then transformed with a mutagenized fragment of DNA partially spanning the two genes, and Fol⁺ transformants are screened for decreased squalene synthase activity.

The following oligonucleotides are synthesized:

```
PRIMER K     5'-CCTTCTAGTCGTACGTAGTCAGC;
             (SEQ ID NO: 59)

PRIMER L     5'-CCACTGATCTAGAATCTCTTTCTGG
             (SEQ ID NO: 60)
``` and used to amplify a 2.3 kb fragment from *Y. lipolytica* genomic DNA spanning most of the FOL3 gene, using Pfu polymerase. The resulting fragment is cleaved with XbaI and phosphorylated, then ligated into pBluescriptSK⁻ that has been cleaved with KpnI, treated with T4 DNA polymerase (T4pol) in the presence of dNTPs, and subsequently cleaved with XbaI. The resultant plasmid, designated pBS-fol3, is then cleaved with Acc65I and EcoRI, treated with T4pol as above, and ligated to the 3.4 kb EcoRV-SpeI ADE1 fragment (treated with T4pol) from pMB4529.

The resulting plasmid, pBSfol3Δade, can be cleaved with BsiWI and XbaI to liberate a 5.5 kb fragment that is used to transform the GRBPua strains described above to adenine prototrophy. Resulting Ade⁺ transformants are screened for a folinic acid requirement, and for homologous integration by PCR analysis.

Strains that harbor the resultant fol3ΔADE1 allele can be transformed with a 3.5 kb DNA fragment generated by mutagenic PCR amplification using the primers:

```
PRIMER M     5'-GGCTCATTGCGCATGCTAACATCG;
             (SEQ ID NO: 61)

PRIMER N     5'-CGACGATGCTATGAGCTTCTAGACG,
             (SEQ ID NO: 62)
``` and *Y. lipolytica* genomic DNA as template. The resulting fragment containing the N-terminal three-quarters of the FOL3 ORF and the C-terminal nine-tenths of the ERG9 ORF is used to transform strains. The resulting Fol⁺ Ade⁺ transformants are screened for decreased squalene synthase activity by sensitivity to agents such as zaragozic acid, itraconazole, or fluconazole. Additionally, the resulting transformants are screened for increased carotenoid production.

7B. Alternatively, the PCR fragment produced in 7A could be cloned and altered in such a way as to remove the 3'-untranslated region of ERG9 gene. Replacement of the fol3ΔADE1 disruption by this fragment results in decreased expression of squalene synthase [Schuldiner et al. (2005), Cell 123:507-519][Muhlrad and Parker (1999), RNA 5:1299-1307], which can be confirmed as in 7A. This approach may also be used in a Fol⁺ Ade⁻ strain, using the ADE1 marker to disrupt the ERG9 3'-UTR.

7C. In still another approach, partially defective ERG9 alleles can be identified in *S. cerevisiae* using plasmid shuffling techniques [Boeke et al. (1987), Methods Enzymol. 154:164-175], and using drug sensitivities as a phenotype. Defective genes can be transferred to *Y. lipolytica* using standard molecular genetic techniques.

Example 8

Treatment of *Y. lipolytica* Strains Producing Carotenoid With Inhibitor of an Isoprenoid Biosynthesis Competitor Polypeptide Results in Increased Carotenoid Production Cultures produced in Example 2 are treated with the squalene synthase inhibitor, zaragozic acid (zaragozic acid at 0.5 µM) and monitored for β-carotene production, as described above.

Example 9

Constructing an Oleaginous Strain of *Saccharomyces crevisiae*

The genes encoding the two subunits of ATP-citrate lyase from *N. crassa*, the AMP deaminase from *Saccharomyces cerevisiae*, and the cytosolic malic enzyme from *M. circinelloides* are overexpressed in *S. cereviseae* strains in order to increase the total lipid content. Similar approaches to enhance lipid production could be employed in other host organisms such as *Xanthophyllomyces dendrorhous* (*Phaffia rhodozyma*), using the same, homologous, or functionally similar oleaginic polypeptides.

Qiagen RNAEasy kits (Qiagen, Valencia, Calif.) are used to prepare messenger RNA from lyophilized biomass prepared from cultures of *N. crassa*. Subsequently, RT-PCR is performed in two reactions containing the mRNA template and either of the following primer pairs.

```
acl1:
1fwd:   5' CACACGGATCCTATAatgccttccgcaacgaccg
           (SEQ ID NO: 63)

1rev:   5' CACACACTAGttaaatttggacctcaacacgaccc
           (SEQ ID NO: 64)

acl2:
2fwd:   5' CACACGGATCCAATATAAatgtctgcgaagagcatcctcg
           (SEQ ID NO: 65)

2rev:   5' CACACGCATGCttaagcttggaactccaccgcac
           (SEQ ID NO: 66)
```

The resulting fragment from the acl1 reaction is cleaved with SpeI and BamHI, and that from the acl2 reaction is cleaved with BamHI and SphI, and both are ligated together into YEp24 that has been digested with NheI and SphI, creating the plasmid "p12". The bi-directional GAL1-10 promoter is amplified from *S. cerevisiae* genomic DNA using the primers.

```
gal10:
5' CACACGGATCCaattttcaaaaattcttactttttttttggatggac
(SEQ ID NO: 67)

gal1:
5' CACACGGATCCtttttctccttgacgttaaagtatagagg,
(SEQ ID NO: 68)
``` and the resulting 0.67 kb fragment is cleaved with BamHI and ligated in either orientation to BamHI-digested "p12" to create "p1gal2" and "p2gal1", containing GAL1-acl1/GAL10-acl2 and GAL10-acl1/GAL1-acl2, respectively (Genbank accession: acl1: CAB91740.2; acl2: CAB91741.2).

In order to amplify the *S. cereviseae* gene encoding AMP deaminase and a promoter suitable for expressing this gene, *S. cerevisiae* genomic DNA is amplified using two primer pairs in separate reactions:

```
AMD1 ORF:
AMD1FWD:   5' CACACGAGCTCAAAAatggacaatcaggctacacagag
              (SEQ ID NO: 69)

AMD1rev:   5' CACACCCTAGGtcactttcttcaatggttctcttgaa
              attg
              (SEQ ID NO: 70)

GAL7p:
gal7prox:  5' CACACGAGCTCggaatattcaactgttttttttatca
              tgttgatg
              (SEQ ID NO: 71)

gal7dist:  5' CACACGGAtccttcttgaaaatatgcactctatatctt
              ttag,
              (SEQ ID NO: 72)
``` and the resulting fragment from the AMD1 reaction (2.4 kb) is cleaved with SacI and AvrII, and that from the GAL7 reaction (0.7 kb) is cleaved with BamHI and SphI, and both are ligated together into YEp13 that has been digested with NheI and BamHI, creating the plasmid "pAMPD". This plasmid carries the *S. cerevisiae* gene, AMD1, encoding AMP deaminase, under the control of the galactose-inducible GAL7 promoter.

Messenger RNA is prepared from lyophilized biomass of *M. circinelloides*, as described above, and the mRNA template is used in a RT-PCR reaction with two primers:

```
MAEfwd:
5' CACACGCTAGCTACAAAatgttgtcactcaaacgcatagcaac
(SEQ ID NO: 73)

MAErev:
5' CACACGTCGACttaatgatctcggtatacgagaggaac,
(SEQ ID NO: 74)
``` and the resulting fragment is cleaved with NheI and SalI, and ligated to XbaI- and XhoI-digested pRS413TEF (Mumberg, D. et al. (1995) Gene, 156:119-122), creating the plasmid "pTEFMAE", which contains sequences encoding the cytosolic $NADP^+$-dependant malic enzyme from *M. circinelloides* (E.C. 1.1.1.40; mce gene; Genbank accession: AY209191) under the control of the constitutive TEF1 promoter.

The plasmids "p1gal2", "pAMPD", and "pTEFMAE" are sequentially transformed into a strain of *S. cereviseae* to restore prototrophy for uracil ("p1gal2"), leucine ("pAMPD"), and histidine ("pTEFMAE") (Guthrie and Fink Methods in Enzymology 194:1-933, 1991). The resulting transformants are tested for total lipid content following shake flask testing in either synthetic complete (SC) medium lacking uracil, leucine and histidine, as described in Example 3, or in a 2-step fermentation process. In the 2-step process, 1.5 ml of cells from an overnight 2 ml roll tube culture containing SC medium lacking uracil, leucine and histidine are centrifuged, washed in distilled water, and resuspended in 20 ml of a nitrogen-limiting medium suitable for lipid accumulation (30 g/L glucose, 1.5 g/L yeast extract, 0.5 g/L $NH_4Cl$, 7 g/L $KH_2PO_4$, 5 g/L $Na_2HPO_4\text{-}12H_2O$, 1.5 g/L $MgSO_4\text{-}7H_2O$, 0.08 g/L $FeCl_3\text{-}6H_2O$, 0.01 g/L $ZnSO_4\text{-}7H_2O$, 0.1 g/L $CaCl_2\text{-}2H_2O$, 0.1 mg/L $MnSO_4\text{-}5H_2O$, 0.1 mg/L $CuSO_4\text{-}5H_2O$, 0.1 mg/L $Co(NO_3)_2\text{-}6H_2O$; pH 5.5 (J Am Oil Chem Soc 70:891-894 (1993)).

Intracellular lipid content of the modified and control *S. cerevisiae* strains is analyzed using the fluorescent probe, Nile Red (J Microbiol Meth (2004) 56:331-338). In brief, cells diluted in buffer are stained with Nile Red, excited at 488 nm, and the fluorescent emission spectra in the wavelength region of 400-700 nm are acquired and compared to the corresponding spectra from cells not stained with Nile Red. To confirm results from the rapid estimation method, the total lipid content is determined by gas chromatographic analysis of the total fatty acids directly transmethylesterified from dried cells, as described (Appl Microbiol Biotechnol. 2002 November;60(3):275-80). Non-transformed *S. cerevisiae* strains produce 6% and 10% total lipid (dry cell weight basis) after growth in YPD and lipid accumulation medium, respectively. Yeast strains expressing the multiple oleaginic polypeptides produce 17% and 25% total lipid following growth in YPD and lipid accumulation medium, respectively.

Example 10

Introduction of Heterologous Carotene Hydroxylase into *Y. lipolytica* Strains Producing Carotenoid for Production of Zeaxanthin MF578 (tef-carRP tef-carB) was transformed with pMB4692 that had been cleaved with SalI. Several Ura+ colonies inferred to contain tef-crtZ by PCR analysis were able to produce zeaxanthin in YPD shake flasks, and in one case, all of the carotene was depleted.

The following tables are referenced throughout the description:

TABLE 1

Examples of acetyl-CoA carboxylase polypeptides.

| Row | Gen bank ACCESSION | Genbank GI |
|---|---|---|
| 1 | XP_410263 | 49097606 |
| 2 | XP_329580 | 32418204 |
| 3 | XP_386756 | 46124405 |
| 4 | XP_367702 | 39972623 |
| 5 | XP_501721 | 50548503 |
| 6 | EAK99708 | 46440402 |
| 7 | XP_457211 | 50413128 |
| 8 | NP_982612 | 45184894 |
| 9 | XP_449236 | 50293649 |
| 10 | NP_593271 | 19114183 |
| 11 | NP_014413 | 6324343 |
| 12 | XP_455355 | 50310667 |
| 13 | T42531 | 11272737 |
| 14 | AAA20073 | 171504 |
| 15 | EAL20176 | 50257469 |
| 16 | XP_571316 | 58268320 |
| 17 | XP_402244 | 49076566 |
| 18 | S60200 | 2133343 |
| 19 | BAA24410 | 2804173 |
| 20 | P32874 | 1708192 |
| 21 | S55089 | 7438088 |
| 22 | NP_990836 | 45382859 |
| 23 | CAE01471 | 32526576 |
| 24 | AAR37018 | 40019048 |
| 25 | NP_001... | 57164283 |
| 26 | NP_776649 | 27806341 |
| 27 | CAI25271 | 56205878 |
| 28 | XP_109883 | 51828611 |
| 29 | NP_942134 | 38679971 |
| 30 | NP_942131 | 38679960 |
| 31 | NP_942135 | 38679974 |
| 32 | NP_942136 | 38679977 |
| 33 | AAP94122 | 33112885 |
| 34 | NP_071529 | 11559962 |
| 35 | 2006242A | 740964 |

TABLE 1-continued

Examples of acetyl-CoA carboxylase polypeptides.

| Row | Gen bank ACCESSION | Genbank GI |
|---|---|---|
| 36 | AAS13685 | 42405896 |
| 37 | NP_598665 | 48976025 |
| 38 | Q13085 | 2493311 |
| 39 | XP_548250 | 57091783 |
| 40 | XP_314071 | 58385597 |
| 41 | CAG08536 | 47226520 |
| 42 | NP_724636 | 24586460 |
| 43 | NP_610342 | 24586458 |
| 44 | NP_001084 | 4501855 |
| 45 | NP_446374 | 16758804 |
| 46 | EAL63219 | 60465120 |
| 47 | NP_921034 | 37533464 |
| 48 | T07084 | 7438099 |
| 49 | AAP78896 | 32264940 |
| 50 | AAO62903 | 29123370 |
| 51 | BAA07012 | 1100253 |
| 52 | AAL02056 | 15558947 |
| 53 | AAG40563 | 11869927 |
| 54 | D86483 | 25293894 |
| 55 | T07920 | 7438090 |
| 56 | A57710 | 2130099 |
| 57 | AAO62902 | 29123376 |
| 58 | 2208491A | 1588584 |
| 59 | T09538 | 7438102 |
| 60 | CAC19875 | 12057067 |
| 61 | AAP78897 | 32264942 |
| 62 | T02235 | 7438095 |
| 63 | AAG40564 | 11869928 |
| 64 | E86483 | 25293893 |
| 65 | CAC84161 | 20975574 |
| 66 | T07081 | 7438097 |
| 67 | CAC19876 | 12057069 |

TABLE 2

Examples of pyruvate decarboxylase polypeptides.

| Row | Genbank ACCESSION | Genbank GI |
|---|---|---|
| 1 | 1QPBB | 7245977 |
| 2 | CAA54522 | 871533 |
| 3 | 1PYDB | 515237 |
| 4 | CAA28380 | 4109 |
| 5 | 1PVDB | 1127233 |
| 6 | CAA33709 | 4114 |
| 7 | AAN77243 | 25992752 |
| 8 | NP_013235 | 6323163 |
| 9 | Q6FJA3 | 57012668 |
| 10 | S36363 | 486942 |
| 11 | Q12629 | 52788279 |
| 12 | AAP75898 | 37359468 |
| 13 | S70684 | 2131152 |
| 14 | NP_011601 | 6321524 |
| 15 | AAQ73618 | 34500072 |
| 16 | NP_983270 | 45185554 |
| 17 | AAF78895 | 8745337 |
| 18 | CAB65554 | 6689662 |
| 19 | AAP75899 | 37359470 |
| 20 | NP_982469 | 45184751 |
| 21 | CAA97091 | 1945321 |
| 22 | S50700 | 1086157 |
| 23 | XP_446491 | 50288125 |
| 24 | XP_462338 | 50427451 |
| 25 | AAC03164 | 17066784 |
| 26 | EAK96569 | 46437219 |
| 27 | XP_457131 | 50412425 |
| 28 | AAC03165 | 2734883 |
| 29 | XP_459224 | 50421349 |
| 30 | CAH56494 | 52673248 |
| 31 | XP_502647 | 50550349 |

TABLE 2-continued

Examples of pyruvate decarboxylase polypeptides.

| Row | Genbank ACCESSION | Genbank GI |
|---|---|---|
| 32 | NP_010203 | 6320123 |
| 33 | BAA04886 | 1786148 |
| 34 | XP_449074 | 50293325 |
| 35 | EAL04098 | 46444826 |
| 36 | CAD60727 | 27803024 |
| 37 | T38759 | 25777585 |
| 38 | XP_331173 | 32421459 |
| 39 | NP_594083 | 19114995 |
| 40 | XP_401609 | 49075036 |
| 41 | XP_390010 | 46136637 |
| 42 | XP_409025 | 49095128 |
| 43 | NP_984350 | 45188127 |
| 44 | AAD16178 | 4323053 |
| 45 | P87208 | 2501326 |
| 46 | EAL18331 | 50255598 |
| 47 | XP_567475 | 58260130 |
| 48 | AAM73540 | 21666011 |
| 49 | AAM73539 | 21666009 |
| 50 | XP_502508 | 50550071 |
| 51 | CAA93158 | 1177659 |
| 52 | XP_412533 | 49123327 |
| 53 | P51844 | 1706333 |
| 54 | XP_455842 | 50311631 |
| 55 | CAA61155 | 3688422 |
| 56 | XP_444902 | 50284947 |
| 57 | CAA47319 | 4118 |

TABLE 3

Examples of isocitrate dehydrogenase polypeptides.

| Row | Genbank ACCESSION | Genbank GI |
|---|---|---|
| 1 | O13285 | 3023996 |
| 2 | EAK91676 | 46432179 |
| 3 | O13285 | 3023996 |
| 4 | EAK94305 | 46434909 |
| 5 | XP_451683 | 50303483 |
| 6 | XP_459772 | 50422415 |
| 7 | O13294 | 27805482 |
| 8 | XP_460289 | 50423413 |
| 9 | XP_390523 | 46137663 |
| 10 | XP_367343 | 39971905 |
| 11 | XP_323176 | 32405126 |
| 12 | XP_445447 | 50286037 |
| 13 | AAK76730 | 15027826 |
| 14 | NP_010217 | 6320137 |
| 15 | NP_984921 | 45190667 |
| 16 | AAK76731 | 15027827 |
| 17 | P79089 | 3023999 |
| 18 | NP_013275 | 6323203 |
| 19 | XP_407136 | 49091350 |
| 20 | NP_982520 | 45184802 |
| 21 | XP_446953 | 50289047 |
| 22 | XP_445184 | 50285511 |
| 23 | XP_455638 | 50311227 |
| 24 | AAA64516 | 736722 |
| 25 | NP_970434 | 42525054 |
| 26 | AAT93173 | 51013759 |
| 27 | XP_569233 | 58264154 |
| 28 | XP_569234 | 58264156 |
| 29 | XP_403726 | 49080406 |
| 30 | XP_503571 | 50552322 |
| 31 | XP_458151 | 50428131 |
| 32 | O13302 | 13124301 |
| 33 | XP_409927 | 49096934 |
| 34 | XP_385909 | 46122711 |
| 35 | XP_365293 | 39967489 |
| 36 | NP_983873 | 45187650 |
| 37 | XP_455266 | 50310493 |

TABLE 3-continued

Examples of isocitrate dehydrogenase polypeptides.

| Row | Genbank ACCESSION | Genbank GI |
|---|---|---|
| 38 | NP_594397 | 19115309 |
| 39 | XP_324955 | 32408949 |
| 40 | CAE81942 | 38636405 |
| 41 | NP_014361 | 6324291 |
| 42 | XP_446479 | 50288101 |
| 43 | XP_567378 | 58259936 |
| 44 | XP_398944 | 49069310 |
| 45 | XP_502479 | 50550013 |
| 46 | EAK96238 | 46436883 |
| 47 | EAK96305 | 46436951 |
| 48 | XP_461797 | 50426401 |
| 49 | XP_328403 | 32415850 |
| 50 | CAF31997 | 42820684 |
| 51 | XP_389756 | 46136129 |
| 52 | XP_363786 | 39952139 |
| 53 | AAL73035 | 18463935 |
| 54 | XP_405140 | 49086142 |
| 55 | NP_595203 | 19111995 |
| 56 | NP_014779 | 6324709 |
| 57 | XP_447564 | 50290265 |
| 58 | NP_985684 | 45198655 |
| 59 | XP_566837 | 58258849 |
| 60 | XP_454086 | 50308171 |
| 61 | XP_398943 | 49069308 |

TABLE 4

Examples of ATP-citrate lyase polypeptides.

| Row | Genbank ACCESSION | Genbank GI |
|---|---|---|
| 1 | XP_327071 | 32413182 |
| 2 | O93988 | 30912679 |
| 3 | XP_370222 | 39977669 |
| 4 | XP_406573 | 49090008 |
| 5 | XP_504787 | 50554757 |
| 6 | Q9P7W3 | 30912748 |
| 7 | XP_398620 | 49068662 |
| 8 | NP_596202 | 19112994 |
| 9 | XP_567460 | 58260100 |
| 10 | NP_001008 | 56118260 |
| 11 | XP_418154 | 50760837 |
| 12 | AAH84253 | 54038148 |
| 13 | NP_942127 | 38569423 |
| 14 | NP_001087 | 38569421 |
| 15 | P53396 | 20141248 |
| 16 | AAL34316 | 17028103 |
| 17 | NP_001002 | 50540366 |
| 18 | AAH84776 | 54311201 |
| 19 | S21173 | 105392 |
| 20 | AAT94429 | 51092031 |
| 21 | AAD34754 | 28372804 |
| 22 | AAH21502 | 18204829 |
| 23 | XP_319323 | 58392375 |
| 24 | NP_725514 | 24653990 |
| 25 | EAL26601 | 54637198 |
| 26 | CAE56725 | 39579419 |
| 27 | CAE64663 | 39593194 |
| 28 | XP_511495 | 55645405 |
| 29 | CAF95829 | 47210997 |
| 30 | AAO22565 | 27754223 |
| 31 | AAL33788 | 17065616 |
| 32 | CAB46077 | 5304837 |
| 33 | CAF96044 | 47204726 |
| 34 | AAK13318 | 13160653 |
| 35 | AAQ75159 | 34558815 |
| 36 | AAQ75128 | 34558783 |
| 37 | XP_537640 | 57091075 |
| 38 | XP_327069 | 32413178 |
| 39 | CAB76164 | 7160184 |

TABLE 4-continued

Examples of ATP-citrate lyase polypeptides.

| Row | Genbank ACCESSION | Genbank GI |
|---|---|---|
| 40 | XP_370223 | 39977671 |
| 41 | XP_386215 | 46123323 |
| 42 | CAA10666 | 7159697 |
| 43 | XP_406572 | 49090004 |
| 44 | XP_503231 | 50551515 |
| 45 | NP_593246 | 19114158 |
| 46 | XP_398620 | 49068662 |
| 47 | XP_567460 | 58260100 |
| 48 | AAT94429 | 51092031 |
| 49 | NP_725514 | 24653990 |
| 50 | AAD34754 | 28372804 |
| 51 | EAL26601 | 54637198 |
| 52 | XP_319323 | 58392375 |
| 53 | AAH84776 | 54311201 |
| 54 | BAB00624 | 9229902 |
| 55 | NP_001008 | 56118260 |
| 56 | AAH84253 | 54038148 |
| 57 | AAH56378 | 38614162 |
| 58 | NP_001087 | 38569421 |
| 59 | NP_942127 | 38569423 |
| 60 | P53396 | 20141248 |
| 61 | XP_511495 | 55645405 |
| 62 | NP_058683 | 8392839 |
| 63 | NP_001002 | 50540366 |
| 64 | S21173 | 105392 |
| 65 | NP_508280 | 17551266 |
| 66 | CAE64663 | 39593194 |
| 67 | CAE56725 | 39579419 |
| 68 | NP_506267 | 17557344 |
| 69 | XP_537640 | 57091075 |
| 70 | CAF96059 | 47204551 |
| 71 | F96633 | 25404292 |
| 72 | AAM91141 | 22136126 |
| 73 | NP_849634 | 30681854 |
| 74 | AAO23582 | 27764922 |
| 75 | AAM65078 | 21593129 |
| 76 | CAC86996 | 15919089 |
| 77 | AAQ75158 | 34558814 |
| 78 | AAQ75127 | 34558782 |

TABLE 5

Examples of malic enzyme polypeptides.

| Row | Genbank ACCESSION | Genbank GI |
|---|---|---|
| 1 | NP_012896 | 6322823 |
| 2 | XP_448858 | 50292851 |
| 3 | XP_454793 | 50309563 |
| 4 | NP_986598 | 45201028 |
| 5 | XP_460887 | 50424595 |
| 6 | EAK97738 | 46438407 |
| 7 | XP_504112 | 50553402 |
| 8 | XP_330094 | 32419237 |
| 9 | XP_380981 | 46107844 |
| 10 | XP_411070 | 49102552 |
| 11 | XP_362875 | 39946676 |
| 12 | NP_587760 | 19075260 |
| 13 | NP_978189 | 42780942 |
| 14 | YP_035982 | 49481098 |
| 15 | YP_027934 | 49184682 |
| 16 | YP_018438 | 47527089 |
| 17 | ZP_002365 | 47565532 |
| 18 | YP_083209 | 52143619 |
| 19 | XP_571672 | 58269032 |
| 20 | NP_391586 | 16080758 |
| 21 | YP_092693 | 52786864 |
| 22 | NP_831516 | 30019885 |
| 23 | YP_093460 | 52787631 |
| 24 | YP_081030 | 52082239 |

TABLE 5-continued

Examples of malic enzyme polypeptides.

| Row | Genbank ACCESSION | Genbank GI |
|---|---|---|
| 25 | NP_822689 | 29828055 |
| 26 | O34389 | 33517449 |
| 27 | EAL19111 | 50256386 |
| 28 | NP_825047 | 29830413 |
| 29 | ZP_002340 | 47096498 |
| 30 | NP_928837 | 37525493 |
| 31 | NP_230833 | 15641201 |
| 32 | NP_934257 | 37679648 |
| 33 | NP_761613 | 27366085 |
| 34 | AC1314 | 25283688 |
| 35 | YP_055602 | 50842375 |
| 36 | YP_095310 | 52841511 |
| 37 | ZP_002315 | 47093832 |
| 38 | AC1686 | 25283689 |
| 39 | YP_126594 | 54294179 |
| 40 | YP_123567 | 54297198 |
| 41 | EAJ76260 | 44510091 |
| 42 | YP_114273 | 53803890 |
| 43 | NP_797637 | 28898032 |
| 44 | YP_040250 | 49483026 |
| 45 | ZP_001276 | 53693400 |
| 46 | YP_044961 | 50083451 |
| 47 | YP_128226 | 54295811 |
| 48 | NP_719387 | 24375344 |
| 49 | XP_572853 | 58271394 |
| 50 | NP_252161 | 15598667 |
| 51 | ZP_001368 | 46164263 |
| 52 | YP_125345 | 54298976 |
| 53 | NP_793695 | 28871076 |
| 54 | YP_096964 | 52843165 |
| 55 | EAH92280 | 44245125 |
| 56 | YP_154988 | 56459707 |
| 57 | EAI68195 | 44354928 |
| 58 | YP_070054 | 51595863 |
| 59 | YP_133025 | 54303032 |
| 60 | NP_969623 | 42524243 |
| 61 | NP_856009 | 31793516 |
| 62 | DECARBOXY | ATING)) |
| 63 | NP_935035 | 37680426 |
| 64 | YP_050922 | 50121755 |
| 65 | E70705 | 7431223 |
| 66 | NP_216848 | 57116971 |
| 67 | DECARBOXY | ATING)) |
| 68 | YP_143786 | 55980489 |
| 69 | YP_130202 | 54309182 |
| 70 | NP_415996 | 16129438 |
| 71 | NP_819843 | 29654151 |
| 72 | NP_753809 | 26247769 |
| 73 | NP_707611 | 56479957 |
| 74 | F85728 | 25283682 |
| 75 | YP_163690 | 56552851 |
| 76 | YP_150562 | 56413487 |
| 77 | NP_720610 | 24378655 |
| 78 | NP_460525 | 16764910 |
| 79 | ZP_003193 | 48865537 |
| 80 | NP_784797 | 28377905 |
| 81 | T13496 | 7431227 |
| 82 | AAV65766 | 55793550 |
| 83 | A97096 | 25283683 |
| 84 | YP_193951 | 58337366 |
| 85 | H97096 | 25283684 |
| 86 | ZP_003237 | 48870993 |
| 87 | ZP_001460 | 41689468 |
| 88 | D86737 | 25283676 |
| 89 | ZP_002870 | 48825851 |
| 90 | ZP_001439 | 34762975 |
| 91 | 1922245A | 737262 |
| 92 | YP_169914 | 56708018 |
| 93 | YP_055027 | 50841800 |
| 94 | ZP_000625 | 23023297 |
| 95 | NP_296302 | 15807565 |
| 96 | NP_285599 | 15807938 |
| 97 | YP_132069 | 54302076 |
| 98 | CAA50716 | 467569 |

TABLE 5-continued

Examples of malic enzyme polypeptides.

| Row | Genbank ACCESSION | Genbank GI |
|---|---|---|
| 99 | ZP_002906 | 48833596 |
| 100 | ZP_003155 | 48861632 |
| 101 | NP_773109 | 27381580 |
| 102 | AAQ95658 | 37622953 |
| 103 | CAC19505 | 56204311 |
| 104 | AAH80660 | 51873855 |
| 105 | P40927 | 729986 |
| 106 | AAT02533 | 46850200 |
| 107 | BAC37086 | 26346875 |
| 108 | T02763 | 7431235 |
| 109 | XP_387367 | 46125627 |
| 110 | AAC50613 | 1465733 |
| 111 | CAA39421 | 669118 |
| 112 | CAA39420 | 669117 |
| 113 | NP_032641 | 6678912 |
| 114 | CAA39419 | 581228 |
| 115 | AAB01380 | 1335389 |
| 116 | JC4160 | 1085347 |
| 117 | E96828 | 25283677 |
| 118 | BAD87910 | 57899974 |
| 119 | EAJ77083 | 44511304 |
| 120 | P13697 | 266504 |
| 121 | NP_036732 | 7106353 |
| 122 | YP_065939 | 51246055 |
| 123 | CAC18164 | 16944467 |
| 124 | XP_322953 | 32404680 |
| 125 | AAK91502 | 18460985 |
| 126 | AAQ88396 | 37147841 |
| 127 | NP_001003 | 57525624 |
| 128 | 1GQ2P | 21465488 |
| 129 | AAO26053 | 28195290 |
| 130 | AAH84250 | 54038006 |
| 131 | XP_362590 | 39946106 |
| 132 | AAH03287 | 13096987 |
| 133 | Q29558 | 2497785 |
| 134 | XP_532217 | 57094622 |
| 135 | P28227 | 126734 |
| 136 | NP_496968 | 17537199 |
| 137 | NP_914533 | 34906372 |
| 138 | AAD10504 | 4096786 |
| 139 | AAO67523 | 50897495 |
| 140 | P43279 | 1170871 |
| 141 | AAK83074 | 15077109 |
| 142 | AAP33011 | 30575690 |
| 143 | AAN86690 | 27357017 |
| 144 | P78715 | 41017288 |
| 145 | AAP32204 | 30526303 |
| 146 | AAV31249 | 54287505 |
| 147 | T06402 | 7431232 |
| 148 | Q99KE1 | 55583978 |
| 149 | XP_399922 | 49071266 |
| 150 | P36444 | 547886 |
| 151 | AAO30034 | 28059162 |
| 152 | AAK83073 | 15077107 |
| 153 | NP_002387 | 4505145 |
| 154 | AAA33487 | 168528 |
| 155 | BAA74735 | 4239891 |
| 156 | NP_989634 | 45383538 |
| 157 | 1GZ3D | 31615316 |
| 158 | AAW56450 | 57791240 |
| 159 | AAT02534 | 46850202 |
| 160 | S29742 | 422339 |
| 161 | 1O0SB | 34811253 |
| 162 | P27443 | 126732 |
| 163 | T06401 | 7431231 |
| 164 | AAL16175 | 16226466 |
| 165 | AAF73006 | 8118507 |
| 166 | AAK97530 | 15420975 |
| 167 | EAI90348 | 44385841 |
| 168 | P51615 | 1708924 |
| 169 | AAA19575 | 169327 |
| 170 | S43718 | 1084300 |
| 171 | P34105 | 1346485 |
| 172 | AAS38597 | 42733630 |
| 173 | BAC54101 | 27530932 |
| 174 | AAT02535 | 46850204 |
| 175 | CAB66003 | 6706333 |
| 176 | AAH84860 | 54311418 |
| 177 | CAA39422 | 669119 |
| 178 | NP_916713 | 34910732 |
| 179 | CAA56354 | 510876 |
| 180 | DEFBC | 7427668 |
| 181 | JC5967 | 7431234 |
| 182 | NP_197960 | 15239517 |
| 183 | NP_651959 | 21356279 |
| 184 | CAB64263 | 6634090 |
| 185 | BAB20887 | 54606800 |
| 186 | EAL27424 | 54638022 |
| 187 | NP_006671 | 5729920 |
| 188 | AAB08874 | 1561774 |
| 189 | 1PJLH | 33358128 |
| 190 | 1GZ4D | 22218682 |
| 191 | 1QR6B | 5822327 |
| 192 | 1PJ3D | 39654475 |
| 193 | P22178 | 126736 |
| 194 | XP_410305 | 49097690 |
| 195 | AAH22472 | 18490280 |

TABLE 6

Examples of AMP deaminase polypeptides.

| Row | Genbank ACCESSION | Genbank GI |
|---|---|---|
| 1 | AAA34420 | 171053 |
| 2 | XP_446684 | 50288509 |
| 3 | NP_983153 | 45185436 |
| 4 | XP_453337 | 50306727 |
| 5 | EAL02322 | 46443037 |
| 6 | XP_460211 | 50423261 |
| 7 | XP_503822 | 50552824 |
| 8 | XP_413009 | 49131023 |
| 9 | XP_360256 | 39941438 |
| 10 | XP_381547 | 46108978 |
| 11 | XP_330167 | 32419447 |
| 12 | CAB97316 | 16945394 |
| 13 | T50996 | 11359582 |
| 14 | NP_595153 | 19111945 |
| 15 | EAL22226 | 50259553 |
| 16 | XP_402237 | 49076548 |
| 17 | CAA62797 | 995562 |
| 18 | AAF65407 | 7638159 |
| 19 | XP_537039 | 57088163 |
| 20 | AAH49119 | 29145073 |
| 21 | XP_569691 | 58265070 |
| 22 | AAD56303 | 5922018 |
| 23 | NP_004028 | 21264318 |
| 24 | A44313 | 345738 |
| 25 | CAI19307 | 56206061 |
| 26 | AAA62126 | 644509 |
| 27 | CAI19305 | 56206059 |
| 28 | XP_310497 | 58424203 |
| 29 | CAI19306 | 56206060 |
| 30 | AAC50308 | 608499 |
| 31 | CAG06825 | 47229629 |
| 32 | NP_727741 | 45551453 |
| 33 | NP_727739 | 45551452 |
| 34 | NP_727740 | 24641890 |
| 35 | AAN09337 | 22832227 |
| 36 | T01259 | 7484807 |
| 37 | XP_506591 | 51963676 |
| 38 | NP_850294 | 30687456 |
| 39 | CAG07509 | 47228777 |
| 40 | NP_494974 | 32564190 |

TABLE 6-continued

Examples of AMP deaminase polypeptides.

| Row | Genbank ACCESSION | Genbank GI |
|---|---|---|
| 41 | T15771 | 7497030 |
| 42 | CAE59064 | 39596837 |
| 43 | NP_494973 | 32564194 |
| 44 | BAA06505 | 1321635 |
| 45 | NP_000471 | 4502079 |
| 46 | S68147 | 2134756 |
| 47 | AAH56380 | 38614134 |
| 48 | O08739 | 2494043 |
| 49 | NP_113732 | 13928736 |
| 50 | O09178 | 2494044 |
| 51 | XP_420973 | 50747746 |
| 52 | NP_956142 | 41054127 |
| 53 | CAG01709 | 47222742 |
| 54 | NP_957187 | 41053780 |
| 55 | XP_392957 | 48104570 |
| 56 | AAH07183 | 13938134 |
| 57 | CAG05605 | 47220579 |
| 58 | NP_620231 | 20302047 |
| 59 | XP_540247 | 57098851 |
| 60 | CAF99638 | 47230445 |
| 61 | XP_513671 | 55587796 |
| 62 | CAI18828 | 56203368 |
| 63 | CAI18829 | 56203369 |
| 64 | CAI18830 | 56203370 |
| 65 | EAA19931 | 23484684 |
| 66 | CAH99706 | 56500932 |
| 67 | XP_131103 | 38076931 |
| 68 | CAH77387 | 56523366 |

TABLE 7

Examples of acetoacetyl-CoA thiolase polypeptides.

| Row | Genbank ACCESSION | Genbank GI |
|---|---|---|
| 1 | P10551 | 135758 |
| 2 | Q04677 | 418002 |
| 3 | Q12598 | 34925109 |
| 4 | T10247 | 7433657 |
| 5 | T42741 | 11257345 |
| 6 | AAL18924 | 16417944 |
| 7 | AAM67058 | 21618008 |
| 8 | AAO51605 | 28829030 |
| 9 | AAU95618 | 53854350 |
| 10 | AAU95619 | 53854352 |
| 11 | BAA97003 | 8777413 |
| 12 | CAE76429 | 38567134 |
| 13 | EAK90852 | 46431255 |
| 14 | EAL32264 | 54643520 |
| 15 | NP_015297 | 6325229 |
| 16 | NP_568694 | 30695411 |
| 17 | NP_572414 | 24640423 |
| 18 | NP_596686 | 19113478 |
| 19 | NP_851154 | 30695409 |
| 20 | NP_908411 | 34894172 |
| 21 | NP_974900 | 42573608 |
| 22 | NP_974901 | 42573610 |
| 23 | NP_984262 | 45188039 |
| 24 | XP_389497 | 46134945 |
| 25 | XP_401186 | 49074048 |
| 26 | XP_405546 | 49087148 |
| 27 | XP_449306 | 50293789 |
| 28 | XP_449306 | 50293789 |
| 29 | XP_450298 | 50899020 |
| 30 | XP_453599 | 50307241 |
| 31 | XP_460741 | 50424309 |
| 32 | XP_500646 | 50546253 |

TABLE 8

Examples of HMG-CoA synthase polypeptides.

| Row | Genbank ACCESSION | Genbank GI |
|---|---|---|
| 1 | B55729 | 1083370 |
| 2 | P54869 | 1708235 |
| 3 | S13887 | 86312 |
| 4 | S27197 | 284048 |
| 5 | AAA37076 | 387072 |
| 6 | AAF89580 | 9621905 |
| 7 | AAH00297 | 33991031 |
| 8 | AAH31363 | 21618633 |
| 9 | AAH42929 | 27552834 |
| 10 | AAH79694 | 50925193 |
| 11 | AAH83543 | 54035469 |
| 12 | AAO52569 | 28830079 |
| 13 | AAP35966 | 30583443 |
| 14 | BAB23657 | 12836439 |
| 15 | BAC04559 | 21754758 |
| 16 | BAC05233 | 21758044 |
| 17 | CAA52032 | 1772495 |
| 18 | CAC18553 | 11602786 |
| 19 | CAG33131 | 48145817 |
| 20 | CAH92111 | 55730782 |
| 21 | CAI22408 | 56205097 |
| 22 | EAK97451 | 46438115 |
| 23 | EAL25034 | 54635631 |
| 24 | NP_002121 | 54020720 |
| 25 | NP_013580 | 6323509 |
| 26 | NP_032282 | 31560689 |
| 27 | NP_058964 | 8393538 |
| 28 | NP_593859 | 19114771 |
| 29 | NP_666054 | 31981842 |
| 30 | NP_725570 | 24654139 |
| 31 | NP_775117 | 27465521 |
| 32 | NP_957379 | 41055180 |
| 33 | NP_983739 | 45187516 |
| 34 | NP_990742 | 45382279 |
| 35 | NP_999545 | 47523816 |
| 36 | XP_315872 | 58387870 |
| 37 | XP_323241 | 32405256 |
| 38 | XP_368218 | 39973655 |
| 39 | XP_389442 | 46134253 |
| 40 | XP_397202 | 48141273 |
| 41 | XP_402977 | 49078452 |
| 42 | XP_409060 | 49095198 |
| 43 | XP_446972 | 50289085 |
| 44 | XP_453529 | 50307101 |
| 45 | XP_456470 | 50405663 |
| 46 | XP_506052 | 50557288 |
| 47 | XP_513693 | 55587844 |
| 48 | XP_536483 | 57085299 |
| 49 | XP_569805 | 58265298 |
| 50 | XP_571930 | 58269548 |

TABLE 9

Examples of HMG-CoA reductase polypeptides.

| Row | Genbank ACCESSION | Genbank GI |
|---|---|---|
| 1 | A23586 | 90238 |
| 2 | O74164 | 11132850 |
| 3 | P51639 | 1708252 |
| 4 | P54960 | 1708251 |
| 5 | Q12649 | 18276268 |
| 6 | Q29512 | 2495262 |
| 7 | Q9Y7D2 | 11133211 |
| 8 | S30338 | 422383 |
| 9 | S72194 | 7450066 |
| 10 | AAA36989 | 387052 |
| 11 | AAA37077 | 305355 |
| 12 | AAA49740 | 214237 |
| 13 | AAD20975 | 9817458 |

TABLE 9-continued

Examples of HMG-CoA reductase polypeptides.

| Row | Genbank ACCESSION | Genbank GI |
|---|---|---|
| 14 | AAH74197 | 49257596 |
| 15 | AAL09351 | 15824453 |
| 16 | AAO85434 | 29468180 |
| 17 | AAP72015 | 32165622 |
| 18 | AAR02862 | 45272118 |
| 19 | AAT92819 | 51013051 |
| 20 | BAC20567 | 23574646 |
| 21 | CAA63970 | 4376229 |
| 22 | CAE47850 | 41581201 |
| 23 | CAF92135 | 47213283 |
| 24 | CAH92577 | 55731745 |
| 25 | EAK94577 | 46435190 |
| 26 | EAL20195 | 50257490 |
| 27 | AAF80374 | 8886086 |
| 28 | NP_013555 | 6323483 |
| 29 | NP_013636 | 6323565 |
| 30 | NP_032281 | 56119096 |
| 31 | NP_037266 | 40538852 |
| 32 | NP_588235 | 19075735 |
| 33 | NP_985010 | 45190756 |
| 34 | NP_989816 | 45383193 |
| 35 | NP_999724 | 47551099 |
| 36 | XP_324892 | 32408825 |
| 37 | XP_364130 | 39955070 |
| 38 | XP_389373 | 46134115 |
| 39 | XP_400629 | 49072680 |
| 40 | XP_405730 | 49087632 |
| 41 | XP_407954 | 49092986 |
| 42 | XP_449268 | 50293713 |
| 43 | XP_451740 | 50303597 |
| 44 | XP_458872 | 50420671 |
| 45 | XP_503558 | 50552167 |
| 46 | XP_536323 | 57084803 |
| 47 | XP_571450 | 58268588 |

TABLE 10

Examples of mevalonate kinase polypeptides.

| Row | Genbank ACCESSION | Genbank GI |
|---|---|---|
| 1 | XP_386088 | 46123069 |
| 2 | XP_408006 | 49093090 |
| 3 | XP_370449 | 39978123 |
| 4 | EAL04797 | 46445529 |
| 5 | XP_322935 | 32404644 |
| 6 | NP_001007 | 55925207 |
| 7 | XP_460851 | 50424525 |
| 8 | XP_567851 | 58260882 |
| 9 | XP_567850 | 58260880 |
| 10 | AAQ02416 | 33303805 |
| 11 | CAA53059 | 450346 |
| 12 | AAH16140 | 16359371 |
| 13 | AAH05606 | 13542811 |
| 14 | XP_403111 | 49078786 |
| 15 | XP_452532 | 50305147 |
| 16 | CAG08527 | 47226511 |
| 17 | XP_446138 | 50287417 |
| 18 | AAO51522 | 28828936 |
| 19 | NP_985191 | 45190937 |
| 20 | XP_500956 | 50546973 |
| 21 | NP_013935 | 6323864 |
| 22 | AAD45421 | 5578718 |
| 23 | NP_920723 | 37532842 |
| 24 | NP_851084 | 30690651 |
| 25 | AAL18925 | 16417946 |
| 26 | NP_788338 | 28573850 |
| 27 | AAU20834 | 51988124 |
| 28 | AAU87813 | 52839819 |
| 29 | AAU20835 | 51988125 |
| 30 | YP_183887 | 57641409 |
| 31 | NP_143478 | 14591399 |
| 32 | BAA24409 | 2804172 |
| 33 | NP_126232 | 14520757 |
| 34 | XP_522574 | 55639331 |
| 35 | NP_071114 | 11499870 |
| 36 | XP_423949 | 50797461 |
| 37 | NP_633786 | 21227864 |
| 38 | ZP_002971 | 48840229 |
| 39 | EAH50787 | 44170778 |
| 40 | NP_615566 | 20089491 |
| 41 | 1VISA | 40890012 |
| 42 | EAK03559 | 44549994 |
| 43 | NP_248080 | 15669275 |
| 44 | 1KKHA | 20150886 |
| 45 | Q50559 | 2497518 |
| 46 | CAF88123 | 47200914 |
| 47 | NP_275189 | 15678075 |
| 48 | EAI88745 | 44383877 |
| 49 | ZP_002040 | 46141948 |
| 50 | XP_543435 | 57105916 |
| 51 | EAI38920 | 44313360 |
| 52 | NP_148611 | 14602065 |
| 53 | EAD08953 | 43286228 |
| 54 | EAD45697 | 43361720 |
| 55 | YP_134862 | 55377012 |
| 56 | NP_720650 | 24378695 |
| 57 | NP_614276 | 20094429 |
| 58 | E84270 | 25409931 |
| 59 | NP_691146 | 23097680 |
| 60 | ZP_003233 | 48870579 |
| 61 | AAG02440 | 9937386 |
| 62 | EAD12278 | 43292898 |
| 63 | NP_498328 | 17555862 |
| 64 | EAB31483 | 42928976 |
| 65 | ZP_003319 | 50590618 |
| 66 | NP_814642 | 29375488 |
| 67 | AC1434 | 25514495 |
| 68 | ZP_003577 | 53796847 |
| 69 | EAD82048 | 43454743 |
| 70 | CAE73618 | 39586491 |
| 71 | YP_012624 | 46906235 |
| 72 | NP_988455 | 45358898 |
| 73 | ZP_002348 | 47097293 |
| 74 | ZP_002862 | 48824993 |
| 75 | ZP_002307 | 47093020 |
| 76 | NP_597102 | 19173299 |
| 77 | CAD24422 | 20429111 |
| 78 | NP_785308 | 28378416 |
| 79 | EAA39098 | 29247539 |
| 80 | NP_819638 | 29653946 |
| 81 | EAH49746 | 44168765 |
| 82 | EAH49745 | 44168764 |
| 83 | NP_378182 | 15922513 |
| 84 | ZP_000459 | 23002259 |
| 85 | H90181 | 25393827 |
| 86 | YP_054120 | 50405028 |
| 87 | BAB07790 | 9695270 |
| 88 | AAG02435 | 9937379 |
| 89 | NP_560495 | 18313828 |
| 90 | YP_187834 | 57866187 |
| 91 | EAK40782 | 44602942 |
| 92 | CAC51370 | 15212070 |
| 93 | AAG02424 | 9937364 |
| 94 | YP_185521 | 57651465 |
| 95 | YP_040044 | 49482820 |
| 96 | YP_194037 | 58337452 |
| 97 | D86675 | 25400965 |
| 98 | NP_763916 | 27467279 |
| 99 | CAF89434 | 47197810 |
| 100 | EAF38333 | 43767792 |
| 101 | EAK46841 | 44611394 |
| 102 | H89827 | 25507776 |
| 103 | ZP_003149 | 48861061 |

TABLE 10-continued

Examples of mevalonate kinase polypeptides.

| Row | Genbank ACCESSION | Genbank GI |
|---|---|---|
| 104 | EAK17824 | 44570143 |
| 105 | EAH86276 | 44235719 |
| 106 | YP_118418 | 54024176 |
| 107 | ZP_003196 | 48865749 |
| 108 | AAG02430 | 9937372 |
| 109 | NP_269075 | 15674901 |
| 110 | NP_802520 | 28896170 |
| 111 | AAL97579 | 19748102 |
| 112 | ZP_003666 | 56808907 |
| 113 | NP_965060 | 42519130 |
| 114 | NP_819639 | 29653947 |
| 115 | EAD97024 | 43484567 |
| 116 | BAD86800 | 57753870 |

TABLE 11

Examples of phosphomevalonate kinase polypeptides.

| Row | Genbank ACCESSION | Genbank GI |
|---|---|---|
| 1 | AAA34596 | 171479 |
| 2 | XP_452514 | 50305111 |
| 3 | NP_985210 | 45190956 |
| 4 | XP_446144 | 50287429 |
| 5 | XP_462340 | 50427455 |
| 6 | EAL04096 | 46444824 |
| 7 | EAL03941 | 46444668 |
| 8 | XP_503619 | 50552418 |
| 9 | XP_389940 | 46136497 |
| 10 | XP_329795 | 32418634 |
| 11 | XP_369652 | 39976529 |
| 12 | XP_406448 | 49089559 |
| 13 | NP_593421 | 19114333 |
| 14 | XP_568385 | 58261950 |
| 15 | EAL17628 | 50254887 |
| 16 | AAL18926 | 16417948 |
| 17 | BAD43274 | 51969164 |
| 18 | BAD44652 | 51971975 |
| 19 | XP_398375 | 49068172 |
| 20 | BAD44486 | 51971643 |
| 21 | F90479 | 25393214 |
| 22 | YP_194039 | 58337454 |

TABLE 12

Examples of mevalonate pyrophosphate decarboxylase polypeptides.

| Row | Genbank ACCESSION | Genbank GI |
|---|---|---|
| 1 | AAT93171 | 51013755 |
| 2 | 1FI4A | 13786942 |
| 3 | XP_455548 | 50311049 |
| 4 | XP_445335 | 50285813 |
| 5 | XP_456912 | 50409853 |
| 6 | NP_986435 | 45200865 |
| 7 | AAF19399 | 6625790 |
| 8 | XP_328845 | 32416734 |
| 9 | XP_505041 | 50555265 |
| 10 | NP_594027 | 19114939 |
| 11 | XP_364905 | 39963452 |
| 12 | XP_390600 | 46137817 |
| 13 | XP_408551 | 49094180 |
| 14 | AAA34506 | 7544604 |
| 15 | EAL18927 | 50256200 |
| 16 | XP_568247 | 58261674 |
| 17 | XP_402794 | 49077992 |
| 18 | AAH81784 | 51980639 |

TABLE 12-continued

Examples of mevalonate pyrophosphate decarboxylase polypeptides.

| Row | Genbank ACCESSION | Genbank GI |
|---|---|---|
| 19 | EAL00166 | 46440864 |
| 20 | NP_619597 | 20149736 |
| 21 | NP_112324 | 13592005 |
| 22 | BAC40852 | 26354448 |
| 23 | XP_546783 | 57087071 |
| 24 | Q99JF5 | 23814095 |
| 25 | AAH63907 | 39645379 |
| 26 | CAF99534 | 47230341 |
| 27 | AAP35576 | 30582699 |
| 28 | AAP36301 | 30584105 |
| 29 | AAL18927 | 16417950 |
| 30 | AAV32433 | 54292590 |
| 31 | AAP68208 | 31711704 |
| 32 | AAM64988 | 21593039 |
| 33 | NP_566995 | 18410026 |
| 34 | XP_423130 | 50771155 |
| 35 | AAM65192 | 21593243 |
| 36 | NP_001007 | 55925435 |
| 37 | NP_573068 | 28571205 |
| 38 | BAD27942 | 50252009 |
| 39 | T47584 | 11281655 |
| 40 | XP_307373 | 31196851 |
| 41 | CAE73245 | 39591192 |
| 42 | NP_496966 | 17537201 |
| 43 | XP_393230 | 48121058 |
| 44 | G90479 | 25393662 |
| 45 | NP_496967 | 17537203 |
| 46 | NP_691147 | 23097681 |
| 47 | EAL29282 | 54640164 |
| 48 | AD1434 | 25515042 |
| 49 | ZP_002308 | 47093021 |
| 50 | YP_012625 | 46906236 |
| 51 | ZP_002348 | 47097294 |
| 52 | NP_819637 | 29653945 |
| 53 | NP_376888 | 15921219 |
| 54 | ZP_003319 | 50590617 |
| 55 | NP_585805 | 19074299 |
| 56 | YP_187835 | 57866188 |
| 57 | CAD24423 | 20429112 |
| 58 | AAG02431 | 9937373 |
| 59 | NP_763917 | 27467280 |
| 60 | AAG02446 | 9937394 |
| 61 | ZP_002863 | 48824994 |
| 62 | AAG02441 | 9937387 |
| 63 | YP_185522 | 57651466 |
| 64 | A89828 | 25505863 |
| 65 | NP_814641 | 29375487 |
| 66 | YP_040045 | 49482821 |
| 67 | NP_785307 | 28378415 |
| 68 | ZP_003196 | 48865750 |
| 69 | ZP_003233 | 48870580 |
| 70 | E86675 | 25400967 |
| 71 | EAE31110 | 43552684 |
| 72 | BAB07791 | 9695271 |
| 73 | CAC51371 | 15212071 |
| 74 | ZP_000459 | 23002258 |
| 75 | NP_965061 | 42519131 |
| 76 | BAD86801 | 57753871 |
| 77 | YP_194038 | 58337453 |
| 78 | YP_118419 | 54024177 |
| 79 | EAK18820 | 44571499 |
| 80 | EAI85935 | 44379784 |
| 81 | NP_721336 | 24379381 |
| 82 | D95044 | 25388338 |
| 83 | AAG02456 | 9937408 |
| 84 | C97914 | 25511486 |
| 85 | EAK47683 | 44612560 |
| 86 | EAB86425 | 43039778 |
| 87 | YP_140971 | 55822530 |
| 88 | YP_139081 | 55820639 |
| 89 | BAD07376 | 40882372 |
| 90 | NP_968512 | 42523132 |
| 91 | EAI06705 | 44265427 |
| 92 | YP_060018 | 50914046 |

TABLE 12-continued

Examples of mevalonate pyrophosphate decarboxylase polypeptides.

| Row | Genbank ACCESSION | Genbank GI |
|---|---|---|
| 93 | AAG02451 | 9937401 |
| 94 | NP_269076 | 15674902 |
| 95 | ZP_003666 | 56808906 |
| 96 | NP_688323 | 22537472 |
| 97 | NP_735832 | 25011437 |
| 98 | EAC40267 | 43149093 |
| 99 | AAL97580 | 19748103 |
| 100 | EAI76915 | 44367119 |
| 101 | EAD35042 | 43339207 |
| 102 | YP_073129 | 51598941 |
| 103 | EAI90092 | 44385501 |
| 104 | BAB07818 | 9711347 |
| 105 | EAD72850 | 43433025 |
| 106 | NP_212820 | 15595031 |
| 107 | YP_124337 | 54297968 |
| 108 | YP_096056 | 52842257 |
| 109 | EAA39903 | 29248368 |
| 110 | EAH06252 | 44088237 |
| 111 | YP_127354 | 54294939 |
| 112 | EAD45753 | 43361830 |
| 113 | NP_802519 | 28896169 |

TABLE 13

Examples of IPP isomerase polypeptides.

| Row | Genbank ACCESSION | Genbank GI |
|---|---|---|
| 1 | NP_015208 | 6325140 |
| 2 | XP_448008 | 50291151 |
| 3 | NP_983828 | 45187605 |
| 4 | XP_455121 | 50310203 |
| 5 | XP_462358 | 50427491 |
| 6 | EAL01685 | 46442395 |
| 7 | XP_504974 | 50555131 |
| 8 | XP_328425 | 32415894 |
| 9 | XP_367200 | 39971619 |
| 10 | XP_389898 | 46136413 |
| 11 | XP_404716 | 49085144 |
| 12 | CAD37150 | 21627818 |
| 13 | NP_595164 | 19111956 |
| 14 | XP_566641 | 58258457 |
| 15 | XP_402453 | 49077100 |
| 16 | O35586 | 6225528 |
| 17 | AAP36609 | 30584713 |
| 18 | AAF37873 | 7188790 |
| 19 | NP_445991 | 16758306 |
| 20 | O42641 | 6225529 |
| 21 | BAA33979 | 3790386 |
| 22 | Q13907 | 6225527 |
| 23 | AAH22418 | 48257241 |
| 24 | AAH19227 | 48257312 |
| 25 | AAH57827 | 35505325 |
| 26 | NP_004499 | 40018633 |
| 27 | AAH89786 | 58477715 |
| 28 | CAH91844 | 55730243 |
| 29 | XP_418561 | 50732281 |
| 30 | AAH06999 | 48257093 |
| 31 | CAF98782 | 47225155 |
| 32 | NP_808875 | 29366820 |
| 33 | XP_507622 | 55633353 |
| 34 | AAH82648 | 52139082 |
| 35 | NP_001011 | 58332496 |
| 36 | AAF29976 | 6856556 |
| 37 | AAG10423 | 9971806 |
| 38 | O48964 | 6225525 |
| 39 | AAF29973 | 6856550 |
| 40 | AAF29977 | 6856558 |
| 41 | AAQ84167 | 35186998 |
| 42 | AAF29974 | 6856552 |

TABLE 13-continued

Examples of IPP isomerase polypeptides.

| Row | Genbank ACCESSION | Genbank GI |
|---|---|---|
| 43 | Q39472 | 6225526 |
| 44 | S49588 | 1085973 |
| 45 | AAL91980 | 19568939 |
| 46 | BAB40973 | 13603406 |
| 47 | AAF29975 | 6856554 |
| 48 | T52027 | 25493162 |
| 49 | AAL91979 | 19568937 |
| 50 | T46812 | 11362218 |
| 51 | T51248 | 11362217 |
| 52 | BAB40974 | 13603408 |
| 53 | O48965 | 6225532 |
| 54 | XP_225509 | 34877710 |
| 55 | XP_506401 | 51963472 |
| 56 | AAF29978 | 6856560 |
| 57 | AAH76541 | 50369278 |
| 58 | AAT94033 | 51038230 |
| 59 | XP_225502 | 34876517 |
| 60 | Q39471 | 6225533 |
| 61 | AAB67743 | 1213450 |
| 62 | NP_197148 | 22326844 |
| 63 | BAB09611 | 9759126 |
| 64 | AAD41766 | 5305669 |
| 65 | AAB67741 | 1213442 |
| 66 | XP_395125 | 48101420 |
| 67 | AAN28784 | 23505849 |
| 68 | AAF36996 | 7110585 |
| 69 | BAB16690 | 15289752 |
| 70 | AAQ14869 | 33340598 |
| 71 | BAC65421 | 28971819 |
| 72 | S71369 | 2129625 |
| 73 | AAF29979 | 6856562 |
| 74 | AAF29980 | 6856564 |
| 75 | AAP21674 | 30267831 |
| 76 | Q39664 | 6225534 |
| 77 | NP_650962 | 24648688 |
| 78 | AAM50284 | 21429130 |
| 79 | XP_321388 | 58395620 |
| 80 | Q9BXS1 | 20978506 |
| 81 | T07979 | 7484383 |
| 82 | XP_225508 | 34876527 |
| 83 | AAT92102 | 51011386 |
| 84 | XP_225507 | 34876555 |
| 85 | XP_344623 | 34876537 |
| 86 | S44843 | 630677 |
| 87 | XP_225498 | 27687955 |
| 88 | AAT08468 | 47013849 |
| 89 | EAI79636 | 44370808 |
| 90 | CAE75055 | 39587401 |
| 91 | EAL04047 | 46444775 |
| 92 | XP_225528 | 34876543 |
| 93 | XP_544282 | 57040602 |
| 94 | XP_225511 | 27688013 |
| 95 | P26173 | 114853 |
| 96 | EAJ04069 | 44405322 |
| 97 | EAH27496 | 44127513 |
| 98 | AAF91499 | 9653280 |
| 99 | AAM48661 | 21328655 |
| 100 | EAK17826 | 44570145 |
| 101 | EAD59515 | 43391069 |
| 102 | YP_128702 | 54307682 |
| 103 | EAK66656 | 44639203 |
| 104 | YP_118189 | 54023947 |
| 105 | T50740 | 11282665 |
| 106 | ZP_002077 | 46193541 |
| 107 | EAK16470 | 44568229 |
| 108 | YP_165403 | 56695056 |
| 109 | EAD08775 | 43285885 |
| 110 | YP_195623 | 58616494 |
| 111 | EAI38918 | 44313358 |
| 112 | NP_930583 | 37527239 |
| 113 | YP_160254 | 56478665 |
| 114 | EAH69842 | 44206571 |
| 115 | EAK26254 | 44582307 |
| 116 | AAR24381 | 38569721 |

TABLE 13-continued

Examples of IPP isomerase polypeptides.

| Row | Genbank ACCESSION | Genbank GI |
|---|---|---|
| 117 | AAM48607 | 21328600 |
| 118 | EAD82049 | 43454744 |
| 119 | ZP_001924 | 45914126 |
| 120 | YP_056780 | 50843553 |
| 121 | YP_050880 | 50121713 |
| 122 | EAF29235 | 43749645 |
| 123 | NP_630823 | 21225044 |
| 124 | Q82MJ7 | 34582349 |
| 125 | ZP_003374 | 52010110 |
| 126 | AAS75819 | 45737905 |
| 127 | Q8KP37 | 30913023 |
| 128 | XP_507621 | 55633351 |
| 129 | XP_344621 | 34876521 |
| 130 | XP_346322 | 34880719 |
| 131 | YP_152060 | 56414985 |
| 132 | AAT42442 | 48429280 |
| 133 | Q9KK75 | 13878536 |
| 134 | NP_806649 | 29143307 |
| 135 | YP_063124 | 50955836 |
| 136 | Q8FND7 | 46395593 |
| 137 | CAF20647 | 41326485 |
| 138 | Q8NN99 | 23821718 |
| 139 | Q7X5H2 | 46395586 |
| 140 | NP_336246 | 15841209 |
| 141 | Q83MJ9 | 46395588 |
| 142 | P60923 | 46395576 |
| 143 | Q8FE75 | 31563050 |
| 144 | 1R67A | 38493022 |
| 145 | Q9KWD1 | 13878537 |
| 146 | Q7VEU0 | 46395585 |
| 147 | B84333 | 25410326 |
| 148 | NP_417365 | 16130791 |
| 149 | E85944 | 25355426 |
| 150 | 1HZTA | 15826050 |
| 151 | 1PVFB | 50513321 |
| 152 | EAD63579 | 43403471 |
| 153 | 1I9AB | 13786886 |
| 154 | YP_012992 | 46906603 |
| 155 | ZP_002293 | 47091503 |
| 156 | EAI37194 | 44310821 |
| 157 | YP_137864 | 55380014 |
| 158 | CAD92056 | 42516867 |
| 159 | 1OW2B | 42543244 |

TABLE 14

Examples of FPP synthase polypeptides.

| Row | Genbank ACCESSION | Genbank GI |
|---|---|---|
| 1 | Q92250 | 2497455 |
| 2 | XP_363065 | 39948036 |
| 3 | XP_386960 | 46124813 |
| 4 | Q92235 | 3122099 |
| 5 | XP_412149 | 49116518 |
| 6 | XP_503599 | 50552378 |
| 7 | NP_593299 | 19114211 |
| 8 | CAD42869 | 21955860 |
| 9 | XP_448787 | 50292709 |
| 10 | NP_012368 | 6322294 |
| 11 | T42081 | 7433997 |
| 12 | EAK93751 | 46434339 |
| 13 | XP_451300 | 50302727 |
| 14 | XP_571137 | 58267962 |
| 15 | XP_460720 | 50424267 |
| 16 | NP_984739 | 45190485 |
| 17 | BAD15361 | 46367743 |
| 18 | S71433 | 7433991 |
| 19 | CAA65643 | 1523990 |
| 20 | XP_399061 | 49069544 |

TABLE 14-continued

Examples of FPP synthase polypeptides.

| Row | Genbank ACCESSION | Genbank GI |
|---|---|---|
| 21 | S71432 | 7433990 |
| 22 | AAH68912 | 46249832 |
| 23 | 1FPS | 1065289 |
| 24 | P08836 | 3915686 |
| 25 | AAH83515 | 53733369 |
| 26 | 1UBX | 1942050 |
| 27 | 1UBY | 1942051 |
| 28 | AAF37872 | 7188788 |
| 29 | NP_803463 | 29135293 |
| 30 | AAK63847 | 14488053 |
| 31 | AAV58896 | 55710092 |
| 32 | T06272 | 7433988 |
| 33 | JC4846 | 2117737 |
| 34 | P05369 | 120478 |
| 35 | O24241 | 25452945 |
| 36 | O24242 | 25452946 |
| 37 | AAH59125 | 37590777 |
| 38 | AAH48497 | 28913418 |
| 39 | AAP74720 | 32329199 |
| 40 | CAG11850 | 47225367 |
| 41 | AAM51429 | 21436457 |
| 42 | AAP74719 | 32329197 |
| 43 | AAM08927 | 20135548 |
| 44 | XP_537252 | 57089113 |
| 45 | AAQ56011 | 34013692 |
| 46 | AAQ14872 | 33340604 |
| 47 | AAQ14871 | 33340602 |
| 48 | AAD17204 | 4324960 |
| 49 | AAH87886 | 56789674 |
| 50 | AAK68152 | 14573639 |
| 51 | AAA52423 | 182399 |
| 52 | S66470 | 2129849 |
| 53 | CAA29064 | 4725 |
| 54 | CAI12715 | 55957735 |
| 55 | BAA03523 | 40788949 |
| 56 | P14324 | 1346031 |
| 57 | S66471 | 2129850 |
| 58 | AAA35820 | 182405 |
| 59 | CAA59170 | 1491641 |
| 60 | BAB16687 | 15289750 |
| 61 | CAA72793 | 1922251 |
| 62 | CAH91070 | 55728661 |
| 63 | AAK58594 | 14279425 |
| 64 | AAB07264 | 1146159 |
| 65 | Q09152 | 21431776 |
| 66 | O64905 | 6016044 |
| 67 | BAB60822 | 14422406 |
| 68 | S52009 | 1076319 |
| 69 | NP_917118 | 34911542 |
| 70 | AAD32648 | 4894899 |
| 71 | AAA40960 | 203582 |
| 72 | AAR27053 | 38684029 |
| 73 | AAU43998 | 52353430 |
| 74 | AAL82595 | 18958450 |
| 75 | NP_917069 | 34911444 |
| 76 | XP_228802 | 34879769 |
| 77 | BAD81810 | 56785155 |
| 78 | AAN62522 | 24796660 |
| 79 | NP_595334 | 19112126 |
| 80 | T52066 | 25458583 |
| 81 | AAL49067 | 17946048 |
| 82 | CAA08919 | 3395483 |
| 83 | XP_547662 | 57089869 |
| 84 | EAL26135 | 54636732 |
| 85 | BAB60821 | 14422404 |
| 86 | AAP74721 | 32329201 |
| 87 | XP_496902 | 51466663 |
| 88 | XP_474182 | 50929309 |
| 89 | CAA87327 | 1160178 |
| 90 | BAD20729 | 47776234 |
| 91 | BAC53873 | 30984142 |
| 92 | BAB69490 | 15991313 |
| 93 | NP_974565 | 42572937 |
| 94 | CAA08918 | 5678609 |

TABLE 14-continued

Examples of FPP synthase polypeptides.

| Row | Genbank ACCESSION | Genbank GI |
|---|---|---|
| 95 | AAP86267 | 32527731 |
| 96 | AAO17735 | 30522953 |
| 97 | AAK71861 | 14647139 |
| 98 | AAL73357 | 18478919 |
| 99 | AAO63552 | 29124957 |
| 100 | CAI00471 | 56498227 |
| 101 | NP_701155 | 23508486 |
| 102 | XP_474180 | 50929305 |
| 103 | AAL73358 | 18478922 |
| 104 | EAH48995 | 44167328 |
| 105 | NP_493027 | 17508563 |
| 106 | CAE71711 | 39580204 |
| 107 | XP_487220 | 51766977 |

TABLE 15

Examples of GGPP synthase polypetides.

| Row | Genbank ACCESSION | Genbank GI |
|---|---|---|
| 1 | AAT92871 | 51013155 |
| 2 | XP_447025 | 50289191 |
| 3 | NP_984623 | 45190369 |
| 4 | XP_390273 | 46137163 |
| 5 | XP_404791 | 49085320 |
| 6 | XP_368486 | 39974191 |
| 7 | Q92236 | 6831550 |
| 8 | AAO85432 | 29468176 |
| 9 | XP_572774 | 58271236 |
| 10 | XP_502923 | 50550901 |
| 11 | AAK11525 | 13021716 |
| 12 | XP_326920 | 32412880 |
| 13 | CAF32032 | 42820719 |
| 14 | BAD29965 | 50355599 |
| 15 | XP_384767 | 46117498 |
| 16 | BAD29970 | 50355631 |
| 17 | CAB89115 | 7649674 |
| 18 | CAG09545 | 47229030 |
| 19 | CAI13753 | 55960163 |
| 20 | AAH69913 | 47124116 |
| 21 | AAH67768 | 45709211 |
| 22 | XP_455003 | 50309979 |
| 23 | P56966 | 9296978 |
| 24 | NP_001007 | 56090562 |
| 25 | AAT65717 | 49409613 |
| 26 | NP_956329 | 41053321 |
| 27 | BAA90525 | 6899844 |
| 28 | XP_405729 | 49087630 |
| 29 | AAK11531 | 13021724 |
| 30 | XP_412280 | 49119197 |
| 31 | AAC05273 | 2944400 |
| 32 | NP_523958 | 24660002 |
| 33 | XP_402074 | 49076128 |
| 34 | EAL30191 | 54641441 |
| 35 | XP_536340 | 57084951 |
| 36 | XP_424685 | 50811194 |
| 37 | AAH06798 | 13905030 |
| 38 | AAP06018 | 29841005 |
| 39 | XP_460338 | 50423511 |
| 40 | AAC05595 | 2957271 |
| 41 | EAK92197 | 46432727 |
| 42 | XP_535573 | 57108760 |
| 43 | AAH83212 | 53734594 |
| 44 | XP_486466 | 51827552 |
| 45 | CAH18006 | 51469024 |
| 46 | CAA75568 | 3549881 |
| 47 | XP_397455 | 48143654 |
| 48 | XP_410947 | 49101294 |
| 49 | XP_381914 | 46109712 |
| 50 | XP_364478 | 39959279 |

TABLE 15-continued

Examples of GGPP synthase polypetides.

| Row | Genbank ACCESSION | Genbank GI |
|---|---|---|
| 51 | XP_360889 | 39942704 |
| 52 | XP_369218 | 39975655 |
| 53 | XP_406544 | 49089926 |
| 54 | XP_367595 | 39972409 |
| 55 | XP_363775 | 39952117 |
| 56 | XP_368486 | 39974191 |
| 57 | XP_390273 | 46137163 |
| 58 | Q92236 | 6831550 |
| 59 | AAK11525 | 13021716 |
| 60 | CAF32032 | 42820719 |
| 61 | XP_404791 | 49085320 |
| 62 | AAO85432 | 29468176 |
| 63 | BAD29965 | 50355599 |
| 64 | BAD29970 | 50355631 |
| 65 | BAA90525 | 6899844 |
| 66 | AAT65717 | 49409613 |
| 67 | XP_384767 | 46117498 |
| 68 | CAB89115 | 7649674 |
| 69 | XP_572774 | 58271236 |
| 70 | AAK11531 | 13021724 |
| 71 | XP_502923 | 50550901 |
| 72 | CAI13753 | 55960163 |
| 73 | CAG09545 | 47229030 |
| 74 | XP_412280 | 49119197 |
| 75 | P56966 | 9296978 |
| 76 | NP_001007 | 56090562 |
| 77 | AAH69913 | 47124116 |
| 78 | AAH67768 | 45709211 |
| 79 | NP_956329 | 41053321 |
| 80 | EAL30191 | 54641441 |
| 81 | XP_424685 | 50811194 |
| 82 | XP_536340 | 57084951 |
| 83 | NP_523958 | 24660002 |
| 84 | AAC05273 | 2944400 |
| 85 | XP_405729 | 49087630 |
| 86 | AAC05595 | 2957271 |
| 87 | XP_402074 | 49076128 |
| 88 | AAP06018 | 29841005 |
| 89 | AAH06798 | 13905030 |
| 90 | XP_535573 | 57108760 |
| 91 | AAH83212 | 53734594 |
| 92 | AAP21085 | 30097620 |
| 93 | NP_984623 | 45190369 |
| 94 | XP_447025 | 50289191 |
| 95 | AAT92871 | 51013155 |
| 96 | XP_486466 | 51827552 |
| 97 | XP_410947 | 49101294 |
| 98 | XP_397455 | 48143654 |
| 99 | XP_455003 | 50309979 |
| 100 | EAK92197 | 46432727 |
| 101 | XP_381914 | 46109712 |
| 102 | XP_460338 | 50423511 |
| 103 | CAH18006 | 51469024 |
| 104 | XP_360889 | 39942704 |
| 105 | XP_406544 | 49089926 |
| 106 | XP_364478 | 39959279 |
| 107 | XP_363775 | 39952117 |
| 108 | XP_367595 | 39972409 |
| 109 | XP_369218 | 39975655 |
| 110 | C39273 | 483124 |
| 111 | BAB79600 | 18143445 |
| 112 | BAA14124 | 216682 |
| 113 | AAN85596 | 27228290 |
| 114 | AAA32797 | 413730 |
| 115 | Q08291 | 585326 |
| 116 | S52584 | 1073293 |
| 117 | S53722 | 1076576 |
| 118 | AAC44848 | 1842242 |
| 119 | BAA19583 | 1944371 |
| 120 | S71230 | 2129674 |
| 121 | BAA23157 | 2578822 |
| 122 | AAC77874 | 3885426 |
| 123 | CAB38744 | 4490594 |
| 124 | BAA78047 | 4958920 |

TABLE 15-continued

Examples of GGPP synthase polypetides.

| Row | Genbank ACCESSION | Genbank GI |
|---|---|---|
| 125 | BAA82613 | 5631295 |
| 126 | CAB56064 | 5912297 |
| 127 | BAA86284 | 6277254 |
| 128 | T11021 | 7447356 |
| 129 | AAF78199 | 8650415 |
| 130 | AAG10424 | 9971808 |
| 131 | CAC10561 | 10637876 |
| 132 | T50879 | 11279298 |
| 133 | BAB01343 | 11994221 |
| 134 | Q42698 | 13431546 |
| 135 | Q43133 | 13431547 |
| 136 | P54976 | 13878921 |
| 137 | BAB50600 | 14023995 |
| 138 | BAB60678 | 14325238 |
| 139 | BAB60820 | 14422402 |
| 140 | NP_189589 | 15228704 |
| 141 | NP_188651 | 15231055 |
| 142 | NP_188069 | 15231869 |
| 143 | NP_188073 | 15231881 |
| 144 | AAL01997 | 15553715 |
| 145 | AAL01998 | 15553717 |
| 146 | NP_252732 | 15599238 |
| 147 | NP_245470 | 15602398 |
| 148 | NP_390308 | 16079484 |
| 149 | NP_440010 | 16329282 |
| 150 | NP_440010 | 16329282 |
| 151 | AAL17614 | 17352451 |
| 152 | NP_520343 | 17546941 |
| 153 | AAL76349 | 18645048 |
| 154 | AAM21638 | 20386366 |
| 155 | AAM21639 | 20386368 |
| 156 | NP_622916 | 20807745 |
| 157 | AAM48650 | 21328644 |
| 158 | NP_659794 | 21492720 |
| 159 | AAM64496 | 21592547 |
| 160 | AAM65107 | 21593158 |
| 161 | NP_680811 | 22297564 |
| 162 | ZP_000474 | 23003800 |
| 163 | ZP_001252 | 23469933 |
| 164 | NP_698760 | 23502633 |
| 165 | E84566 | 25313373 |
| 166 | F85434 | 25313385 |
| 167 | AC1245 | 25313389 |
| 168 | E83997 | 25313393 |
| 169 | G84566 | 25313395 |
| 170 | AH2910 | 25315863 |
| 171 | D87505 | 25398795 |
| 172 | A89932 | 25505949 |
| 173 | F97685 | 25520741 |
| 174 | AI3285 | 25527013 |
| 175 | BAC42571 | 26450928 |
| 176 | NP_785195 | 28378303 |
| 177 | NP_790546 | 28867927 |
| 178 | AAO63392 | 28950937 |
| 179 | AAO93113 | 29893480 |
| 180 | NP_833891 | 30022260 |
| 181 | AAP59037 | 31621279 |
| 182 | ZP_001374 | 32039216 |
| 183 | NP_864766 | 32471772 |
| 184 | NP_875521 | 33240579 |
| 185 | NP_881399 | 33593755 |
| 186 | NP_884694 | 33597051 |
| 187 | NP_888456 | 33600896 |
| 188 | NP_893187 | 33861626 |
| 189 | NP_894940 | 33863380 |
| 190 | NP_896835 | 33865276 |
| 191 | NP_896835 | 33865276 |
| 192 | AAQ65086 | 34365549 |
| 193 | NP_945877 | 39933601 |
| 194 | NP_946867 | 39934591 |
| 195 | NP_952815 | 39996864 |
| 196 | AAR37805 | 40062934 |
| 197 | AAR37858 | 40062988 |
| 198 | AAR98495 | 41018904 |
| 199 | AAR99082 | 41059107 |
| 200 | NP_965349 | 42519419 |
| 201 | NP_980544 | 42783297 |
| 202 | EAA96348 | 42858148 |
| 203 | EAB36506 | 42939031 |
| 204 | EAB36642 | 42939300 |
| 205 | EAC39208 | 43146996 |
| 206 | EAD26007 | 43320598 |
| 207 | EAE43084 | 43576643 |
| 208 | EAE70061 | 43630884 |
| 209 | EAF70308 | 43832107 |
| 210 | EAG88494 | 44055952 |
| 211 | EAH52060 | 44173220 |
| 212 | EAH78354 | 44221788 |
| 213 | EAH84117 | 44231960 |
| 214 | EAI11762 | 44272832 |
| 215 | EAI49391 | 44328289 |
| 216 | EAI54846 | 44336042 |
| 217 | EAI68356 | 44355138 |
| 218 | EAI68713 | 44355672 |
| 219 | EAI69401 | 44356609 |
| 220 | EAI73873 | 44362658 |
| 221 | EAJ73634 | 44506168 |
| 222 | EAJ77351 | 44511694 |
| 223 | EAK70639 | 44644254 |
| 224 | ZP_001751 | 45523854 |
| 225 | AAS76253 | 45752710 |
| 226 | ZP_001957 | 45916757 |
| 227 | 1RTRB | 46015556 |
| 228 | ZP_001863 | 46105954 |
| 229 | ZP_002002 | 46107045 |
| 230 | ZP_001711 | 46132567 |
| 231 | ZP_002073 | 46192680 |
| 232 | ZP_002074 | 46192861 |
| 233 | AAS82860 | 46241274 |
| 234 | ZP_002108 | 46308696 |
| 235 | YP_010568 | 46579760 |
| 236 | BAD18313 | 47076770 |
| 237 | ZP_002315 | 47093750 |
| 238 | ZP_002335 | 47095946 |
| 239 | AAT35222 | 47531118 |
| 240 | ZP_002401 | 47569437 |
| 241 | ZP_002435 | 47573473 |
| 242 | ZP_002626 | 48728941 |
| 243 | ZP_002702 | 48765678 |
| 244 | ZP_002705 | 48766028 |
| 245 | ZP_002732 | 48768894 |
| 246 | ZP_002914 | 48834438 |
| 247 | ZP_003024 | 48848203 |
| 248 | ZP_003129 | 48858958 |
| 249 | ZP_003177 | 48863841 |
| 250 | ZP_003225 | 48869790 |
| 251 | AAT51323 | 49086036 |
| 252 | ZP_003301 | 49236117 |
| 253 | YP_034222 | 49476181 |
| 254 | YP_040995 | 49483771 |
| 255 | YP_043579 | 49486358 |
| 256 | AAT71982 | 50253560 |
| 257 | AAT90315 | 50952782 |
| 258 | YP_066435 | 51246551 |
| 259 | YP_075673 | 51892982 |
| 260 | YP_085511 | 52141318 |
| 261 | YP_092166 | 52786337 |
| 262 | ZP_001298 | 53691368 |
| 263 | YP_105136 | 53716444 |
| 264 | YP_111769 | 53722784 |
| 265 | ZP_003630 | 54030933 |
| 266 | YP_129021 | 54308001 |
| 267 | AAV74395 | 56122554 |
| 268 | AAV74396 | 56122556 |
| 269 | YP_148246 | 56420928 |
| 270 | YP_156518 | 56461237 |
| 271 | YP_162590 | 56551751 |
| 272 | YP_171470 | 56750769 |

TABLE 15-continued

Examples of GGPP synthase polypetides.

| Row | Genbank ACCESSION | Genbank GI |
|---|---|---|
| 273 | YP_175959 | 56964228 |
| 274 | YP_186407 | 57650478 |
| 275 | YP_190690 | 58038726 |
| 276 | AAW66658 | 58201026 |
| 277 | YP_194187 | 58337602 |
| 278 | YP_197469 | 58579257 |
| 279 | YP_201938 | 58582922 |
| 280 | YP_196510 | 58617311 |

TABLE 16

Examples of squalene synthase polypeptides.

| Row | Genbank ACCESSION | Genbank GI |
|---|---|---|
| 1 | AAA34597 | 171481 |
| 2 | CAA42583 | 3686 |
| 3 | Q9HGZ6 | 51704336 |
| 4 | BAB12207 | 9955387 |
| 5 | XP_453457 | 50306959 |
| 6 | Q752X9 | 51701405 |
| 7 | O74165 | 51701378 |
| 8 | XP_458579 | 50420093 |
| 9 | EAK95451 | 46436082 |
| 10 | P78589 | 2499979 |
| 11 | Q9Y753 | 51701459 |
| 12 | XP_407513 | 49092104 |
| 13 | XP_364394 | 39958237 |
| 14 | Q7S4Z6 | 51701416 |
| 15 | CAD60581 | 27764301 |
| 16 | XP_389557 | 46135731 |
| 17 | NP_595363 | 19112155 |
| 18 | B48057 | 477750 |
| 19 | NP_034321 | 34328173 |
| 20 | CAH92517 | 55731622 |
| 21 | AAF00038 | 6002565 |
| 22 | P53798 | 1706773 |
| 23 | NP_004453 | 31542632 |
| 24 | AAP36671 | 30584837 |
| 25 | 1EZFC | 11514497 |
| 26 | AAH09251 | 14328083 |
| 27 | AAH84016 | 54035372 |
| 28 | I52090 | 2136196 |
| 29 | XP_420043 | 50745256 |
| 30 | AAH81810 | 51858605 |
| 31 | CAE48363 | 50841455 |
| 32 | XP_569783 | 58265254 |
| 33 | XP_569782 | 58265252 |
| 34 | XP_534557 | 57105080 |
| 35 | XP_401989 | 49075920 |

TABLE 17

Examples of phytoene dehydrogenase polypeptides.

| Row | Genbank ACCESSION |
|---|---|
| 1 | 1613414B |
| 2 | 1613414F |
| 3 | 1904206A |
| 4 | 2121278A |
| 5 | A86203 |
| 6 | A96612 |
| 7 | A99470 |
| 8 | AAA24820 |
| 9 | AAA34001 |
| 10 | AAA50313 |

TABLE 17-continued

Examples of phytoene dehydrogenase polypeptides.

| Row | Genbank ACCESSION |
|---|---|
| 11 | AAA64981 |
| 12 | AAA91161 |
| 13 | AAA99519 |
| 14 | AAC44798 |
| 15 | AAC44850 |
| 16 | AAC48983 |
| 17 | AAF78201 |
| 18 | AAG10426 |
| 19 | AAG14399 |
| 20 | AAG28700 |
| 21 | AAG50743 |
| 22 | AAH85048 |
| 23 | AAK51545 |
| 24 | AAK51557 |
| 25 | AAK64299 |
| 26 | AAL02000 |
| 27 | AAL15300 |
| 28 | AAL38046 |
| 29 | AAL73986 |
| 30 | AAL80005 |
| 31 | AAL91366 |
| 32 | AAM45380 |
| 33 | AAM48646 |
| 34 | AAM63349 |
| 35 | AAM94364 |
| 36 | AAN75037 |
| 37 | AAN85599 |
| 38 | AAO24235 |
| 39 | AAO46892 |
| 40 | AAO46894 |
| 41 | AAO53257 |
| 42 | AAO53258 |
| 43 | AAO64750 |
| 44 | AAO93135 |
| 45 | AAP59036 |
| 46 | AAP79175 |
| 47 | AAQ04224 |
| 48 | AAQ04225 |
| 49 | AAQ65246 |
| 50 | AAQ65246 |
| 51 | AAQ88931 |
| 52 | AAR37797 |
| 53 | AAR37802 |
| 54 | AAR37850 |
| 55 | AAR37855 |
| 56 | AAR86105 |
| 57 | AAR98491 |
| 58 | AAR98494 |
| 59 | AAR98733 |
| 60 | AAS17750 |
| 61 | AAT01639 |
| 62 | AAT35222 |
| 63 | AAT74579 |
| 64 | AAT74580 |
| 65 | AAT76050 |
| 66 | AAT76434 |
| 67 | AAT90316 |
| 68 | AAU34019 |
| 69 | AAW23161 |
| 70 | AB2035 |
| 71 | AB2064 |
| 72 | AC2446 |
| 73 | AF1557 |
| 74 | AF2029 |
| 75 | AG2103 |
| 76 | AG2509 |
| 77 | AH1199 |
| 78 | AI2185 |
| 79 | AI2273 |
| 80 | B55548 |
| 81 | B84327 |
| 82 | B90061 |
| 83 | BAA14127 |
| 84 | BAA20276 |

TABLE 17-continued

Examples of phytoene dehydrogenase polypeptides.

| Row | Genbank ACCESSION |
|---|---|
| 85 | BAA76534 |
| 86 | BAB10768 |
| 87 | BAB50520 |
| 88 | BAB51896 |
| 89 | BAB68552 |
| 90 | BAB79603 |
| 91 | BAB82461 |
| 92 | BAB82462 |
| 93 | BAB98016 |
| 94 | BAC75676 |
| 95 | BAC77668 |
| 96 | BAC77671 |
| 97 | BAD07279 |
| 98 | BAD07280 |
| 99 | BAD07287 |
| 100 | BAD07288 |
| 101 | CAA52098 |
| 102 | CAA60479 |
| 103 | CAA66626 |
| 104 | CAB38739 |
| 105 | CAB38743 |
| 106 | CAB40843 |
| 107 | CAB56041 |
| 108 | CAB56062 |
| 109 | CAB59726 |
| 110 | CAB65434 |
| 111 | CAB94794 |
| 112 | CAC85667 |
| 113 | CAD19989 |
| 114 | CAD27442 |
| 115 | CAD55814 |
| 116 | CAE00192 |
| 117 | CAE83576 |
| 118 | CAF19330 |
| 119 | CAF21094 |
| 120 | CAF21337 |
| 121 | CAH91165 |
| 122 | E90061 |
| 123 | EAA90383 |
| 124 | EAA98598 |
| 125 | EAB09790 |
| 126 | EAB14136 |
| 127 | EAB18725 |
| 128 | EAB29729 |
| 129 | EAB30992 |
| 130 | EAB41377 |
| 131 | EAB54727 |
| 132 | EAB76679 |
| 133 | EAB87028 |
| 134 | EAB92587 |
| 135 | EAB94459 |
| 136 | EAB96864 |
| 137 | EAC01884 |
| 138 | EAC38895 |
| 139 | EAC60360 |
| 140 | EAD05874 |
| 141 | EAD05999 |
| 142 | EAD20520 |
| 143 | EAE06978 |
| 144 | EAE70773 |
| 145 | EAF04985 |
| 146 | EAF51354 |
| 147 | EAF62819 |
| 148 | EAF75453 |
| 149 | EAG09111 |
| 150 | EAG19412 |
| 151 | EAG23070 |
| 152 | EAG25053 |
| 153 | EAG25054 |
| 154 | EAG29279 |
| 155 | EAG39845 |
| 156 | EAG56100 |
| 157 | EAG63013 |
| 158 | EAG68633 |
| 159 | EAG71574 |
| 160 | EAG89835 |
| 161 | EAH04928 |
| 162 | EAH04936 |
| 163 | EAH08586 |
| 164 | EAH22597 |
| 165 | EAH22853 |
| 166 | EAH31648 |
| 167 | EAH55579 |
| 168 | EAH68071 |
| 169 | EAH73302 |
| 170 | EAH79041 |
| 171 | EAH86965 |
| 172 | EAH97108 |
| 173 | EAH99977 |
| 174 | EAI01660 |
| 175 | EAI03576 |
| 176 | EAI06784 |
| 177 | EAI11087 |
| 178 | EAI15261 |
| 179 | EAI15547 |
| 180 | EAI17521 |
| 181 | EAI21398 |
| 182 | EAI29728 |
| 183 | EAI38468 |
| 184 | EAI43591 |
| 185 | EAI51589 |
| 186 | EAI58453 |
| 187 | EAI72974 |
| 188 | EAI77885 |
| 189 | EAI78272 |
| 190 | EAI80262 |
| 191 | EAI83937 |
| 192 | EAI86664 |
| 193 | EAJ00517 |
| 194 | EAJ05570 |
| 195 | EAJ08238 |
| 196 | EAJ15524 |
| 197 | EAJ18144 |
| 198 | EAJ20649 |
| 199 | EAJ21683 |
| 200 | EAJ24413 |
| 201 | EAJ28774 |
| 202 | EAJ30522 |
| 203 | EAJ35157 |
| 204 | EAJ37407 |
| 205 | EAJ39929 |
| 206 | EAJ54356 |
| 207 | EAJ54959 |
| 208 | EAJ56207 |
| 209 | EAJ58447 |
| 210 | EAJ59958 |
| 211 | EAJ63347 |
| 212 | EAJ66054 |
| 213 | EAJ67637 |
| 214 | EAJ69812 |
| 215 | EAJ74441 |
| 216 | EAJ76472 |
| 217 | EAJ76473 |
| 218 | EAJ80355 |
| 219 | EAJ80839 |
| 220 | EAJ81408 |
| 221 | EAJ86174 |
| 222 | EAJ87600 |
| 223 | EAJ88203 |
| 224 | EAJ88682 |
| 225 | EAJ92341 |
| 226 | EAJ94774 |
| 227 | EAJ97555 |
| 228 | EAJ97958 |
| 229 | EAK07654 |
| 230 | EAK08513 |
| 231 | EAK08529 |
| 232 | EAK10609 |

TABLE 17-continued

Examples of phytoene dehydrogenase polypeptides.

| Row | Genbank ACCESSION |
|---|---|
| 233 | EAK10614 |
| 234 | EAK12902 |
| 235 | EAK13034 |
| 236 | EAK15092 |
| 237 | EAK22483 |
| 238 | EAK23222 |
| 239 | EAK24187 |
| 240 | EAK24674 |
| 241 | EAK28785 |
| 242 | EAK34731 |
| 243 | EAK34742 |
| 244 | EAK36883 |
| 245 | EAK37522 |
| 246 | EAK42705 |
| 247 | EAK43213 |
| 248 | EAK52580 |
| 249 | EAK53452 |
| 250 | EAK58759 |
| 251 | EAK62665 |
| 252 | EAK63558 |
| 253 | F84187 |
| 254 | F90272 |
| 255 | G87635 |
| 256 | G90413 |
| 257 | H83880 |
| 258 | H84320 |
| 259 | JC7723 |
| 260 | NP_060220 |
| 261 | NP_080435 |
| 262 | NP_193157 |
| 263 | NP_214383 |
| 264 | NP_276913 |
| 265 | NP_293819 |
| 266 | NP_294534 |
| 267 | NP_294585 |
| 268 | NP_295972 |
| 269 | NP_338490 |
| 270 | NP_376437 |
| 271 | NP_377056 |
| 272 | NP_388895 |
| 273 | NP_441167 |
| 274 | NP_441254 |
| 275 | NP_442491 |
| 276 | NP_442727 |
| 277 | NP_562475 |
| 278 | NP_568712 |
| 279 | NP_601630 |
| 280 | NP_601630 |
| 281 | NP_616426 |
| 282 | NP_624522 |
| 283 | NP_626360 |
| 284 | NP_630834 |
| 285 | NP_643053 |
| 286 | NP_647302 |
| 287 | NP_659552 |
| 288 | NP_661086 |
| 289 | NP_661546 |
| 290 | NP_661701 |
| 291 | NP_662300 |
| 292 | NP_681023 |
| 293 | NP_681127 |
| 294 | NP_682351 |
| 295 | NP_693380 |
| 296 | NP_693382 |
| 297 | NP_737250 |
| 298 | NP_763380 |
| 299 | NP_786524 |
| 300 | NP_822198 |
| 301 | NP_822828 |
| 302 | NP_827278 |
| 303 | NP_851528 |
| 304 | NP_857496 |
| 305 | NP_868798 |
| 306 | NP_869339 |
| 307 | NP_870237 |
| 308 | NP_874530 |
| 309 | NP_874561 |
| 310 | NP_874977 |
| 311 | NP_892236 |
| 312 | NP_892265 |
| 313 | NP_892458 |
| 314 | NP_893232 |
| 315 | NP_894882 |
| 316 | NP_895385 |
| 317 | NP_895793 |
| 318 | NP_895829 |
| 319 | NP_896854 |
| 320 | NP_896994 |
| 321 | NP_898304 |
| 322 | NP_898346 |
| 323 | NP_902647 |
| 324 | NP_923340 |
| 325 | NP_923639 |
| 326 | NP_923813 |
| 327 | NP_925079 |
| 328 | NP_931515 |
| 329 | NP_936379 |
| 330 | NP_940208 |
| 331 | NP_945754 |
| 332 | NP_946860 |
| 333 | NP_946866 |
| 334 | NP_948851 |
| 335 | NP_962004 |
| 336 | NP_968600 |
| 337 | NP_974222 |
| 338 | NP_974545 |
| 339 | O49901 |
| 340 | P17059 |
| 341 | P54971 |
| 342 | P54978 |
| 343 | P54979 |
| 344 | P54981 |
| 345 | P54982 |
| 346 | P74306 |
| 347 | Q01671 |
| 348 | Q02861 |
| 349 | Q38893 |
| 350 | Q40406 |
| 351 | Q9FV46 |
| 352 | Q9SE20 |
| 353 | Q9SMJ3 |
| 354 | Q9ZTN9 |
| 355 | Q9ZTP4 |
| 356 | S29314 |
| 357 | S32171 |
| 358 | S49624 |
| 359 | S52586 |
| 360 | S65060 |
| 361 | T10701 |
| 362 | T31463 |
| 363 | T46822 |
| 364 | T48646 |
| 365 | T50745 |
| 366 | T50749 |
| 367 | T50893 |
| 368 | T50910 |
| 369 | T51119 |
| 370 | T51123 |
| 371 | XP_324732 |
| 372 | XP_383241 |
| 373 | XP_401825 |
| 374 | XP_470568 |
| 375 | XP_473486 |
| 376 | XP_477063 |
| 377 | XP_525801 |
| 378 | XP_540198 |
| 379 | YP_006049 |
| 380 | YP_013621 |

TABLE 17-continued

Examples of phytoene dehydrogenase polypeptides.

| Row | Genbank ACCESSION |
|---|---|
| 381 | YP_024310 |
| 382 | YP_041986 |
| 383 | YP_041988 |
| 384 | YP_044561 |
| 385 | YP_044564 |
| 386 | YP_062471 |
| 387 | YP_117947 |
| 388 | YP_120612 |
| 389 | YP_135077 |
| 390 | YP_136483 |
| 391 | YP_145331 |
| 392 | YP_145348 |
| 393 | YP_171014 |
| 394 | YP_172823 |
| 395 | YP_173078 |
| 396 | YP_173207 |
| 397 | YP_184572 |
| 398 | YP_187368 |
| 399 | YP_187371 |
| 400 | YP_187371 |
| 401 | YP_187371 |
| 402 | ZP_000490 |
| 403 | ZP_000509 |
| 404 | ZP_000518 |
| 405 | ZP_000566 |
| 406 | ZP_000627 |
| 407 | ZP_000627 |
| 408 | ZP_001073 |
| 409 | ZP_001081 |
| 410 | ZP_001091 |
| 411 | ZP_001116 |
| 412 | ZP_001117 |
| 413 | ZP_001119 |
| 414 | ZP_001124 |
| 415 | ZP_001510 |
| 416 | ZP_001591 |
| 417 | ZP_001593 |
| 418 | ZP_001602 |
| 419 | ZP_001614 |
| 420 | ZP_001645 |
| 421 | ZP_001650 |
| 422 | ZP_001722 |
| 423 | ZP_001746 |
| 424 | ZP_001752 |
| 425 | ZP_001770 |
| 426 | ZP_001777 |
| 427 | ZP_001787 |
| 428 | ZP_001837 |
| 429 | ZP_001867 |
| 430 | ZP_002073 |
| 431 | ZP_002077 |
| 432 | ZP_002339 |
| 433 | ZP_002680 |
| 434 | ZP_002705 |
| 435 | ZP_002771 |
| 436 | ZP_002892 |
| 437 | ZP_002916 |
| 438 | ZP_002963 |
| 439 | ZP_003022 |
| 440 | ZP_003036 |
| 441 | ZP_003107 |
| 442 | ZP_003202 |
| 443 | ZP_003258 |
| 444 | ZP_003268 |
| 445 | ZP_003269 |
| 446 | ZP_003276 |
| 447 | ZP_003283 |
| 448 | ZP_003557 |
| 449 | ZP_003559 |
| 450 | ZP_003565 |
| 451 | ZP_003577 |
| 452 | ZP_003593 |
| 453 | ZP_003595 |
| 441 | ZP_003685 |

TABLE 18

Examples of phytoene synthase and lycopene cyclase polypeptides.

| Row | Genbank Accession | Genbank GI |
|---|---|---|
| 1 | 1613414C | 227040 |
| 2 | A49558 | 1076590 |
| 3 | AAA19428 | 506623 |
| 4 | AAA32836 | 413732 |
| 5 | AAA64982 | 148413 |
| 6 | AAB87738 | 29893495 |
| 7 | AAC44849 | 1842243 |
| 8 | AAD38051 | 13542332 |
| 9 | AAF78202 | 8650418 |
| 10 | AAF82616 | 9081847 |
| 11 | AAG10427 | 9971814 |
| 12 | AAG28701 | 11066678 |
| 13 | AAK07734 | 18476085 |
| 14 | AAK07735 | 18476089 |
| 15 | AAK15621 | 13195243 |
| 16 | AAL02001 | 15553721 |
| 17 | AAL76346 | 18645045 |
| 18 | AAL82578 | 21326700 |
| 19 | AAM45379 | 21360353 |
| 20 | AAM48647 | 21328641 |
| 21 | AAM62787 | 21553694 |
| 22 | AAM94363 | 22296799 |
| 23 | AAN85600 | 27228294 |
| 24 | AAO24767 | 27903500 |
| 25 | AAO39835 | 28403302 |
| 26 | AAO46895 | 37729028 |
| 27 | AAO47570 | 33465823 |
| 28 | AAO73816 | 33465821 |
| 29 | AAP22038 | 30349414 |
| 30 | AAP55451 | 32350232 |
| 31 | AAP55453 | 32350236 |
| 32 | AAP55461 | 32350252 |
| 33 | AAP55471 | 32350272 |
| 34 | AAP55484 | 32350298 |
| 35 | AAP55486 | 32350302 |
| 36 | AAP56083 | 32349564 |
| 37 | AAP56124 | 32349646 |
| 38 | AAP56127 | 32349652 |
| 39 | AAP56136 | 32349670 |
| 40 | AAP56148 | 32349694 |
| 41 | AAP56155 | 32349708 |
| 42 | AAP56156 | 32349710 |
| 43 | AAP56157 | 32349712 |
| 44 | AAP56158 | 32349714 |
| 45 | AAP79176 | 32307542 |
| 46 | AAQ91837 | 37499616 |
| 47 | AAR08445 | 38037628 |
| 48 | AAR31885 | 39842609 |
| 49 | AAR37803 | 40062932 |
| 50 | AAR37856 | 40062986 |
| 51 | AAR86104 | 40456029 |
| 52 | AAR87868 | 40557193 |
| 53 | AAR98492 | 41018901 |
| 54 | AAS02284 | 41394357 |
| 55 | AAS17009 | 42491736 |
| 56 | AAS18307 | 42521626 |
| 57 | AAT28184 | 47498515 |
| 58 | AAT35222 | 47531118 |
| 59 | AAT38473 | 47779181 |
| 60 | AAT46069 | 48686711 |
| 61 | AAT74581 | 50313418 |

TABLE 18-continued

Examples of phytoene synthase and lycopene cyclase polypeptides.

| Row | Genbank Accession | Genbank GI |
|---|---|---|
| 62 | AAT90319 | 50952786 |
| 63 | AAV74394 | 56122551 |
| 64 | AAW23162 | 56698928 |
| 65 | AC2035 | 25366683 |
| 66 | AC2035 | 25366683 |
| 67 | BAB18514 | 11344507 |
| 68 | BAB79604 | 18143449 |
| 69 | BAD07278 | 40809739 |
| 70 | BAD07286 | 40809755 |
| 71 | BAD62106 | 54291340 |
| 72 | BAD62107 | 54291341 |
| 73 | C90061 | 25506636 |
| 74 | CAA47625 | 19347 |
| 75 | CAA68575 | 19341 |
| 76 | CAB07958 | 1934837 |
| 77 | CAB38740 | 4490590 |
| 78 | CAB51949 | 5690074 |
| 79 | CAB56063 | 5912296 |
| 80 | CAB86388 | 7453011 |
| 81 | CAB93661 | 8250520 |
| 82 | CAB94795 | 8574392 |
| 83 | CAC19567 | 11990226 |
| 84 | CAC27383 | 12584564 |
| 85 | CAD19988 | 18307500 |
| 86 | CAD29284 | 57282088 |
| 87 | CAE76609 | 38567321 |
| 88 | E37802 | 95606 |
| 89 | E84320 | 25410251 |
| 90 | EAA98758 | 42863045 |
| 91 | EAB01965 | 42869439 |
| 92 | EAB04170 | 42873822 |
| 93 | EAB07138 | 42879858 |
| 94 | EAB09791 | 42885235 |
| 95 | EAB19826 | 42905452 |
| 96 | EAB35029 | 42936011 |
| 97 | EAB41375 | 42948740 |
| 98 | EAB78706 | 43024004 |
| 99 | EAB92586 | 43052355 |
| 100 | EAC06949 | 43081493 |
| 101 | EAC18360 | 43104624 |
| 102 | EAC25793 | 43119723 |
| 103 | EAC29883 | 43128092 |
| 104 | EAC32813 | 43133973 |
| 105 | EAC33105 | 43134560 |
| 106 | EAC38486 | 43145552 |
| 107 | EAC52233 | 43173313 |
| 108 | EAC60029 | 43189028 |
| 109 | EAC68026 | 43204953 |
| 110 | EAC96197 | 43261031 |
| 111 | EAD08701 | 43285745 |
| 112 | EAD20866 | 43310220 |
| 113 | EAD32755 | 43334458 |
| 114 | EAD38008 | 43345761 |
| 115 | EAD50152 | 43370658 |
| 116 | EAD50402 | 43371147 |
| 117 | EAD81123 | 43452903 |
| 118 | EAD93882 | 43478303 |
| 119 | EAE12860 | 43516265 |
| 120 | EAE16121 | 43522884 |
| 121 | EAE31084 | 43552634 |
| 122 | EAE35665 | 43561764 |
| 123 | EAE44717 | 43579862 |
| 124 | EAE46627 | 43583580 |
| 125 | EAE47846 | 43586023 |
| 126 | EAE72264 | 43635190 |
| 127 | EAE76009 | 43642573 |
| 128 | EAE86335 | 43662748 |
| 129 | EAE89581 | 43669163 |
| 130 | EAF18881 | 43728007 |
| 131 | EAF64277 | 43819669 |
| 132 | EAF67931 | 43827263 |
| 133 | EAF84745 | 43861327 |
| 134 | EAF94004 | 43880040 |
| 135 | EAG06083 | 43903395 |
| 136 | EAG21950 | 43933540 |
| 137 | EAG43625 | 43973477 |
| 138 | EAG50171 | 43985555 |
| 139 | EAG57517 | 43999205 |
| 140 | EAG62787 | 44009110 |
| 141 | EAG65580 | 44014171 |
| 142 | EAG68110 | 44018715 |
| 143 | EAG72283 | 44026322 |
| 144 | EAG78750 | 44037938 |
| 145 | EAG80445 | 44041116 |
| 146 | EAG93220 | 44064453 |
| 147 | EAH04927 | 44085694 |
| 148 | EAH08972 | 44093217 |
| 149 | EAH10377 | 44095788 |
| 150 | EAH22151 | 44117864 |
| 151 | EAH31461 | 44134654 |
| 152 | EAH50033 | 44169323 |
| 153 | EAH64480 | 44196848 |
| 154 | EAH79040 | 44223009 |
| 155 | EAH99976 | 44255671 |
| 156 | EAI02786 | 44259828 |
| 157 | EAI02787 | 44259829 |
| 158 | EAI03575 | 44260943 |
| 159 | EAI05900 | 44264266 |
| 160 | EAI61004 | 44344824 |
| 161 | EAI70669 | 44358327 |
| 162 | EAI83938 | 44377067 |
| 163 | EAJ05110 | 44406802 |
| 164 | EAJ05569 | 44407471 |
| 165 | EAJ08876 | 44412338 |
| 166 | EAJ35156 | 44449986 |
| 167 | EAJ38900 | 44455130 |
| 168 | EAJ49645 | 44470504 |
| 169 | EAJ54357 | 44477026 |
| 170 | EAJ60475 | 44485647 |
| 171 | EAJ64125 | 44492007 |
| 172 | EAJ67499 | 44497025 |
| 173 | EAJ76471 | 44510405 |
| 174 | EAJ76950 | 44511114 |
| 175 | EAJ78637 | 44513596 |
| 176 | EAJ78787 | 44513824 |
| 177 | EAJ79616 | 44515082 |
| 178 | EAJ80356 | 44516200 |
| 179 | EAJ81914 | 44518489 |
| 180 | EAJ87417 | 44526623 |
| 181 | EAK08514 | 44557109 |
| 182 | EAK08523 | 44557119 |
| 183 | EAK12901 | 44563097 |
| 184 | EAK22180 | 44576315 |
| 185 | EAK24859 | 44580262 |
| 186 | EAK28345 | 44585276 |
| 187 | EAK34732 | 44594324 |
| 188 | EAK34736 | 44594329 |
| 189 | EAK37296 | 44597942 |
| 190 | EAK37521 | 44598256 |
| 191 | EAK56335 | 44624430 |
| 192 | G84363 | 25410528 |
| 193 | NP_274195 | 15677043 |
| 194 | NP_284085 | 15794263 |
| 195 | NP_294586 | 15805888 |
| 196 | NP_388961 | 16078144 |
| 197 | NP_441168 | 16330440 |
| 198 | NP_443763 | 16519643 |
| 199 | NP_624523 | 21218744 |
| 200 | NP_630832 | 21225053 |
| 201 | NP_662273 | 21674208 |
| 202 | NP_682350 | 22299103 |
| 203 | NP_693381 | 23099915 |
| 204 | NP_786525 | 28379633 |
| 205 | NP_822199 | 29827565 |
| 206 | NP_822829 | 29828195 |
| 207 | NP_851527 | 30795077 |
| 208 | NP_868799 | 32475805 |
| 209 | NP_874560 | 33239618 |

TABLE 18-continued

Examples of phytoene synthase and lycopene cyclase polypeptides.

| Row | Genbank Accession | Genbank GI |
|---|---|---|
| 210 | NP_879992 | 33592348 |
| 211 | NP_884101 | 33596458 |
| 212 | NP_889809 | 33602249 |
| 213 | NP_892264 | 33860703 |
| 214 | NP_895828 | 33864268 |
| 215 | NP_898345 | 33866786 |
| 216 | NP_902648 | 34498433 |
| 217 | NP_902649 | 34498434 |
| 218 | NP_924690 | 37521313 |
| 219 | NP_931516 | 37528171 |
| 220 | NP_946861 | 39934585 |
| 221 | NP_949079 | 39936803 |
| 222 | NP_962005 | 41409169 |
| 223 | NP_968601 | 42523221 |
| 224 | O07333 | 3913360 |
| 225 | P08196 | 585746 |
| 226 | P21683 | 30923192 |
| 227 | P37269 | 585009 |
| 228 | P37271 | 27735222 |
| 229 | P37272 | 585749 |
| 230 | P53797 | 1709885 |
| 231 | P54975 | 1706137 |
| 232 | P54977 | 1706139 |
| 233 | P65860 | 54041032 |
| 234 | Q9SSU8 | 8928282 |
| 235 | Q9UUQ6 | 34922667 |
| 236 | S22474 | 7489041 |
| 237 | S32170 | 321671 |
| 238 | S52587 | 1073300 |
| 239 | S56668 | 2129505 |
| 240 | S68307 | 2130144 |
| 241 | T10702 | 7484346 |
| 242 | T46594 | 11291807 |
| 243 | T50746 | 11356347 |
| 244 | T50895 | 11291816 |
| 245 | XP_324765 | 32408567 |
| 246 | XP_383242 | 46114448 |
| 247 | XP_403902 | 49080862 |
| 248 | YP_006040 | 46255128 |
| 249 | YP_103126 | 53723680 |
| 250 | YP_112342 | 53723357 |
| 251 | YP_117945 | 54023703 |
| 252 | YP_120611 | 54026369 |
| 253 | YP_136628 | 55378778 |
| 254 | YP_136629 | 55378779 |
| 255 | YP_145340 | 55978284 |
| 256 | YP_145343 | 55978287 |
| 257 | YP_160917 | 56479328 |
| 258 | YP_160918 | 56479329 |
| 259 | YP_162605 | 56551766 |
| 260 | YP_172822 | 56752121 |
| 261 | YP_187369 | 57652299 |
| 262 | YP_192648 | 58040684 |
| 263 | ZP_000044 | 22956752 |
| 264 | ZP_001091 | 53688068 |
| 265 | ZP_001591 | 53763709 |
| 266 | ZP_001657 | 45514234 |
| 267 | ZP_001690 | 46132223 |
| 268 | ZP_001746 | 45523280 |
| 269 | ZP_001837 | 53771530 |
| 270 | ZP_001867 | 45546711 |
| 271 | ZP_002096 | 46204978 |
| 272 | ZP_002248 | 46324513 |
| 273 | ZP_002450 | 47575031 |
| 274 | ZP_002680 | 48763469 |
| 275 | ZP_002710 | 48766450 |
| 276 | ZP_002791 | 48782680 |
| 277 | ZP_002892 | 48832182 |
| 278 | ZP_002916 | 48834623 |
| 279 | ZP_003036 | 48849426 |
| 280 | ZP_003269 | 48893702 |
| 281 | ZP_003351 | 52007802 |
| 282 | ZP_003487 | 53730362 |
| 283 | ZP_003501 | 53759405 |
| 284 | ZP_003591 | 53798896 |
| 285 | ZP_003628 | 54030691 |

TABLE 19

Examples of carotenoid ketolase polypeptides.

| Row | Accession Number | GI Number |
|---|---|---|
| 1 | AAA99932 | 609575 |
| 2 | AAB48668 | 1870215 |
| 3 | AAC25611 | 2541936 |
| 4 | AAF78203 | 8650419 |
| 5 | AAH16427 | 16741158 |
| 6 | AAN03484 | 22597194 |
| 7 | AAN85497 | 26541510 |
| 8 | AAN86030 | 33439708 |
| 9 | AAO64399 | 28976134 |
| 10 | AAQ23139 | 33621091 |
| 11 | AAT35222 | 47531118 |
| 12 | AAT35555 | 47558911 |
| 13 | AAV41372 | 55139370 |
| 14 | AB2307 | 25530134 |
| 15 | AF2204 | 25533132 |
| 16 | BAB54999 | 14028447 |
| 17 | BAB58879 | 14270087 |
| 18 | BAC98366 | 37360914 |
| 19 | CAA60674 | 2654318 |
| 20 | CAB56059 | 5912292 |
| 21 | D87673 | 25398945 |
| 22 | EAA79304 | 42823978 |
| 23 | EAA80363 | 42826055 |
| 24 | EAA81403 | 42828115 |
| 25 | EAA84711 | 42834481 |
| 26 | EAB82380 | 43031476 |
| 27 | EAB86624 | 43040184 |
| 28 | EAC05755 | 43079085 |
| 29 | EAD12219 | 43292778 |
| 30 | EAD71182 | 43427899 |
| 31 | EAD94927 | 43480380 |
| 32 | EAF11582 | 43712986 |
| 33 | EAF98072 | 43888329 |
| 34 | EAG19345 | 43928738 |
| 35 | EAG38273 | 43963688 |
| 36 | EAG79800 | 44039853 |
| 37 | EAG96474 | 44070318 |
| 38 | EAH00349 | 44077315 |
| 39 | EAH36448 | 44143633 |
| 40 | EAH40683 | 44151265 |
| 41 | EAH53180 | 44175316 |
| 42 | EAH96648 | 44250729 |
| 43 | EAI05260 | 44263397 |
| 44 | EAI17468 | 44281329 |
| 45 | EAI53009 | 44333409 |
| 46 | EAI54054 | 44334878 |
| 47 | EAI67818 | 44354362 |
| 48 | EAI68153 | 44354875 |
| 49 | EAI89684 | 44384943 |
| 50 | EAJ27674 | 44439188 |
| 51 | EAJ45589 | 44464684 |
| 52 | EAJ45589 | 44464684 |
| 53 | EAJ67118 | 44496466 |
| 54 | EAJ74221 | 44507022 |
| 55 | EAJ74653 | 44507662 |
| 56 | EAJ88396 | 44528064 |
| 57 | EAJ88887 | 44528792 |
| 58 | EAK06069 | 44553531 |
| 59 | EAK11467 | 44561166 |
| 60 | EAK16824 | 44568733 |
| 61 | EAK28828 | 44585942 |

TABLE 19-continued

Examples of carotenoid ketolase polypetides.

| Row | Accession Number | GI Number |
|---|---|---|
| 62 | EAK28828 | 44585942 |
| 63 | EAK31112 | 44589271 |
| 64 | EAK42591 | 44605441 |
| 65 | NP_045063 | 11465545 |
| 66 | NP_081575 | 27754029 |
| 67 | NP_338204 | 15843167 |
| 68 | NP_440788 | 16330060 |
| 69 | NP_441220 | 16330492 |
| 70 | NP_682690 | 22299443 |
| 71 | NP_770721 | 27379192 |
| 72 | NP_848964 | 30468077 |
| 73 | NP_857223 | 31794730 |
| 74 | NP_881760 | 33594116 |
| 75 | NP_882469 | 33594826 |
| 76 | NP_886657 | 33599097 |
| 77 | NP_895643 | 33864083 |
| 78 | NP_896386 | 33864827 |
| 79 | NP_897461 | 33865902 |
| 80 | NP_924674 | 37521297 |
| 81 | NP_927525 | 37524181 |
| 82 | NP_947075 | 39934799 |
| 83 | P54972 | 1706150 |
| 84 | Q39982 | 2498257 |
| 85 | Q44261 | 2498256 |
| 86 | T31123 | 11361063 |
| 87 | XP_330780 | 32420673 |
| 88 | XP_368852 | 39974923 |
| 89 | XP_380194 | 46102628 |
| 90 | XP_383758 | 46115480 |
| 91 | XP_405100 | 49086048 |
| 92 | XP_409222 | 49095522 |
| 93 | YP_102417 | 53725671 |
| 94 | YP_108945 | 53719959 |
| 95 | YP_132414 | 54302421 |
| 96 | YP_154670 | 56459389 |
| 97 | YP_166682 | 56696325 |
| 98 | YP_168846 | 56698471 |
| 99 | YP_172377 | 56751676 |
| 100 | ZP_001068 | 23124870 |
| 101 | ZP_001112 | 53688676 |
| 102 | ZP_001607 | 53764743 |
| 103 | ZP_001757 | 46118877 |
| 104 | ZP_001787 | 53736018 |
| 105 | ZP_002218 | 46321435 |
| 106 | ZP_002456 | 47575608 |
| 107 | ZP_003028 | 48848557 |
| 108 | ZP_003107 | 48856640 |
| 109 | ZP_003264 | 48893204 |
| 110 | ZP_003458 | 53688805 |
| 111 | ZP_003513 | 53763576 |

TABLE 20

Examples of carotenoid hydroxylase polypetides.

| Row | Genbank ACCESSION | Genbank GI |
|---|---|---|
| 1 | AAC44852 | 1842246 |
| 2 | AAC49443 | 1575296 |
| 3 | AAD54243 | 5852870 |
| 4 | AAG10430 | 9971820 |
| 5 | AAG10793 | 9988836 |
| 6 | AAG33636 | 11245486 |
| 7 | AAL80006 | 19071768 |
| 8 | AAM44971 | 21280903 |
| 9 | AAM51300 | 21436107 |
| 10 | AAM77007 | 21734857 |
| 11 | AAN85601 | 27228295 |
| 12 | AAO53295 | 28911949 |
| 13 | AAS48097 | 44887642 |

TABLE 20-continued

Examples of carotenoid hydroxylase polypetides.

| Row | Genbank ACCESSION | Genbank GI |
|---|---|---|
| 14 | AAS55552 | 45184599 |
| 15 | AAS88426 | 46326968 |
| 16 | AAT48741 | 49036137 |
| 17 | AAT84408 | 50844570 |
| 18 | AAV85452 | 56267980 |
| 19 | AAV85453 | 56267982 |
| 20 | BAA14129 | 216687 |
| 21 | BAB79605 | 18143450 |
| 22 | BAC77670 | 31790567 |
| 23 | BAD07283 | 40809749 |
| 24 | BAD07291 | 40809765 |
| 25 | CAA70427 | 2956671 |
| 26 | CAA70888 | 2956717 |
| 27 | CAB55625 | 5870598 |
| 28 | CAB55626 | 5870600 |
| 29 | CAB56060 | 5912293 |
| 30 | CAC06712 | 9968545 |
| 31 | CAC95130 | 33145986 |
| 32 | EAB30128 | 42926157 |
| 33 | EAC49462 | 43167766 |
| 34 | EAC86129 | 43241003 |
| 35 | EAD61089 | 43395962 |
| 36 | EAD76156 | 43443111 |
| 37 | EAD88640 | 43467793 |
| 38 | EAE27903 | 43546376 |
| 39 | EAE28203 | 43546980 |
| 40 | EAE78743 | 43647896 |
| 41 | EAF12173 | 43714211 |
| 42 | EAH29370 | 44130906 |
| 43 | EAH44202 | 44158360 |
| 44 | EAI00766 | 44256844 |
| 45 | EAI29017 | 44298625 |
| 46 | EAJ30844 | 44443849 |
| 47 | EAJ72524 | 44504516 |
| 48 | EAK10611 | 44559981 |
| 49 | EAK53455 | 44620561 |
| 50 | EAK63955 | 44635271 |
| 51 | H90469 | 25394049 |
| 52 | NP_745389 | 26989964 |
| 53 | NP_922503 | 37536402 |
| 54 | P54973 | 1706152 |
| 55 | Q44262 | 2498258 |
| 56 | S52982 | 1073291 |
| 57 | XP_473611 | 50928167 |
| 58 | YP_024309 | 48478603 |
| 59 | ZP_003055 | 48851297 |
| 60 | ZP_003107 | 48856620 |

TABLE 21

Examples of astaxanthin synthase polypeptides and putative astaxanthin synthase polypeptides.

| Row | Genbank ACCESSION | Genbank GI |
|---|---|---|
| 1 | AAM56288 | 21501451 |
| 2 | XP_571276 | 58268240 |
| 3 | EAL20013 | 50257304 |
| 4 | XP_401804 | 49075484 |
| 5 | XP_397817 | 49067054 |
| 6 | XP_399595 | 49070612 |
| 7 | XP_403279 | 49079218 |
| 8 | XP_382294 | 46110473 |
| 9 | XP_406021 | 49088382 |
| 10 | XP_381224 | 46108332 |
| 11 | XP_391479 | 46139577 |
| 12 | XP_569261 | 58264210 |
| 13 | EAL22841 | 50260180 |
| 14 | XP_359866 | 39940658 |

TABLE 22

Examples of carotenoid epsilon hydroxylase polypeptides.

| ACCESSION | GI | PROTEIN DESCRIPTION |
|---|---|---|
| ABB52076 | 79155148 | putative epsilon-ring carotene hydroxylase [*Daucus carota* subsp. *sativus*] |
| BAD94136 | 62319017 | Cytochrom P450-like protein [*Arabidopsis thaliana*] |
| ABD28565 | 87162770 | E-class P450, group I [*Medicago truncatula*] |
| AAT28222 | 47498772 | putative 97B2-like cytochrome P450 [*Ginkgo biloba*] |
| ABC68396 | 85001685 | cytochrome P450 monooxygenase CYP97A [*Glycine max*] |
| ABC59110 | 84514203 | cytochrome P450 monooxygenase CYP97B [*Medicago truncatula*] |
| NP_190881 | 42565881 | LUT1 (LUTEIN DEFICIENT 1); oxygen binding [*Arabidopsis thaliana*] |
| ABB47954 | 78708979 | cytochrome P450 monooxygenase, putative [*Oryza sativa* (*japonica* cultivar-group)] |
| NP_922604 | 37536604 | putative cytochrome P450 monooxygenase [*Oryza sativa* (*japonica* cultivar-group)] |

TABLE 23

Examples of lycopene cyclase polypeptides, beta and epsilon subunits.

| ACCESSION | GI | PROTEIN DESCRIPTION |
|---|---|---|
| AAK07431 | 12746307 | lycopene epsilon-cyclase [*Adonis palaestina*] |
| ABB52073 | 79154988 | putative lycopene epsilon cyclase [*Daucus carota* subsp. *sativus*] |
| Q38932 | 27735211 | Lycopene epsilon cyclase, chloroplast precursor |
| AAB53336 | 1399181 | lycopene epsilon cyclase |
| AAG10428 | 9971816 | epsilon cyclase [*Tagetes erecta*] |
| AAK07434 | 12746313 | lycopene epsilon-cyclase [*Lactuca sativa*] |
| AAM45382 | 21360359 | epsilon cyclase [*Tagetes erecta*] |
| O65837 | 11132841 | Lycopene epsilon cyclase, chloroplast precursor |
| AAL69394 | 18419661 | lycopene epsilon-cyclase [*Spinacia oleracea*] |
| BAE79549 | 87299433 | lycopene epsilon-cyclase [*Chrysanthemum* x *morifolium*] |
| XP_463351 | 50901836 | putative lycopene epsilon-cyclase [*Oryza sativa* (*japonica* cultivar-group)] |
| AAS48096 | 44887640 | epsilon lycopene cyclase [*Citrus sinensis*] |
| AAX92679 | 62638188 | lycopene epsilon cyclase [*Citrus maxima*] |
| AAL92114 | 19569601 | lycopene epsilon-cyclase [*Citrus* x *paradisi*] |
| AAK07433 | 12746311 | lycopene epsilon-cyclase [*Solanum tuberosum*] |
| AAL47019 | 17864021 | lycopene epsilon-cyclase [*Citrus sinensis*] |
| AAT46065 | 48686703 | chloroplast lycopene epsilon-cyclase precursor [*Chlamydomonas reinhardtii*] |
| BAD07293 | 40809769 | lycopene epsilon-cyclase [*Citrus limon*] |
| BAD07285 | 40809753 | lycopene epsilon-cyclase [*Citrus sinensis*] |
| BAD07277 | 40809737 | lycopene epsilon-cyclase [*Citrus unshiu*] |
| EAJ62839 | 44489138 | unknown [environmental sequence] |
| BAE43547 | 73993068 | putative lycopene beta cyclase [*Taxodium distichum* var. *distichum*] |
| BAE43550 | 73993074 | putative lycopene beta cyclase [*Taxodium distichum* var. *distichum*] |
| BAE43557 | 73993088 | putative lycopene beta cyclase [*Taxodium distichum* var. *imbricarium*] |
| BAE43558 | 73993090 | putative lycopene beta cyclase [*Taxodium distichum* var. *imbricarium*] |
| BAE43553 | 73993080 | putative lycopene beta cyclase [*Taxodium distichum* var. *imbricarium*] |
| BAE43545 | 73993064 | putative lycopene beta cyclase [*Taxodium distichum* var. *distichum*] |
| BAE43556 | 73993086 | putative lycopene beta cyclase [*Taxodium distichum* var. *imbricarium*] |
| BAE43552 | 73993078 | putative lycopene beta cyclase [*Taxodium distichum* var. *distichum*] |
| BAE43560 | 73993094 | putative lycopene beta cyclase [*Taxodium distichum* var. *imbricarium*] |
| BAE43554 | 73993082 | putative lycopene beta cyclase [*Taxodium distichum* var. *imbricarium*] |
| BAE43551 | 73993076 | putative lycopene beta cyclase [*Taxodium distichum* var. *distichum*] |
| BAE43519 | 73993012 | putative lycopene beta cyclase [*Cryptomeria japonica*] |
| BAE43535 | 73993044 | putative lycopene beta cyclase [*Cryptomeria japonica*] |
| BAE43541 | 73993056 | putative lycopene beta cyclase [*Cryptomeria japonica*] |
| BAE43542 | 73993058 | putative lycopene beta cyclase [*Cryptomeria japonica*] |
| BAE43517 | 73993008 | putative lycopene beta cyclase [*Cryptomeria japonica*] |

TABLE 23-continued

Examples of lycopene cyclase polypeptides, beta and epsilon subunits.

| ACCESSION | GI | PROTEIN DESCRIPTION |
|---|---|---|
| BAE43534 | 73993042 | putative lycopene beta cyclase [*Cryptomeria japonica*] |
| BAE43537 | 73993048 | putative lycopene beta cyclase [*Cryptomeria japonica*] |
| BAE43533 | 73993040 | putative lycopene beta cyclase [*Cryptomeria japonica*] |
| BAD02774 | 38603277 | putative lycopene beta cyclase [*Cryptomeria japonica*] |
| BAD02766 | 38603261 | putative lycopene beta cyclase [*Cryptomeria japonica*] |
| BAE43540 | 73993054 | putative lycopene beta cyclase [*Cryptomeria japonica*] |
| BAE43514 | 73993002 | putative lycopene beta cyclase [*Cryptomeria japonica*] |
| BAE43544 | 73993062 | putative lycopene beta cyclase [*Cryptomeria japonica*] |
| BAE43538 | 73993050 | putative lycopene beta cyclase [*Cryptomeria japonica*] |
| BAE43528 | 73993030 | putative lycopene beta cyclase [*Cryptomeria japonica*] |
| BAE43546 | 73993066 | putative lycopene beta cyclase [*Taxodium distichum* var. *distichum*] |
| BAE43526 | 73993026 | putative lycopene beta cyclase [*Cryptomeria japonica*] |
| BAE43543 | 73993060 | putative lycopene beta cyclase [*Cryptomeria japonica*] |
| BAD02742 | 38603213 | putative lycopene beta cyclase [*Cryptomeria japonica*] |
| BAD02770 | 38603269 | putative lycopene beta cyclase [*Cryptomeria japonica*] |
| BAE43522 | 73993018 | putative lycopene beta cyclase [*Cryptomeria japonica*] |
| BAE43559 | 73993092 | putative lycopene beta cyclase [*Taxodium distichum* var. *imbricarium*] |
| BAE43527 | 73993028 | putative lycopene beta cyclase [*Cryptomeria japonica*] |
| BAE43548 | 73993070 | putative lycopene beta cyclase [*Taxodium distichum* var. *distichum*] |
| AAF44700 | 14550425 | lycopene beta-cyclase [*Citrus sinensis*] |
| BAE43555 | 73993084 | putative lycopene beta cyclase [*Taxodium distichum* var. *imbricarium*] |
| BAE43549 | 73993072 | putative lycopene beta cyclase [*Taxodium distichum* var. *distichum*] |
| AAU14144 | 51922063 | lycopene beta-cyclase [*Citrus sinensis*] |
| AAN86060 | 27261727 | lycopene cyclase [*Citrus unshiu*] |
| AAR89632 | 40756518 | lycopene-beta-cyclase [*Citrus maxima*] |
| AAM21152 | 20530862 | lycopene beta-cyclase [*Citrus sinensis*] |
| AAD38049 | 13959731 | lycopene cyclase [*Citrus x paradisi*] |
| AAU05146 | 51511939 | lycopene beta-cyclase [*Citrus sinensis*] |
| AAU05145 | 51511937 | lycopene beta-cyclase [*Citrus sinensis*] |
| AAK07430 | 12746305 | lycopene beta-cyclase [*Adonis palaestina*] |
| ABB72443 | 82394885 | lycopene beta-cyclase [*Citrus sinensis*] |
| BAE79544 | 87299423 | lycopene beta-cyclase [*Chrysanthemum* x *morifolium*] |
| BAE78471 | 85717882 | lycopene beta cyclase [*Taraxacum officinale*] |
| Q43415 | 11133019 | Lycopene beta cyclase, chloroplast precursor |
| AAF23013 | 6665782 | lycopene epsilon-cyclase [*Daucus carota*] |
| ABB52071 | 79154899 | putative lycopene beta cyclase [*Daucus carota* subsp. *sativus*] |
| AAW88382 | 59665024 | lycopene beta-cyclase [*Lycium barbarum*] |
| AAG10429 | 9971818 | beta cyclase [*Tagetes erecta*] |
| AAM45381 | 21360357 | beta cyclase [*Tagetes erecta*] |
| AAM14335 | 20259239 | putative lycopene beta cyclase [*Arabidopsis thaliana*] |
| AAO18661 | 27728515 | lycopene beta-cyclase [*Zea mays*] |
| AAA81880 | 735882 | lycopene cyclase |
| Q43503 | 11133022 | Lycopene beta cyclase, chloroplast precursor |
| S66350 | 2129931 | lycopene beta-cyclase (EC 5.5.1.—) - tomato |
| XP_464409 | 50905841 | putative lycopene beta-cyclase [*Oryza sativa* (japonica cultivar-group)] |
| CAD70565 | 45237491 | lycopene cyclase [*Bixa orellana*] |
| Q43578 | 11133025 | Lycopene beta cyclase, chloroplast precursor |
| AAL92175 | 19569782 | beta-lycopene cyclase [*Sandersonia aurantiaca*] |
| AAX54906 | 61742130 | putative chloroplast lycopene beta cyclase precursor [*Chlamydomonas reinhardtii*] |
| S66349 | 2129954 | lycopene beta-cyclase (EC 5.5.1.—) - common tobacco |
| AAG21133 | 10644119 | chromoplast-specific lycopene beta-cyclase [*Lycopersicon esculentum*] |
| CAB92977 | 8247354 | neoxanthin synthase [*Solanum tuberosum*] |
| CAB93342 | 8249885 | neoxanthin synthase [*Lycopersicon esculentum*] |
| Q9SEA0 | 11131528 | Capsanthin/capsorubin synthase, chloroplast precursor |
| Q42435 | 12643508 | Capsanthin/capsorubin synthase, chloroplast precursor |
| AAO64977 | 37730608 | lycopene beta cyclase [*Haematococcus pluvialis*] |
| Q40424 | 11133011 | Lycopene beta cyclase, chloroplast precursor |
| ABB52072 | 79154940 | putative capsanthin-capsorubin synthase [*Daucus carota* subsp. *sativus*] |
| AAQ02668 | 33304511 | lycopene cyclase [*Setaria italica*] |
| CAA54961 | 840729 | putative chromoplastic oxydo-reductase [*Capsicum annuum*] |
| EAJ62838 | 44489136 | unknown [environmental sequence] |
| YP_401079 | 81300871 | Lycopene cyclase, beta and epsilon [*Synechococcus elongatus* PCC 7942] |
| YP_172741 | 56752040 | lycopene cyclase [*Synechococcus elongatus* PCC 6301] |
| ZP_011 . . . | 88808972 | lycopene beta cyclase [*Synechococcus* sp. WH 7805] |
| EAK50052 | 44615956 | unknown [environmental sequence] |

TABLE 23-continued

Examples of lycopene cyclase polypeptides, beta and epsilon subunits.

| ACCESSION | GI | PROTEIN DESCRIPTION |
|---|---|---|
| NP_892751 | 33861190 | putative lycopene epsilon cyclase [*Prochlorococcus marinus* subsp. *pastoris* str. CCMP1986] |
| NP_875182 | 33240240 | Lycopene epsilon cyclase [*Prochlorococcus marinus* subsp. *marinus* str. CCMP1375] |
| YP_382237 | 78213458 | Lycopene cyclase, beta and epsilon [*Synechococcus* sp. CC9605] |
| YP_397130 | 78779018 | Lycopene cyclase, beta and epsilon [*Prochlorococcus marinus* str. MIT 9312] |
| NP_896821 | 33865262 | lycopene beta cyclase [*Synechococcus* sp. WH 8102] |
| YP_397570 | 78779458 | Lycopene cyclase, beta and epsilon [*Prochlorococcus marinus* str. MIT 9312] |
| ZP_010 . . . | 87302144 | lycopene cyclase [*Synechococcus* sp. WH 5701] |
| EAK17149 | 44569190 | unknown [environmental sequence] |
| YP_291882 | 72382527 | lycopene cyclase, beta and epsilon [*Prochlorococcus marinus* str. NATL2A] |
| NP_875528 | 33240586 | Lycopene beta cyclase related dehydrogenase [*Prochlorococcus marinus* subsp. *marinus* str. CCMP1375] |
| NP_893181 | 33861620 | putative lycopene beta cyclase [*Prochlorococcus marinus* subsp. *pastoris* str. CCMP1986] |
| NP_895600 | 33864040 | putative lycopene epsilon cyclase [*Prochlorococcus marinus* str. MIT 9313] |
| EAI47456 | 44325573 | unknown [environmental sequence] |
| YP_291268 | 72381913 | lycopene cyclase, beta and epsilon [*Prochlorococcus marinus* str. NATL2A] |
| ZP_010 . . . | 84517806 | Lycopene beta cyclase related dehydrogenase [*Prochlorococcus marinus* str. MIT 9211] |
| AAF34191 | 6970079 | lycopene epsilon cyclase [*Daucus carota*] |
| ZP_010 . . . | 84518202 | Lycopene epsilon cyclase [*Prochlorococcus marinus* str. MIT 9211] |
| YP_376736 | 78184301 | Lycopene cyclase, beta and epsilon [*Synechococcus* sp. CC9902] |
| ZP_003 . . . | 66796756 | Lycopene cyclase, beta and epsilon [*Deinococcus geothermalis* DSM 11300] |
| NP_894954 | 33863394 | putative lycopene beta cyclase [*Prochlorococcus marinus* str. MIT 9313] |
| AAT76051 | 50365502 | lycopene cyclase [*Citrus clementina*] |
| EAK22047 | 44576122 | unknown [environmental sequence] |
| NP_294525 | 15805827 | lycopene cyclase [*Deinococcus radiodurans* R1] |

TABLE 24

Examples of carotenoid glucosyltransferase polypeptides.

| ACCESSION | GI | PROTEIN DESCRIPTION |
|---|---|---|
| AAA21261 | 148395 | CrtX [*Pantoea agglomerans*] |
| AAN85597 | 27228291 | Zeaxanthin Glucosyl Transferase [*Pantoea stewartii*] |
| BAB79601 | 18143446 | crtX [*Pantoea agglomerans* pv. *milletiae*] |
| AAZ73147 | 72536082 | zeaxanthin glucosyl transferase [*Enterobacteriaceae bacterium* DC413] |
| AAZ73128 | 72536060 | zeaxanthin glucosyl transferase [*Enterobacteriaceae bacterium* DC260] |
| AAZ73140 | 72536074 | zeaxanthin glucosyl transferase [*Enterobacteriaceae bacterium* DC416] |
| Q01330 | 231911 | Zeaxanthin glucosyl transferase |
| ZP_006 . . . | 71674312 | UDP-glycosyltransferase, MGT [*Trichodesmium erythraeum* IMS101] |
| NP_439972 | 16329244 | zeaxanthin glucosyl transferase [*Synechocystis* sp. PCC 6803] |
| EAH29368 | 44130903 | unknown [environmental sequence] |
| ZP_005 . . . | 67926135 | zeaxanthin glucosyl transferase, hypothetical protein [*Crocosphaera watsonii* WH 8501] |
| YP_378763 | 78188425 | hypothetical protein Cag_0447 [*Chlorobium chlorochromatii* CaD3] |
| ZP_005 . . . | 68549418 | Glycosyl transferase, group 1 [*Pelodictyon phaeoclathratiforme* BU-1] |
| ZP_010 . . . | 85713606 | glycosyl transferase, group 1 [*Nitrobacter* sp. Nb-311A] |
| YP_317171 | 75674750 | glycosyl transferase, group 1 [*Nitrobacter winogradskyi* Nb-255] |
| ZP_006 . . . | 69929171 | Glycosyl transferase, group 1 [*Nitrobacter hamburgensis* X14] |
| ZP_009 . . . | 84500589 | hypothetical protein OB2597_11541 [*Oceanicola batsensis* HTCC2597] |

TABLE 24-continued

Examples of carotenoid glucosyltransferase polypeptides.

| ACCESSION | GI | PROTEIN DESCRIPTION |
|---|---|---|
| ZP_009 . . . | 83953176 | hypothetical protein NAS141_12746 [*Sulfitobacter* sp. NAS-14.1] |
| ZP_009 . . . | 83942121 | hypothetical protein EE36_07793 [*Sulfitobacter* sp. EE-36] |
| YP_508020 | 89052569 | glycosyl transferase, group 1 [*Jannaschia* sp. CCS1] |
| ZP_010 . . . | 85704103 | hypothetical protein ROS217_13931 [*Roseovarius* sp. 217] |
| ZP_009 . . . | 83370850 | probable glycosyltransferase [*Rhodobacter sphaeroides* ATCC 17025] |
| ZP_006 . . . | 69934465 | Glycosyl transferase, group 1 [*Paracoccus denitrificans* PD1222] |
| ZP_009 . . . | 83949880 | probable glycosyltransferase [*Roseovarius nubinhibens* ISM] |
| YP_376237 | 78183803 | putative glycosyltransferase [*Synechococcus* sp. CC9902] |
| YP_376129 | 78183695 | probable glycosyltransferase [*Synechococcus* sp. CC9902] |
| YP_374296 | 78186253 | hypothetical protein Plut_0365 [*Pelodictyon luteolum* DSM 273] |
| ZP_010 . . . | 87301651 | Putative glycosyltransferase [*Synechococcus* sp. WH 5701] |
| ZP_011 . . . | 88809938 | Putative glycosyltransferase [*Synechococcus* sp. WH 7805] |
| BAE47471 | 78483937 | carotenoid glucosyltransferase [*Paracoccus* sp. N81106] |
| ZP_010 . . . | 87303273 | probable glycosyltransferase [*Synechococcus* sp. WH 5701] |
| YP_376127 | 78183693 | probable glycosyltransferase [*Synechococcus* sp. CC9902] |
| YP_501334 | 88196509 | hypothetical protein SAOUHSC_02880 [*Staphylococcus aureus* subsp. *aureus* NCTC 8325] |
| YP_187370 | 57652300 | glycosyl transferase, group 2 family protein [*Staphylococcus aureus* subsp. *aureus* COL] |
| CAA66627 | 1340131 | unnamed protein product [*Staphylococcus aureus*] |
| YP_041987 | 49484763 | putative glycosyl transferase [*Staphylococcus aureus* subsp. *aureus* MRSA252] |
| YP_417885 | 82752144 | hypothetical protein SAB2436c [*Staphylococcus aureus* RF122] |
| YP_252404 | 70725490 | hypothetical protein SH0489 [*Staphylococcus haemolyticus* JCSC1435] |
| NP_693379 | 23099913 | hypothetical protein OB2458 [*Oceanobacillus iheyensis* HTE831] |
| ZP_008 . . . | 82501285 | conserved hypothetical protein [*Caldicellulosiruptor saccharolyticus* DSM 8903] |
| ZP_010 . . . | 87303565 | hypothetical protein WH5701_09900 [*Synechococcus* sp. WH 5701] |

TABLE 25

Examples of acyl CoA: diacyglycerol acyltransferase (DGAT) polypeptides.

| ACCESSION | GI | PROTEIN DESCRIPTION |
|---|---|---|
| XP_957022 | 85082953 | hypothetical protein [*Neurospora crassa* N150] |
| XP_386864 | 46124621 | hypothetical protein FG06688.1 [*Gibberella zeae* PH-1] |
| XP_755172 | 71000982 | diacylglycerol O-acyltransferase DGAT [*Aspergillus fumigatus* Af293] |
| XP_663763 | 67539978 | hypothetical protein AN6159.2 [*Aspergillus nidulans* FGSC A4] |
| BAE65302 | 83775179 | unnamed protein product [*Aspergillus oryzae*] |
| XP_502557 | 50550169 | hypothetical protein [*Yarrowia lipolytica*] |
| AAS78662 | 56199782 | diacylglycerol acyltransferase [*Glycine max*] |
| ABB84383 | 82582915 | diacylglycerol acyltransferase [*Jatropha curcas*] |
| AAV31083 | 54145459 | 1,2-diacyl-sn-glycerol: acyl-CoA acyltransferase [*Euonymus alatus*] |
| AAG23696 | 10803053 | diacylglycerol acyltransferase [*Perilla frutescens*] |
| AAF64065 | 7576941 | putative diacylglycerol acyltransferase [*Brassica napus*] |
| AAS01606 | 41387497 | acyl-CoA: diacylglycerol acyltransferase 1 [*Olea europaea*] |
| AAT73629 | 50299542 | acyl CoA: diacylglycerol acyltransferase [*Glycine max*] |
| AAM03340 | 67043496 | putative diacylglycerol acyltransferase [*Tropaeolum majus*] |
| XP_645633 | 66824557 | hypothetical protein DDB0202877 [*Dictyostelium discoideum*] |
| AAF19345 | 6625653 | diacylglycerol acylCoA acyltransferase [*Nicotiana tabacum*] |
| AAY40785 | 63376239 | diacylglycerol acyltransferase DGAT2 [*Brassica juncea*] |
| AAW47581 | 57231736 | diacylglycerol acyltransferase [*Oryza sativa (japonica* cultivar-group)] |
| AAR11479 | 38146080 | diacylglycerol acyltransferase [*Ricinus communis*] |
| AAY40784 | 63376226 | diacylglycerol acyltransferase DGAT1 [*Brassica juncea*] |
| AAP68322 | 31711932 | At2g19450 [*Arabidopsis thaliana*] |
| AAW51456 | 57545061 | diacylglycerol acyltransferase [*Lotus corniculatus* var. *japonicus*] |

TABLE 25-continued

Examples of acyl CoA: diacyglycerol acyltransferase (DGAT) polypeptides.

| ACCESSION | GI | PROTEIN DESCRIPTION |
|---|---|---|
| AAD45536 | 5579408 | putative diacylglycerol acyltransferase [*Brassica napus*] |
| BAD53762 | 53791817 | putative acyl-CoA: diacylglycerol acyltransferase [*Oryza sativa* (*japonica* cultivar-group)] |
| NP_956024 | 41054343 | hypothetical protein LOC325875 [*Danio rerio*] |
| AAL49962 | 18642598 | diacylglycerol acyltransferase 1 [*Bos taurus*] |
| XP_930884 | 89028385 | similar to Diacylglycerol O-acyltransferase 1 (Diglyceride acyltransferase) (ACAT-related gene) [*Homo sapiens*] |
| NP_777118 | 27819636 | diacylglycerol O-acyltransferase 1 [*Bos taurus*] |
| Q9GMF1 | 18202926 | Diacylglycerol O-acyltransferase 1 (Diglyceride acyltransferase) |
| NP_036211 | 6912332 | diacylglycerol O-acyltransferase 1 [*Homo sapiens*] |
| AAH06263 | 34782946 | DGAT1 protein [*Homo sapiens*] |
| XP_780515 | 72006039 | similar to Diacylglycerol O-acyltransferase 1 [*Strongylocentrotus purpuratus*] |
| AAD40881 | 5225382 | putative diacylglycerol acyltransferase [*Brassica napus*] |
| XP_539214 | 73974769 | similar to Diacylglycerol O-acyltransferase 1 (ACAT related gene product 1) isoform 1 [*Canis familiaris*] |
| AAZ22403 | 71063860 | diacylglycerol O-acyltransferase 1 [*Bubalus bubalis*] |
| NP_999216 | 47522918 | diacylglycerol acyltransferase [*Sus scrofa*] |
| NP_001 . . . | 50539976 | hypothetical protein LOC436731 [*Danio rerio*] |
| XP_849176 | 73974767 | similar to Diacylglycerol O-acyltransferase 1 (ACAT related gene product 1) isoform 2 [*Canis familiaris*] |
| NP_505828 | 71997360 | H19N07.4 [*Caenorhabditis elegans*] |
| AAF82410 | 9049538 | diacylglycerol acyltransferase [*Caenorhabditis elegans*] |
| CAE75170 | 39591950 | Hypothetical protein CBG23107 [*Caenorhabditis briggsae*] |
| XP_626337 | 66358318 | diacylglycerol acyltransferase 1 [*Cryptosporidium parvum* Iowa II] |
| XP_668402 | 67624239 | acyl-CoA: diacylglycerol acyltransferase 1-related enzyme [*Cryptosporidium hominis* TU502] |
| AAP94208 | 33113253 | acyl-CoA: diacylglycerol acyltransferase 1-related enzyme [*Toxoplasma gondii*] |
| AAP94209 | 33113255 | acyl-CoA: diacylglycerol acyltransferase 1-related enzyme [*Toxoplasma gondii*] |
| XP_579557 | 62652535 | PREDICTED: diacylglycerol O-acyltransferase 1 [*Rattus norvegicus*] |
| BAC66171 | 29170489 | diacylglycerol acyltransferase [*Mus musculus*] |
| Q9ERM3 | 18202872 | Diacylglycerol O-acyltransferase 1 (Diglyceride acyltransferase) |
| AAL78366 | 18698659 | acyl coenzyme A: diacylglycerol acyltransferase [*Drosophila melanogaster*] |
| NP_995724 | 45552403 | CG31991-PD, isoform D [*Drosophila melanogaster*] |
| NP_724017 | 24584734 | CG31991-PC, isoform C [*Drosophila melanogaster*] |
| XP_858062 | 73974765 | similar to Diacylglycerol O-acyltransferase 1 (ACAT related gene product 1) isoform 3 [*Canis familiaris*] |
| XP_728984 | 82915156 | hypothetical protein PY01256 [*Plasmodium yoelii yoelii* str. 17XNL] |
| CAG11944 | 47225461 | unnamed protein product [*Tetraodon nigroviridis*] |
| BAD27526 | 50199438 | acyl-CoA: diacylglycerol acyltransferase [eukaryotic synthetic construct] |
| XP_317656 | 31226099 | ENSANGP00000002281 [*Anopheles gambiae* str. PEST] |
| AAV59457 | 55733950 | putative diacylglycerol acyltransferase [*Oryza sativa* (*japonica* cultivar-group)] |
| EAL33593 | 54644853 | GA16599-PA [*Drosophila pseudoobscura*] |
| XP_678753 | 68073677 | diacylglycerol O-acyltransferase [*Plasmodium berghei* strain ANKA] |
| XP_520014 | 55631434 | PREDICTED: similar to Diacylglycerol O-acyltransferase 1 (Diglyceride acyltransferase) [*Pan troglodytes*] |
| CAG10815 | 47219451 | unnamed protein product [*Tetraodon nigroviridis*] |
| XP_624754 | 66522700 | PREDICTED: similar to ENSANGP00000002281 [*Apis mellifera*] |
| CAC69884 | 15620769 | diacylglycerol acyltransferase I [*Rattus norvegicus*] |
| XP_686181 | 68363630 | PREDICTED: similar to Diacylglycerol O-acyltransferase 1 (Diglyceride acyltransferase) [*Danio rerio*] |
| XP_734008 | 70921323 | diacylglycerol O-acyltransferase [*Plasmodium chabaudi chabaudi*] |
| XP_673128 | 68062248 | hypothetical protein PB300300.00.0 [*Plasmodium berghei* strain ANKA] |
| AAS72376 | 45642963 | acyl-CoA: cholesterol acyltransferase beta [*Toxoplasma gondii*] |
| AAS72375 | 45642961 | acyl-CoA: cholesterol acyltransferase alpha [*Toxoplasma gondii*] |
| NP_586145 | 19074639 | STEROL O-ACYLTRANSFERASE [*Encephalitozoon cuniculi* GB-M1] |
| XP_640280 | 66812202 | hypothetical protein DDB0205259 [*Dictyostelium discoideum*] |

TABLE 25-continued

Examples of acyl CoA: diacyglycerol acyltransferase (DGAT) polypeptides.

| ACCESSION | GI | PROTEIN DESCRIPTION |
|---|---|---|
| AAY40783 | 63376221 | diacylglycerol acyltransferase [*Brassica juncea*] |
| XP_765774 | 71032265 | diacylglycerol O-acyltransferase [*Theileria parva* strain Muguga] |
| Q876L2 | 34582301 | Sterol O-acyltransferase 2 (Sterol-ester synthase 2) |
| XP_571260 | 58268208 | sterol O-acyltransferase [*Cryptococcus neoformans* var. *neoformans* JEC21] |
| EAL20032 | 50257323 | hypothetical protein CNBF3580 [*Cryptococcus neoformans* var. *neoformans* B-3501A] |
| XP_954478 | 84999514 | acyl transferase [*Theileria annulata* strain Ankara] |
| XP_505086 | 50555355 | hypothetical protein [*Yarrowia lipolytica*] |
| NP_588558 | 19076058 | hypothetical protein SPCP1E11.05c [*Schizosaccharomyces pombe* 972h-] |
| AAC49441 | 1389739 | acyl-CoA: sterol acyltransferase |
| NP_014416 | 6324346 | Acyl-CoA: sterol acyltransferase, isozyme of Are1p; Are2p [*Saccharomyces cerevisiae*] |
| XP_750354 | 70991010 | sterol o-acyltransferase APE2 [*Aspergillus fumigatus* Af293] |
| XP_382192 | 46110268 | hypothetical protein FG02016.1 [*Gibberella zeae* PH-1] |
| BAE54934 | 83764790 | unnamed protein product [*Aspergillus oryzae*] |
| XP_885914 | 76617939 | similar to Sterol O-acyltransferase 2 (Cholesterol acyltransferase 2) (ACAT-2) isoform 2 [*Bos taurus*] |
| XP_591251 | 76617937 | similar to Sterol O-acyltransferase 2 (Cholesterol acyltransferase 2) (ACAT-2) isoform 1 [*Bos taurus*] |
| BAC00846 | 21392392 | AcylCoA: Cholesterol Acyltransferase 2 [*Rattus norvegicus*] |
| NP_649816 | 28571583 | CG8112-PA [*Drosophila melanogaster*] |
| NP_666176 | 22122547 | sterol O-acyltransferase 2 [*Mus musculus*] |
| O88908 | 18202245 | Sterol O-acyltransferase 2 (Cholesterol acyltransferase 2) (ACAT-2) |
| XP_761502 | 71022545 | hypothetical protein UM05355.1 [*Ustilago maydis* 521] |
| NP_714950 | 40254723 | sterol O-acyltransferase 2 [*Rattus norvegicus*] |
| EAQ86094 | 88178626 | hypothetical protein CHGG_07347 [*Chaetomium globosum* CBS 148.51] |
| XP_461395 | 50425599 | hypothetical protein DEHA0F25652g [*Debaryomyces hansenii* CBS767] |
| XP_661812 | 67527926 | hypothetical protein AN4208.2 [*Aspergillus nidulans* FGSC A4] |
| AAH96091 | 64654094 | Sterol O-acyltransferase 2 [*Homo sapiens*] |
| O75908 | 18202149 | Sterol O-acyltransferase 2 (Cholesterol acyltransferase 2) (ACAT-2) |
| AAH96090 | 64652990 | Sterol O-acyltransferase 2 [*Homo sapiens*] |
| AAK48829 | 13898623 | acyl coenzyme A: cholesterol acyltransferase-2 [*Homo sapiens*] |
| XP_543637 | 73996435 | PREDICTED: similar to sterol O-acyltransferase 2 [*Canis familiaris*] |
| O77759 | 18202176 | Sterol O-acyltransferase 2 (Cholesterol acyltransferase 2) (ACAT-2) |
| AAO32474 | 28564191 | ARE2 [*Saccharomyces castellii*] |
| XP_323485 | 32405744 | hypothetical protein [*Neurospora crassa*] |
| NP_982606 | 45184888 | AAR065Cp [*Eremothecium gossypii*] |
| NP_593708 | 19114620 | hypothetical protein SPAC13G7.06 [*Schizosaccharomyces pombe* 972h-] |
| AAO32554 | 28564940 | ARE2 [*Saccharomyces kluyveri*] |
| EAL28962 | 54639560 | GA20833-PA [*Drosophila pseudoobscura*] |
| XP_449806 | 50294790 | hypothetical protein CAGL0M10571g [*Candida glabrata* CBS138] |
| NP_033256 | 84619697 | sterol O-acyltransferase 1 [*Mus musculus*] |
| Q61263 | 18202591 | Sterol O-acyltransferase 1 (Cholesterol acyltransferase 1) (ACAT-1) |
| BAC34925 | 26342537 | unnamed protein product [*Mus musculus*] |
| XP_452607 | 50305295 | unnamed protein product [*Kluyveromyces lactis*] |
| NP_001 . . . | 77735363 | hypothetical protein LOC504287 [*Bos taurus*] |
| Q60457 | 18202585 | Sterol O-acyltransferase 1 (Cholesterol acyltransferase 1) (ACAT-1) |
| XP_320321 | 58393811 | ENSANGP00000016512 [*Anopheles gambiae* str. PEST] |
| XP_320320 | 58393809 | ENSANGP00000016486 [*Anopheles gambiae* str. PEST] |
| O70536 | 18202126 | Sterol O-acyltransferase 1 (Cholesterol acyltransferase 1) (ACAT-1) |
| XP_714776 | 68482533 | acyl-CoA cholesterol acyltransferase [*Candida albicans* SC5314] |
| P84285 | 56404462 | Sterol O-acyltransferase 2 (Sterol-ester synthase) (ASAT) |
| AAH77916 | 50416229 | Soat1-prov protein [*Xenopus laevis*] |
| XP_692855 | 68364838 | PREDICTED: similar to Soat1-prov protein [*Danio rerio*] |
| CAI13574 | 55960156 | sterol O-acyltransferase (acyl-Coenzyme A: cholesterol acyltransferase) 1 [*Homo sapiens*] |
| AAL56227 | 18028942 | cholesterol acyltransferase 1 [*Gorilla gorilla*] |
| AAL56228 | 18028944 | cholesterol acyltransferase 1 [*Pongo pygmaeus*] |

TABLE 25-continued

Examples of acyl CoA: diacyglycerol acyltransferase (DGAT) polypeptides.

| ACCESSION | GI | PROTEIN DESCRIPTION |
|---|---|---|
| AAC37532 | 4878022 | acyl-coenzyme A: cholesterol acyltransferase [*Homo sapiens*] |
| 2201440A | 1585676 | acyl-CoA/cholesterol acyltransferase |
| Q876L3 | 34582302 | Sterol O-acyltransferase 1 (Sterol-ester synthase 1) |
| BAE01048 | 67969393 | unnamed protein product [*Macaca fascicularis*] |
| XP_514030 | 55588858 | PREDICTED: hypothetical protein XP_514030 [*Pan troglodytes*] |
| XP_547445 | 73961286 | similar to Sterol O-acyltransferase 1 (Cholesterol acyltransferase 1) (ACAT-1) [*Canis familiaris*] |
| EAQ84619 | 88177151 | hypothetical protein CHGG_08633 [*Chaetomium globosum* CBS 148.51] |
| O77761 | 18202178 | Sterol O-acyltransferase 1 (Cholesterol acyltransferase 1) (ACAT-1) |
| XP_422267 | 50751122 | PREDICTED: similar to Sterol O-acyltransferase 1 (Cholesterol acyltransferase 1) (ACAT-1) [*Gallus gallus*] |
| XP_693284 | 68392980 | PREDICTED: similar to Sterol O-acyltransferase 1 (Cholesterol acyltransferase 1) (ACAT-1) [*Danio rerio*] |
| AAT92940 | 51013293 | YCR048W [*Saccharomyces cerevisiae*] |
| XP_956576 | 85080625 | hypothetical protein [*Neurospora crassa* N150] |
| XP_624691 | 66564061 | PREDICTED: similar to ENSANGP00000016486 [*Apis mellifera*] |
| CAF96514 | 47222847 | unnamed protein product [*Tetraodon nigroviridis*] |
| XP_788209 | 72085563 | PREDICTED: similar to sterol O-acyltransferase 1 [*Strongylocentrotus purpuratus*] |
| XP_445307 | 50285757 | unnamed protein product [*Candida glabrata*] |
| CAE70002 | 39596364 | Hypothetical protein CBG16409 [*Caenorhabditis briggsae*] |
| CAG07990 | 47225647 | unnamed protein product [*Tetraodon nigroviridis*] |
| NP_510623 | 17549960 | B0395.2 [*Caenorhabditis elegans*] |
| AAX28331 | 76157393 | SJCHGC04421 protein [*Schistosoma japonicum*] |
| CAI96158 | 66347204 | Diacylglycerol O-acyltransferase [*Bubalus bubalis*] |
| XP_390039 | 46136695 | hypothetical protein FG09863.1 [*Gibberella zeae* PH-1] |
| XP_643169 | 66819019 | hypothetical protein DDB0203882 [*Dictyostelium discoideum*] |
| AAO53095 | 28850306 | hypothetical protein [*Dictyostelium discoideum*] |
| AAB06959 | 1515472 | acyl-CoA: cholesterol acyltransferase [*Oryctolagus cuniculus*] |
| NP_945619 | 39933343 | putative alginate o-acetyltransferase AlgI [*Rhodopseudomonas palustris* CGA009] |
| ZP_008 . . . | 77691302 | Membrane bound O-acyl transferase, MBOAT [*Rhodopseudomonas palustris* BisB5] |
| XP_465546 | 50908115 | putative wax synthase [*Oryza sativa* (japonica cultivar-group)] |

TABLE 29

Examples of Prenyldiphosphate synthase polypeptides

| Accession | GI | Description |
|---|---|---|
| 29A: Bacteria Proteins that require a mitochondrial targeting sequence ||| 
| ZP_009 . . . | 83373595 | Trans-hexaprenyltranstransferase [*Rhodobacter sphaeroides* ATCC 17029] |
| ZP_009 . . . | 83371280 | Trans-hexaprenyltranstransferase [*Rhodobacter sphaeroides* ATCC 17025] |
| CAD24417 | 20429105 | decaprenyl diphosphate synthase [*Paracoccus zeaxanthinifaciens*] |
| ZP_010 . . . | 85705714 | Geranylgeranyl pyrophosphate synthase/Polyprenyl synthetase [*Roseovarius* sp. 217] |
| ZP_010 . . . | 84515724 | decaprenyl diphosphate synthase [*Loktanella vestfoldensis* SKA53] |
| YP_165582 | 56695234 | decaprenyl diphosphate synthase [*Silicibacter pomeroyi* DSS-3] |
| ZP_010 . . . | 86139019 | decaprenyl diphosphate synthase [*Roseobacter* sp. MED193] |
| ZP_009 . . . | 83941379 | decaprenyl diphosphate synthase [*Sulfitobacter* sp. EE-36] |
| ZP_009 . . . | 83854856 | decaprenyl diphosphate synthase [*Sulfitobacter* sp. NAS-14. 1] |
| ZP_006 . . . | 69299873 | Farnesyltranstransferase [*Silicibacter* sp. TM1040] |
| ZP_010 . . . | 84683979 | Geranylgeranyl pyrophosphate synthase/Polyprenyl synthetase [*Rhodobacterales bacterium* HTCC2654] |
| ZP_009 . . . | 84500217 | decaprenyl diphosphate synthase [*Oceanicola batsensis* HTCC2597] |
| ZP_009 . . . | 83952381 | decaprenyl diphosphate synthase [*Roseovarius nubinhibens* ISM] |
| ZP_006 . . . | 69937106 | Trans-hexaprenyltranstransferase [*Paracoccus denitrificans* PD1222] |
| ZP_005 . . . | 68180845 | Trans-hexaprenyltranstransferase [*Jannaschia* sp. CCS1] |
| ZP_008 . . . | 78495595 | Polyprenyl synthetase [*Rhodopseudomonas palustris* BisB18] |
| AAY82368 | 67866738 | decaprenyl diphosphate synthase [*Agrobacterium tumefaciens*] |
| NP_353656 | 15887975 | hypothetical protein AGR_C_1125 [*Agrobacterium tumefaciens* str. C58] |

TABLE 29-continued

Examples of Prenyldiphosphate synthase polypeptides

| Accession | GI | Description |
|---|---|---|
| ZP_008... | 77688465 | Farnesyltranstransferase [*Rhodopseudomonas palustris* BisB5] |
| NP_531334 | 17934544 | octaprenyl-diphosphate synthase [*Agrobacterium tumefaciens* str. C58] |
| YP_484709 | 86748213 | Farnesyltranstransferase [*Rhodopseudomonas palustris* HaA2] |
| AAP56240 | 37903500 | decaprenyl diphosphate synthase [*Agrobacterium tumefaciens*] |
| YP_192388 | 58040424 | Decaprenyl diphosphate synthase [*Gluconobacter oxydans* 621H] |
| | | 29B: Subunit 1- Proteins that contain mitochondrial targeting sequence |
| T43193 | 11279237 | trans-pentaprenyltranstransferase homolog - fission yeast (*Schizosaccharomyces pombe*) |
| AAD28559 | 4732024 | trans-prenyltransferase [*Homo sapiens*] |
| AAI07275 | 78070698 | Trans-prenyltransferase [*Mus musculus*] |
| BAE48216 | 81157931 | subunit 1 of decaprenyl diphosphate synthase [*Homo sapiens*] |
| AAH49211 | 29165656 | PDSS1 protein [*Homo sapiens*] |
| Q33DR2 | 85700953 | Decaprenyl-diphosphate synthase subunit 1 (Solanesyl-diphosphate synthase subunit 1) (Trans-prenyltransferase) |
| XP_507706 | 55633583 | PREDICTED: similar to TPRT protein [*Pan troglodytes*] |
| XP_586717 | 76632198 | PREDICTED: similar to trans-prenyltransferase [*Bos taurus*] |
| XP_849908 | 73948851 | PREDICTED: similar to trans-prenyltransferase [*Canis familiaris*] |
| | | 29C: Subunit 2- Proteins that contain mitochondrial targeting sequence |
| O13851 | 60389474 | Decaprenyl-diphosphate synthase subunit 2 (Decaprenyl pyrophosphate synthetase subunit 2) |
| BAE48218 | 81157935 | subunit 2 of solanesyl diphosphate synthase [*Mus musculus*] |
| BAE48217 | 81157933 | subunit 2 of decaprenyl diphosphate synthase [*Homo sapiens*] |

TABLE 30

Examples of PHB-Polyprenyltransferase polypeptides

| GI | PROTEIN DESCRIPTION |
|---|---|
| 51013645 | YNR041C [*Saccharomyces cerevisiae*] |
| 50285815 | unnamed protein product [*Candida glabrata*] |
| 50311051 | unnamed protein product [*Kluyveromyces lactis*] |
| 45200866 | AGL231Wp [*Eremothecium gossypii*] |
| 50555263 | hypothetical protein [*Yarrowia lipolytica*] |
| 68473193 | para-hydroxybenzoate: polyprenyl transferase [*Candida albicans* SC5314] |
| 50410039 | hypothetical protein DEHA0A14212g [*Debaryomyces hansenii* CBS767] |
| 83769349 | unnamed protein product [*Aspergillus oryzae*] |
| 70994900 | para-hydroxybenzoate-polyprenyltransferase precursor [*Aspergillus fumigatus* Af293] |
| 19114131 | hypothetical protein SPAC56F8. 04c [*Schizosaccharomyces pombe* 972h-] |
| 39973573 | hypothetical protein MG01067. 4 [*Magnaporthe grisea* 70-15] |
| 85078920 | protein related to para-hydroxybenzoate polyprenyltransferase precursor [*Neurospora crassa* N150] |
| 76660839 | PREDICTED: similar to para-hydroxybenzoate-polyprenyltransferase, mitochondrial [*Bos taurus*] |
| 52138578 | para-hydroxybenzoate-polyprenyltransferase, mitochondrial [*Homo sapiens*] |
| 18088424 | COQ2 protein [*Homo sapiens*] |
| 47221448 | unnamed protein product [*Tetraodon nigroviridis*] |
| 58385249 | ENSANGP00000012220 [*Anopheles gambiae* str. PEST] |
| 50746583 | PREDICTED: similar to hypothetical protein CL640 [*Gallus gallus*] |
| 54638587 | GA21912-PA [*Drosophila pseudoobscura*] |
| 21355567 | CG9613-PA [*Drosophila melanogaster*] |
| 71005862 | hypothetical protein UM01450. 1 [*Ustilago maydis* 521] |

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A genetically engineered *Yarrowia* fungus characterized by:
   a. the fungus is oleaginous in that it can accumulate lipid to at least 20% of its dry cell weight; and
   b. as a result of genetic engineering, the *Yarrowia* fungus produces at least one carotenoid, and can accumulate the produced carotenoid to at least 1% of its dry cell weight.

2. The *Yarrowia* fungus of claim 1 wherein the *Yarrowia* fungus is a strain of *Yarrowia lipolytica*.

3. The *Yarrowia* fungus of claim 1 wherein the fungus contains at least one oleaginic modification.

4. The *Yarrowia* fungus of claim 3 wherein the at least one oleaginic modification alters oleaginicity of the fungus.

5. The *Yarrowia* fungus of claim 3 wherein the fungus further comprises more than one carotenogenic modification.

6. The *Yarrowia* fungus of claim 3 wherein the at least one oleaginic modification increases expression or activity of at least one oleaginic polypeptide.

7. The *Yarrowia* fungus of claim 3, wherein the at least one oleaginic modification decreases expression or activity of at least one oleaginic polypeptide.

8. The *Yarrowia* fungus of claim 3, wherein the at least one oleaginic modification increases expression or activity of at least one oleaginic polypeptide and decreases expression or activity of at least one other oleaginic polypeptide.

9. The *Yarrowia* fungus of claim 6 or 7, wherein the at least one oleaginic polypeptide is selected from the group consisting of acetyl-CoA carboxylase polypeptide, pyruvate decarboxylase polypeptide, isocitrate dehydrogenase polypeptide, ATP-citrate lyase polypeptide, malic enzyme polypeptide, AMP deaminase polypeptide, and combinations thereof.

10. The *Yarrowia* fungus of claim 6 or 7 wherein the least one oleaginic polypeptide is at least one polypeptide selected from the group consisting of a polypeptide in any one of Tables 1 through 6.

11. The *Yarrowia* fungus of any one of claims 6-8, wherein the at least one oleaginic modification comprises expression of at least one heterologous oleaginic polypeptide in the fungus.

12. The *Yarrowia* fungus of claim 11, wherein the at least one oleaginic modification comprises expression of at least one heterologous gene encoding the at least one heterologous oleaginic polypeptide.

13. The *Yarrowia* fungus of claim 11, wherein the at least one heterologous oleaginic polypeptide comprises an animal polypeptide, a mammalian polypeptide, an insect polypeptide, a plant polypeptide, a fungal polypeptide, a yeast polypeptide, an algal polypeptide, a bacterial polypeptide, a cyanobacterial polypeptide, an archaebacterial polypeptide, or a protozoal polypeptide.

14. The *Yarrowia* fungus of claim 11, wherein the at least one heterologous oleaginic polypeptide comprises at least two heterologous oleaginic polypeptides.

15. The *Yarrowia* fungus of claim 14, wherein the at least two heterologous oleaginic polypeptides are from a single source organism.

16. The *Yarrowia* fungus of claim 14, wherein the at least two heterologous oleaginic polypeptides are from at least two different source organisms.

17. The *Yarrowia* fungus of claim 1 wherein the fungus contains more than one carotenogenic modification.

18. The *Yarrowia* fungus of claim 17 wherein the carotenogenic modifications confers to the fungus the ability to produce the at least one carotenoid to a level at least 1% of its dry cell weight.

19. The *Yarrowia* fungus of claim 17 wherein the carotenogenic modifications confers to the fungus the ability to produce at least one carotenoid which the fungus does not naturally produce.

20. The *Yarrowia* fungus of claim 17 wherein the fungus further comprises at least one oleaginic modification wherein the oleaginic modification alters oleaginicity of the fungus.

21. The *Yarrowia* fungus of claim 17, wherein the carotenogenic modifications confer the ability to the fungus to produce the at least one carotenoid to a level selected from the group consisting of at least 2%, at least 3%, at least 5%, and at least 10% of the fungus' dry cell weight.

22. The *Yarrowia* fungus of claim 17, wherein the carotenoids are selected from the group consisting of astaxanthin, β-carotene, canthaxanthin, zeaxanthin, lutein, lycopene, and combinations thereof.

23. The *Yarrowia* fungus of claim 17 wherein the predominant type of carotenoid is astaxanthin.

24. The *Yarrowia* fungus of claim 17, wherein at least one of the carotenogenic modifications increases expression or activity of a carotenogenic polypeptide.

25. The *Yarrowia* fungus of claim 17, wherein at least one of the carotenogenic modifications decreases expression or activity of a carotenogenic polypeptide.

26. The *Yarrowia* fungus of claim 17, wherein at least one of the carotenogenic modifications increases expression or activity of at least one carotenogenic polypeptide and decreases expression or activity of at least one other carotenogenic polypeptide.

27. The *Yarrowia* fungus of any one of claims 24-26, wherein the carotenogenic modifications comprises expression of at least one heterologous carotenogenic polypeptide.

28. The *Yarrowia* fungus of claim 27 wherein the carotenogenic modifications comprises expression of at least one heterologous gene encoding the at least one heterologous carotenogenic polypeptide.

29. The *Yarrowia* fungus of claim 24 or 25, wherein the carotenogenic polypeptide is selected from the group consisting of: isoprenoid biosynthesis polypeptides, carotenoid biosynthesis polypeptides, isoprenoid biosynthesis competitor polypeptides, and combinations thereof.

30. The *Yarrowia* fungus of claim 29 wherein the isoprenoid biosynthesis polypeptides are selected from the group consisting of: acetoacetyl-CoA thiolase polypeptide, HMG-CoA synthase polypeptide, HMG-CoA reductase polypeptide, mevalonate kinase polypeptide, phosphomevalonate kinase polypeptide, mevalonate pyrophosphate decarboxylase polypeptide, IPP isomerase polypeptide, FPP synthase polypeptide, and GGPP synthase polypeptide.

31. The *Yarrowia* fungus of claim 29, wherein the carotenoid biosynthesis polypeptides are selected from the group consisting of: phytoene synthase polypeptide, phytoene dehydrogenase polypeptide, lycopene cyclase polypeptide, carotenoid ketolase polypeptide, carotenoid hydroxylase polypeptide, astaxanthin synthase polypeptide, carotenoid epsilon hydroxylase polypeptide, carotenoid glucosyltransferase polypeptide, lycopene cyclase (beta and epsilon subunits) polypeptides, and acyl CoA:diacyglycerol acyltransferase polypeptide.

32. The *Yarrowia* fungus of claim 29, wherein the isoprenoid biosynthesis competitor polypeptides are selected from the group consisting of squalene synthase polypeptide, prenyldiphosphate synthase and PHB polyprenyltransferase.

33. The *Yarrowia* fungus of claim 29, wherein the carotenogenic polypeptide is selected from the group consisting of any of the polypeptides of any one of Tables 7-25, Table 29, and Table 30, and combinations thereof.

34. The *Yarrowia* fungus of any one of claims 24-26, wherein the carotenogenic modifications comprises an animal polypeptide, a mammalian polypeptide, an insect polypeptide, a plant polypeptide, a fungal polypeptide, a yeast polypeptide, an algal polypeptide, a bacterial polypeptide, cyanobacterial polypeptide, an archaebacterial polypeptide, or a protozoal polypeptide.

35. The *Yarrowia* fungus of any one of claims 24-26, wherein the carotenogenic modifications comprises at least two heterologous carotenogenic polypeptides.

36. The *Yarrowia* fungus of claim 35, wherein the at least two heterologous carotenogenic polypeptides are from a single source organism.

37. The *Yarrowia* fungus of claim 35, wherein the at least two heterologous carotenogenic polypeptides are from at least two different source organisms.

38. A *Yarrowia* fungus according to claim 1 wherein the *Yarrowia* fungus accumulates the produced at least one carotenoid to a level selected from the group consisting of:
above 1%, above 2%, above 3%, above 5%, and above 10% of the fungus' dry cell weight.

39. A *Yarrowia* fungus according to claim 1 characterized in that the *Yarrowia* fungus accumulates lipid in the form of cytoplasmic bodies.

40. The *Yarowia* fungus of claim 39 wherein the at least one carotenoid accumulates in the cytoplasmic oil bodies.

41. A strain of *Yarrowia lipolytica* comprising one or more modifications selected from the group consisting of an oleaginic modification, a carotenogenic modification, and combinations thereof, such that the strain accumulates from 1% to 10% of its dry cell weight as at least one carotenoid.

42. The strain of claim 41 further characterized in that it accumulates from 20% to 50% of its dry cell weight as lipid.

43. The strain of claim 42, wherein the strain accumulates from 20% to 50% of its dry cell weight as lipid in the form of cytoplasmic oil bodies.

44. The strain of claim 41, wherein the strain comprises a carotenogenic modification selected from the group consisting of:
a. expression of a polypeptide selected from a group consisting of a truncated endogenous HMG CoA reductase polypeptide that lacks the N-terminal membrane spanning domain, acetoacetyl-CoA thiolase, HMG-CoA synthase, FPP synthase, and GGPP synthase;
b. expression of a heterologous polypeptide selected from the group consisting of phytoene synthase, phytoene desaturase, lycopene cyclase, carotenoid ketolase, carotenoid hydroxylase, and combinations thereof.

45. The strain of any one of claims 41-44, wherein the strain accumulates 1-10% of its dry cell weight as β-carotene.

46. The strain of claim 41, wherein the strain comprises a carotenogenic modification selected from the group consisting of:
a. expression of a polypeptide selected from a group consisting of a truncated endogenous HMG CoA reductase polypeptide that lacks the N-terminal membrane spanning domain, acetoacetyl-CoA thiolase, HMG-CoA synthase, FPP synthase, and GGPP synthase;
b. expression of a heterologous polypeptide selected from the group consisting of phytoene synthase, phytoene desaturase, lycopene cyclase, carotenoid ketolase, carotenoid hydroxylase, astaxanthin synthase, carotenoid epsilon hydroxylase, lycopene cyclase (beta and epsilon subunits), carotenoid glucosyltransferase, acyl CoA:diacylglycerol acyltransferase, and combinations thereof.

47. The strain of any one of claim 41-43 or 46, wherein the strain accumulates 1-10% of its dry cell weight as astaxanthin or lutein.

48. A method of producing a carotenoid, the method comprising steps of:
a. cultivating the fungus of claim 1 under conditions that allow production of the carotenoid;
b. and isolating the produced carotenoid.

49. The method of claim 48, wherein the step of isolating comprises fractionating the cultivation medium to obtain at least one carotenoid-enriched fraction.

50. The method of claim 48, wherein: the step of cultivating comprises cultivating the fungus under conditions that allow accumulation of the carotenoid in cytoplasmic oil bodies; and the step of isolating comprises isolating oil derived from the cytoplasmic oil bodies.

51. The method of claim 48, wherein the carotenoid is selected from the group consisting of astaxanthin, β-carotene, canthaxanthin, zeaxanthin, lutein, lycopene, and combinations thereof.

52. The method of claim 48, wherein the carotenoid comprises astaxanthin.

53. A method of preparing a food or feed additive containing a carotenoid, the method comprising steps of:
a. cultivating the fungus of claim 1 under conditions that allow production of the carotenoid;
b. isolating the carotenoid; and
c. combining the isolated carotenoid with one or more other food or feed additive components.

\* \* \* \* \*

SEQUENCE LISTING

<160> NUMBER OF SEQ ID NOS: 83

<210> SEQ ID NO 1

-continued

```
<211> LENGTH: 984
<212> TYPE: DNA
<213> ORGANISM: Artificial
<220> FEATURE:
<223> OTHER INFORMATION: Y. lipolytica

<400> SEQUENCE: 1
atggattata acagcgcgga tttcaaggag atatggggca aggccgccga caccgcgctg    60
ctgggaccgt acaactacct cgccaacaac cggggccaca acatcagaga acacttgatc   120
gcagcgttcg gagcggttat caaggtggac aagagcgatc tcgagaccat ttcgcacatc   180
accaagattt tgcataactc gtcgctgctt gttgatgacg tggaagacaa ctcgatgctc   240
cgacgaggcc tgccggcagc ccattgtctg tttggagtcc cccaaaccat caactccgcc   300
aactacatgt actttgtggc tctgcaggag gtgctcaagc tcaagtctta tgatgccgtc   360
tccattttca ccgaggaaat gatcaacttg catagaggtc agggtatgga tctctactgg   420
agagaaacac tcacttgccc ctcggaagac gagtatctgg atggtggt gcacaagacc    480
ggtggactgt ttcggctggc tctgagactt atgctgtcgg tggcatcgaa acaggaggac   540
catgaaaaga tcaactttga tctcacacac cttaccgaca cactgggagt catttaccag   600
attctggatg attacctcaa cctgcagtcc acggaattga ccgagaacaa gggattctgc   660
gaagatatca gcgaaggaaa gttttcgttt ccgctgattc acagcatacg caccaacccg   720
gataaccacg agattctcaa cattctcaaa cagcgaacaa gcgacgcttc actcaaaaag   780
tacgccgtgg actacatgag aacagaaacc aagagtttcg actactgcct caagaggata   840
caggccatgt cactcaaggc aagttcgtac attgatgatc tagcagcagc tggccacgat   900
gtctccaagc tacgagccat tttgcattat tttgtgtcca cctctgactg tgaggagaga   960
aagtactttg aggatgcgca gtga                                          984

<210> SEQ ID NO 2
<211> LENGTH: 327
<212> TYPE: PRT
<213> ORGANISM: Artificial
<220> FEATURE:
<223> OTHER INFORMATION: Y. lipolytica

<400> SEQUENCE: 2

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140
```

-continued

```
Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
            165                 170                 175

Lys Gln Glu Asp His Glu Lys Ile Asn Phe Asp Leu Thr His Leu Thr
        180                 185                 190

Asp Thr Leu Gly Val Ile Tyr Gln Ile Leu Asp Tyr Leu Asn Leu
    195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
ctgggtgacc tggaagcctt                                              20

<210> SEQ ID NO 4
<211> LENGTH: 23
<212> TYPE: DNA
<213> ORGANISM: Artificial
<220> FEATURE:
<223> OTHER INFORMATION: Primer

<400> SEQUENCE: 4
aagatcaatc cgtagaagtt cag                                          23

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
aagcgattac aatcttcctt tgg                                          23

<210> SEQ ID NO 6
<211> LENGTH: 22
<212> TYPE: DNA
<213> ORGANISM: Artificial
<220> FEATURE:
<223> OTHER INFORMATION: Primer
```

```
<400> SEQUENCE: 6
ccagtccatc aactcagtct ca                                        22

<210> SEQ ID NO 7
<211> LENGTH: 23
<212> TYPE: DNA
<213> ORGANISM: Artificial
<220> FEATURE:
<223> OTHER INFORMATION: Primer

<400> SEQUENCE: 7
gcattgctta ttacgaagac tac                                       23

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
ccactgtcct ccactacaaa cac                                       23

<210> SEQ ID NO 9
<211> LENGTH: 31
<212> TYPE: DNA
<213> ORGANISM: Artificial
<220> FEATURE:
<223> OTHER INFORMATION: Primer

<400> SEQUENCE: 9
cacaaacgcg ttcactgcgc atcctcaaag t                              31

<210> SEQ ID NO 10
<211> LENGTH: 37
<212> TYPE: DNA
<213> ORGANISM: Artificial
<220> FEATURE:
<223> OTHER INFORMATION: Primer

<400> SEQUENCE: 10
cacaatctag acacaaatgg attataacag cgcggat                        37

<210> SEQ ID NO 11
<211> LENGTH: 31
<212> TYPE: DNA
<213> ORGANISM: Artificial
<220> FEATURE:
<223> OTHER INFORMATION: Primer

<400> SEQUENCE: 11
cacaaactag tttgccacct acaagccaga t                              31

<210> SEQ ID NO 12
<211> LENGTH: 31
<212> TYPE: DNA
<213> ORGANISM: Artificial
<220> FEATURE:
<223> OTHER INFORMATION: Primer

<400> SEQUENCE: 12
cacaaggtac caatgtgaaa gtgcgcgtga t                              31

<210> SEQ ID NO 13
```

```
<211> LENGTH: 28
<212> TYPE: DNA
<213> ORGANISM: Artificial
<220> FEATURE:
<223> OTHER INFORMATION: Primer

<400> SEQUENCE: 13
cacaaggtac cagagaccgg gttggcgg                                               28

<210> SEQ ID NO 14
<211> LENGTH: 40
<212> TYPE: DNA
<213> ORGANISM: Artificial
<220> FEATURE:
<223> OTHER INFORMATION: Primer

<400> SEQUENCE: 14
cacaagcggc cgcgctagca tggggatcga tctcttatat                                  40

<210> SEQ ID NO 15
<211> LENGTH: 41
<212> TYPE: DNA
<213> ORGANISM: Artificial
<220> FEATURE:
<223> OTHER INFORMATION: Primer

<400> SEQUENCE: 15
cacaagcggc cgcgctagcg aatgattctt atactcagaa g                                41

<210> SEQ ID NO 16
<211> LENGTH: 40
<212> TYPE: DNA
<213> ORGANISM: Artificial
<220> FEATURE:
<223> OTHER INFORMATION: Primer

<400> SEQUENCE: 16
cacaagcggc cgcacgcgtg caattaacag atagtttgcc                                  40

<210> SEQ ID NO 17
<211> LENGTH: 33
<212> TYPE: DNA
<213> ORGANISM: Artificial
<220> FEATURE:
<223> OTHER INFORMATION: Primer

<400> SEQUENCE: 17
cacaagctag ctggggatgc gatctcttat atc                                         33

<210> SEQ ID NO 18
<211> LENGTH: 36
<212> TYPE: DNA
<213> ORGANISM: Artificial
<220> FEATURE:
<223> OTHER INFORMATION: Primer

<400> SEQUENCE: 18
cacaaacgcg tttaaatggt atttagattt ctcatt                                      36

<210> SEQ ID NO 19
<211> LENGTH: 36
<212> TYPE: DNA
<213> ORGANISM: Artificial
<220> FEATURE:
<223> OTHER INFORMATION: Primer

<400> SEQUENCE: 19
```

-continued cacaatctag acacaaatgc tgctcaccta catgga                                36

<210> SEQ ID NO 20
<211> LENGTH: 1906
<212> TYPE: DNA
<213> ORGANISM: Artificial
<220> FEATURE:
<223> OTHER INFORMATION: M. circinelloides

<400> SEQUENCE: 20

| | | |
|---|---|---|
| atgctgctca cctacatgga agtccacctc tactacacgc tgcctgtgct gggcgtcctg | 60 |
| tcctggctgt cgcggccgta ctacacagcc accgatgcgc tcaaattcaa atttctgaca | 120 |
| ctggttgcct tcacgaccgc ctccgcctgg acaactaca ttgtctacca caaggcgtgg | 180 |
| tcctactgcc ccacctgcgt caccgctgtc attggctacg tgcccttgga ggagtacatg | 240 |
| ttcttcatca tcatgactct gttgaccgtg gcattcacca atctggtgat gcgctggcac | 300 |
| ctgcacagct tctttatcag gcctgaaacg cccgtcatgc agtccgtcct ggtccgtctt | 360 |
| gtccccataa cagccttatt aatcactgca tacaaggctt gggtaagcaa acaaacaaat | 420 |
| gatgtgccgc atcgcatttt aatattaacc attgcataca cagcatttgg cggtccctgg | 480 |
| aaagccactg ttctacggat catgcatttt gtggtacgcc tgtccggttt tggccttatt | 540 |
| gtggtttggt gctggcgagt acatgatgcg tcgtccgctg gcggtgctcg tctccattgc | 600 |
| gctgcccacg ctgtttctct gctgggtcga tgtcgtcgct attggcgccg gcacatggga | 660 |
| catttcgctg gccacaagca ccggcaagtt cgtcgtgccc cacctgcccg tggaggaatt | 720 |
| catgttcttt gcgctaatta ataccgtttt ggtatttggt acgtgtgcga tcgatcgcac | 780 |
| gatggcgatc ctccacctgt tcaaaaacaa gagtccttat cagcgcccat accagcacag | 840 |
| caagtcgttc ctccaccaga tcctcgagat gacctgggcc ttctgtttac ccgaccaagt | 900 |
| gctgcattca gacacattcc acgacctgtc cgtcagctgg gacatcctgc gcaaggcctc | 960 |
| caagtccttt tacacggcct ctgctgtctt tcccggcgac gtgcgccaag agctcggtgt | 1020 |
| gctatacgcc ttttgcagag ccacggacga tctctgcgac aacgagcagg tccctgtgca | 1080 |
| gacgcgaaag gagcagctga tactgacaca tcagttcgtc agcgatctgt ttggccaaaa | 1140 |
| gacaagcgcg ccgactgcca ttgactggga ctttacaac gaccaactgc ctgcctcgtg | 1200 |
| catctctgcc ttcaagtcgt tcacccgttt gcgccatgtg ctggaagctg agccatcaa | 1260 |
| ggaactgctc gacgggtaca agtgggattt ggagcgtcgc tccatcaggg atcaggagga | 1320 |
| tctcagatat tactcagctt gtgtcgccag cagtgttggt gaaatgtgca ctcgcatcat | 1380 |
| actggcccac gccgacaagc ccgcctcccg ccagcaaaca cagtggatca ttcagcgtgc | 1440 |
| gcgtgaaatg ggtctggtac tccaatatac aaacattgca agagacattg tcaccgacag | 1500 |
| cgaggaactg gcagatgct acctgcctca ggattggctt accgagaagg aggtggcgct | 1560 |
| gattcaaggc ggccttgccc gagaaattgg cgaggagcga ttgctctcac tgtcgcatcg | 1620 |
| cctcatctac caggcagacg agctcatggt ggttgccaac aagggcatcg acaagctgcc | 1680 |
| cagccattgt caaggcggcg tgcgtgcggc ctgcaacgtc tatgcttcca ttggcaccaa | 1740 |
| gctcaagtct tacaagcacc actatcccag cagagcacat gtcggcaatt cgaaacgagt | 1800 |
| ggaaattgct cttcttagcg tatacaacct ttacaccgcg ccaattgcga ctagtagtac | 1860 |
| cacacattgc agacagggaa aaatgagaaa tctaaatacc atttaa | 1906 |

<210> SEQ ID NO 21

<211> LENGTH: 613
<212> TYPE: PRT
<213> ORGANISM: Artificial
<220> FEATURE:
<223> OTHER INFORMATION: M. circinelloides

<400> SEQUENCE: 21

Met Leu Leu Thr Tyr Met Glu Val His Leu Tyr Tyr Thr Leu Pro Val
1               5                   10                  15

Leu Gly Val Leu Ser Trp Leu Ser Arg Pro Tyr Tyr Thr Ala Thr Asp
            20                  25                  30

Ala Leu Lys Phe Lys Phe Leu Thr Leu Val Ala Phe Thr Thr Ala Ser
        35                  40                  45

Ala Trp Asp Asn Tyr Ile Val Tyr His Lys Ala Trp Ser Tyr Cys Pro
    50                  55                  60

Thr Cys Val Thr Ala Val Ile Gly Tyr Val Pro Leu Glu Glu Tyr Met
65                  70                  75                  80

Phe Phe Ile Ile Met Thr Leu Leu Thr Val Ala Phe Thr Asn Leu Val
                85                  90                  95

Met Arg Trp His Leu His Ser Phe Phe Ile Arg Pro Glu Thr Pro Val
            100                 105                 110

Met Gln Ser Val Leu Val Arg Leu Val Pro Ile Thr Ala Leu Leu Ile
        115                 120                 125

Thr Ala Tyr Lys Ala Trp His Leu Ala Val Pro Gly Lys Pro Leu Phe
    130                 135                 140

Tyr Gly Ser Cys Ile Leu Trp Tyr Ala Cys Pro Val Leu Ala Leu Leu
145                 150                 155                 160

Trp Phe Gly Ala Gly Glu Tyr Met Met Arg Arg Pro Leu Ala Val Leu
                165                 170                 175

Val Ser Ile Ala Leu Pro Thr Leu Phe Leu Cys Trp Val Asp Val Val
            180                 185                 190

Ala Ile Gly Ala Gly Thr Trp Asp Ile Ser Leu Ala Thr Ser Thr Gly
        195                 200                 205

Lys Phe Val Val Pro His Leu Pro Val Glu Glu Phe Met Phe Phe Ala
    210                 215                 220

Leu Ile Asn Thr Val Leu Val Phe Gly Thr Cys Ala Ile Asp Arg Thr
225                 230                 235                 240

Met Ala Ile Leu His Leu Phe Lys Asn Lys Ser Pro Tyr Gln Arg Pro
                245                 250                 255

Tyr Gln His Ser Lys Ser Phe Leu His Gln Ile Leu Glu Met Thr Trp
            260                 265                 270

Ala Phe Cys Leu Pro Asp Gln Val Leu His Ser Asp Thr Phe His Asp
        275                 280                 285

Leu Ser Val Ser Trp Asp Ile Leu Arg Lys Ala Ser Lys Ser Phe Tyr
    290                 295                 300

Thr Ala Ser Ala Val Phe Pro Gly Asp Val Arg Gln Glu Leu Gly Val
305                 310                 315                 320

Leu Tyr Ala Phe Cys Arg Ala Thr Asp Leu Cys Asp Asn Glu Gln
                325                 330                 335

Val Pro Val Gln Thr Arg Lys Glu Gln Leu Ile Leu Thr His Gln Phe
            340                 345                 350

Val Ser Asp Leu Phe Gly Gln Lys Thr Ser Ala Pro Thr Ala Ile Asp
        355                 360                 365

Trp Asp Phe Tyr Asn Asp Gln Leu Pro Ala Ser Cys Ile Ser Ala Phe
    370                 375                 380

```
Lys Ser Phe Thr Arg Leu Arg His Val Leu Glu Ala Gly Ala Ile Lys
385                 390                 395                 400

Glu Leu Leu Asp Gly Tyr Lys Trp Asp Leu Glu Arg Arg Ser Ile Arg
                405                 410                 415

Asp Gln Glu Asp Leu Arg Tyr Tyr Ser Ala Cys Val Ala Ser Ser Val
                420                 425                 430

Gly Glu Met Cys Thr Arg Ile Ile Leu Ala His Ala Asp Lys Pro Ala
            435                 440                 445

Ser Arg Gln Gln Thr Gln Trp Ile Ile Gln Arg Ala Arg Glu Met Gly
        450                 455                 460

Leu Val Leu Gln Tyr Thr Asn Ile Ala Arg Asp Ile Val Thr Asp Ser
465                 470                 475                 480

Glu Glu Leu Gly Arg Cys Tyr Leu Pro Gln Asp Trp Leu Thr Glu Lys
                485                 490                 495

Glu Val Ala Leu Ile Gln Gly Gly Leu Ala Arg Glu Ile Gly Glu Glu
            500                 505                 510

Arg Leu Leu Ser Leu Ser His Arg Leu Ile Tyr Gln Ala Asp Glu Leu
        515                 520                 525

Met Val Val Ala Asn Lys Gly Ile Asp Lys Leu Pro Ser His Cys Gln
530                 535                 540

Gly Gly Val Arg Ala Ala Cys Asn Val Tyr Ala Ser Ile Gly Thr Lys
545                 550                 555                 560

Leu Lys Ser Tyr Lys His His Tyr Pro Ser Arg Ala His Val Gly Asn
                565                 570                 575

Ser Lys Arg Val Glu Ile Ala Leu Leu Ser Val Tyr Asn Leu Tyr Thr
            580                 585                 590

Ala Pro Ile Ala Thr Ser Ser Thr His Cys Arg Gln Gly Lys Met
        595                 600                 605

Arg Asn Leu Asn Thr
    610

<210> SEQ ID NO 22
<211> LENGTH: 17
<212> TYPE: DNA
<213> ORGANISM: Artificial
<220> FEATURE:
<223> OTHER INFORMATION: Primer

<400> SEQUENCE: 22
gtaaaacgac ggccagt                                                    17

<210> SEQ ID NO 23
<211> LENGTH: 38
<212> TYPE: DNA
<213> ORGANISM: Artificial
<220> FEATURE:
<223> OTHER INFORMATION: Primer

<400> SEQUENCE: 23
cacacggtct catgccaagc cttgtatgca gtgattaa                             38

<210> SEQ ID NO 24
<211> LENGTH: 19
<212> TYPE: DNA
<213> ORGANISM: Artificial
<220> FEATURE:
<223> OTHER INFORMATION: Primer

<400> SEQUENCE: 24
```
ccactgtgtt tgctggcgg                                              19

<210> SEQ ID NO 25
<211> LENGTH: 34
<212> TYPE: DNA
<213> ORGANISM: Artificial
<220> FEATURE:
<223> OTHER INFORMATION: Primer

<400> SEQUENCE: 25
cacacggtct ctggcatttg gcggtccctg gaaa                             34

<210> SEQ ID NO 26
<211> LENGTH: 35
<212> TYPE: DNA
<213> ORGANISM: Artificial
<220> FEATURE:
<223> OTHER INFORMATION: Primer

<400> SEQUENCE: 26
cacaaacgcg tttaaatgac attagagtta tgaac                            35

<210> SEQ ID NO 27
<211> LENGTH: 37
<212> TYPE: DNA
<213> ORGANISM: Artificial
<220> FEATURE:
<223> OTHER INFORMATION: Primer

<400> SEQUENCE: 27
cacaatctag acacaaatgt ccaagaaaca cattgtc                          37

<210> SEQ ID NO 28
<211> LENGTH: 17
<212> TYPE: DNA
<213> ORGANISM: Artificial
<220> FEATURE:
<223> OTHER INFORMATION: Primer

<400> SEQUENCE: 28
gtaaaacgac ggccagt                                                17

<210> SEQ ID NO 29
<211> LENGTH: 31
<212> TYPE: DNA
<213> ORGANISM: Artificial
<220> FEATURE:
<223> OTHER INFORMATION: Primer

<400> SEQUENCE: 29
cacaaggtct caagcacgca tcccggaact g                                31

<210> SEQ ID NO 30
<211> LENGTH: 32
<212> TYPE: DNA
<213> ORGANISM: Artificial
<220> FEATURE:
<223> OTHER INFORMATION: Primer

<400> SEQUENCE: 30
cacacggtct caggcatgtc gccctacgat gc                               32

<210> SEQ ID NO 31
<211> LENGTH: 35
<212> TYPE: DNA

```
<213> ORGANISM: Artificial
<220> FEATURE:
<223> OTHER INFORMATION: Primer

<400> SEQUENCE: 31
cacacggtct catgcttgca cccacaaaga atagg                              35

<210> SEQ ID NO 32
<211> LENGTH: 17
<212> TYPE: DNA
<213> ORGANISM: Artificial
<220> FEATURE:
<223> OTHER INFORMATION: Primer

<400> SEQUENCE: 32
caggaaacag ctatgac                                                  17

<210> SEQ ID NO 33
<211> LENGTH: 36
<212> TYPE: DNA
<213> ORGANISM: Artificial
<220> FEATURE:
<223> OTHER INFORMATION: Primer

<400> SEQUENCE: 33
cacacggtct cttgcccata tacatggtct gaaacg                             36

<210> SEQ ID NO 34
<211> LENGTH: 1740
<212> TYPE: DNA
<213> ORGANISM: Artificial
<220> FEATURE:
<223> OTHER INFORMATION: M. circinelloides

<400> SEQUENCE: 34
atgtccaaga aacacattgt cattatcggt gctggcgtgg gtggcacggc tacagctgct    60
cgtttggccc gcgaaggctt caaggtcact gtggtggaga aaaacgactt tggtggcggc   120
cgctgctcct tgatccatca ccagggccat cgctttgatc agggcccgtc gctctacctg   180
atgcccaagt actttgagga cgcctttgcc gatctggacg agcgcattca agaccacctg   240
gagctgctgc gatgcgacaa caactacaag gtgcactttg acgacggtga gtcgatccag   300
ctgtcgtctg acttgacacg catgaaggct gaattggacc gcgtggaggg ccccttggt   360 tttggccgat tcctggattt catgaaagag acacacatcc actacgaaag cggcaccctg   420
attgcgctca agaagaattt cgaatccatc tgggacctga ttcgcatcaa gtacgctcca   480
gagatctttc gcttgcacct gtttggcaag atctacgacc gcgcttccaa gtacttcaag   540
accaagaaga tgcgcatggc attcacgttt cagaccatgt atatgggcat gtcgccctac   600
gatgcgcctg ctgtctacag cctgttgcag tacaccgagt tcgctgaagg catctggtat   660
ccccgtggcg gcttcaacat ggtggttcag aagctagagg cgattgcaaa gcaaaagtac   720
gatgccgagt ttatctacaa tgcgcctgtt gccaagatta acaccgatga tgccaccaaa   780
caagtgacag gtgtaacctt ggaaaatggc cacatcatcg atgccgatgc ggttgtgtgt   840
aacgcagatc tggtctatgc ttatcacaat ctgttgcctc cctgccgatg gacgcaaaac   900
acactggctt ccaagaaatt gacgtcttct tccatttcct tctactggtc catgtccacc   960
aaggtgcctc aattggacgt gcacaacatc ttttggccg aggcttatca ggagagcttt  1020
gacgaaatct tcaaggactt tggcctgcct tctgaagcct ccttctacgt caatgtgccc  1080
tctcgcatcg atccttctgc tgctcccgac ggcaaggact ctgtcattgt cttggtgcct  1140
```

-continued

```
attggtcata tgaagagcaa gacgggcgat gcttccaccg agaactaccc ggccatggtg    1200
gacaaggcac gcaagatggt gctggctgtg attgagcgtc gtctgggcat gtcgaatttc    1260
gccgacttga ttgagcatga gcaagtcaat gatcccgctg tatggcagag caagttcaat    1320
ctgtggagag gctcaattct gggtttgtct catgatgtgc ttcaggtgct gtggttccgt    1380
cccagcacaa aggattctac cggtcgttat gataacctat tctttgtggg tgcaagcacg    1440
catcccggaa ctggtgttcc cattgtcctt gcaggaagca agctcacctc tgaccaagtt    1500
gtcaagagct ttggaaagac gcccaagcca agaaagatcg agatggagaa cacgcaagca    1560
cctttggagg agcctgatgc tgaatcgaca ttccctgtgt ggttctggtt gcgcgctgcc    1620
tttggggtca tgtttatgtt cttttacttc ttccctcaat ccaatggcca aacgcccgca    1680
tcttttatca ataatttgtt acctgaagta ttccgcgttc ataactctaa tgtcatttaa    1740
```

<210> SEQ ID NO 35
<211> LENGTH: 579
<212> TYPE: PRT
<213> ORGANISM: Artificial Sequence
<220> FEATURE:
<223> OTHER INFORMATION: M. circinelloides

<400> SEQUENCE: 35

Met Ser Lys Lys His Ile Val Ile Ile Gly Ala Gly Val Gly Thr
1               5                   10                  15

Ala Thr Ala Ala Arg Leu Ala Arg Glu Gly Phe Lys Val Thr Val Val
            20                  25                  30

Glu Lys Asn Asp Phe Gly Gly Gly Arg Cys Ser Leu Ile His His Gln
        35                  40                  45

Gly His Arg Phe Asp Gln Gly Pro Ser Leu Tyr Leu Met Pro Lys Tyr
    50                  55                  60

Phe Glu Asp Ala Phe Ala Asp Leu Asp Glu Arg Ile Gln Asp His Leu
65                  70                  75                  80

Glu Leu Leu Arg Cys Asp Asn Asn Tyr Lys Val His Phe Asp Asp Gly
                85                  90                  95

Glu Ser Ile Gln Leu Ser Ser Asp Leu Thr Arg Met Lys Ala Glu Leu
            100                 105                 110

Asp Arg Val Glu Gly Pro Leu Gly Phe Gly Arg Phe Leu Asp Phe Met
        115                 120                 125

Lys Glu Thr His Ile His Tyr Glu Ser Gly Thr Leu Ile Ala Leu Lys
    130                 135                 140

Lys Asn Phe Glu Ser Ile Trp Asp Leu Ile Arg Ile Lys Tyr Ala Pro
145                 150                 155                 160

Glu Ile Phe Arg Leu His Leu Phe Gly Lys Ile Tyr Asp Arg Ala Ser
                165                 170                 175

Lys Tyr Phe Lys Thr Lys Lys Met Arg Met Ala Phe Thr Phe Gln Thr
            180                 185                 190

Met Tyr Met Gly Met Ser Pro Tyr Asp Ala Pro Ala Val Tyr Ser Leu
        195                 200                 205

Leu Gln Tyr Thr Glu Phe Ala Glu Gly Ile Trp Tyr Pro Arg Gly Gly
    210                 215                 220

Phe Asn Met Val Val Gln Lys Leu Glu Ala Ile Ala Lys Gln Lys Tyr
225                 230                 235                 240

Asp Ala Glu Phe Ile Tyr Asn Ala Pro Val Ala Lys Ile Asn Thr Asp
                245                 250                 255

Asp Ala Thr Lys Gln Val Thr Gly Val Thr Leu Glu Asn Gly His Ile
            260                 265                 270

Ile Asp Ala Asp Ala Val Val Cys Asn Ala Asp Leu Val Tyr Ala Tyr
        275                 280                 285

His Asn Leu Leu Pro Pro Cys Arg Trp Thr Gln Asn Thr Leu Ala Ser
    290                 295                 300

Lys Lys Leu Thr Ser Ser Ile Ser Phe Tyr Trp Ser Met Ser Thr
305                 310                 315                 320

Lys Val Pro Gln Leu Asp Val His Asn Ile Phe Leu Ala Glu Ala Tyr
                325                 330                 335

Gln Glu Ser Phe Asp Glu Ile Phe Lys Asp Phe Gly Leu Pro Ser Glu
            340                 345                 350

Ala Ser Phe Tyr Val Asn Val Pro Ser Arg Ile Asp Pro Ser Ala Ala
        355                 360                 365

Pro Asp Gly Lys Asp Ser Val Ile Val Leu Val Pro Ile Gly His Met
    370                 375                 380

Lys Ser Lys Thr Gly Asp Ala Ser Thr Glu Asn Tyr Pro Ala Met Val
385                 390                 395                 400

Asp Lys Ala Arg Lys Met Val Leu Ala Val Ile Glu Arg Arg Leu Gly
                405                 410                 415

Met Ser Asn Phe Ala Asp Leu Ile Glu His Glu Gln Val Asn Asp Pro
            420                 425                 430

Ala Val Trp Gln Ser Lys Phe Asn Leu Trp Arg Gly Ser Ile Leu Gly
        435                 440                 445

Leu Ser His Asp Val Leu Gln Val Leu Trp Phe Arg Pro Ser Thr Lys
    450                 455                 460

Asp Ser Thr Gly Arg Tyr Asp Asn Leu Phe Phe Val Gly Ala Ser Thr
465                 470                 475                 480

His Pro Gly Thr Gly Val Pro Ile Val Leu Ala Gly Ser Lys Leu Thr
                485                 490                 495

Ser Asp Gln Val Val Lys Ser Phe Gly Lys Thr Pro Lys Pro Arg Lys
            500                 505                 510

Ile Glu Met Glu Asn Thr Gln Ala Pro Leu Glu Pro Asp Ala Glu
        515                 520                 525

Ser Thr Phe Pro Val Trp Phe Trp Leu Arg Ala Ala Phe Trp Val Met
    530                 535                 540

Phe Met Phe Phe Tyr Phe Phe Pro Gln Ser Asn Gly Gln Thr Pro Ala
545                 550                 555                 560

Ser Phe Ile Asn Asn Leu Leu Pro Glu Val Phe Arg Val His Asn Ser
                565                 570                 575

Asn Val Ile

<210> SEQ ID NO 36
<211> LENGTH: 32
<212> TYPE: DNA
<213> ORGANISM: Artificial
<220> FEATURE:
<223> OTHER INFORMATION: Primer

<400> SEQUENCE: 36
cattcactag tggtgtgttc tgtggagcat tc                              32

<210> SEQ ID NO 37
<211> LENGTH: 36
<212> TYPE: DNA
<213> ORGANISM: Artificial

<220> FEATURE:
<223> OTHER INFORMATION: Primer

<400> SEQUENCE: 37
cacacggtct catcgaggtg tagtggtagt gcagtg         36

<210> SEQ ID NO 38
<211> LENGTH: 1740
<212> TYPE: DNA
<213> ORGANISM: Artificial
<220> FEATURE:
<223> OTHER INFORMATION: Y. lipolytica

<400> SEQUENCE: 38

| | |
|---|---|
| atgtccaaga aacacattgt cattatcggt gctggcgtgg gtggcacggc tacagctgct | 60 |
| cgtttggccc gcgaaggctt caaggtcact gtggtggaga aaacgacttt ggtggcggc | 120 |
| cgctgctcct tgatccatca ccagggccat cgctttgatc agggcccgtc gctctacctg | 180 |
| atgcccaagt actttgagga cgcctttgcc gatctggacg agcgcattca agaccacctg | 240 |
| gagctgctgc gatgcgacaa caactacaag gtgcactttg acgacggtga gtcgatccag | 300 |
| ctgtcgtctg acttgacacg catgaaggct gaattggacc gcgtggaggg ccccttggt | 360 |
| tttggccgat tcctggattt catgaaagag acacacatcc actacgaaag cggcaccctg | 420 |
| attgcgctca agaagaattt cgaatccatc tgggacctga ttcgcatcaa gtacgctcca | 480 |
| gagatctttc gcttgcacct gtttggcaag atctacgacc gcgcttccaa gtacttcaag | 540 |
| accaagaaga tgcgcatggc attcacgttt cagaccatgt atatgggcat gtcgccctac | 600 |
| gatgcgcctg ctgtctacag cctgttgcag tacaccgagt tcgctgaagg catctggtat | 660 |
| ccccgtggcg gcttcaacat ggtggttcag aagctagagg cgattgcaaa gcaaaagtac | 720 |
| gatgccgagt ttatctacaa tgcgcctgtt gccaagatta acaccgatga tgccaccaaa | 780 |
| caagtgacag gtgtaacctt ggaaaatggc cacatcatcg atgccgatgc ggttgtgtgt | 840 |
| aacgcagatc tggtctatgc ttatcacaat ctgttgcctc cctgccgatg gacgcaaaac | 900 |
| acactggctt ccaagaaatt gacgtcttct tccatttcct tctactgtc catgtccacc | 960 |
| aaggtgcctc aattggacgt gcacaacatc tttttggccg aggcttatca ggagagcttt | 1020 |
| gacgaaatct tcaaggactt tggcctgcct tctgaagcct ccttctacgt caatgtgccc | 1080 |
| tctcgcatcg atccttctgc tgctcccgac ggcaaggact ctgtcattgt cttggtgcct | 1140 |
| attggtcata tgaagagcaa gacgggcgat gcttccaccg agaactaccc ggccatggtg | 1200 |
| gacaaggcac gcaagatggt gctggctgtg attgagcgtc gtctgggcat gtcgaatttc | 1260 |
| gccgacttga ttgagcatga gcaagtcaat gatcccgctg tatggcagag caagttcaat | 1320 |
| ctgtggagag gctcaattct gggtttgtct catgatgtgc ttcaggtgct gtggttccgt | 1380 |
| cccagcacaa aggattctac cggtcgttat gataacctat tctttgtggg tgcaagcacg | 1440 |
| catcccggaa ctggtgttcc cattgtcctt gcaggaagca agctcacctc tgaccaagtt | 1500 |
| gtcaagagct ttggaaagac gcccaagcca agaaagatcg agatggagaa cacgcaagca | 1560 |
| cctttggagg agcctgatgc tgaatcgaca ttccctgtgt ggttctggtt gcgcgctgcc | 1620 |
| ttttgggtca tgtttatgtt cttttacttc ttccctcaat ccaatggcca aacgcccgca | 1680 |
| tcttttatca ataatttgtt acctgaagta ttccgcgttc ataactctaa tgtcattaa | 1740 |

<210> SEQ ID NO 39
<211> LENGTH: 579
<212> TYPE: PRT

<213> ORGANISM: Artificial
<220> FEATURE:
<223> OTHER INFORMATION: Y. lipolytica

<400> SEQUENCE: 39

```
Met Ser Lys Lys His Ile Val Ile Gly Ala Gly Val Gly Gly Thr
 1               5                  10                  15

Ala Thr Ala Ala Arg Leu Ala Arg Glu Gly Phe Lys Val Thr Val Val
            20                  25                  30

Glu Lys Asn Asp Phe Gly Gly Arg Cys Ser Leu Ile His His Gln
            35                  40                  45

Gly His Arg Phe Asp Gln Gly Pro Ser Leu Tyr Leu Met Pro Lys Tyr
        50                  55                  60

Phe Glu Asp Ala Phe Ala Asp Leu Asp Glu Arg Ile Gln Asp His Leu
65                  70                  75                  80

Glu Leu Leu Arg Cys Asp Asn Asn Tyr Lys Val His Phe Asp Asp Gly
                85                  90                  95

Glu Ser Ile Gln Leu Ser Ser Asp Leu Thr Arg Met Lys Ala Glu Leu
            100                 105                 110

Asp Arg Val Glu Gly Pro Leu Gly Phe Gly Arg Phe Leu Asp Phe Met
            115                 120                 125

Lys Glu Thr His Ile His Tyr Glu Ser Gly Thr Leu Ile Ala Leu Lys
130                 135                 140

Lys Asn Phe Glu Ser Ile Trp Asp Leu Ile Arg Ile Lys Tyr Ala Pro
145                 150                 155                 160

Glu Ile Phe Arg Leu His Leu Phe Gly Lys Ile Tyr Asp Arg Ala Ser
                165                 170                 175

Lys Tyr Phe Lys Thr Lys Lys Met Arg Met Ala Phe Thr Phe Gln Thr
            180                 185                 190

Met Tyr Met Gly Met Ser Pro Tyr Asp Ala Pro Ala Val Tyr Ser Leu
        195                 200                 205

Leu Gln Tyr Thr Glu Phe Ala Glu Gly Ile Trp Tyr Pro Arg Gly Gly
    210                 215                 220

Phe Asn Met Val Val Gln Lys Leu Glu Ala Ile Ala Lys Gln Lys Tyr
225                 230                 235                 240

Asp Ala Glu Phe Ile Tyr Asn Ala Pro Val Ala Lys Ile Asn Thr Asp
                245                 250                 255

Asp Ala Thr Lys Gln Val Thr Gly Val Thr Leu Glu Asn Gly His Ile
            260                 265                 270

Ile Asp Ala Asp Ala Val Val Cys Asn Ala Asp Leu Val Tyr Ala Tyr
        275                 280                 285

His Asn Leu Leu Pro Pro Cys Arg Trp Thr Gln Asn Thr Leu Ala Ser
    290                 295                 300

Lys Lys Leu Thr Ser Ser Ser Ile Ser Phe Tyr Trp Ser Met Ser Thr
305                 310                 315                 320

Lys Val Pro Gln Leu Asp Val His Asn Ile Phe Leu Ala Glu Ala Tyr
                325                 330                 335

Gln Glu Ser Phe Asp Glu Ile Phe Lys Asp Phe Gly Leu Pro Ser Glu
            340                 345                 350

Ala Ser Phe Tyr Val Asn Val Pro Ser Arg Ile Asp Pro Ser Ala Ala
        355                 360                 365

Pro Asp Gly Lys Asp Ser Val Ile Val Leu Val Pro Ile Gly His Met
    370                 375                 380

Lys Ser Lys Thr Gly Asp Ala Ser Thr Glu Asn Tyr Pro Ala Met Val
```

```
                385                 390                 395                 400
Asp Lys Ala Arg Lys Met Val Leu Ala Val Ile Glu Arg Arg Leu Gly
                405                 410                 415

Met Ser Asn Phe Ala Asp Leu Ile Glu His Glu Gln Val Asn Asp Pro
            420                 425                 430

Ala Val Trp Gln Ser Lys Phe Asn Leu Trp Arg Gly Ser Ile Leu Gly
        435                 440                 445

Leu Ser His Asp Val Leu Gln Val Leu Trp Phe Arg Pro Ser Thr Lys
    450                 455                 460

Asp Ser Thr Gly Arg Tyr Asp Asn Leu Phe Phe Val Gly Ala Ser Thr
465                 470                 475                 480

His Pro Gly Thr Gly Val Pro Ile Val Leu Ala Gly Ser Lys Leu Thr
                485                 490                 495

Ser Asp Gln Val Val Lys Ser Phe Gly Lys Thr Pro Lys Pro Arg Lys
            500                 505                 510

Ile Glu Met Glu Asn Thr Gln Ala Pro Leu Glu Pro Asp Ala Glu
        515                 520                 525

Ser Thr Phe Pro Val Trp Phe Trp Leu Arg Ala Ala Phe Trp Val Met
    530                 535                 540

Phe Met Phe Tyr Phe Phe Pro Gln Ser Asn Gly Gln Thr Pro Ala
545                 550                 555                 560

Ser Phe Ile Asn Asn Leu Leu Pro Glu Val Phe Arg Val His Asn Ser
                565                 570                 575

Asn Val Ile
```

<210> SEQ ID NO 40
<211> LENGTH: 36
<212> TYPE: DNA
<213> ORGANISM: Artificial
<220> FEATURE:
<223> OTHER INFORMATION: Primer

<400> SEQUENCE: 40
ttctagacac aaaaatggct gcagaccaat tggtga         36

<210> SEQ ID NO 41
<211> LENGTH: 33
<212> TYPE: DNA
<213> ORGANISM: Artificial
<220> FEATURE:
<223> OTHER INFORMATION: Primer

<400> SEQUENCE: 41
cattaattct tctaaaggac gtattttctt atc         33

<210> SEQ ID NO 42
<211> LENGTH: 21
<212> TYPE: DNA
<213> ORGANISM: Artificial
<220> FEATURE:
<223> OTHER INFORMATION: Primer

<400> SEQUENCE: 42
gttctctgga cgacctagag g         21

<210> SEQ ID NO 43
<211> LENGTH: 33
<212> TYPE: DNA
<213> ORGANISM: Artificial
<220> FEATURE:

<223> OTHER INFORMATION: Primer

<400> SEQUENCE: 43

| cacacacgcg tacacctatg accgtatgca aat | 33 |

<210> SEQ ID NO 44
<211> LENGTH: 40
<212> TYPE: DNA
<213> ORGANISM: Artificial
<220> FEATURE:
<223> OTHER INFORMATION: Primer

<400> SEQUENCE: 44

| cacactctag acacaaaaat gacccagtct gtgaaggtgg | 40 |

<210> SEQ ID NO 45
<211> LENGTH: 1503
<212> TYPE: DNA
<213> ORGANISM: Artificial
<220> FEATURE:
<223> OTHER INFORMATION: Y. lipolytica

<400> SEQUENCE: 45

| atgacccagt ctgtgaaggt ggttgagaag cacgttccta tcgtcattga gaagcccagc | 60 |
| gagaaggagg aggacacctc ttctgaagac tccattgagc tgactgtcgg aaagcagccc | 120 |
| aagcccgtga ccgagacccg ttctctggac gacctagagg ctatcatgaa ggcaggtaag | 180 |
| accaagcttc tggaggacca cgaggttgtc aagctctctc tcgagggcaa gcttcctttg | 240 |
| tatgctcttg agaagcagct tggtgacaac acccgagctg ttggcatccg acgatctatc | 300 |
| atctcccagc agtctaatac caagacttta gagacctcaa agcttcctta cctgcactac | 360 |
| gactacgacc gtgttttgg agcctgttgc gagaacgtta ttggttacat gcctctcccc | 420 |
| gttggtgttg ctggccccat gaacattgat ggcaagaact accacattcc tatggccacc | 480 |
| actgagggtt gtcttgttgc ctcaaccatg cgaggttgca aggccatcaa cgccggtggc | 540 |
| ggtgttacca ctgtgcttac tcaggacggt atgacgag gtccttgtgt tccttcccc | 600 |
| tctctcaagc gggctggagc cgctaagatc tggcttgatt ccgaggaggg tctcaagtcc | 660 |
| atgcgaaagg ccttcaactc cacctctcga tttgctcgtc tccagtctct tcactctacc | 720 |
| cttgctggta acctgctgtt tattcgattc cgaaccacca ctggtgatgc catgggcatg | 780 |
| aacatgatct ccaagggcgt cgaacactct ctggccgtca tggtcaagga gtacggcttc | 840 |
| cctgatatgg acattgtgtc tgtctcgggt aactactgca ctgacaagaa gcccgcagcg | 900 |
| atcaactgga tcgaaggccg aggcaagagt gttgttgccg aagccaccat ccctgctcac | 960 |
| attgtcaagt ctgttctcaa aagtgaggtt gacgctcttg ttgagctcaa catcagcaag | 1020 |
| aatctgatcg gtagtgccat ggctggctct gtgggaggtt caatgcaca cgccgcaaac | 1080 |
| ctggtgaccg ccatctacct tgccactggc caggatcctg ctcagaatgt cgagtcttcc | 1140 |
| aactgcatca cgctgatgag caacgtcgac ggtaacctgc tcatctccgt ttccatgcct | 1200 |
| tctatcgagg tcggtaccat tggtggaggt actattttgg agccccaggg ggctatgctg | 1260 |
| gagatgcttg gcgtgcgagg tcctcacatc gagaccccg tgccaacgc ccaacagctt | 1320 |
| gctcgcatca ttgcttctgg agttcttgca gcggagcttt cgctgtgttc tgctcttgct | 1380 |
| gccggccatc ttgtgcaaag tcatatgacc acaaccggt cccaggctcc tactccggcc | 1440 |
| aagcagtctc aggccgatct gcagcgtcta caaaacggtt cgaatatttg catacggtca | 1500 |
| tag | 1503 |

<210> SEQ ID NO 46
<211> LENGTH: 500
<212> TYPE: PRT
<213> ORGANISM: Artificial
<220> FEATURE:
<223> OTHER INFORMATION: Y. lipolytica

<400> SEQUENCE: 46

| | | | | | | | | | | | | | | | |
|---|---|---|---|---|---|---|---|---|---|---|---|---|---|---|---|
| Met | Thr | Gln | Ser | Val | Lys | Val | Val | Glu | Lys | His | Val | Pro | Ile | Val | Ile |
| 1 | | | | 5 | | | | | 10 | | | | | 15 | |
| Glu | Lys | Pro | Ser | Glu | Lys | Glu | Glu | Asp | Thr | Ser | Ser | Glu | Asp | Ser | Ile |
| | | | 20 | | | | | 25 | | | | | 30 | | |
| Glu | Leu | Thr | Val | Gly | Lys | Gln | Pro | Lys | Pro | Val | Thr | Glu | Thr | Arg | Ser |
| | | | | 35 | | | | | 40 | | | | | 45 | |
| Leu | Asp | Asp | Leu | Glu | Ala | Ile | Met | Lys | Ala | Gly | Lys | Thr | Lys | Leu | Leu |
| | | 50 | | | | | 55 | | | | | 60 | | | |
| Glu | Asp | His | Glu | Val | Val | Lys | Leu | Ser | Leu | Glu | Gly | Lys | Leu | Pro | Leu |
| 65 | | | | | 70 | | | | | 75 | | | | | 80 |
| Tyr | Ala | Leu | Glu | Lys | Gln | Leu | Gly | Asp | Asn | Thr | Arg | Ala | Val | Gly | Ile |
| | | | | 85 | | | | | 90 | | | | | 95 | |
| Arg | Arg | Ser | Ile | Ile | Ser | Gln | Gln | Ser | Asn | Thr | Lys | Thr | Leu | Glu | Thr |
| | | | | 100 | | | | | 105 | | | | | 110 | |
| Ser | Lys | Leu | Pro | Tyr | Leu | His | Tyr | Asp | Tyr | Asp | Arg | Val | Phe | Gly | Ala |
| | | | 115 | | | | | 120 | | | | | 125 | | |
| Cys | Cys | Glu | Asn | Val | Ile | Gly | Tyr | Met | Pro | Leu | Pro | Val | Gly | Val | Ala |
| | | 130 | | | | | 135 | | | | | 140 | | | |
| Gly | Pro | Met | Asn | Ile | Asp | Gly | Lys | Asn | Tyr | His | Ile | Pro | Met | Ala | Thr |
| 145 | | | | | 150 | | | | | 155 | | | | | 160 |
| Thr | Glu | Gly | Cys | Leu | Val | Ala | Ser | Thr | Met | Arg | Gly | Cys | Lys | Ala | Ile |
| | | | | 165 | | | | | 170 | | | | | 175 | |
| Asn | Ala | Gly | Gly | Gly | Val | Thr | Thr | Val | Leu | Thr | Gln | Asp | Gly | Met | Thr |
| | | | | 180 | | | | | 185 | | | | | 190 | |
| Arg | Gly | Pro | Cys | Val | Ser | Phe | Pro | Ser | Leu | Lys | Arg | Ala | Gly | Ala | Ala |
| | | | 195 | | | | | 200 | | | | | 205 | | |
| Lys | Ile | Trp | Leu | Asp | Ser | Glu | Glu | Gly | Leu | Lys | Ser | Met | Arg | Lys | Ala |
| | | 210 | | | | | 215 | | | | | 220 | | | |
| Phe | Asn | Ser | Thr | Ser | Arg | Phe | Ala | Arg | Leu | Gln | Ser | Leu | His | Ser | Thr |
| 225 | | | | | 230 | | | | | 235 | | | | | 240 |
| Leu | Ala | Gly | Asn | Leu | Leu | Phe | Ile | Arg | Phe | Arg | Thr | Thr | Thr | Gly | Asp |
| | | | | 245 | | | | | 250 | | | | | 255 | |
| Ala | Met | Gly | Met | Asn | Met | Ile | Ser | Lys | Gly | Val | Glu | His | Ser | Leu | Ala |
| | | | | 260 | | | | | 265 | | | | | 270 | |
| Val | Met | Val | Lys | Glu | Tyr | Gly | Phe | Pro | Asp | Met | Asp | Ile | Val | Ser | Val |
| | | | 275 | | | | | 280 | | | | | 285 | | |
| Ser | Gly | Asn | Tyr | Cys | Thr | Asp | Lys | Lys | Pro | Ala | Ala | Ile | Asn | Trp | Ile |
| | | | 290 | | | | | 295 | | | | | 300 | | | |
| Glu | Gly | Arg | Gly | Lys | Ser | Val | Val | Ala | Glu | Ala | Thr | Ile | Pro | Ala | His |
| 305 | | | | | 310 | | | | | 315 | | | | | 320 |
| Ile | Val | Lys | Ser | Val | Leu | Lys | Ser | Glu | Val | Asp | Ala | Leu | Val | Glu | Leu |
| | | | | 325 | | | | | 330 | | | | | 335 | |
| Asn | Ile | Ser | Lys | Asn | Leu | Ile | Gly | Ser | Ala | Met | Ala | Gly | Ser | Val | Gly |
| | | | | 340 | | | | | 345 | | | | | 350 | |
| Gly | Phe | Asn | Ala | His | Ala | Ala | Asn | Leu | Val | Thr | Ala | Ile | Tyr | Leu | Ala |
| | | | 355 | | | | | 360 | | | | | 365 | | |

```
Thr Gly Gln Asp Pro Ala Gln Asn Val Glu Ser Ser Asn Cys Ile Thr
    370                 375                 380

Leu Met Ser Asn Val Asp Gly Asn Leu Leu Ile Ser Val Ser Met Pro
385                 390                 395                 400

Ser Ile Glu Val Gly Thr Ile Gly Gly Thr Ile Leu Glu Pro Gln
                405                 410                 415

Gly Ala Met Leu Glu Met Leu Gly Val Arg Gly Pro His Ile Glu Thr
                420                 425                 430

Pro Gly Ala Asn Ala Gln Gln Leu Ala Arg Ile Ile Ala Ser Gly Val
                435                 440                 445

Leu Ala Ala Glu Leu Ser Leu Cys Ser Ala Leu Ala Ala Gly His Leu
    450                 455                 460

Val Gln Ser His Met Thr His Asn Arg Ser Gln Ala Pro Thr Pro Ala
465                 470                 475                 480

Lys Gln Ser Gln Ala Asp Leu Gln Arg Leu Gln Asn Gly Ser Asn Ile
                485                 490                 495

Cys Ile Arg Ser
            500

<210> SEQ ID NO 47
<211> LENGTH: 551
<212> TYPE: DNA
<213> ORGANISM: Artificial Sequence
<220> FEATURE:
<223> OTHER INFORMATION: Novosphingobium aromaticivorans

<400> SEQUENCE: 47
ttctagacac aaaaatgggt ggagccatgc agaccctcgc tgctatcctg atcgtcctcg      60
gtacagtgct cgctatggag tttgtcgctt ggtcttctca taagtatatc atgcatggct    120
tcggatgggg atggcataga gaccatcacg agccccatga gggatttctt gagaagaatg    180
acttatacgc catcgttggc gctgccctct cgatactcat gtttgccctc ggctctccca    240
tgatcatggg cgctgacgcc tggtggcccg gaacctggat cggactcggt gtcctcttct    300
atggtgtcat ctataccctc gtgcacgacg gtctggtgca ccaacgatgg tttagatggg    360
tgcctaaacg aggttacgcc aaacgactcg tgcaggccca taagctgcac acgccacca    420 ttggcaagga aggaggcgtc tcattcggtt tcgtgttcgc ccgagatccc gccgttctga    480
agcaggagct tcgagctcaa cgagaagcag gtatcgccgt gctgcgagag ctgtggacg    540 gctagacgcg t                                                         551

<210> SEQ ID NO 48
<211> LENGTH: 815
<212> TYPE: DNA
<213> ORGANISM: Artificial Sequence
<220> FEATURE:
<223> OTHER INFORMATION: Sargasso Sea environmental isolate

<400> SEQUENCE: 48
ttctagacac aaaaatgact cgatctattt cctggccttc cacctactgg cacctccagc     60
cctcctgttc ttcttgggtc gcaaacgaat tctctcctca agcccgaaaa ggtctcgtcc    120
tcgctggtct cattggttcc gcttggctgc ttactctcgg acttggcttt tcccttcccc    180
tccatcaaac gagctggctt ctcatcggtt gtctcgttct ccttagatct ttcctgcaca    240
ccggactttt tatcgttgcc catgacgcta tgcacgcttc tcttgttcct gaccaccctg    300
gccttaaccg ttggattgga cgtgtctgtc ttctcatgta tgctggactc tcctacaaaa    360
```

```
gatgctgccg aaatcaccgt cgacaccacc aagcccctga acagttgaa gaccctgact    420 accaacgatg cactaacaac aatatcctcg actggtacgt tcactttatg ggaaattacc    480
tcggatggca acaattgctt aatctctctt gcgtttggct cgctctcacc ttccgtgttt    540
ctgactactc tgctcaattc ttccacctgc tccttttctc tgtccttcct ctcatcgtct    600
cctcctgtca actcttcctc gtgggaacct ggctgccaca ccgacgaggc gctactactc    660
gacccggcgt taccactcga tccctgaact tccaccctgc tctttccttc gctgcttgct    720
accacttcgg ttaccaccgt gaacaccatg aatctccctc tactccttgg ttccaacttc    780
ctaaactccg agaaggttct ctcatctaaa cgcgt                              815
```

<210> SEQ ID NO 49
<211> LENGTH: 29
<212> TYPE: DNA
<213> ORGANISM: Artificial
<220> FEATURE:
<223> OTHER INFORMATION: Primer

<400> SEQUENCE: 49

```
cacacggtac ctgtaggttg ggttgggtg                                       29
```

<210> SEQ ID NO 50
<211> LENGTH: 45
<212> TYPE: DNA
<213> ORGANISM: Artificial
<220> FEATURE:
<223> OTHER INFORMATION: Primer

<400> SEQUENCE: 50

```
cacacggatc ctgtttaatt caagaatgaa tatagagaag agaag                     45
```

<210> SEQ ID NO 51
<211> LENGTH: 42
<212> TYPE: DNA
<213> ORGANISM: Artificial
<220> FEATURE:
<223> OTHER INFORMATION: Primer

<400> SEQUENCE: 51

```
cacacggatc cacatcaaca atggcatctg ccacccttcc cc                        42
```

<210> SEQ ID NO 52
<211> LENGTH: 31
<212> TYPE: DNA
<213> ORGANISM: Artificial
<220> FEATURE:
<223> OTHER INFORMATION: Primer

<400> SEQUENCE: 52

```
cacacggatc caagtgctga cgcggaactt g                                    31
```

<210> SEQ ID NO 53
<211> LENGTH: 37
<212> TYPE: DNA
<213> ORGANISM: Artificial
<220> FEATURE:
<223> OTHER INFORMATION: Primer

<400> SEQUENCE: 53

```
cacaccgtct caaatgacca atttcctgat cgtcgtc                              37
```

<210> SEQ ID NO 54

```
<211> LENGTH: 29
<212> TYPE: DNA
<213> ORGANISM: Artificial
<220> FEATURE:
<223> OTHER INFORMATION: Primer

<400> SEQUENCE: 54
cacacagatc tcacgtgcgc tcctgcgcc                                    29

<210> SEQ ID NO 55
<211> LENGTH: 32
<212> TYPE: DNA
<213> ORGANISM: Artificial
<220> FEATURE:
<223> OTHER INFORMATION: Primer

<400> SEQUENCE: 55
cacaccctag gccatgagcg cacatgccct gc                                32

<210> SEQ ID NO 56
<211> LENGTH: 30
<212> TYPE: DNA
<213> ORGANISM: Artificial
<220> FEATURE:
<223> OTHER INFORMATION: Primer

<400> SEQUENCE: 56
cacacaagct ttcatgcggt gtccccttg                                    30

<210> SEQ ID NO 57
<211> LENGTH: 14
<212> TYPE: DNA
<213> ORGANISM: Artificial
<220> FEATURE:
<223> OTHER INFORMATION: Primer

<400> SEQUENCE: 57
aattcgcggc cgct                                                    14

<210> SEQ ID NO 58
<211> LENGTH: 10
<212> TYPE: DNA
<213> ORGANISM: Artificial
<220> FEATURE:
<223> OTHER INFORMATION: Primer

<400> SEQUENCE: 58
agcggccgcg                                                         10

<210> SEQ ID NO 59
<211> LENGTH: 23
<212> TYPE: DNA
<213> ORGANISM: Artificial
<220> FEATURE:
<223> OTHER INFORMATION: Primer

<400> SEQUENCE: 59
ccttctagtc gtacgtagtc agc                                          23

<210> SEQ ID NO 60
<211> LENGTH: 25
<212> TYPE: DNA
<213> ORGANISM: Artificial
<220> FEATURE:
<223> OTHER INFORMATION: Primer

<400> SEQUENCE: 60
```
ccactgatct agaatctctt tctgg            25

<210> SEQ ID NO 61
<211> LENGTH: 24
<212> TYPE: DNA
<213> ORGANISM: Artificial
<220> FEATURE:
<223> OTHER INFORMATION: Primer

<400> SEQUENCE: 61
ggctcattgc gcatgctaac atcg             24

<210> SEQ ID NO 62
<211> LENGTH: 25
<212> TYPE: DNA
<213> ORGANISM: Artificial
<220> FEATURE:
<223> OTHER INFORMATION: Primer

<400> SEQUENCE: 62
cgacgatgct atgagcttct agacg            25

<210> SEQ ID NO 63
<211> LENGTH: 34
<212> TYPE: DNA
<213> ORGANISM: Artificial
<220> FEATURE:
<223> OTHER INFORMATION: Primer

<400> SEQUENCE: 63
cacacggatc ctataatgcc ttccgcaacg accg            34

<210> SEQ ID NO 64
<211> LENGTH: 35
<212> TYPE: DNA
<213> ORGANISM: Artificial
<220> FEATURE:
<223> OTHER INFORMATION: Primer

<400> SEQUENCE: 64
cacacactag ttaaatttgg acctcaacac gaccc           35

<210> SEQ ID NO 65
<211> LENGTH: 40
<212> TYPE: DNA
<213> ORGANISM: Artificial
<220> FEATURE:
<223> OTHER INFORMATION: Primer

<400> SEQUENCE: 65
cacacggatc caatataaat gtctgcgaag agcatcctcg       40

<210> SEQ ID NO 66
<211> LENGTH: 34
<212> TYPE: DNA
<213> ORGANISM: Artificial
<220> FEATURE:
<223> OTHER INFORMATION: Primer

<400> SEQUENCE: 66
cacacgcatg cttaagcttg gaactccacc gcac            34

<210> SEQ ID NO 67
<211> LENGTH: 47
<212> TYPE: DNA

```
<213> ORGANISM: Artificial
<220> FEATURE:
<223> OTHER INFORMATION: Primer

<400> SEQUENCE: 67
cacacggatc caattttcaa aaattcttac ttttttttg gatggac            47

<210> SEQ ID NO 68
<211> LENGTH: 41
<212> TYPE: DNA
<213> ORGANISM: Artificial
<220> FEATURE:
<223> OTHER INFORMATION: Primer

<400> SEQUENCE: 68
cacacggatc cttttttctc cttgacgtta aagtatagag g                 41

<210> SEQ ID NO 69
<211> LENGTH: 38
<212> TYPE: DNA
<213> ORGANISM: Artificial
<220> FEATURE:
<223> OTHER INFORMATION: Primer

<400> SEQUENCE: 69
cacacgagct caaaaatgga caatcaggct acacagag                     38

<210> SEQ ID NO 70
<211> LENGTH: 42
<212> TYPE: DNA
<213> ORGANISM: Artificial
<220> FEATURE:
<223> OTHER INFORMATION: Primer

<400> SEQUENCE: 70
cacaccctag gtcacttttc ttcaatggtt ctcttgaaat tg                42

<210> SEQ ID NO 71
<211> LENGTH: 46
<212> TYPE: DNA
<213> ORGANISM: Artificial
<220> FEATURE:
<223> OTHER INFORMATION: Primer

<400> SEQUENCE: 71
cacacgagct cggaatattc aactgttttt ttttatcatg ttgatg            46

<210> SEQ ID NO 72
<211> LENGTH: 41
<212> TYPE: DNA
<213> ORGANISM: Artificial
<220> FEATURE:
<223> OTHER INFORMATION: Primer

<400> SEQUENCE: 72
cacacggatc cttcttgaaa atatgcactc tatatcttta g                 41

<210> SEQ ID NO 73
<211> LENGTH: 43
<212> TYPE: DNA
<213> ORGANISM: Artificial
<220> FEATURE:
<223> OTHER INFORMATION: Primer

<400> SEQUENCE: 73
cacacgctag ctacaaaatg ttgtcactca aacgcatagc aac               43
```

<210> SEQ ID NO 74
<211> LENGTH: 38
<212> TYPE: DNA
<213> ORGANISM: Artificial
<220> FEATURE:
<223> OTHER INFORMATION: Primer

<400> SEQUENCE: 74
cacacgtcga cttaatgatc tcggtatacg agaggaac                              38

<210> SEQ ID NO 75
<211> LENGTH: 1124
<212> TYPE: PRT
<213> ORGANISM: Artificial Sequence
<220> FEATURE:
<223> OTHER INFORMATION: Aspergillus nidulans

<400> SEQUENCE: 75

Met Ala Ser Val Leu Ile Arg Arg Lys Phe Gly Thr Glu Gly Gly Ser
1               5                   10                  15

Asp Ala Glu Pro Ser Trp Leu Lys Arg Gln Val Thr Gly Cys Leu Gln
            20                  25                  30

Ser Ile Ser Arg Arg Ala Cys Ile His Pro Ile His Thr Ile Val Val
        35                  40                  45

Ile Ala Leu Leu Ala Ser Thr Thr Tyr Val Gly Leu Leu Glu Gly Ser
    50                  55                  60

Leu Phe Asp Ser Phe Arg Asn Ser Asn Asn Val Ala Gly His Val Asp
65                  70                  75                  80

Val Asp Ser Leu Leu Leu Gly Asn Arg Ser Leu Arg Leu Gly Glu Gly
                85                  90                  95

Thr Ser Trp Lys Trp Gln Val Glu Asp Ser Leu Asn Gln Asp Asp Gln
            100                 105                 110

Lys Val Gly Asn Pro Glu Leu Lys Arg Glu Val Asp Gln His Leu Ala
        115                 120                 125

Leu Thr Thr Leu Ile Phe Pro Asp Ser Ile Ser Lys Ser Ala Ser Thr
    130                 135                 140

Ala Pro Ala Ala Asp Ala Leu Pro Val Pro Ala Asn Ala Ser Ala Gln
145                 150                 155                 160

Leu Leu Pro His Thr Pro Asn Leu Phe Ser Pro Phe Ser His Asp Ser
                165                 170                 175

Ser Leu Val Phe Thr Leu Pro Phe Asp Gln Val Pro Gln Phe Leu Arg
            180                 185                 190

Ala Val Gln Glu Leu Pro Asp Pro Thr Leu Glu Asp Asp Glu Gly Glu
        195                 200                 205

Gln Lys Arg Trp Ile Met Arg Ala Thr Arg Gly Pro Val Ser Gly Pro
    210                 215                 220

Asn Gly Thr Ile Ser Ser Trp Leu Ser Asp Ala Trp Ser Ser Phe Val
225                 230                 235                 240

Asp Leu Ile Lys His Ala Glu Thr Ile Asp Ile Ile Met Thr Leu
                245                 250                 255

Gly Tyr Leu Ala Met Tyr Leu Ser Phe Ala Ser Leu Glu Phe Ser Met
            260                 265                 270

Lys Gln Leu Gly Ser Lys Phe Trp Leu Ala Thr Thr Val Leu Phe Ser
        275                 280                 285

Gly Met Phe Ala Phe Leu Phe Gly Leu Leu Val Thr Thr Lys Phe Gly
    290                 295                 300

-continued

```
Val Pro Leu Asn Leu Leu Leu Ser Glu Gly Leu Pro Glu Leu Val
305                 310                 315                 320

Thr Thr Ile Gly Phe Glu Lys Pro Ile Ile Leu Thr Arg Ala Val Leu
            325                 330                 335

Ser Ala Ser Ile Asp Lys Lys Arg Gln Gly Ser Ala Thr Ser Thr Pro
                340                 345                 350

Ser Ser Ile Gln Asp Ser Ile Gln Thr Ala Ile Arg Glu Gln Gly Phe
            355                 360                 365

Glu Ile Ile Arg Asp Tyr Cys Ile Glu Ile Ser Ile Leu Ile Ala Gly
    370                 375                 380

Ala Ala Ser Gly Val Gln Gly Gly Leu Gln Gln Phe Cys Phe Leu Ala
385                 390                 395                 400

Ala Trp Ile Leu Phe Phe Asp Cys Ile Leu Leu Phe Thr Phe Tyr Thr
                405                 410                 415

Thr Ile Leu Cys Ile Lys Leu Glu Ile Thr Arg Ile Arg Arg His Val
            420                 425                 430

Thr Leu Arg Lys Ala Leu Glu Glu Asp Gly Thr Thr Gln Ser Val Ala
    435                 440                 445

Glu Lys Val Ala Ser Ser Asn Asp Trp Phe Gly Ala Gly Ser Asp Asn
450                 455                 460

Ser Asp Ala Asp Ala Ser Val Phe Gly Arg Lys Ile Lys Ser Asn
465                 470                 475                 480

Asn Val Arg Arg Phe Lys Phe Leu Met Val Gly Gly Phe Val Leu Val
                485                 490                 495

Asn Val Val Asn Met Thr Ala Ile Pro Phe Arg Asn Ser Ser Leu Ser
            500                 505                 510

Pro Leu Cys Asn Val Phe Ser Pro Thr Pro Ile Asp Pro Phe Lys Val
    515                 520                 525

Ala Glu Asn Gly Leu Asp Ala Thr Tyr Val Ser Ala Lys Ser Gln Lys
530                 535                 540

Leu Glu Leu Val Thr Val Val Pro Pro Ile Lys Val Lys Leu Glu Tyr
545                 550                 555                 560

Pro Ser Val His Tyr Ala Lys Leu Gly Glu Ser Gln Ser Ile Glu Ile
                565                 570                 575

Glu Tyr Thr Asp Gln Leu Leu Asp Ala Val Gly Gly His Val Leu Asn
            580                 585                 590

Gly Val Leu Lys Ser Ile Glu Asp Pro Val Ile Ser Lys Trp Ile Thr
    595                 600                 605

Ala Val Leu Thr Ile Ser Ile Val Leu Asn Gly Tyr Leu Phe Asn Ala
610                 615                 620

Ala Arg Trp Ser Ile Lys Glu Pro Gln Ala Ala Pro Ala Pro Lys Glu
625                 630                 635                 640

Pro Ala Lys Pro Lys Val Tyr Pro Lys Thr Asp Leu Asn Ala Gly Pro
                645                 650                 655

Lys Arg Ser Met Glu Glu Cys Glu Ala Met Leu Lys Ala Lys Lys Ala
            660                 665                 670

Ala Tyr Leu Ser Asp Glu Leu Leu Ile Glu Leu Ser Leu Ser Gly Lys
    675                 680                 685

Leu Pro Gly Tyr Ala Leu Leu Lys Ser Leu Glu Asn Glu Glu Leu Met
690                 695                 700

Ser Arg Val Asp Ala Phe Leu Arg Ala Val Lys Leu Arg Arg Ala Val
705                 710                 715                 720
```

-continued

```
Val Ser Arg Thr Pro Ala Thr Ser Ala Val Thr Ser Ser Leu Glu Thr
                725                 730                 735

Ser Lys Leu Pro Tyr Lys Asp Tyr Asn Tyr Ala Leu Val His Gly Ala
            740                 745                 750

Cys Cys Glu Asn Val Ile Gly Thr Leu Pro Leu Pro Leu Gly Val Ala
            755                 760                 765

Gly Pro Leu Val Thr Asp Gly Gln Ser Tyr Phe Ile Pro Met Ala Thr
        770                 775                 780

Ile Glu Gly Val Leu Val Ala Ser Ala Ser Arg Gly Ala Lys Ala Ile
785                 790                 795                 800

Asn Ala Gly Gly Gly Ala Val Ile Val Leu Thr Gly Asp Gly Met Thr
                805                 810                 815

Arg Gly Pro Cys Val Gly Phe Pro Thr Leu Ala Arg Ala Ala Ala Ala
            820                 825                 830

Lys Val Trp Leu Asp Ser Glu Glu Gly Lys Ser Val Met Thr Ala Ala
            835                 840                 845

Phe Asn Ser Thr Ser Arg Phe Ala Arg Leu Gln His Leu Lys Thr Ala
850                 855                 860

Leu Ala Gly Thr Tyr Leu Tyr Ile Arg Phe Lys Thr Thr Thr Gly Asp
865                 870                 875                 880

Ala Met Gly Met Asn Met Ile Ser Lys Gly Val Glu Lys Ala Leu His
                885                 890                 895

Val Met Ala Thr Glu Cys Gly Phe Asp Asp Met Ala Thr Ile Ser Val
                900                 905                 910

Ser Gly Asn Phe Cys Thr Asp Lys Lys Ala Ala Ala Leu Asn Trp Ile
            915                 920                 925

Asp Gly Arg Gly Lys Ser Val Val Ala Glu Ala Ile Ile Pro Gly Asp
            930                 935                 940

Val Val Arg Asn Val Leu Lys Ser Asp Val Asp Ala Leu Val Glu Leu
945                 950                 955                 960

Asn Thr Ser Lys Asn Leu Ile Gly Ser Ala Met Ala Gly Ser Leu Gly
                965                 970                 975

Gly Phe Asn Ala His Ala Ser Asn Ile Val Thr Ala Ile Phe Leu Ala
            980                 985                 990

Thr Gly Asp Pro Ala Gln Asn Val Glu Ser Ser Ser Cys Ile Thr Thr
        995                 1000                1005

Met Lys Asn Thr Asn Gly Asn Leu Gln Thr Ala Val Ser Met Pro
    1010                1015                1020

Ser Ile Glu Val Gly Thr Ile Gly Gly Gly Thr Ile Leu Glu Ala
    1025                1030                1035

Gln Gly Ala Met Ile Leu Asp Ile Leu Gly Val Arg Gly Ser His
    1040                1045                1050

Pro Thr Asn Pro Gly Asp Asn Ala Arg Gln Leu Ala Arg Ile Val
    1055                1060                1065

Ala Ala Ala Val Leu Ala Gly Phe Leu Ser Leu Cys Ser Ala Leu
    1070                1075                1080

Ala Ala Gly His Leu Val Arg Ala His Met Ala His Asn Arg Ser
    1085                1090                1095

Ala Ala Pro Thr Arg Ser Ala Thr Pro Val Ser Ala Ala Val Gly
    1100                1105                1110

Ala Thr Arg Gly Leu Ser Met Thr Ser Ser Arg
    1115                1120
```

<210> SEQ ID NO 76
<211> LENGTH: 1210
<212> TYPE: PRT
<213> ORGANISM: Gibberella zeae

<400> SEQUENCE: 76

| | | | | | | | | | | | | | | |
|---|---|---|---|---|---|---|---|---|---|---|---|---|---|---|
| Met | Ala | Ser | Ile | Leu | Leu | Pro | Lys | Lys | Phe | Arg | Gly | Glu | Thr | Ala | Pro |
| 1 | | | | 5 | | | | | 10 | | | | | 15 | |
| Ala | Glu | Lys | Thr | Thr | Pro | Ser | Trp | Ala | Ser | Lys | Arg | Leu | Thr | Pro | Ile |
| | | | 20 | | | | | 25 | | | | | 30 | | |
| Ala | Gln | Phe | Ile | Ser | Arg | Leu | Ala | Cys | Ser | His | Pro | Ile | His | Thr | Val |
| | | | 35 | | | | | 40 | | | | | 45 | | |
| Val | Leu | Val | Ala | Val | Leu | Ala | Ser | Thr | Ser | Tyr | Val | Gly | Leu | Leu | Gln |
| 50 | | | | | 55 | | | | | 60 | | | | | |
| Glu | Ser | Phe | Phe | Ser | Thr | Asp | Leu | Pro | Thr | Val | Gly | Lys | Ala | Asp | Trp |
| 65 | | | | | 70 | | | | | 75 | | | | | 80 |
| Ser | Ser | Leu | Val | Glu | Gly | Ser | Arg | Val | Leu | Arg | Ala | Gly | Pro | Glu | Thr |
| | | | | 85 | | | | | 90 | | | | | 95 | |
| Ala | Trp | Asn | Trp | Lys | Ala | Ile | Glu | Gln | Asp | Ser | Ile | Gln | His | Ala | Gly |
| | | | 100 | | | | | 105 | | | | | 110 | | |
| Ala | Asp | Ala | Asp | His | Leu | Ala | Leu | Leu | Thr | Leu | Val | Phe | Pro | Asp | Thr |
| | | | 115 | | | | | 120 | | | | | 125 | | |
| His | Ser | Ala | Glu | Ser | Ser | Thr | Ala | Pro | Arg | Ser | Ser | His | Val | Pro |
| | 130 | | | | | 135 | | | | | 140 | | | | |
| Val | Pro | Gln | Asn | Leu | Ser | Ile | Thr | Pro | Leu | Pro | Ser | Thr | Lys | Asn | Ser |
| 145 | | | | | 150 | | | | | 155 | | | | | 160 |
| Phe | Thr | Ala | Tyr | Ser | Gln | Asp | Ser | Ile | Leu | Ala | Tyr | Ser | Leu | Pro | Tyr |
| | | | | 165 | | | | | 170 | | | | | 175 | |
| Ala | Glu | Gly | Pro | Asp | Val | Val | Gln | Trp | Ala | Asn | Asn | Ala | Trp | Thr | Glu |
| | | | 180 | | | | | 185 | | | | | 190 | | |
| Phe | Leu | Asp | Leu | Leu | Lys | Asn | Ala | Glu | Thr | Leu | Asp | Ile | Val | Ile | Met |
| | | | 195 | | | | | 200 | | | | | 205 | | |
| Phe | Leu | Gly | Tyr | Thr | Ala | Met | His | Leu | Thr | Phe | Val | Ser | Leu | Phe | Leu |
| | 210 | | | | | 215 | | | | | 220 | | | | |
| Ser | Met | Arg | Lys | Ile | Gly | Ser | Lys | Phe | Trp | Leu | Gly | Ile | Cys | Thr | Leu |
| 225 | | | | | 230 | | | | | 235 | | | | | 240 |
| Phe | Ser | Ser | Val | Phe | Ala | Phe | Leu | Phe | Gly | Leu | Ile | Val | Thr | Thr | Lys |
| | | | | 245 | | | | | 250 | | | | | 255 | |
| Leu | Gly | Val | Pro | Ile | Ser | Val | Ile | Leu | Leu | Ser | Glu | Gly | Leu | Pro | Phe |
| | | | 260 | | | | | 265 | | | | | 270 | | |
| Leu | Val | Val | Thr | Ile | Gly | Phe | Glu | Lys | Asn | Ile | Val | Leu | Thr | Arg | Ala |
| | | | 275 | | | | | 280 | | | | | 285 | | |
| Val | Met | Ser | His | Ala | Ile | Glu | His | Arg | Arg | Gln | Ile | Gln | Asn | Ser | Lys |
| | 290 | | | | | 295 | | | | | 300 | | | | |
| Ser | Gly | Lys | Gly | Ser | Pro | Glu | Arg | Ser | Met | Gln | Asn | Val | Ile | Gln | Tyr |
| 305 | | | | | 310 | | | | | 315 | | | | | 320 |
| Ala | Val | Gln | Ser | Ala | Ile | Lys | Glu | Lys | Gly | Phe | Glu | Ile | Met | Arg | Asp |
| | | | | 325 | | | | | 330 | | | | | 335 | |
| Tyr | Ala | Ile | Glu | Ile | Val | Ile | Leu | Ala | Leu | Gly | Ala | Ala | Ser | Gly | Val |
| | | | 340 | | | | | 345 | | | | | 350 | | |
| Gln | Gly | Gly | Leu | Gln | His | Phe | Cys | Phe | Leu | Ala | Ala | Trp | Thr | Leu | Phe |
| | | | 355 | | | | | 360 | | | | | 365 | | |
| Phe | Asp | Phe | Ile | Leu | Leu | Phe | Thr | Phe | Tyr | Thr | Ala | Ile | Leu | Ser | Ile |
| | 370 | | | | | 375 | | | | | 380 | | | | |

```
Lys Leu Glu Ile Asn Arg Ile Lys Arg His Val Asp Met Arg Met Ala
385                 390                 395                 400

Leu Glu Asp Asp Gly Val Ser Arg Arg Val Ala Glu Asn Val Ala Lys
            405                 410                 415

Ser Asp Gly Asp Trp Thr Arg Val Lys Gly Asp Ser Ser Leu Phe Gly
        420                 425                 430

Arg Lys Ser Ser Val Pro Thr Phe Lys Val Leu Met Ile Leu Gly
    435                 440                 445

Phe Ile Phe Val Asn Ile Val Asn Ile Cys Ser Ile Pro Phe Arg Asn
450                 455                 460

Pro Arg Ser Leu Ser Thr Ile Arg Thr Trp Ala Ser Ser Leu Gly Gly
465                 470                 475                 480

Val Val Ala Pro Leu Ser Val Asp Pro Phe Lys Val Ala Ser Asn Gly
            485                 490                 495

Leu Asp Ala Ile Leu Ala Ala Lys Ser Asn Asn Arg Pro Thr Leu
            500                 505                 510

Val Thr Val Leu Thr Pro Ile Lys Tyr Glu Leu Glu Tyr Pro Ser Ile
        515                 520                 525

His Tyr Ala Leu Gly Ser Ala Ile Asn Gly Asn Asn Ala Glu Tyr Thr
        530                 535                 540

Asp Ala Phe His His His Phe Gln Gly Tyr Gly Val Gly Gly Arg Met
545                 550                 555                 560

Val Gly Gly Ile Leu Lys Ser Leu Glu Asp Pro Val Leu Ser Lys Trp
                565                 570                 575

Ile Val Ile Ala Leu Ala Leu Ser Val Ala Leu Asn Gly Tyr Leu Phe
                580                 585                 590

Asn Val Ala Arg Trp Gly Ile Lys Asp Pro Asn Val Pro Glu His Asn
                595                 600                 605

Ile Asp Arg Asn Glu Leu Ala Arg Ala Gln Gln Phe Asn Asp Thr Gly
610                 615                 620

Ser Ala Thr Leu Pro Leu Gly Glu Tyr Val Pro Pro Thr Pro Met Arg
625                 630                 635                 640

Thr Glu Pro Ser Thr Pro Ala Ile Thr Asp Asp Glu Ala Glu Gly Leu
                645                 650                 655

Gln Met Thr Lys Ala Arg Ser Asp Lys Leu Pro Asn Arg Pro Asn Glu
                660                 665                 670

Glu Leu Glu Lys Leu Leu Ala Glu Lys Arg Val Lys Glu Met Ser Asp
        675                 680                 685

Glu Glu Leu Val Ser Leu Ser Met Arg Cys Lys Ile Pro Gly Tyr Ala
690                 695                 700

Leu Leu Lys Thr Leu Gly Asp Phe Thr Arg Ala Val Lys Ile Arg Arg
705                 710                 715                 720

Ser Ile Ile Ala Arg Asn Arg Ala Thr Ser Asp Leu Thr His Ser Leu
            725                 730                 735

Glu Arg Ser Lys Leu Pro Phe Glu Lys Tyr Asn Trp Glu Arg Val Phe
        740                 745                 750

Cys Ala Cys Cys Glu Asn Val Ile Gly Tyr Met Pro Leu Pro Val Gly
            755                 760                 765

Val Ala Gly Arg Leu Val Thr Asp Gly Gln Ser Tyr Phe Ile Pro Met
        770                 775                 780

Ala Thr Thr Glu Gly Val Leu Val Ala Ser Ala Ser Arg Gly Cys Lys
785                 790                 795                 800

Ala Ile Asn Ala Gly Gly Gly Ala Val Thr Val Leu Thr Ala Asp Gly
```

-continued

```
                805                 810                 815
Met Thr Arg Gly Pro Cys Val Ala Phe Glu Thr Leu Glu Arg Ala Gly
                820                 825                 830

Ala Ala Lys Leu Trp Ile Asp Ser Glu Ala Gly Ser Asp Ile Met Lys
                835                 840                 845

Lys Ala Phe Asn Ser Thr Ser Arg Phe Ala Arg Leu Gln Ser Met Lys
                850                 855                 860

Thr Ala Leu Ala Gly Thr Asn Leu Tyr Ile Arg Phe Lys Thr Thr Thr
865                 870                 875                 880

Gly Asp Ala Met Gly Met Asn Ile Ile Ser Lys Gly Val Glu His Ala
                885                 890                 895

Leu Ser Val Met Ser Asn Glu Ala Gly Phe Asp Asp Met Gln Ile Val
                900                 905                 910

Ser Val Ser Gly Asn Tyr Cys Thr Asp Lys Lys Ala Ala Ala Leu Asn
                915                 920                 925

Trp Ile Asp Gly Arg Gly Lys Gly Val Val Ala Glu Ala Ile Ile Pro
                930                 935                 940

Gly Asp Val Val Arg Ser Val Leu Lys Ser Asp Val Asp Ala Leu Val
945                 950                 955                 960

Glu Leu Asn Ile Ser Lys Asn Ile Ile Gly Ser Ala Met Ala Gly Ser
                965                 970                 975

Val Gly Gly Phe Asn Ala His Ala Ala Asn Ile Val Ala Ala Ile Phe
                980                 985                 990

Leu Ala Thr Gly Gln Asp Pro Ala Gln Val Val Glu Ser Ala Asn Cys
                995                 1000                1005

Ile Thr Leu Met Lys Asn Leu Arg Gly Ala Leu Gln Thr Ser Val
                1010                1015                1020

Ser Met Pro Ser Leu Glu Val Gly Thr Leu Gly Gly Gly Thr Ile
                1025                1030                1035

Leu Glu Pro Gln Ser Ala Met Leu Asp Leu Leu Gly Val Arg Gly
                1040                1045                1050

Ser His Pro Thr Asn Pro Gly Asp Asn Ser Arg Arg Leu Ala Arg
                1055                1060                1065

Ile Ile Gly Ala Ser Val Leu Ala Gly Glu Leu Ser Leu Cys Ser
                1070                1075                1080

Ala Leu Ala Ala Gly His Leu Val Arg Ala His Met Gln His Asn
                1085                1090                1095

Arg Ser Ala Ala Pro Ser Arg Ser Thr Thr Pro Ala Pro Met Thr
                1100                1105                1110

Pro Val Arg Ser Phe Asp Thr Lys Val Arg Cys Gln Pro Asn Asn
                1115                1120                1125

Lys Asp Ile Arg Asn Ile Leu Leu Thr Gln His Pro Ser Lys Pro
                1130                1135                1140

Thr Ile Thr Tyr Ser Lys Arg Val Ile Lys Ser Thr Ile His Leu
                1145                1150                1155

Asn Pro Leu Ile Leu Ala Leu Phe Asp Asn Ser Val Gln Thr Arg
                1160                1165                1170

Asp Val Gln Leu Gly Asp Gln Val Ser Thr Arg Gly Thr Leu Asp
                1175                1180                1185

Ala Val Gly Gly Pro Gln Gly Gly Val Ala Ala Gly Gly Val
                1190                1195                1200

Ala Arg Arg Val Val Gly Ser
                1205                1210
```

<210> SEQ ID NO 77
<211> LENGTH: 1173
<212> TYPE: PRT
<213> ORGANISM: Neurospora crassa

<400> SEQUENCE: 77

```
Met Ile Ala Ser Ser Leu Leu Pro Ser Lys Phe Arg Gly Glu Gln Pro
1               5                   10                  15

Ala Thr Gln Ala Ala Thr Pro Ser Trp Ile Asn Lys Lys Val Thr Pro
            20                  25                  30

Pro Leu Gln Lys Leu Ser Lys Ile Thr Ser Ser Asn Pro Ile His Thr
        35                  40                  45

Ile Val Ile Val Ala Leu Leu Ala Ser Ser Ser Tyr Ile Gly Leu Leu
    50                  55                  60

Gln Asn Ser Leu Phe Asn Val Thr Arg Ser Val Arg Lys Ala Glu Trp
65                  70                  75                  80

Glu Ser Leu Gln Ala Gly Ser Arg Met Leu Arg Ala Gly Ala Asn Thr
                85                  90                  95

Glu Trp Asn Trp Gln Asn His Asp Pro Glu Ala Pro Val Pro Ala Asn
            100                 105                 110

Ala Asn His Leu Ala Leu Leu Thr Leu Val Phe Pro Asp Thr Ala Glu
        115                 120                 125

Ser Gly Pro Val Val Ala Gln Thr Asn Thr Val Pro Leu Pro Ser Asn
    130                 135                 140

Leu Ser Thr Thr Pro Leu Pro Ser Thr Ala Ile Ser Phe Thr Tyr Ser
145                 150                 155                 160

Gln Asp Ser Ala Leu Ala Phe Ser Leu Pro Tyr Ser Gln Ala Pro Glu
                165                 170                 175

Phe Leu Ala Asn Ala Gln Glu Ile Pro Asn Ala Val Ser Ser Gln Glu
            180                 185                 190

Thr Ile Glu Thr Glu Arg Gly His Glu Lys Lys Met Trp Ile Met Lys
        195                 200                 205

Ala Ala Arg Val Gln Thr Arg Ser Ser Thr Val Lys Trp Val Gln Asn
    210                 215                 220

Ala Trp Val Glu Phe Thr Asp Leu Leu Arg Asn Ala Glu Thr Leu Asp
225                 230                 235                 240

Ile Ile Ile Met Ala Leu Gly Tyr Ile Ser Met His Leu Thr Phe Val
                245                 250                 255

Ser Leu Phe Leu Ser Met Arg Arg Met Gly Ser Asn Phe Trp Leu Ala
            260                 265                 270

Thr Ser Val Ile Phe Ser Ile Phe Ala Phe Leu Phe Gly Leu Leu
        275                 280                 285

Val Thr Thr Lys Leu Gly Val Pro Met Asn Met Val Leu Leu Ser Glu
    290                 295                 300

Gly Leu Pro Phe Leu Val Val Thr Ile Gly Phe Glu Lys Asn Ile Val
305                 310                 315                 320

Leu Thr Arg Ala Val Leu Ser His Ala Ile Asp His Arg Arg Pro Thr
                325                 330                 335

Glu Lys Ser Gly Lys Pro Ser Lys Gln Ala Asp Ser Ala His Ser Ile
            340                 345                 350

Gln Ser Ala Ile Gln Leu Ala Ile Lys Glu Lys Gly Phe Asp Ile Val
        355                 360                 365

Lys Asp Tyr Ala Ile Glu Ala Gly Ile Leu Val Leu Gly Ala Ala Ser
```

-continued

```
            370                 375                 380
Gly Val Gln Gly Gly Leu Gln Gln Phe Cys Phe Leu Ala Ala Trp Ile
385                 390                 395                 400

Leu Phe Phe Asp Cys Ile Leu Leu Phe Ser Phe Tyr Thr Ala Ile Leu
                    405                 410                 415

Cys Ile Lys Leu Phe Ile Asn Arg Ile Lys Arg His Val Gln Met Arg
                420                 425                 430

Lys Ala Leu Glu Glu Asp Gly Val Ser Arg Arg Val Ala Glu Lys Val
            435                 440                 445

Ala Gln Ser Asn Asp Trp Pro Arg Ala Asp Gly Lys Asp Gln Pro Gly
        450                 455                 460

Thr Thr Ile Phe Gly Arg Gln Leu Lys Ser Thr His Ile Pro Lys Phe
465                 470                 475                 480

Lys Val Met Met Val Thr Gly Phe Val Leu Ile Asn Val Leu Asn Leu
                    485                 490                 495

Cys Thr Ile Pro Phe Arg Ser Ala Asn Ser Ile Ser Ser Ile Ser Ser
                500                 505                 510

Trp Ala Arg Gly Leu Gly Gly Val Val Thr Pro Pro Val Asp Pro
            515                 520                 525

Phe Lys Val Ala Ser Asn Gly Leu Asp Ile Ile Leu Glu Ala Ala Arg
        530                 535                 540

Ala Asp Gly Arg Glu Thr Thr Val Thr Val Leu Thr Pro Ile Arg Tyr
545                 550                 555                 560

Glu Leu Glu Tyr Pro Ser Thr His Tyr Asp Leu Pro Gln Lys Ser Ala
                    565                 570                 575

Glu Val Glu Gly Gly Asp Tyr Ala Asn Leu Gly Gly Tyr Gly Gly Arg
                580                 585                 590

Met Val Gly Ser Ile Leu Lys Ser Leu Glu Asp Pro Thr Leu Ser Lys
            595                 600                 605

Trp Ile Val Val Ala Leu Ala Leu Ser Val Ala Leu Asn Gly Tyr Leu
        610                 615                 620

Phe Asn Ala Ala Arg Trp Gly Ile Lys Asp Pro Asn Val Pro Asp His
625                 630                 635                 640

Pro Ile Asn Pro Lys Glu Leu Asp Glu Ala Gln Lys Phe Asn Asp Thr
                    645                 650                 655

Ala Ser Ala Thr Leu Pro Leu Gly Glu Tyr Met Lys Pro Thr Ala Pro
                660                 665                 670

Ser Ser Pro Val Ala Pro Leu Thr Pro Ser Ser Thr Asp Asp Glu Asn
            675                 680                 685

Asp Ala Gln Ala Lys Glu Asn Arg Ala Val Thr Leu Ala Ala Gln Arg
        690                 695                 700

Ala Thr Thr Ile Arg Ser Gln Gly Glu Leu Asp Lys Met Thr Ala Glu
705                 710                 715                 720

Lys Arg Thr His Glu Leu Asn Asp Glu Thr Val His Leu Ser Leu
                    725                 730                 735

Lys Gly Lys Ile Pro Gly Tyr Ala Leu Glu Lys Thr Leu Lys Asp Phe
                740                 745                 750

Thr Arg Ala Val Lys Val Arg Arg Ser Ile Ile Ser Arg Thr Lys Ala
            755                 760                 765

Thr Thr Glu Leu Thr Asn Ile Leu Asp Arg Ser Lys Leu Pro Tyr Gln
        770                 775                 780

Asn Val Asn Trp Ala Gln Val His Gly Ala Cys Cys Glu Asn Val Ile
785                 790                 795                 800
```

```
Gly Tyr Met Pro Leu Pro Val Gly Val Ala Gly Pro Leu Val Thr Asp
                805                 810                 815

Gly Gln Ser Phe Phe Val Pro Met Ala Thr Thr Glu Gly Val Leu Val
                820                 825                 830

Ala Ser Thr Ser Arg Gly Cys Lys Ala Ile Asn Ser Gly Gly Gly Ala
                835                 840                 845

Val Thr Val Leu Thr Ala Asp Gly Met Thr Arg Gly Pro Cys Val Gln
                850                 855                 860

Phe Glu Thr Leu Glu Arg Ala Gly Ala Ala Lys Leu Trp Leu Asp Ser
865                 870                 875                 880

Glu Lys Gly Gln Ser Ile Met Lys Lys Ala Phe Asn Ser Thr Ser Arg
                885                 890                 895

Phe Arg Ala Leu Glu Thr Met Lys Thr Ala Met Ala Gly Thr Asn Leu
                900                 905                 910

Tyr Ile Arg Phe Lys Ile Thr Thr Gly Asp Ala Met Gly Met Asn Met
                915                 920                 925

Ile Ser Lys Gly Val Glu His Ala Leu Ser Val Met Tyr Asn Glu Gly
                930                 935                 940

Phe Glu Asp Met Asn Ile Val Ser Leu Ser Gly Asn Tyr Cys Thr Asp
945                 950                 955                 960

Lys Lys Ala Ala Ala Ile Asn Val Ile Asp Gly Arg Gly Lys Ser Val
                965                 970                 975

Val Ala Glu Ala Ile Ile Pro Ala Asp Val Val Lys Asn Val Leu Lys
                980                 985                 990

Thr Asp Val Asp Thr Leu Val Glu Leu Asn Val Asn Lys Asn Thr Ile
        995                 1000                1005

Gly Ser Ala Met Ala Gly Ser Met Gly Gly Phe Asn Ala His Ala
        1010                1015                1020

Ala Asn Ile Val Ala Ala Ile Phe Leu Ala Thr Gly Gln Asp Pro
        1025                1030                1035

Ala Gln Val Val Glu Ser Ala Asn Cys Ile Thr Leu Met Arg Asn
        1040                1045                1050

Leu Arg Gly Asn Leu Gln Ile Ser Val Ser Met Pro Ser Ile Glu
        1055                1060                1065

Val Gly Thr Leu Gly Gly Gly Thr Ile Leu Glu Pro Gln Ser Ala
        1070                1075                1080

Met Leu Asp Met Leu Gly Val Arg Gly Pro His Pro Thr Asn Pro
        1085                1090                1095

Gly Glu Asn Ala Arg Arg Leu Ala Arg Ile Val Ala Ala Ala Val
        1100                1105                1110

Leu Ala Gly Glu Leu Ser Leu Cys Ser Ala Leu Ala Ala Gly His
        1115                1120                1125

Leu Val Lys Ala His Met Ala His Asn Arg Ser Ala Pro Pro Thr
        1130                1135                1140

Arg Thr Ser Thr Pro Ala Pro Ala Ala Ala Ala Gly Leu Thr Met
        1145                1150                1155

Thr Ser Ser Asn Pro Asn Ala Ala Ala Val Glu Arg Ser Arg Arg
        1160                1165                1170

<210> SEQ ID NO 78
<211> LENGTH: 1045
<212> TYPE: PRT
<213> ORGANISM: Saccharomyces cerevisiae
```

<400> SEQUENCE: 78

```
Met Ser Leu Pro Leu Lys Thr Ile Val His Leu Val Lys Pro Phe Ala
1               5                   10                  15

Cys Thr Ala Arg Phe Ser Ala Arg Tyr Pro Ile His Val Ile Val Val
            20                  25                  30

Ala Val Leu Leu Ser Ala Ala Tyr Leu Ser Val Thr Gln Ser Tyr
        35                  40                  45

Leu Asn Glu Trp Lys Leu Asp Ser Asn Gln Tyr Ser Thr Tyr Leu Ser
    50                  55                  60

Ile Lys Pro Asp Glu Leu Phe Glu Lys Cys Thr His Tyr Tyr Arg Ser
65                  70                  75                  80

Pro Val Ser Asp Thr Trp Lys Leu Leu Ser Ser Lys Glu Ala Ala Asp
                85                  90                  95

Ile Tyr Thr Pro Phe His Tyr Leu Ser Thr Ile Ser Phe Gln Ser
            100                 105                 110

Lys Asp Asn Ser Thr Thr Leu Pro Ser Leu Asp Asp Val Ile Tyr Ser
            115                 120                 125

Val Asp His Thr Arg Tyr Leu Leu Ser Glu Glu Pro Lys Ile Pro Thr
        130                 135                 140

Glu Leu Val Ser Glu Asn Gly Thr Lys Trp Arg Leu Arg Asn Asn Ser
145                 150                 155                 160

Asn Phe Ile Leu Asp Leu His Asn Ile Tyr Arg Asn Met Val Lys Gln
                165                 170                 175

Phe Ser Asn Lys Thr Ser Glu Phe Asp Gln Phe Asp Leu Phe Ile Ile
            180                 185                 190

Leu Ala Ala Tyr Leu Thr Leu Phe Tyr Thr Leu Cys Cys Leu Phe Asn
        195                 200                 205

Asp Met Arg Lys Ile Gly Ser Lys Phe Trp Leu Ser Phe Ser Ala Leu
    210                 215                 220

Ser Asn Ser Ala Cys Ala Leu Tyr Leu Ser Leu Tyr Thr Thr His Ser
225                 230                 235                 240

Leu Leu Lys Lys Pro Ala Ser Leu Leu Ser Leu Val Ile Gly Leu Pro
                245                 250                 255

Phe Thr Val Val Ile Ile Gly Glu Lys His Lys Val Arg Leu Ala Ala
            260                 265                 270

Phe Ser Leu Gln Lys Phe His Arg Ile Ser Ile Asp Lys Lys Ile Thr
        275                 280                 285

Val Ser Asn Ile Ile Tyr Glu Ala Met Phe Gln Glu Gly Ala Tyr Leu
    290                 295                 300

Ile Arg Asp Tyr Leu Phe Tyr Ile Ser Ser Phe Ile Gly Cys Ala Ile
305                 310                 315                 320

Tyr Ala Arg His Leu Pro Gly Leu Val Asn Phe Cys Ile Leu Ser Thr
                325                 330                 335

Phe Met Leu Val Phe Asp Leu Leu Leu Ser Ala Thr Phe Tyr Ser Ala
            340                 345                 350

Ile Leu Ser Met Lys Leu Phe Ile Asn Ile Ile His Arg Ser Thr Val
        355                 360                 365

Ile Arg Gln Thr Leu Glu Glu Asp Gly Val Val Pro Thr Thr Ala Asp
    370                 375                 380

Ile Ile Tyr Lys Asp Glu Thr Ala Ser Glu Pro His Phe Leu Arg Ser
385                 390                 395                 400

Asn Val Ala Ile Ile Leu Gly Lys Ala Ser Val Ile Gly Leu Leu Leu
                405                 410                 415
```

```
Leu Ile Asn Leu Tyr Val Phe Thr Asp Lys Leu Asn Ala Thr Ile Leu
            420                 425                 430
Asn Thr Val Tyr Phe Asp Ser Thr Ile Tyr Ser Leu Pro Asn Phe Ile
        435                 440                 445
Asn Tyr Lys Asp Ile Gly Asn Leu Ser Asn Gln Val Ile Ile Ser Val
    450                 455                 460
Leu Pro Lys Gln Tyr Tyr Thr Pro Leu Lys Lys Tyr His Gln Ile Glu
465                 470                 475                 480
Asp Ser Val Leu Leu Ile Ile Asp Ser Val Ser Asn Ala Ile Arg Asp
            485                 490                 495
Gln Phe Ile Ser Lys Leu Leu Phe Phe Ala Phe Ala Val Ser Ile Ser
            500                 505                 510
Ile Asn Val Tyr Leu Leu Asn Ala Ala Lys Ile His Thr Gly Tyr Met
        515                 520                 525
Asn Phe Gln Pro Gln Ser Asn Lys Ile Asp Asp Leu Val Val Gln Gln
    530                 535                 540
Lys Ser Ala Thr Ile Glu Phe Ser Glu Thr Arg Ser Met Pro Leu Ala
545                 550                 555                 560
Ser Gly Leu Glu Thr Pro Val Thr Ala Lys Asp Ile Ile Ile Ser Glu
            565                 570                 575
Glu Ile Gln Asn Asn Glu Cys Val Tyr Ala Leu Ser Ser Gln Asp Glu
            580                 585                 590
Pro Ile Arg Pro Leu Ser Asn Leu Val Glu Leu Met Glu Lys Glu Gln
        595                 600                 605
Leu Lys Asn Met Asn Asn Thr Glu Val Ser Asn Leu Val Val Asn Gly
    610                 615                 620
Lys Leu Pro Leu Tyr Ser Leu Glu Lys Lys Leu Glu Asp Thr Leu Arg
625                 630                 635                 640
Ala Val Leu Val Arg Arg Lys Ala Leu Ser Thr Leu Ala Glu Ser Pro
            645                 650                 655
Ile Leu Val Ser Glu Lys Leu Pro Phe Arg Asn Tyr Asp Tyr Asp Arg
            660                 665                 670
Val Phe Gly Ala Cys Cys Glu Asn Val Ile Gly Tyr Met Pro Ile Pro
        675                 680                 685
Val Gly Val Ile Gly Pro Leu Ile Thr Asp Gly Thr Ser Tyr His Ile
    690                 695                 700
Pro Met Ala Thr Thr Glu Gly Cys Leu Val Ala Ser Ala Met Pro Gly
705                 710                 715                 720
Cys Lys Ala Ile Asn Ala Gly Gly Ala Thr Thr Val Leu Thr Lys
            725                 730                 735
Asp Gly Met Thr Arg Gly Pro Val Val Arg Phe Pro Thr Leu Ile Arg
            740                 745                 750
Ser Gly Ala Cys Lys Ile Trp Leu Asp Ser Glu Glu Gly Gln Asn Ser
        755                 760                 765
Ile Lys Lys Ala Phe Asn Ser Thr Ser Arg Phe Ala Arg Leu Gln His
    770                 775                 780
Thr Gln Thr Cys Leu Ala Gly Asp Leu Leu Phe Met Arg Phe Arg Thr
785                 790                 795                 800
Thr Thr Gly Asp Ala Met Gly Met Asn Met Ile Ser Lys Gly Val Glu
            805                 810                 815
Tyr Ser Leu Lys Gln Met Val Glu Glu Tyr Gly Trp Glu Asp Met Glu
            820                 825                 830
```

-continued

```
Val Val Ser Val Ser Gly Asn Tyr Cys Thr Asp Lys Lys Pro Ala Ala
        835                 840                 845

Ile Asn Trp Ile Glu Gly Arg Gly Lys Ser Val Val Ala Glu Ala Thr
850                 855                 860

Ile Pro Gly Asp Val Val Lys Ser Val Leu Lys Ser Asp Val Ser Ala
865                 870                 875                 880

Leu Val Glu Leu Asn Ile Ser Lys Asn Ile Val Gly Ser Ala Met Ala
                885                 890                 895

Gly Ser Val Gly Gly Phe Asn Ala His Ala Ala Asn Leu Val Thr Ala
                900                 905                 910

Leu Phe Leu Ala Leu Gly Gln Asp Pro Ala Gln Asn Val Glu Ser Ser
                915                 920                 925

Asn Cys Ile Thr Leu Met Lys Glu Val Asp Gly Asp Leu Arg Ile Ser
                930                 935                 940

Val Ser Met Pro Ser Ile Glu Val Gly Thr Ile Gly Gly Gly Thr Val
945                 950                 955                 960

Leu Glu Pro Gln Gly Ala Met Leu Asp Leu Leu Gly Val Arg Gly Pro
                965                 970                 975

His Pro Thr Glu Pro Gly Ala Asn Ala Arg Gln Leu Ala Arg Ile Ile
                980                 985                 990

Ala Cys Ala Val Leu Ala Gly Glu  Leu Ser Leu Cys Ser  Ala Leu Ala
                995                1000                1005

Ala Gly  His Leu Val Gln Ser  His Met Thr His Asn  Arg Lys Thr
                1010                1015                1020

Asn Lys  Ala Asn Glu Leu Pro  Gln Pro Ser Asn Lys  Gly Pro Pro
                1025                1030                1035

Cys Lys  Thr Ser Ala Leu Leu
                1040                1045

<210> SEQ ID NO 79
<211> LENGTH: 1052
<212> TYPE: PRT
<213> ORGANISM: Saccharomyces cerevisiae

<400> SEQUENCE: 79

Met Pro Pro Leu Phe Lys Gly Leu Lys Gln Met Ala Lys Pro Leu Ala
1               5                   10                  15

Tyr Val Ser Arg Phe Ser Ala Lys Pro Pro Ile His Ile Ile Leu Phe
                20                  25                  30

Ser Leu Ile Ile Ser Ala Phe Ala Tyr Leu Ser Val Ile Gln Tyr Tyr
                35                  40                  45

Phe Asn Gly Trp Gln Leu Asp Ser Asn Ser Val Phe Glu Thr Ala Pro
50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Ser
                100                 105                 110

Pro Asn Glu Thr Asp Ser Ile Pro Glu Leu Ala Asn Thr Val Phe Glu
                115                 120                 125

Lys Asp Asn Thr Lys Tyr Leu Leu Gln Glu Asp Leu Ser Val Ser Lys
                130                 135                 140

Glu Thr Ser Ser Thr Asp Gly Thr Lys Trp Arg Leu Arg Ser Asp Arg
145                 150                 155                 160
```

-continued

```
Lys Ser Leu Phe Asp Val Lys Thr Leu Ala Tyr Ser Leu Tyr Asp Val
            165                 170                 175
Phe Ser Glu Asn Val Thr Gln Ala Asp Pro Phe Asp Val Leu Ile Met
            180                 185                 190
Val Thr Ala Tyr Leu Met Met Phe Tyr Thr Ile Phe Gly Leu Phe Asn
            195                 200                 205
Asp Met Arg Lys Thr Gly Ser Asn Phe Trp Leu Ser Ala Ser Thr Val
210                 215                 220
Val Asn Ser Ala Ser Ser Leu Phe Leu Ala Leu Tyr Val Thr Gln Cys
225                 230                 235                 240
Ile Leu Gly Lys Glu Val Ser Ala Leu Thr Leu Phe Glu Gly Leu Pro
            245                 250                 255
Phe Leu Val Val Val Gly Phe Lys His Lys Ile Lys Ile Ala Gln
            260                 265                 270
Tyr Ala Leu Glu Lys Phe Glu Arg Val Gly Leu Ser Lys Arg Ile Thr
            275                 280                 285
Thr Asp Glu Ile Val Phe Glu Ser Val Ser Glu Gly Gly Arg Leu
290                 295                 300
Ile Gln Asp His Leu Leu Cys Ile Phe Ala Phe Ile Gly Cys Met Tyr
305                 310                 315                 320
Ala His Gln Leu Lys Thr Leu Thr Asn Phe Cys Ile Leu Ser Ala Phe
            325                 330                 335
Ile Leu Ile Phe Glu Leu Ile Leu Thr Pro Thr Phe Tyr Ser Ala Ile
            340                 345                 350
Leu Ala Leu Arg Leu Glu Met Asn Val Ile His Arg Ser Thr Ile Ile
            355                 360                 365
Ile Gly Gln Thr Leu Glu Glu Asp Gly Val Val Pro Ser Thr Ala Arg
            370                 375                 380
Ile Ile Ser Lys Ala Glu Lys Lys Ser Val Ser Ser Phe Leu Asn Leu
385                 390                 395                 400
Ser Val Val Val Ile Thr Met Lys Leu Ser Val Ile Leu Leu Phe Val
            405                 410                 415
Phe Ile Asn Phe Tyr Asn Phe Gly Ala Asn Trp Val Asn Asp Ala Phe
            420                 425                 430
Asn Ser Leu Tyr Phe Asp Lys Glu Arg Val Ser Leu Pro Asp Phe Ile
            435                 440                 445
Thr Ser Asn Ala Ser Glu Asn Phe Lys Glu Gln Ala Ile Val Ser Val
            450                 455                 460
Thr Pro Leu Leu Tyr Tyr Lys Pro Ile Lys Ser Tyr Gln Arg Ile Glu
465                 470                 475                 480
Asp Met Val Leu Leu Leu Arg Asn Val Ser Val Ala Ile Arg Asp
            485                 490                 495
Arg Phe Val Ser Lys Leu Val Leu Ser Ala Leu Val Cys Ser Ala Val
            500                 505                 510
Ile Asn Val Tyr Leu Leu Asn Ala Ala Arg Ile His Thr Ser Tyr Thr
            515                 520                 525
Ala Asp Gln Leu Val Lys Thr Glu Val Thr Lys Lys Ser Phe Thr Ala
            530                 535                 540
Pro Val Gln Lys Ala Ser Thr Pro Val Leu Thr Asn Lys Thr Val Ile
545                 550                 555                 560
Ser Gly Ser Lys Val Lys Ser Leu Ser Ser Ala Gln Ser Ser Ser Ser
            565                 570                 575
```

```
Gly Pro Ser Ser Ser Glu Glu Asp Asp Ser Arg Asp Ile Glu Ser
            580                 585                 590

Leu Asp Lys Lys Ile Arg Pro Leu Glu Glu Leu Glu Ala Leu Leu Ser
    595                 600                 605

Ser Gly Asn Thr Lys Gln Leu Lys Asn Lys Glu Val Ala Ala Leu Val
610                 615                 620

Thr His Gly Lys Leu Pro Leu Tyr Ala Leu Glu Lys Lys Leu Gly Asp
625                 630                 635                 640

Thr Thr Arg Ala Val Ala Val Arg Arg Lys Ala Leu Ser Ile Leu Ala
                645                 650                 655

Glu Ala Pro Val Leu Ala Ser Asp Arg Leu Pro Tyr Lys Asn Tyr Asp
                660                 665                 670

Tyr Asp Arg Val Phe Gly Ala Cys Cys Glu Asn Val Ile Gly Tyr Met
            675                 680                 685

Pro Leu Pro Val Gly Val Ile Gly Pro Leu Val Thr Asp Gly Thr Ser
        690                 695                 700

Tyr His Ile Pro Met Ala Thr Thr Glu Gly Cys Leu Val Ala Ser Ala
705                 710                 715                 720

Met Arg Gly Cys Lys Ala Ile Asn Ala Gly Gly Gly Ala Thr Thr Val
                725                 730                 735

Leu Thr Lys Asp Gly Met Ile Arg Gly Pro Val Val Arg Phe Pro Thr
                740                 745                 750

Leu Lys Arg Ser Gly Ala Cys Lys Ile Trp Leu Asp Ser Glu Glu Gly
            755                 760                 765

Gln Asn Ala Ile Lys Lys Ala Phe Asn Ser Thr Ser Arg Phe Ala Arg
        770                 775                 780

Leu Gln His Ile Gln Thr Cys Leu Ala Gly Asp Leu Leu Phe Met Arg
785                 790                 795                 800

Phe Arg Thr Thr Thr Ser Asp Ala Met Gly Met Asn Met Ile Ser Lys
                805                 810                 815

Gly Val Glu Tyr Ser Leu Lys Gln Met Val Glu Glu Tyr Gly Trp Glu
                820                 825                 830

Asp Met Glu Val Val Ser Val Ser Gly Asn Tyr Cys Thr Asp Lys Lys
            835                 840                 845

Pro Ala Ala Ile Asn Trp Ile Glu Gly Arg Gly Lys Ser Val Val Ala
        850                 855                 860

Glu Ala Thr Ile Pro Gly Asp Val Val Arg Lys Val Leu Lys Ser Asp
865                 870                 875                 880

Val Ser Ala Leu Val Glu Leu Asn Ile Ala Lys Asn Leu Val Gly Ser
                885                 890                 895

Ala Met Ala Gly Ser Val Gly Gly Glu Asn Ala His Ala Ala Asn Leu
                900                 905                 910

Val Thr Ala Val Phe Leu Ala Leu Gly Asp Pro Ala Gln Asn Val Glu
            915                 920                 925

Ser Ser Asn Cys Ile Thr Leu Met Lys Glu Val Asp Gly Asp Leu Arg
        930                 935                 940

Ile Ser Val Ser Met Pro Ser Ile Glu Val Gly Thr Ile Gly Gly Gly
945                 950                 955                 960

Thr Val Leu Glu Pro Gln Gly Ala Met Leu Asp Leu Leu Ser Val Arg
                965                 970                 975

Gly Pro His Ala Thr Ala Pro Gly Thr Asn Ala Arg Gln Leu Ala Arg
            980                 985                 990

Ile Val Ala Cys Ala Val Leu Ala  Gly Glu Leu Ser Leu  Cys Ala Ala
```

```
                995                 1000                1005
Leu Ala  Ala Gly His Leu Val  Gln Ser His Met Thr  His Asn Arg
    1010             1015                 1020

Lys Pro  Ala Glu Pro Thr Lys  Pro Asn Asn Leu Asp  Ala Thr Asp
    1025             1030                 1035

Ile Asn  Arg Leu Lys Asp Gly  Ser Val Thr Cys Ile  Lys Ser
    1040             1045                 1050

<210> SEQ ID NO 80
<211> LENGTH: 999
<212> TYPE: PRT
<213> ORGANISM: Yarrowia lipolytica

<400> SEQUENCE: 80

Met Leu Gln Ala Ala Ile Gly Lys Ile Val Gly Phe Ala Val Asn Arg
1               5                   10                  15

Pro Ile His Thr Val Val Leu Thr Ser Ile Val Ala Ser Thr Ala Tyr
            20                  25                  30

Leu Ala Leu Leu Asp Ile Ala Ile Pro Gly Glu Glu Gly Thr Gln Pro
        35                  40                  45

Ile Ser Tyr Tyr His Pro Ala Ala Lys Ser Tyr Asp Asn Pro Ala Asp
    50                  55                  60

Trp Thr His Ile Ala Glu Ala Asp Ile Pro Ser Asp Ala Tyr Arg Leu
65                  70                  75                  80

Ala Phe Ala Gln Ile Arg Val Ser Asp Val Gln Gly Gly Glu Ala Pro
                85                  90                  95

Thr Ile Pro Gly Ala Val Ala Val Ser Asp Leu Asp His Arg Ile Val
            100                 105                 110

Met Asp Tyr Lys Gln Trp Ala Pro Trp Thr Ala Ser Asn Glu Gln Ile
        115                 120                 125

Ala Ser Glu Asn His Ile Trp Lys His Ser Phe Lys Asp His Val Ala
    130                 135                 140

Phe Ser Trp Ile Lys Trp Phe Arg Trp Ala Tyr Leu Arg Leu Ser Thr
145                 150                 155                 160

Leu Ile Gln Gly Ala Asp Asn Phe Asp Ile Ala Val Val Ala Leu Gly
                165                 170                 175

Tyr Leu Ala Met His Tyr Thr Phe Phe Ser Leu Phe Arg Ser Lys Arg
            180                 185                 190

Lys Val Gly Ser His Phe Trp Leu Ala Ser Met Ala Leu Val Ser Ser
        195                 200                 205

Phe Phe Ala Phe Leu Leu Ala Val Val Ala Ser Ser Ser Leu Gly Tyr
    210                 215                 220

Arg Pro Ser Met Ile Thr Met Ser Glu Gly Leu Pro Phe Leu Val Val
225                 230                 235                 240

Ala Ile Gly Phe Asp Arg Lys Val Asn Leu Ala Ser Glu Val Leu Thr
                245                 250                 255

Ser Lys Ser Ser Gln Leu Ala Pro Met Val Gln Val Ile Thr Lys Ile
            260                 265                 270

Ala Ser Lys Ala Leu Phe Glu Tyr Ser Leu Glu Val Ala Ala Leu Phe
        275                 280                 285

Ala Gly Ala Tyr Thr Gly Val Pro Arg Leu Ser Gln Phe Cys Phe Leu
    290                 295                 300

Ser Ala Trp Ile Leu Ile Phe Asp Tyr Met Phe Leu Leu Thr Phe Tyr
305                 310                 315                 320
```

-continued

```
Ser Ala Val Ile Ala Ile Lys Phe Leu Ile Asn His Ile Lys Phe Asn
            325                 330                 335

Arg Met Ile Gln Asp Ala Leu Lys Glu Asp Gly Val Ser Ala Ala Val
            340                 345                 350

Ala Glu Lys Val Ala Asp Ser Ser Pro Asp Ala Lys Leu Asp Arg Lys
            355                 360                 365

Ser Asp Val Ser Leu Phe Gly Ala Ser Gly Ala Ile Ala Val Phe Lys
            370                 375                 380

Ile Phe Met Val Leu Gly Phe Leu Gly Leu Asn Leu Ile Asn Leu Thr
385                 390                 395                 400

Ala Ile Pro His Leu Gly Lys Ala Ala Ala Ala Gln Ser Val Thr
                405                 410                 415

Pro Ile Thr Leu Ser Pro Glu Leu Leu His Ala Ile Pro Ala Ser Val
            420                 425                 430

Pro Val Val Val Thr Phe Val Pro Ser Val Val Tyr Glu His Ser Gln
            435                 440                 445

Leu Ile Leu Gln Leu Glu Asp Ala Leu Thr Phe Phe Leu Ala Ala Cys
    450                 455                 460

Ser Lys Thr Ile Gly Asp Pro Val Ile Ser Lys Tyr Ile Phe Leu Cys
465                 470                 475                 480

Leu Met Val Ser Thr Ala Leu Asn Val Tyr Leu Phe Gly Ala Thr Arg
            485                 490                 495

Glu Val Val Arg Thr Gln Ser Val Lys Val Val Glu Lys His Val Pro
            500                 505                 510

Ile Val Ile Glu Lys Pro Ser Glu Lys Glu Asp Thr Ser Ser Glu
            515                 520                 525

Asp Ser Ile Glu Leu Thr Val Gly Lys Gln Pro Lys Pro Val Thr Glu
    530                 535                 540

Thr Arg Ser Leu Asp Asp Leu Glu Ala Thr Met Lys Ala Gly Lys Thr
545                 550                 555                 560

Lys Leu Leu Glu Asp His Glu Val Val Lys Leu Ser Leu Glu Gly Lys
                565                 570                 575

Leu Pro Leu Tyr Ala Leu Phe Lys Gln Leu Gly Asp Asn Thr Arg Ala
            580                 585                 590

Val Gly Ile Arg Arg Ser Ile Ile Ser Gln Gln Ser Asn Thr Lys Thr
            595                 600                 605

Leu Glu Thr Ser Lys Leu Pro Tyr Leu His Tyr Asp Tyr Asp Arg Val
    610                 615                 620

Phe Gly Ala Cys Cys Glu Asn Val Ile Gly Tyr Met Pro Leu Pro Val
625                 630                 635                 640

Gly Val Ala Gly Pro Met Asn Thr Asp Gly Lys Asn Tyr His Ile Pro
            645                 650                 655

Met Ala Thr Thr Glu Gly Cys Leu Val Ala Ser Thr Met Arg Gly Cys
            660                 665                 670

Lys Ala Ile Asn Ala Gly Gly Gly Val Thr Thr Val Leu Thr Gln Asp
            675                 680                 685

Gly Met Thr Arg Gly Pro Cys Val Ser Phe Pro Ser Leu Lys Arg Ala
            690                 695                 700

Gly Ala Ala Lys Ile Trp Leu Asp Glu Ser Glu Gly Leu Lys Ser Met
705                 710                 715                 720

Arg Lys Ala Phe Asn Ser Thr Ser Arg Phe Ala Arg Leu Gln Ser Leu
            725                 730                 735

His Ser Thr Leu Ala Gly Asn Leu Leu Phe Ile Arg Phe Arg Thr Thr
```

```
                    740                 745                 750
Thr Gly Asp Ala Met Gly Met Asn Met Ile Ser Lys Gly Val Glu His
            755                 760                 765
Ser Leu Ala Val Met Val Lys Glu Tyr Gly Phe Pro Leu Met Asp Ile
        770                 775                 780
Val Ser Val Ser Gly Asn Tyr Cys Thr Asp Lys Lys Pro Ala Ala Ile
785                 790                 795                 800
Asn Trp Ile Glu Gly Arg Gly Lys Ser Val Val Ala Glu Ala Thr Ile
                805                 810                 815
Pro Ala His Ile Val Lys Ser Val Leu Lys Ser Glu Val Asp Ala Leu
            820                 825                 830
Val Glu Leu Asn Ile Ser Lys Asn Leu Ile Gly Ser Ala Met Ala Gly
        835                 840                 845
Ser Val Gly Gly Phe Asn Ala His Ala Ala Asn Leu Val Thr Ala Ile
    850                 855                 860
Tyr Leu Ala Thr Gly Gln Asp Pro Ala Gln Asn Val Glu Ser Ser Asn
865                 870                 875                 880
Cys Ile Thr Leu Met Ser Asn Val Asp Gly Asn Leu Leu Ile Ser Val
                885                 890                 895
Ser Met Pro Ser Ile Glu Val Gly Thr Ile Gly Gly Gly Thr Ile Leu
            900                 905                 910
Glu Pro Gln Gly Ala Met Leu Glu Met Leu Gly Val Arg Gly Pro His
        915                 920                 925
Ile Glu Thr Pro Gly Ala Asn Ala Gln Gln Leu Ala Arg Ile Ile Ala
    930                 935                 940
Ser Gly Val Leu Ala Ala Glu Leu Ser Leu Cys Ser Ala Leu Ala Ala
945                 950                 955                 960
Gly His Leu Val Gln Ser His Met Thr His Asn Arg Ser Gln Ala Pro
                965                 970                 975
Thr Pro Ala Lys Gln Ser Gln Ala Asp Leu Gln Arg Leu Gln Asn Gly
            980                 985                 990
Ser Asn Ile Cys Ile Arg Ser
        995

<210> SEQ ID NO 81
<211> LENGTH: 1203
<212> TYPE: PRT
<213> ORGANISM: Artificial
<220> FEATURE:
<223> OTHER INFORMATION: Primer synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(20)
<223> OTHER INFORMATION: Xaa can be any naturally occurring amino acid
<220> FEATURE:
<221> NAME/KEY: misc_feature
```

-continued

```
<222> LOCATION: (22)..(22)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (77)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (105)..(106)
<223> OTHER INFORMATION: Xaa can be any naturally occurring amino acid
<220> FEATURE:
<221> NAME/KEY: misc_feature
<222> LOCATION: (109)..(111)
<223> OTHER INFORMATION: Xaa can be any naturally occurring amino acid
<220> FEATURE:
<221> NAME/KEY: misc_feature
<222> LOCATION: (113)..(123)
<223> OTHER INFORMATION: Xaa can be any naturally occurring amino acid
<220> FEATURE:
```

```
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (153)..(154)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (170)..(171)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (190)..(233)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (239)..(240)
<223> OTHER INFORMATION: Xaa can be any naturally occurring amino acid
<220> FEATURE:
<221> NAME/KEY: misc_feature
<222> LOCATION: (244)..(245)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
```

```
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (346)..(346)
<223> OTHER INFORMATION: Xaa can be any naturally occurring amino acid
<220> FEATURE:
<221> NAME/KEY: misc_feature
<222> LOCATION: (350)..(350)
<223> OTHER INFORMATION: Xaa can be any naturally occurring amino acid
<220> FEATURE:
<221> NAME/KEY: misc_feature
<222> LOCATION: (353)..(366)
<223> OTHER INFORMATION: Xaa can be any naturally occurring amino acid
<220> FEATURE:
<221> NAME/KEY: misc_feature
<222> LOCATION: (368)..(370)
<223> OTHER INFORMATION: Xaa can be any naturally occurring amino acid
<220> FEATURE:
<221> NAME/KEY: misc_feature
<222> LOCATION: (374)..(374)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (454)..(454)
<223> OTHER INFORMATION: Xaa can be any naturally occurring amino acid
<220> FEATURE:
<221> NAME/KEY: misc_feature
<222> LOCATION: (463)..(463)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (477)..(479)
<223> OTHER INFORMATION: Xaa can be any naturally occurring amino acid
<220> FEATURE:
<221> NAME/KEY: misc_feature
<222> LOCATION: (485)..(485)
<223> OTHER INFORMATION: Xaa can be any naturally occurring amino acid
<220> FEATURE:
<221> NAME/KEY: misc_feature
<222> LOCATION: (487)..(496)
<223> OTHER INFORMATION: Xaa can be any naturally occurring amino acid
<220> FEATURE:
<221> NAME/KEY: misc_feature
<222> LOCATION: (499)..(499)
<223> OTHER INFORMATION: Xaa can be any naturally occurring amino acid
<220> FEATURE:
<221> NAME/KEY: misc_feature
<222> LOCATION: (502)..(502)
```

-continued

```
<223> OTHER INFORMATION: Xaa can be any naturally occurring amino acid
<220> FEATURE:
<221> NAME/KEY: misc_feature
<222> LOCATION: (527)..(527)
<223> OTHER INFORMATION: Xaa can be any naturally occurring amino acid
<220> FEATURE:
<221> NAME/KEY: misc_feature
<222> LOCATION: (529)..(529)
<223> OTHER INFORMATION: Xaa can be any naturally occurring amino acid
<220> FEATURE:
<221> NAME/KEY: misc_feature
<222> LOCATION: (531)..(540)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (548)..(549)
<223> OTHER INFORMATION: Xaa can be any naturally occurring amino acid
<220> FEATURE:
<221> NAME/KEY: misc_feature
<222> LOCATION: (557)..(557)
<223> OTHER INFORMATION: Xaa can be any naturally occurring amino acid
<220> FEATURE:
<221> NAME/KEY: misc_feature
<222> LOCATION: (564)..(564)
<223> OTHER INFORMATION: Xaa can be any naturally occurring amino acid
<220> FEATURE:
<221> NAME/KEY: misc_feature
<222> LOCATION: (571)..(571)
<223> OTHER INFORMATION: Xaa can be any naturally occurring amino acid
<220> FEATURE:
<221> NAME/KEY: misc_feature
<222> LOCATION: (594)..(594)
<223> OTHER INFORMATION: Xaa can be any naturally occurring amino acid
<220> FEATURE:
<221> NAME/KEY: misc_feature
<222> LOCATION: (596)..(598)
<223> OTHER INFORMATION: Xaa can be any naturally occurring amino acid
<220> FEATURE:
<221> NAME/KEY: misc_feature
<222> LOCATION: (600)..(608)
<223> OTHER INFORMATION: Xaa can be any naturally occurring amino acid
<220> FEATURE:
<221> NAME/KEY: misc_feature
<222> LOCATION: (610)..(617)
<223> OTHER INFORMATION: Xaa can be any naturally occurring amino acid
<220> FEATURE:
<221> NAME/KEY: misc_feature
<222> LOCATION: (619)..(619)
<223> OTHER INFORMATION: Xaa can be any naturally occurring amino acid
<220> FEATURE:
<221> NAME/KEY: misc_feature
<222> LOCATION: (622)..(622)
<223> OTHER INFORMATION: Xaa can be any naturally occurring amino acid
<220> FEATURE:
<221> NAME/KEY: misc_feature
<222> LOCATION: (661)..(661)
<223> OTHER INFORMATION: Xaa can be any naturally occurring amino acid
<220> FEATURE:
<221> NAME/KEY: misc_feature
<222> LOCATION: (668)..(672)
<223> OTHER INFORMATION: Xaa can be any naturally occurring amino acid
<220> FEATURE:
<221> NAME/KEY: misc_feature
<222> LOCATION: (675)..(675)
<223> OTHER INFORMATION: Xaa can be any naturally occurring amino acid
<220> FEATURE:
<221> NAME/KEY: misc_feature
<222> LOCATION: (678)..(680)
<223> OTHER INFORMATION: Xaa can be any naturally occurring amino acid
<220> FEATURE:
<221> NAME/KEY: misc_feature
```

-continued

```
<222> LOCATION: (682)..(683)
<223> OTHER INFORMATION: Xaa can be any naturally occurring amino acid
<220> FEATURE:
<221> NAME/KEY: misc_feature
<222> LOCATION: (685)..(687)
<223> OTHER INFORMATION: Xaa can be any naturally occurring amino acid
<220> FEATURE:
<221> NAME/KEY: misc_feature
<222> LOCATION: (690)..(690)
<223> OTHER INFORMATION: Xaa can be any naturally occurring amino acid
<220> FEATURE:
<221> NAME/KEY: misc_feature
<222> LOCATION: (692)..(696)
<223> OTHER INFORMATION: Xaa can be any naturally occurring amino acid
<220> FEATURE:
<221> NAME/KEY: misc_feature
<222> LOCATION: (698)..(699)
<223> OTHER INFORMATION: Xaa can be any naturally occurring amino acid
<220> FEATURE:
<221> NAME/KEY: misc_feature
<222> LOCATION: (701)..(709)
<223> OTHER INFORMATION: Xaa can be any naturally occurring amino acid
<220> FEATURE:
<221> NAME/KEY: misc_feature
<222> LOCATION: (713)..(713)
<223> OTHER INFORMATION: Xaa can be any naturally occurring amino acid
<220> FEATURE:
<221> NAME/KEY: misc_feature
<222> LOCATION: (718)..(719)
<223> OTHER INFORMATION: Xaa can be any naturally occurring amino acid
<220> FEATURE:
<221> NAME/KEY: misc_feature
<222> LOCATION: (721)..(722)
<223> OTHER INFORMATION: Xaa can be any naturally occurring amino acid
<220> FEATURE:
<221> NAME/KEY: misc_feature
<222> LOCATION: (724)..(727)
<223> OTHER INFORMATION: Xaa can be any naturally occurring amino acid
<220> FEATURE:
<221> NAME/KEY: misc_feature
<222> LOCATION: (729)..(729)
<223> OTHER INFORMATION: Xaa can be any naturally occurring amino acid
<220> FEATURE:
<221> NAME/KEY: misc_feature
<222> LOCATION: (732)..(737)
<223> OTHER INFORMATION: Xaa can be any naturally occurring amino acid
<220> FEATURE:
<221> NAME/KEY: misc_feature
<222> LOCATION: (755)..(755)
<223> OTHER INFORMATION: Xaa can be any naturally occurring amino acid
<220> FEATURE:
<221> NAME/KEY: misc_feature
<222> LOCATION: (757)..(757)
<223> OTHER INFORMATION: Xaa can be any naturally occurring amino acid
<220> FEATURE:
<221> NAME/KEY: misc_feature
<222> LOCATION: (763)..(763)
<223> OTHER INFORMATION: Xaa can be any naturally occurring amino acid
<220> FEATURE:
<221> NAME/KEY: misc_feature
<222> LOCATION: (767)..(767)
<223> OTHER INFORMATION: Xaa can be any naturally occurring amino acid
<220> FEATURE:
<221> NAME/KEY: misc_feature
<222> LOCATION: (781)..(789)
<223> OTHER INFORMATION: Xaa can be any naturally occurring amino acid
<220> FEATURE:
<221> NAME/KEY: misc_feature
<222> LOCATION: (805)..(806)
<223> OTHER INFORMATION: Xaa can be any naturally occurring amino acid
<220> FEATURE:
<221> NAME/KEY: misc_feature
<222> LOCATION: (813)..(813)
<223> OTHER INFORMATION: Xaa can be any naturally occurring amino acid
<220> FEATURE:
<221> NAME/KEY: misc_feature
<222> LOCATION: (903)..(903)
<223> OTHER INFORMATION: Xaa can be any naturally occurring amino acid
<220> FEATURE:
```

```
<221> NAME/KEY: misc_feature
<222> LOCATION: (908)..(908)
<223> OTHER INFORMATION: Xaa can be any naturally occurring amino acid
<220> FEATURE:
<221> NAME/KEY: misc_feature
<222> LOCATION: (924)..(924)
<223> OTHER INFORMATION: Xaa can be any naturally occurring amino acid
<220> FEATURE:
<221> NAME/KEY: misc_feature
<222> LOCATION: (981)..(981)
<223> OTHER INFORMATION: Xaa can be any naturally occurring amino acid
<220> FEATURE:
<221> NAME/KEY: misc_feature
<222> LOCATION: (1186)..(1186)
<223> OTHER INFORMATION: Xaa can be any naturally occurring amino acid
<220> FEATURE:
<221> NAME/KEY: misc_feature
<222> LOCATION: (1189)..(1190)
<223> OTHER INFORMATION: Xaa can be any naturally occurring amino acid
<220> FEATURE:
<221> NAME/KEY: misc_feature
<222> LOCATION: (1192)..(1198)
<223> OTHER INFORMATION: Xaa can be any naturally occurring amino acid
<220> FEATURE:
<221> NAME/KEY: misc_feature
<222> LOCATION: (1200)..(1200)
<223> OTHER INFORMATION: Xaa can be any naturally occurring amino acid
<220> FEATURE:
<221> NAME/KEY: misc_feature
<222> LOCATION: (1202)..(1202)
<223> OTHER INFORMATION: Xaa can be any naturally occurring amino acid

<400> SEQUENCE: 81

Xaa Met Ala Ser Xaa Leu Leu Xaa Xaa Arg Phe Xaa Xaa Glu Xaa Xaa
1               5                   10                  15

Xaa Xaa Xaa Xaa Ala Xaa Pro Ser Trp Xaa Xaa Lys Xaa Leu Thr Xaa
            20                  25                  30

Pro Ile Gln Xaa Ile Ser Arg Phe Ala Ala Xaa His Pro Ile His Thr
        35                  40                  45

Ile Val Leu Val Ala Leu Leu Ala Ser Thr Ala Tyr Leu Gly Leu Leu
    50                  55                  60

Gln Xaa Ser Leu Phe Xaa Trp Xaa Leu Xaa Ser Asn Xaa Xaa Xaa Xaa
65                  70                  75                  80

Xaa Xaa Asp Xaa Thr Ser Leu Xaa Xaa Gly Ser Arg Xaa Leu Arg Xaa
                85                  90                  95

Gly Xaa Xaa Thr Xaa Trp Arg Trp Xaa Xaa Ile Asp Xaa Xaa Xaa Ile
            100                 105                 110

Xaa Xaa Xaa Xaa Xaa Xaa Xaa Xaa Xaa Xaa Ala Ala Asp Ala Xaa
        115                 120                 125

His Leu Ala Leu Xaa Thr Leu Val Phe Pro Asp Thr Gln Ser Xaa Glu
    130                 135                 140

Xaa Ala Ser Thr Ile Pro Xaa Ala Xaa Xaa Val Pro Val Pro Xaa Asn
145                 150                 155                 160

Xaa Ser Ile Xaa Leu Leu Pro Xaa Thr Xaa Xaa Ile Phe Thr Xaa Tyr
                165                 170                 175

Ser Gln Asp Ser Ser Leu Xaa Phe Ser Leu Pro Tyr Ser Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Asp Ile Val Xaa Trp Xaa Xaa
225                 230                 235                 240
```

```
Asn Ala Trp Xaa Xaa Phe Ser Asp Leu Ile Lys Asn Ala Asp Thr Phe
            245                 250                 255

Asp Ile Ile Ile Met Xaa Leu Gly Tyr Leu Ala Met His Tyr Thr Phe
            260                 265                 270

Xaa Ser Leu Phe Xaa Ser Met Arg Lys Leu Gly Ser Lys Phe Trp Leu
            275                 280                 285

Ala Thr Ser Xaa Leu Phe Ser Ser Ile Phe Ala Phe Leu Leu Gly Leu
            290                 295                 300

Leu Val Thr Thr Lys Leu Gly Xaa Val Pro Ile Ser Met Leu Leu Leu
305                 310                 315                 320

Ser Glu Gly Leu Pro Phe Leu Val Val Thr Ile Gly Phe Glu Lys Lys
                    325                 330                 335

Ile Val Leu Thr Arg Ala Val Leu Ser Xaa Ala Ile Asp Xaa Arg Arg
                340                 345                 350

Xaa Xaa Xaa Xaa Xaa Xaa Xaa Xaa Xaa Xaa Xaa Xaa Xaa Ser Xaa
                355                 360                 365

Xaa Xaa Ser Ile Gln Xaa Ala Ile Gln Xaa Ala Ile Lys Glu Xaa Gly
            370                 375                 380

Phe Glu Ile Ile Arg Asp Tyr Ala Ile Glu Ile Ser Ile Leu Ile Ala
385                 390                 395                 400

Gly Ala Ala Ser Gly Val Gln Gly Gly Xaa Leu Xaa Gln Phe Cys Phe
                405                 410                 415

Leu Ala Ala Trp Ile Leu Phe Phe Asp Xaa Ile Leu Leu Phe Thr Phe
                420                 425                 430

Tyr Ser Ala Ile Leu Ala Ile Lys Leu Glu Ile Asn Arg Ile Lys Arg
                435                 440                 445

His Val Ile Ile Arg Xaa Ala Leu Glu Glu Asp Gly Val Ser Xaa Ser
            450                 455                 460

Val Ala Glu Lys Val Ala Lys Ser Glu Xaa Asp Trp Xaa Xaa Xaa Lys
465                 470                 475                 480

Gly Ser Asp Ser Xaa Phe Xaa Xaa Xaa Xaa Xaa Xaa Xaa Xaa Xaa
                485                 490                 495

Lys Ser Xaa Ala Ile Xaa Ile Phe Lys Val Leu Met Ile Leu Gly Phe
            500                 505                 510

Val Leu Ile Asn Leu Val Asn Leu Thr Ala Ile Pro Phe Arg Xaa Ala
            515                 520                 525

Xaa Ser Xaa Xaa Xaa Xaa Xaa Xaa Xaa Xaa Xaa Leu Xaa Gly Val
            530                 535                 540

Xaa Ser Pro Xaa Xaa Val Asp Pro Phe Lys Val Ala Xaa Asn Leu Leu
545                 550                 555                 560

Asp Ala Ile Xaa Ala Ala Lys Ser Asn Xaa Arg Glu Thr Leu Val
            565                 570                 575

Thr Val Val Thr Pro Ile Lys Tyr Glu Leu Glu Tyr Pro Ser Ile His
            580                 585                 590

Tyr Xaa Glu Xaa Xaa Xaa Ser Xaa Xaa Xaa Xaa Xaa Xaa Xaa Xaa
    595                 600                 605

Leu Xaa Xaa Xaa Xaa Xaa Xaa Gly Xaa Gly Gly Xaa Met Leu
            610                 615                 620

Gly Ser Val Ser Lys Ser Ile Glu Asp Pro Val Ile Ser Lys Trp Ile
625                 630                 635                 640

Val Ile Ala Leu Ala Leu Ser Ile Ala Leu Asn Val Tyr Leu Phe Asn
                645                 650                 655

Ala Ala Arg Trp Xaa Ile Lys Asp Pro Asn Val Xaa Xaa Xaa Xaa Xaa
```

-continued

```
               660                 665                 670
Glu Val Xaa Glu Leu Xaa Xaa Xaa Gln Xaa Xaa Asn Xaa Xaa Xaa Ser
            675                 680                 685
Ala Xaa Leu Xaa Xaa Xaa Xaa Xaa Ile Xaa Xaa Thr Xaa Xaa Xaa Xaa
            690                 695                 700
Xaa Xaa Xaa Xaa Xaa Thr Pro Ala Xaa Thr Asp Asp Glu Xaa Xaa Ser
705                 710                 715                 720
Xaa Xaa Ser Xaa Xaa Xaa Val Xaa Lys Ile Xaa Xaa Xaa Xaa Xaa
            725                 730                 735
Xaa Ile Arg Ser Leu Glu Glu Leu Glu Ala Leu Leu Ala Ala Lys Lys
            740                 745                 750
Thr Lys Xaa Leu Xaa Asp Glu Glu Val Val Xaa Leu Ser Leu Xaa Gly
            755                 760                 765
Lys Leu Pro Leu Tyr Ala Leu Glu Lys Thr Leu Gly Xaa Xaa Xaa Xaa
            770                 775                 780
Xaa Xaa Xaa Xaa Xaa Asp Phe Thr Arg Ala Val Lys Ile Arg Arg Ser
785                 790                 795                 800
Ile Ile Ser Arg Xaa Xaa Ala Thr Ser Ala Leu Thr Xaa Ser Leu Glu
            805                 810                 815
Ser Ser Lys Leu Pro Tyr Lys Asn Tyr Asn Tyr Asp Arg Val Phe Gly
            820                 825                 830
Ala Cys Cys Glu Asn Val Ile Gly Tyr Met Pro Leu Pro Val Gly Val
            835                 840                 845
Ala Gly Pro Leu Val Ile Asp Gly Gln Ser Tyr His Ile Pro Met Ala
            850                 855                 860
Thr Thr Glu Gly Val Leu Val Ala Ser Ala Ser Arg Gly Cys Lys Ala
865                 870                 875                 880
Ile Asn Ala Gly Gly Gly Ala Val Thr Val Leu Thr Ala Asp Gly Met
            885                 890                 895
Thr Arg Gly Pro Cys Val Xaa Phe Pro Thr Leu Xaa Arg Ala Gly Ala
            900                 905                 910
Ala Lys Ile Trp Leu Asp Ser Glu Glu Gly Gln Xaa Ser Met Lys Lys
            915                 920                 925
Ala Phe Asn Ser Thr Ser Arg Phe Ala Arg Leu Gln His Ile Lys Thr
            930                 935                 940
Ala Leu Ala Gly Thr Leu Leu Phe Ile Arg Phe Lys Thr Thr Thr Gly
945                 950                 955                 960
Asp Ala Met Gly Met Asn Met Ile Ser Lys Gly Val Glu His Ala Leu
                    965                 970                 975
Ser Val Met Val Xaa Glu Tyr Gly Phe Glu Asp Met Glu Ile Val Ser
            980                 985                 990
Val Ser Gly Asn Tyr Cys Thr Asp Lys Lys Pro Ala Ala Ile Asn Trp
            995                1000                1005
Ile Asp Gly Arg Gly Lys Ser Val Val Ala Glu Ala Thr Ile Pro
    1010                1015                1020
Gly Asp Val Val Lys Ser Val Leu Lys Ser Asp Val Asp Ala Leu
    1025                1030                1035
Val Glu Leu Asn Ile Ser Lys Asn Leu Ile Gly Ser Ala Met Ala
    1040                1045                1050
Gly Ser Val Gly Gly Phe Asn Ala His Ala Ala Asn Ile Val Thr
    1055                1060                1065
Ala Ile Phe Leu Ala Thr Gly Gln Asp Pro Ala Gln Asn Val Glu
    1070                1075                1080
```

```
Ser  Ser  Asn  Cys  Ile  Thr  Leu  Met  Lys  Asn  Val  Asp  Gly  Asn  Leu
     1085                1090                     1095

Gln  Ile  Ser  Val  Ser  Met  Pro  Ser  Ile  Glu  Val  Gly  Thr  Ile  Gly
     1100                1105                     1110

Gly  Gly  Thr  Ile  Leu  Glu  Pro  Gln  Gly  Ala  Met  Leu  Asp  Leu  Leu
     1115                1120                     1125

Gly  Val  Arg  Gly  Pro  His  Pro  Thr  Asn  Pro  Gly  Asp  Asn  Ala  Arg
     1130                1135                     1140

Gln  Leu  Ala  Arg  Ile  Ile  Ala  Ala  Ala  Val  Leu  Ala  Gly  Glu  Leu
     1145                1150                     1155

Ser  Leu  Cys  Ser  Ala  Leu  Ala  Ala  Gly  His  Leu  Val  Gln  Ala  His
     1160                1165                     1170

Met  Thr  His  Asn  Arg  Ser  Ala  Ala  Pro  Thr  Arg  Ser  Xaa  Thr  Pro
     1175                1180                     1185

Xaa  Xaa  Ala  Xaa  Xaa  Xaa  Xaa  Xaa  Xaa  Xaa  Thr  Xaa  Ile  Xaa  Ser
     1190                1195                     1200
```

<210> SEQ ID NO 82
<211> LENGTH: 176
<212> TYPE: PRT
<213> ORGANISM: Artificial Sequence
<220> FEATURE:
<223> OTHER INFORMATION: Novosphingobium aromaticivorans

<400> SEQUENCE: 82

```
Met  Gly  Gly  Ala  Met  Gln  Thr  Leu  Ala  Ala  Ile  Leu  Ile  Val  Leu  Gly
1                 5                    10                       15

Thr  Val  Leu  Ala  Met  Glu  Phe  Val  Ala  Trp  Ser  Ser  His  Lys  Tyr  Ile
              20                   25                       30

Met  His  Gly  Phe  Gly  Trp  Gly  Trp  His  Arg  Asp  His  His  Glu  Pro  His
         35                   40                       45

Glu  Gly  Phe  Leu  Glu  Lys  Asn  Asp  Leu  Tyr  Ala  Ile  Val  Gly  Ala  Ala
     50                   55                       60

Leu  Ser  Ile  Leu  Met  Phe  Ala  Leu  Gly  Ser  Pro  Met  Ile  Met  Gly  Ala
65                   70                   75                       80

Asp  Ala  Trp  Trp  Pro  Gly  Thr  Trp  Ile  Gly  Leu  Gly  Val  Leu  Phe  Tyr
                 85                   90                       95

Gly  Val  Ile  Tyr  Thr  Leu  Val  His  Asp  Gly  Leu  Val  His  Gln  Arg  Trp
              100                  105                      110

Phe  Arg  Trp  Val  Pro  Lys  Arg  Gly  Tyr  Ala  Lys  Arg  Leu  Val  Gln  Ala
         115                  120                      125

His  Lys  Leu  His  His  Ala  Thr  Ile  Gly  Lys  Glu  Gly  Gly  Val  Ser  Phe
     130                  135                      140

Gly  Phe  Val  Phe  Ala  Arg  Asp  Pro  Ala  Val  Leu  Lys  Gln  Glu  Leu  Arg
145                  150                  155                      160

Ala  Gln  Arg  Glu  Ala  Gly  Ile  Ala  Val  Leu  Arg  Glu  Ala  Val  Asp  Gly
                 165                  170                      175
```

<210> SEQ ID NO 83
<211> LENGTH: 264
<212> TYPE: PRT
<213> ORGANISM: Artificial Sequence
<220> FEATURE:
<223> OTHER INFORMATION: Sargasso Sea environmental isolate

<400> SEQUENCE: 83

```
Met  Thr  Arg  Ser  Ile  Ser  Trp  Pro  Ser  Thr  Tyr  Trp  His  Leu  Gln  Pro
```

-continued

```
1               5                   10                  15
Ser Cys Ser Ser Trp Val Ala Asn Glu Phe Ser Pro Gln Ala Arg Lys
            20                  25                  30

Gly Leu Val Leu Ala Gly Leu Ile Gly Ser Ala Trp Leu Leu Thr Leu
            35                  40                  45

Gly Leu Gly Phe Ser Leu Pro Leu His Gln Thr Ser Trp Leu Leu Ile
        50              55                  60

Gly Cys Leu Val Leu Leu Arg Ser Phe Leu His Thr Gly Leu Phe Ile
65                  70              75                      80

Val Ala His Asp Ala Met His Ala Ser Leu Val Pro Asp His Pro Gly
                85                  90                  95

Leu Asn Arg Trp Ile Gly Arg Val Cys Leu Leu Met Tyr Ala Gly Leu
            100                 105                 110

Ser Tyr Lys Arg Cys Cys Arg Asn His Arg Arg His His Gln Ala Pro
            115                 120                 125

Glu Thr Val Glu Asp Pro Asp Tyr Gln Arg Cys Thr Asn Asn Asn Ile
        130                 135                 140

Leu Asp Trp Tyr Val His Phe Met Gly Asn Tyr Leu Gly Trp Gln Gln
145                 150                 155                 160

Leu Leu Asn Leu Ser Cys Val Trp Leu Ala Leu Thr Phe Arg Val Ser
            165                 170                 175

Asp Tyr Ser Ala Gln Phe Phe His Leu Leu Leu Phe Ser Val Leu Pro
            180                 185                 190

Leu Ile Val Ser Ser Cys Gln Leu Phe Leu Val Gly Thr Trp Leu Pro
            195                 200                 205

His Arg Arg Gly Ala Thr Thr Arg Pro Gly Val Thr Thr Arg Ser Leu
    210                 215                 220

Asn Phe His Pro Ala Leu Ser Phe Ala Ala Cys Tyr His Phe Gly Tyr
225                 230                 235                 240

His Arg Glu His His Glu Ser Pro Ser Thr Pro Trp Phe Gln Leu Pro
                245                 250                 255

Lys Leu Arg Glu Gly Ser Leu Ile
            260
```